(12) United States Patent
Lazzari et al.

(10) Patent No.: US 8,609,659 B2
(45) Date of Patent: Dec. 17, 2013

(54) SUBSTITUTED 3,8-DIAZABICYCLO[3.2.1]OCTANE COMPOUNDS

(75) Inventors: Paolo Lazzari, Cagliari (IT); Giovanni Loriga, Sassari (IT); Stefania Ruiu, Cagliari (IT); Gabriele Murineddu, Sassari (IT); Luca Pani, Cagliari (IT); Gerard Aime Pinna, Sassari (IT)

(73) Assignee: Neuroscienze Pharmaness S.C.A.R.L., Cagliari (IT)

( * ) Notice: Subject to any disclaimer, the term of this patent is extended or adjusted under 35 U.S.C. 154(b) by 16 days.

(21) Appl. No.: 12/966,371

(22) Filed: Dec. 13, 2010

(65) Prior Publication Data

US 2011/0152238 A1    Jun. 23, 2011

(30) Foreign Application Priority Data

Dec. 18, 2009    (IT) .............................. MI2009A2222

(51) Int. Cl.
*A61K 31/495* (2006.01)
(52) U.S. Cl.
USPC ........... 514/249; 540/607; 544/349; 546/210; 548/530
(58) Field of Classification Search
USPC ........... 514/249; 540/607; 544/349; 546/210; 548/530
See application file for complete search history.

(56) References Cited

U.S. PATENT DOCUMENTS

| | | |
|---|---|---|
| 5,672,601 A | 9/1997 | Cignarella |
| 5,780,589 A | 7/1998 | Lazarus et al. |
| 6,028,084 A | 2/2000 | Barth et al. |
| 6,127,362 A | 10/2000 | Cignarella et al. |
| 7,358,243 B2 | 4/2008 | Peters et al. |
| 2003/0003145 A1 | 1/2003 | Abramovici et al. |
| 2003/0152635 A1 | 8/2003 | Heurtault et al. |
| 2003/0186872 A1 | 10/2003 | Chang et al. |
| 2003/0195217 A1 | 10/2003 | Cignarella et al. |
| 2004/0131692 A1 | 7/2004 | Kreuter et al. |
| 2005/0203123 A1 | 9/2005 | Dolle et al. |
| 2006/0135522 A1 | 6/2006 | Carson et al. |
| 2006/0135763 A1 | 6/2006 | Coats et al. |
| 2006/0148850 A1 | 7/2006 | Brown et al. |
| 2008/0096925 A1 | 4/2008 | Janssens et al. |

FOREIGN PATENT DOCUMENTS

| | | |
|---|---|---|
| WO | WO-01/46198 A3 | 6/2001 |
| WO | WO-01/60823 A1 | 8/2001 |
| WO | WO-02/30935 A1 | 4/2002 |
| WO | WO-02/42309 A1 | 5/2002 |
| WO | WO-2004/011468 A1 | 2/2004 |
| WO | WO-2004/060321 A3 | 7/2004 |
| WO | WO-2004/089372 A1 | 10/2004 |
| WO | WO-2005/066164 A1 | 7/2005 |
| WO | WO-2005/092836 A1 | 10/2005 |
| WO | WO-2005/108402 A1 | 11/2005 |
| WO | WO-2006/113468 A2 | 10/2006 |

OTHER PUBLICATIONS

K.J. Chang et al; "Benzomorphan Sites Are Ligand Recognition Sites of Putative ε-Receptors"; Molecular Pharmacology 26 (1984) pp. 484-488.
D.F. Pacheco et al.; "δ-Opioid receptor agonist SNC80 elicits peripheral antinociception via $\delta_1$ and $\delta_2$ receptors and activation of the L-arginine/nitric oxide/cyclic GMP pathway", Life Sciences 78 (2005) pp. 54-60.
G.A. Pinna et al.; "N-3(9)-Arylpropenyl-N-9(3)-propionyl-3,9-diazabicyclo[3.3.1]nonanes as μ-Opioid Receptor Agonists. Effects on μ-Affinity of Arylalkenyl Chain Modifications" Bioorganic & Medicinal Chemistry, 10 (2002) pp. 1929-1937.
G.A. Pinna et al.; "Synthesis of Novel Diazatricyclodecanes (DTDs). Effects of Structural Variation at the C3' Allyl EnD and at the Phenyl Ring of the Cinnamyl Chain on μ-Receptor Affinity and Opioid Antinociception" Bioorganic & Medicinal Chemistry, 11 (2003) pp. 4015-4026.
K.J. Chang et al.; "A Novel Potent and Selective Nonpeptidic Delta Opioid Receptor Agonist BW373U86" The Journal of Pharmacology and Experimental Therapeutics, 267 (1993) pp. 852-857.
S.N. Calderon et al.; "Probes for Narcotic Receptor Mediated Phenomena. 19.[1] Synthesis of (+)-4-[(αR)-α-((2S,5R)-4-Allyl-2,5-dimethyl-1-piperazinyl)-3-methoxybenzyl]-.N,N-diethylbenzamide (SNC 80): A Highly Selective, Nonpeptide δ Opioid Receptor Agonist" J. Med. Chem. 37 (1994) pp. 2125-2128.
A. Hatzoglou et al.; "The antiproliferative effect of opioid receptor agonists on the T47D human breast cancer cell line, is partially mediated through opioid receptors", European Journal of Pharmacology 296 (1996) pp. 199-207.

(Continued)

*Primary Examiner* — Douglas M Willis
(74) *Attorney, Agent, or Firm* — Arent Fox LLP

(57) ABSTRACT

Diazapolycyclic compounds having affinity for the opioidergic receptors, preferably for the delta opioidergic receptors, with central and/or peripheral activity, having formula:

$$A_1\text{-}D_1\text{-}T_1 \quad (I)$$

wherein:
$A_1$ is a group of formula (II):

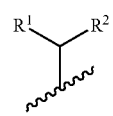

(II)

wherein:
$R^1$ is phenyl wherein one of the ring hydrogen atoms is substituted with a group selected from C(O)R', C(O)OR', C(O)NHR' or C(O)NR$^3$R$^4$, R', R$^3$ and R$^4$, being as defined in the application; R$^2$ is phenyl, optionally substituted
$D_1$ is a diazapolycyclic group
$T_1$ is a group selected from H, alkyl, alkenyl, alkynyl and from the following optionally substituted groups: cycloalkyl, heterocycloalkyl, aryl, heteroaryl, cycloalkylalkyl, heterocycloalkylalkyl, arylalkyl or heteroarylalkyl,
and their hydrates and solvates and pharmaceutically acceptable salts.

10 Claims, No Drawings

(56) References Cited

OTHER PUBLICATIONS

D. Stephan et al.; "Changes in intraocular pressure and pupil size following intramuscular administration of hydromorphone hydrochloride and acepromazine in clinically normal dogs", Veterinary Ophthalmology (2003) 6, 1, pp. 73-76.
J. Dortch-Carnes et al.; "Morphine-stimulated nitric oxide release in rabbit aqueous humor", Experimental Eye Research 84 (2007) pp. 185-190.
R. Alexander et al.; "Remifentanil prevents an icrease in intraocular pressure after succinylcholine and tracheal intubation", British Journal of Anaesthesia 1998, 81 pp. 606-607.
M.J. Glass et al.; "Opioids and food intake: distributed functional neural pathways?" Neuropeptides 33 (5) (1999) pp. 360-368.
A. Saitoh et al.; "Potential Anxiolytic and Antidepressant-Like Activites of SNC80, a Selective δ-Opioid Agonist, in Behavioral Models in Rodents", Journal of Pharmacological Sciences 95 (2004) pp. 374-380.
C. J. Kotzer et al.; "The Antitussive Activity of δ-Opioid Receptor Stimulation in Guinea Pigs", The Journal of Pharmacology and Experimental Therapeutics 292 (2000) pp. 803-809.
G. Dondio et al.; "Discovery of Novel Class of Substituted Pyrrolooctahydroisoquinolines as Potent and Selective δ Opioid Agonists, Based on an Extension of the Message-Address Concept", J. Med. Chem. 40 (1997) pp. 3192-3198.
R. Rozenfeld et al.; "An Emerging Role for the Delta Opioid Receptor in the Regulation of Mu Opioid Receptor Function", The Scientific World Journal 7 (S2) (2007) pp. 64-73.
I. Gomes et al.; "A role for heterodimerization of μ and δ opiate receptors in enchancing morphine analgesia", PNAS 101 (2004) pp. 5135-5139.
E. Abdelhamid et al.; "Selective Blockage of Delta Opioid Receptors Prevents the Development of Morphine Tolerance and Dependence in Mice", The Journal of Pharmacology and Experimental Therapeutics, 258 (1991) pp. 299-303.
Remington; "The Science and Practice of Pharmacy", Mack Publishing Company, vol. II, 1995, p. 1457.
S.N. Calderon et al.; "Probes for Narcotic Receptor Mediated Phenomena. 23.[1] Synthesis, Opioid Receptor Binding, and Bioassay of the Highly Selective δ Agonist (+)-4-[(αR)-α-((2S,5R)-4-Allyl-2,5-dimethyl-1-piperazinyl)-3-methoxybenzyl]-N,N-diethylbenzamide (SNC 80) and Related Novel Nonpeptide δ Opioid Receptor Ligands", J. Med. Chem. 40 (1997) 695-704.
R. K. Mitra; "Physicchemical investigations of microemulsification of eucalyptus oil and water using mixed surfactants (AOT+Brij-35) and butanol", J. Colloid and Interface Science 283 (2005) pp. 564-577.
C. E. McNamee et al.; "Physicochemical Characterization of PEG1500-12-acyloxy-stearate Micelles and Liquid Crystalline Phases", Langmuir, 2005, 21, pp. 8146-8154.
Simovic et al; "Dry Hybrid Lipid-Silica Microcapsules Engineered from Submicron Lipid Droplets and Nanoparticles as a Novel Delivery System for Poorly Soluble Drugs", Pharmaceutics, 6, 2009, pp. 861-872.
Woo-Dong Jang et al.; "Bioinspired application of dendrimers: From bio-mimicry to biomedical applications", Progress in Polymer Science 34, 2009, pp. 1-23.
E. Garcia et al.; "Colloidal carriers and blood-brain barrier (BBB) translocation: A way to deliver drugs to the brain?", International Journal of Pharmaceutics 298 (2005), pp. 274-292.
J. Kreuter, "Nanoparticulate systems for brain delivery of drugs", Advanced Drug Delivery Reviews, 47, 2001, pp. 65-81.
M.T. Peracchia et al.; "Synthesis of a Novel Poly(MePEG cyanoacrylate-co-alkyl cyanoacrylate) Amphiphilic Copolymer for Nanoparticle Technology" Macromolecules, 30, 1997, pp. 846-885.
L. Costantino et al, "Peptide-derivatized biodegradable nanoparticles able to cross the blood-brain barrier", Journal of Controlled Release, 108, 2005, pp. 84-96.
B. Stella et al., "Design of Folic Acid-Conjugated Nanoparticles for Drug Targeting", Journal of Phamaceutical Science, vol. 89, No. 11, Nov. 2000, pp. 1452-1464.
G. Cignarella et al., "Bicyclic Homologs of Piperazine. II. Synthesis of 3,8-Diazabicyclo[3.2.1]octane. New Synthesis of 8-Methyl-3,8-diazabicyclo[3.2.1]octane", J. Org. Chem., 26 (1961) pp. 2747-2750.
E.J. Bilsky et al.; "SNC 80, A Selective, Nonpeptidic and Systemically Active Opioid Delta Agonist", The Journal of Pharmacology and Experimental Therapeutics, Apr. 1995, 273 (1), pp. 359-366.
S.Ruiu et al.; "Synthesis and Characterization of NESS 0327: A Novel Putative Antagonist of the $CB_1$ Cannabinoid Receptor", The Journal of Pharmacology and Experimental Therapeutics, 306(1), 2003, pp. 363-370.
Holl R et al.; "Synthesis and Pharmacological Evaluation of SNC80 Analogues with a Bridged Piperazine Ring" CHEMMEDCHEM, vol. 4, Oct. 13, 2009, pp. 2111-2122.

SUBSTITUTED 3,8-DIAZABICYCLO[3.2.1]OCTANE COMPOUNDS

CROSS-REFERENCE TO RELATED APPLICATIONS

This application claims priority to Italian Application No. MI2009A002222 filed on Dec. 18, 2009.

FIELD OF INVENTION

The present invention relates to pharmaceutical compositions comprising as active principles diazapolycyclic compounds having affinity for opioidergic receptors, the corresponding solvates and pharmaceutically acceptable salts.

More specifically the present invention relates to pharmaceutical compositions wherein the active principles have a high affinity and selectivity for the delta (δ) opioidergic receptors. Preferably the diazapolycyclic compounds are diazabicyclic compounds or diazatricyclic compounds.

Still more specifically the present invention relates to heptane, octane, nonane or decane diazabicyclic compounds and to decane diazatricyclic compounds.

BACKGROUND OF INVENTION

At least three subreceptors of the opioid receptorial system are known: mu (μ), delta (δ) and kappa (k) opioidergic receptors. The presence of epsilon (ε) opioid receptors has also been reported (K. J. Chang et al. in Molecular Pharmacology 26 (1984) 484-488). As regards the delta opioid receptors, the presence of two distinct subreceptors $\delta_1$ and $\delta_2$ has been described (D. F. Pacheco et al. Life Sciences 78 (2005) 54-60).

Diazabicyclic and diazatricyclic compounds having affinity for the opioidergic receptors are known in the art.

In patent application US 2003/195,217 3,9-diazabicyclo[3.3.1]nonane compounds are described, having formula (A1):

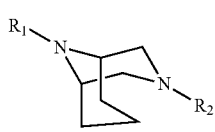
(A1)

wherein $R_1$ and $R_2$, different from each other, are a $C_2$-$C_8$ acyl or group of formula (A1a) or of formula (A1b):

—$CH_2$—CH=C(B)$R_a$ (A1a)

—$CH_2$—$CH_2$—CH(B)$R_a$ (A1b)

wherein:
B has the meaning of:
- $C_6$-$C_{10}$ aryl optionally substituted with the following G1 groups: $C_1$-$C_3$ alkoxy, $C_1$-$C_2$ haloalkyl, $C_1$-$C_3$ alkyl, halogen, CONHR$_b$, COOH, cyano, nitro,
- $C_5$-$C_7$ cycloalkyl group or an aromatic heterocyclo having 5 or 6 atoms, optionally benzocondensed, comprising at least one heteroatom selected from nitrogen, oxygen, sulphur, the heterocycle being optionally substituted with G1 groups herein above defined, $R_a$ has the meaning of hydrogen, $C_1$-$C_4$ alkyl, $C_5$-$C_7$ cycloalkyl or phenyl, optionally substituted with G1 groups.

The compounds of formula (A1) have a central analgesic activity mediated by the opioidergic receptors comparable to that induced by morphine, but with the advantage of lower side effects.

The compounds of formula (A1) has also been dealt with in the paper of G. A. Pinna et al., *Bioorganic & Medicinal Chemistry*, 10 (2002) 1929-1937, wherein the effect of various substituents of the bicyclic structure on the affinity towards opioidergic receptors is pointed out. It is therein shown that both the compounds of the examples of the patent application US 2003/195,217 and those described by G. A. Pinna et al. show a high or good affinity for the μ receptors and a poor or no affinity for the delta receptors.

U.S. Pat. No. 5,672,601 describes 3,8-diaza bicyclo[3.2.1] octane compounds and the corresponding pharmaceutical dosage forms having central analgesic activity mediated by the μ opioidergic receptors. The compounds are shown to be selective towards the μ receptors, with affinity similar to that of the morphine. The compounds have formula (A2):

(A2)

wherein $R_3$ and $R_4$, different from each other, are $C_2$-$C_8$ acyl group or a group of formula —$CH_2$-A-D wherein:
A is —$CH_2$—$CH_2$—, —CH=CH—, or —$CH_2$—C(O)—,
D is selected from the following groups:
- $C_6$-$C_{10}$ aryl, optionally substituted with the following G2 groups: CONHR$_3$, COOH, ciano, nitro, NHCOR$_3$,
- aromatic heterocycle or an alicyclic group with a 5 or 6 atom ring, optionally benzocondensed, comprising at least one heteroatom selected from nitrogen, oxygen, sulphur, said heterocycles being optionally substituted with G2 groups.

Patent application WO 2005/108,402 relates to 3,6 diazabicyclo[3.1.1]heptane derivatives of formula (A3):

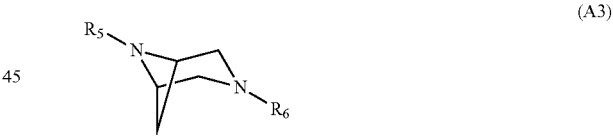
(A3)

wherein $R_5$ and $R_6$, different from each other, are $C_2$-$C_8$ acyl or a group selected from the following formulas (A3a), (A3b), (A3c):

—$CH_2$—CH=C(B$_1$)R$_c$ (A3a)

—$CH_2$—$CH_2$—CH(B$_1$)R$_c$ (A3b)

—$CH_2$—$CH_2$—C(O)B$_1$ (A3c)

wherein:
B$_1$ is selected from the following groups:
- $C_6$-$C_{10}$ aryl, optionally substituted with the following G3 groups: $C_1$-$C_3$ alkoxy, $C_1$-$C_2$ haloalkyl, $C_1$-$C_3$ alkyl, halogen, COOH, cyano, nitro, CONHR$_d$ wherein R$_d$ is a $C_1$-$C_4$ alkyl group,
- $C_5$-$C_7$ cycloalkyl group,
- an aromatic heterocycle having a ring with 5 or 6 atoms, optionally benzocondensed, containing at least one heteroatom selected from nitrogen, oxygen, sulphur, said heterocycle being optionally substituted with G3 groups, $R_c$ has the meaning of hydrogen, $C_1$-$C_4$ alkyl, $C_5$-$C_7$ cycloalkyl or phenyl, optionally substituted with G3 groups as herein above defined.

The compounds show central analgesic activity mediated by the μ opioid receptors.

Another class of diazabicyclic compounds having affinity towards the opioidergic receptors is described in U.S. Pat. No. 7,358,243. In particular, this class of compounds is formed of diazabicyclo nonanes and decanes characterized by high affinity for the μ receptors and having general formula (A4):

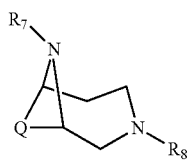

(A4)

wherein Q is —$CH_2$—$CH_2$— or —$CH_2$—$CH_2$—$CH_2$— and one between $R_7$ and $R_8$ is —$CH_2$—$CH_2$—$CH_2$—$R_e$ or —$CH_2$—CH=CH—$R_e$ or —$CH_2$—C≡C—$R_e$, $R_e$ being aryl or heteroaryl and the other between $R_7$ and $R_8$ is —C(O)$R_f$, $R_f$ being alkyl, or cycloalkyl, or cycloalkylalkyl, or aryl or arylalkyl.

U.S. Pat. No. 6,127,362 discloses 9,10-diazatricyclo-[4,4, 1,1$^{2,5}$]-decane compounds and 2,7-diazatricyclo[4,4,0,0$^{3,8}$] decane compounds having analgesic activity, of formula (A5) or (A6):

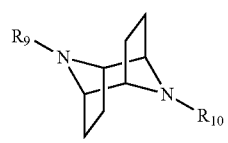

(A5)

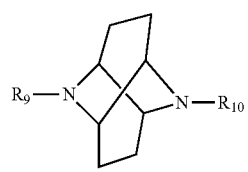

(A6)

wherein $R_9$ and $R_{10}$ are both hydrogen, or are different from each other and they are selected from:
hydrogen, $C_1$-$C_8$ alkyl, $C_2$-$C_{10}$ acyl,
a group Ar selected from:
  phenyl optionally substituted,
  naphthyl optionally substituted,
  heterocyclic group having from 5 to 7 atoms in the ring, containing from 1 to 3 heteroatoms selected from oxygen, nitrogen and sulphur, optionally the heterocyclic group is benzocondensed and is optionally substituted on the benzene ring,
a group of formula —$CH_2$—CH=CH—Ar, wherein Ar is as defined above.

The analgesic activity of the compounds of formula (A5) or (A6) is mediated by the μ opioid receptors, as it results from the affinity and selectivity values of the compounds described in the articles by G. A. Pinna et al., *Bioorganic & Medicinal Chemistry*, 11 (2003) 4015-4026, and by P. Vianello et al., *Journal of Medicinal Chemistry*, 43 (2000) 2115-2123.

Compounds having affinity and selectivity for the delta opioidergic receptors having a non peptidic structure are known in the art.

Morphine derivatives selective for the delta opioid receptors are described in WO 02/30,935 and have formula (A7):

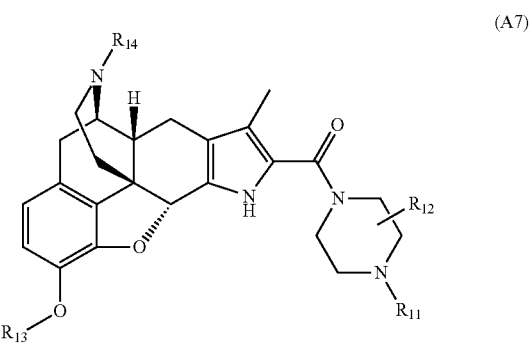

(A7)

wherein $R_{11}$, $R_{12}$, $R_{13}$ and $R_{14}$ have various meanings as reported in the patent application.

Agonist compounds selective of the delta opioid receptors are described in patent application US 2008/0096,925, and have the following formula (A8):

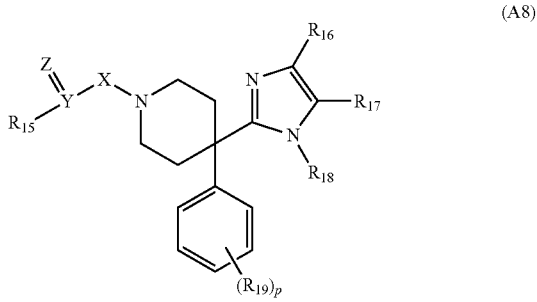

(A8)

wherein $R_{15}$, $R_{16}$, $R_{17}$, $R_{18}$, $R_{19}$, X, Y, Z, p have the various meanings therein reported.

Ligands of the delta opioid receptors are described in patent application US 2006/0148,850 having formula (A9):

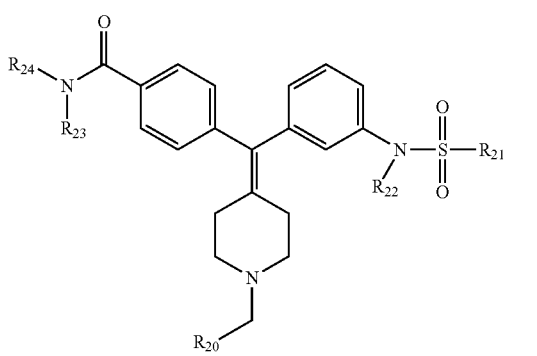

(A9)

wherein $R_{20}$, $R_{21}$, $R_{22}$, $R_{23}$, $R_{24}$ have the various meanings reported therein.

Patent applications US 2006/0135,522 and US 2006/0135,763 disclose compounds modulating the delta opioid receptors having formulas (A10) and (A11) respectively:

(A10)
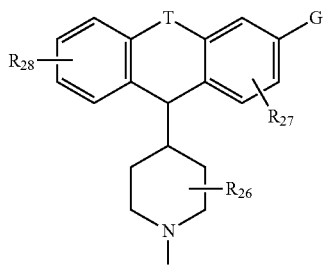

(A11)
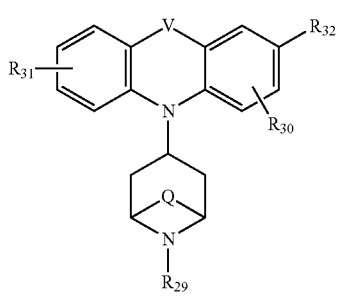

wherein $R_{25}$, $R_{26}$, $R_{27}$, $R_{28}$, $R_{29}$, $R_{30}$, $R_{31}$, $R_{32}$, T, G, V, Q have the various meanings reported in said patent applications.

Other known compounds with affinity and selectivity for the delta opioid receptors are the BW373U86 and SNC80 derivatives described, respectively, by K. J. Chang et al. in J.P.E.T. 267 (1993) 852-857 and by S. N. Calderon et al. in J. Med. Chem. 37 (1994) 2125-2128. The structures of the two compounds are:

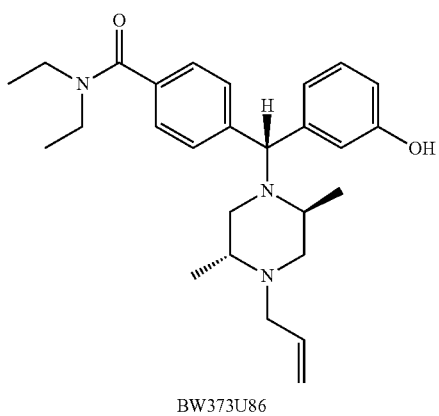

BW373U86

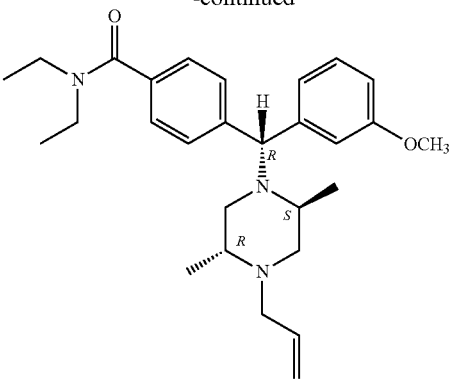

SNC80

The above mentioned patents and patent applications describing the diazabicyclic and diazatricyclic compounds with affinity for the opioidergic receptors disclose the use of said compounds for the pain treatment.

The above mentioned U.S. Pat. No. 7,358,243 indicates that the opioidergic compounds, besides the use for the treatment of different kinds of pain (post-surgery pain, chronic pain such as neuropathic pain), can be used for the therapeutic treatment of other diseases and disorders such as allergic dermatitis, sexual disfunctions, alcoholism, nausea, vomit, depression, tabagism, obesity and disorders related to food intake, use of abuse substances (for example heroin, cocaine), spinal lesions, cerebral trauma, shock, stroke, gastrointestinal disorders. *Eur. J. Pharmacol.* 296 (1996) 199-207 reports the antiproliferative activity of agonist compounds of the opioidergic receptors on a human cell line of breast cancer. The article therefore makes it known the antitumoral activity of said agonist compounds. In the following articles: Veterinary Ophthalmology (2003) 6, 1, 73-76; Exp. Eye Res. 2007 January 84 (1) 185-190; British Journal of Anaesthesia 1998, 81 606-607, the capability of agonist compounds of the opioidergic receptors of reducing the intraocular pressure and thus the use of said compounds for eye pathologies, such as glaucoma, is shown. In the article published in Neuropeptides 33 (5) (1999) 360-368, the effect of compounds modulating the opioidergic receptors on food intake is reported, in particular it is indicated that agonists and antagonists of the opioidergic receptors are capable to increase or decrease the food intake respectively.

Patent application WO 06/113,468 describes the use of compounds modulating the opioidergic receptors for the treatment of arthritis, psoriasis, asthma, cardiac disorders, sexual disfunctions, pain, incontinence and urogenital tract disorders.

Patent application US 2005/203,123 relates to antagonist compounds of the opioidergic receptors and their use for the treatment of gastrointestinal disorders, pain, obesity, Alzheimer and Parkinson diseases and related disorders. The use of opioidergic compounds for the treatment of diabetes and atherosclerosis is described in patent applications WO 05/092,836 and WO 05/066,164.

Patent application WO 04/089,372 describes the use of compounds which modulate the opioidergic receptors for the treatment or prevention of the central nervous system disorders such as anxiety and depression. The antidepressant and relaxing effects of the compound (+)-4-[(aR)-a-((2S,5R)-4-allil-2,5-dimethylpiperazinyl)-3-methoxy-benzyl]-N,N-diethylbenzamide, called SNC80, selective agonist of the delta opioidergic receptors, are reported in Journal of Pharmacological Sciences 95 (2004) 374-380.

Patent application WO 04/060,321 relates to therapeutic compositions comprising agonists of the opioidergic receptors having cardioprotective effects.

Patent applications WO 02/42,309 and WO 01/46,198 describe that opioidergic compounds can be used also as immunostimulants or immunosuppressants.

U.S. Pat. No. 5,780,589 reports the activity of the ligands of the opioid receptors in analgesia, in the modification of the peptide hormone secretion, in the body temperature modulation, in the respiratory depression, in the gastrointestinal functions, in the immune system activity. The patent describes also the use of opioids in the therapeutic treatment of the following pathologies: abuse of alcohol or opiates, neurologic diseases, hormonal disorders, disorders in the neurotransmitter release, neurologic disorders, immune system disfunctions, transplant rejection, pain, shock and cerebral lesions. This patent describes furthermore a new class of selective compounds for the delta opioid receptors having a peptide structure formed of dipeptides, tripeptides and cyclic peptides containing 2',6'-dimethyl-L-tyrosine (Dmt) and 1,2,3,4-tetrahydroisoquinoline-3-carboxylic acid (Tic).

Patent application US 2003/0186,872 describes the use of agonist compounds of the delta opioid receptors for the treatment of sexual disfunctions and in particular for the treatment of the early ejaculation in men.

C. J. Kotzer et al. in J.P.E.T. 292 (2000) 803-809 describe the anticough properties of the delta opioid agonists. In particular the agonist of the delta opioids studied in this reference is the compound called SB 227122 (page 804).

The therapeutic use of compounds having affinity for the μ opioid receptors, as well known from the prior art, can involve undesired effects such as constipation, respiratory depression, motion disturbances, nausea, vomit, sedation, tolerance and dependence. It is furthermore known that the entity of said side effects is lower or even nullified in the case of use of compounds having affinity and selectivity for the delta opioid receptors (G. Dondio et al. J. Med. Chem. 40 (1997) 3192-3198). Recent studies point out the role of the delta opioid receptors in modulating the μ opioid receptors (R. Rozenfeld et al. The Scientific World Journal 7 (S2) (2007) 64-73; I. Gomes et al. PNAS 101 (2004) 5135-5139). Ligands of the delta opioid receptors are capable of modulating the analgesic effect of opioidergic agonists acting prevailingly through the μ opioid receptors, such as morphine, but reducing the effects thereof of the pharmacological dependence and tolerance, (E. E. Abdelhamid et al. J.P.E.T. 258 (1991) 299-303).

BRIEF SUMMARY OF INVENTION

The need was felt to have available compounds having affinity for the opioid receptorial system having the following combination of properties:
high affinity and selectivity for the delta opioid receptors,
lower side effect with respect to the compounds having affinity and selectivity for the μ opioid receptors,
lower side effects with respect to morphine,
effective in reducing the side effects of compounds selected from μ opioid receptor agonists and/or morphine, without substantially modifying the therapeutic effects of said compounds, preferably by increasing and/or prolonging the therapeutic effects of the compounds.
It has been surprisingly and unexpectedly found by the Applicant a new class of compounds having affinity and selectivity for the opioid receptors, and corresponding pharmaceutical compositions, that solve the technical problem described above.

DETAILED DESCRIPTION OF INVENTION

It is an object of the present invention diazapolycyclic compounds having affinity for the opioidergic receptors, preferably for the delta opioidergic receptors, with central and/or peripheral activity, having formula:

$$A_1\text{-}D_1\text{-}T_1 \qquad (I)$$

wherein:
$A_1$ is a group of formula (II):

wherein:
$R^1$ is phenyl wherein one of the hydrogen atoms is substituted with a group selected from C(O)R', C(O)OR', C(O)NHR' or C(O)NR$^3$R$^4$, wherein:
R' is selected from H, alkyl, alkenyl, alkylthio, and from the following optionally substituted groups: cycloalkyl, heterocycloalkyl, aryl, heteroaryl, cycloalkylalkyl, heterocycloalkylalkyl, arylalkyl or heteroarylalkyl,
$R^3$ and $R^4$, equal to or different from each other, have the same meanings as R' excluding H, or together with the nitrogen atom to which they are linked, they form a ring with a number of atoms comprised between 5 and 7,
$R^2$ is phenyl, wherein one or more hydrogen atoms of the ring are optionally substituted with G4 groups, said groups being equal to or different from each other and selected from: halogen, alkyl, cycloalkyl, heterocycloalkyl, phenyl, benzyl, heteroaryl, alkenyl, alkylthio, cyano, SO$_2$NH$_2$, isothiocyanate, OR$^5$, NO$_2$, NHR$^5$ or NR$^6$R$^7$, wherein:
$R^5$ has the same meanings as R',
$R^6$ and $R^7$ have the same meanings as $R^3$ and $R^4$,
$D_1$ is a group selected from the following formulae (D1), (D2) and (D3)

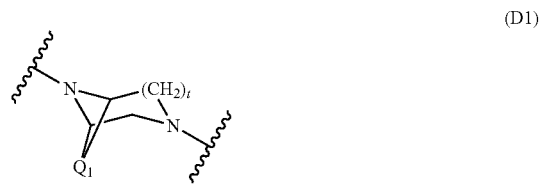

wherein t is an integer equal to 1 or 2,
when t=1 $Q_1$ is selected from —CH$_2$—, —CH$_2$—CH$_2$— or —CH$_2$—CH$_2$—CH$_2$—,
when t=2 $Q_1$ is selected from —CH$_2$—CH$_2$— or —CH$_2$—CH$_2$—CH$_2$—,

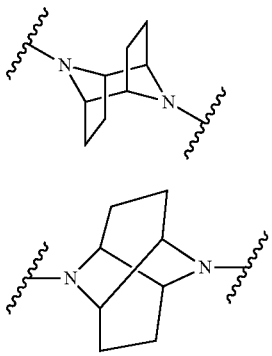

(D2)

(D3)

T₁ is a group selected from H, alkyl, alkenyl, alkynyl, and from the following optionally substituted groups: cycloalkyl, heterocycloalkyl, aryl, heteroaryl, cycloalkylalkyl, heterocycloalkylalkyl, arylalkyl or heteroarylalkyl.

The compounds of the invention can be in the form of the corresponding isomers (geometrical isomers, for example cis-trans, or stereoisomers), or mixtures thereof, further at least one atom of the compounds of formula (I) can be in a different isotopic form, for the radiolabelling.

In $R^1$ one or more hydrogen atoms of the aromatic ring can optionally be substituted with the above mentioned G4 groups, equal to or different from each other.

When R', $R^3$ or $R^4$ have the meaning of cycloalkyl, heterocycloalkyl, aryl, heteroaryl, cycloalkylalkyl, heterocycloalkylalkyl, arylalkyl or heteroarylalkyl groups, one or more hydrogen atoms of the ring can optionally be substituted with one or more substitutent groups G4, equal to or different from each other.

When $R^2$ is phenyl substituted with cycloalkyl, heterocycloalkyl, phenyl, benzyl, or heteroaryl groups, one or more hydrogen atoms of the ring are optionally substituted with one or more groups, equal to or different from each other, selected from the G4 substituents.

When T₁ has the meaning of cycloalkyl, heterocycloalkyl, aryl, heteroaryl, cycloalkylalkyl, heterocycloalkylalkyl, arylalkyl, heteroarylalkyl, one or more hydrogen atoms of the ring of said groups are optionally substituted with one or more groups, equal to or different from each other, selected from the G4 substituents.

Where not otherwise specified, the following definitions hold throughout the present description.

By halogen it is meant an atom selected from fluorine, chlorine, bromine or iodine.

By alkyl it is meant a $C_1$-$C_{20}$ saturated aliphatic chain, linear or optionally branched when possible, wherein one or more hydrogen atoms are optionally substituted with one or more groups, equal to or different from each other, selected from halogen and OH.

By alkenyl it is meant a $C_2$-$C_{20}$ mono- or poly-unsaturated aliphatic chain, linear or optionally branched when possible, preferably mono unsaturated, wherein one or more hydrogen atoms are optionally substituted with one or more groups, equal to or different from each other, selected from halogen and OH.

By cycloalkyl it is meant an aliphatic monocyclic ring, from 3 to 10 carbon atoms, preferably from 4 to 8 carbon atoms, or a polycyclic ring group comprising from 7 to 19 carbon atoms.

By heterocycloalkyl it is meant a cycloalkyl as defined above wherein one or more carbon atoms are substituted by heteroatoms, equal to or different from each other, selected from S, O, N; when the ring is monocyclic, preferably the heteroatoms are no more than 2.

By alkylthio it is meant a —S—$R^8$ substituent wherein $R^8$ is selected from alkyl, cycloalkyl, alkenyl, or heterocycloalkyl.

By heteroaryl it is meant a $C_5$-$C_6$ aromatic ring, or a $C_7$-$C_{19}$ polycyclic ring structure wherein at least one ring is aromatic, wherein at least one atom of said aromatic ring is an heteroatom selected from S, O, N.

By alkynyl it is meant a $C_2$-$C_{20}$ mono- or poly-unsaturated, preferably mono-unsaturated, hydrocarbon chain, wherein the unsaturation is a triple bond, said chain being linear or optionally branched when possible, wherein one or more hydrogen atoms can optionally be substituted with halogen atoms or with OH groups, preferably the chain is a $C_2$-$C_{12}$ hydrocarbon chain.

By aryl it is meant an aromatic monocyclic radical, or a condensed aromatic polycyclic radical, having from 6 to 20 carbon atoms.

By arylalkyl it is meant an alkyl as defined above, preferably $C_1$-$C_7$, linked to an aryl as defined above. As an example of arylalkyl, benzyl can be mentioned.

By heteroarylalkyl it is meant an alkyl as defined above, preferably $C_1$-$C_7$, linked to an heteroaryl as defined above.

By cycloalkylalkyl it is meant an alkyl as defined above, preferably $C_1$-$C_7$, linked to a cycloalkyl as defined above.

By heterocycloalkylalkyl it is meant an alkyl as defined above, preferably $C_1$-$C_7$, linked to an heterocycloalkyl as defined above.

By alkylene it is meant a $C_1$-$C_{20}$ bivalent aliphatic chain, linear or optionally branched when possible, having at each end one free valence, wherein one or more hydrogen atoms of the chain can optionally be substituted with halogen atoms or with OH groups. Preferably the bivalent aliphatic chain is $C_1$-$C_8$, for example selected from the following groups: vinyl, allyl, propen-1-yl, propen-2-yl, but-1-en-1-yl, but-1-en-2-yl, but-1-en-3-yl, but-1-en-4-yl, but-2-en-1-yl, but-2-en-2-yl, 2-methyl-propen-1-yl, 2-methyl-propen-3-yl.

By alkenylene it is meant a bivalent mono- or poly-unsaturated $C_2$-$C_{20}$ hydrocarbon chain, wherein the unsaturation is a double bond, linear or optionally branched when possible, having at each end one free valence, wherein one or more hydrogen atoms can optionally be substituted with halogen atoms or with OH groups, preferably the bivalent hydrocarbon chain is $C_2$-$C_8$.

By alkynylene it is meant a bivalent mono- or poly-unsaturated $C_2$-$C_{20}$ hydrocarbon chain, wherein the unsaturation is a triple bond, linear or optionally branched when possible, having at each end one free valence, wherein one or more hydrogen atoms can optionally be substituted with halogen atoms or with OH groups, preferably the bivalent hydrocarbon chain is $C_2$-$C_8$.

By heteroalkylene it is meant a group having the following meanings: —Ra—O—CO-Ya-, —Ra—S-Ya-, —Ra—N(Rb)—Ya-, —Ra—CO-Ya-, —Ra—O—CO-Ya-, —Ra—CO—O-Ya, —Ra—CO—N(R'b)-Ya-, —Ra—N(R'b)-CO-Ya, —Ra—O—CO—N(R'b)-Ya-, —Ra—N(R'b)-CO—O-Ya-, —Ra—N(R'b)-CO—N(Rc)—Ya-, —Ra—O—CO—O-Ya-, —Ra—N(R'b)-C(=NRd)—N(Rc)—Ya-, —Ra—CS-Ya-, —Ra—OCS-Ya-, —Ra—CS—O-Ya-, —Ra—CS—N(R'b)-Ya-, —Ra—N(R'b)-CS-Ya-, —Ra—O—CS—N(R'b)-Ya-, —Ra—N(R'b)-CS—O-Ya-, —Ra—N(R'b)-CS—N(RC)-Ya-, —RaO-CS—OYa-, —Ra—S—CO-Ya-, —Ra—CO—S-Ya-, —Ra—S—CO—N(R'b)-Ya-, —Ra—N(R'b)-

CO—S-Ya-, —Ra—S—CO—O-Ya-, —Ra—O—CO—S-Ya-, —Ra—S—CO—S-Ya-, —Ra—S—CS-Ya-, —Ra—CS—S-Ya-, —Ra—S—CS—N(R'b)-Ya-, —Ra—N(R'b)-CS—S-Ya-, —Ra—S—CS—S-Ya-, —Ra—O—CS—S-Ya-,
wherein:

Ra is a group selected from $C_1$-$C_6$ alkylene, $C_2$-$C_6$ alkenylene or $C_2$-$C_6$ alkynylene, R'b is an hydrogen atom or a group selected from $C_1$-$C_6$ alkyl, $C_2$-$C_6$ alkenyl or $C_2$-$C_6$ alkynyl, Rc is hydrogen or a group selected from $C_1$-$C_6$ alkyl, $C_2$-$C_6$ alkenyl or $C_2$-$C_6$ alkynyl, Rd is hydrogen or a group selected from $C_1$-$C_6$ alkyl, $C_2$-$C_6$ alkenyl or $C_2$-$C_6$ alkynyl, Ya is a direct bond (free valence) or a group selected from $C_1$-$C_6$ alkylene, $C_2$-$C_6$ alkenylene or $C_2$-$C_6$ alkynylene, wherein each heteroalkylene group contains at least one carbon atom, and one or more hydrogen atoms can be substituted by fluorine or chlorine atoms.

By alkylcycloalkyl it is meant a cycloalkyl as defined above, linked to an alkyl as defined above.

By heteroalkylcycloalkyl it is meant a cycloalkyl as defined above, linked to an heteroalkylene as defined above.

By arylene, heteroarylene, cycloalkylene, heterocycloalkylene, arylalkylene, heteroarylalkylene, alkylcycloalkylene and heteroalkylcycloalkylene are meant respectively an aryl, an heteroaryl, a cycloalkyl, an heterocycloalkyl, an arylalkyl, an heteroarylalkyl, an alkylcycloalkyl, an heteroalkylcycloalkyl, as defined above, wherein one hydrogen atom of the ring is substituted by one free valence.

By delta opioid receptors, the delta ($\delta$) opioid receptors or the $\delta_1$ and $\delta_2$ subreceptors are meant.

By compound having affinity towards the receptors it is meant a compound having in vivo and/or in vitro agonist or antagonist, or partial agonist, or partial antagonist, or inverse agonist, or inverse antagonist, or inverse partial agonist, or inverse partial antagonist activity towards the receptors. The meaning of said terms is known to the skilled in the field.

The preferred compounds of formula (I) are those wherein:

$R^1$ is phenyl wherein the hydrogen atom at the para position of the ring is substituted with a group selected from C(O)R', C(O)OR', C(O)NHR' or C(O)NR$^3$R$^4$, wherein:

R' is selected from the following G5 groups: H, $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings with $C_1$-$C_6$ alkyl chains, $R^3$ and $R^4$, equal to or different from each other, are selected from the above mentioned G5 groups but excluding hydrogen, or $R^3$ and $R^4$ with the nitrogen atom to which they are linked form a ring with a number of atoms from 5 to 7, $R^2$ is phenyl, wherein one or more hydrogen atoms of the ring are optionally substituted with the following G7 groups, equal to or different from each other and selected from: halogen, $C_1$-$C_7$ alkyl, $C_3$-$C_8$ monocyclic cycloalkyl, $C_2$-$C_7$ alkenyl, cyano, $SO_2NH_2$, isothiocyanate, $OR^5$, $NO_2$, $NHR^5$, $NR^6R^7$, alkylthio —S—$R^9$ wherein $R^9$ is $C_1$-$C_7$ alkyl, wherein:

$R^5$ is selected from the G5 groups, $R^6$ and $R^7$, equal to or different from each other, are selected from the above mentioned G5 groups but excluding hydrogen, or $R^6$ and $R^7$ together with the nitrogen atom to which they are linked, form a ring with a number of atoms comprised between 5 and 7, $D_1$ is as defined above, $T_1$ is selected from H, $C_1$-$C_{10}$ alkyl, $C_3$-$C_{10}$ alkenyl, $C_3$-$C_{10}$ alkynyl, monocyclic cycloalkyl, heterocycloalkyl, aryl, heteroaryl, cycloalkylalkyl, heterocycloalkylalkyl, arylalkyl or heteroarylalkyl.

The most preferred compounds of formula (I) are those wherein:

$R^1$ is phenyl wherein the hydrogen at the para position of the ring is substituted with a group selected from C(O)R', C(O)OR', C(O)NHR' or C(O)NR$^3$R$^4$, wherein:

R' is selected from the following G6 groups: $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings substituted with $C_1$-$C_3$ alkyl, $R^3$ and $R^4$, equal to or different from each other, are selected from the above mentioned G6 groups but excluding hydrogen, or $R^3$ and $R^4$ together with the nitrogen atom to which they are linked, form a ring with a number of atoms comprised between 5 and 7, $R^2$ is phenyl wherein one or more hydrogen atoms of the ring are optionally substituted with groups, equal to or different from each other, selected from: halogen, $C_1$-$C_7$ alkyl, cyano, $SO_2NH_2$, isothiocyanate, $OR^5$, $NO_2$, $NHR^5$ or $NR^6R^7$, wherein: $R^5$ is a substituent group selected from hydrogen or $C_1$-$C_7$ alkyl, $R^6$ and $R^7$ together with the nitrogen atom to which they are linked form a ring having a number of atoms comprised between 5 and 7, or $R^6$ and $R^7$, equal to or different from each other, are $C_1$-$C_7$ alkyl, $D_1$ is as defined above, $T_1$ is a group selected from H, $C_1$-$C_7$ alkyl, $C_3$-$C_7$ alkenyl, $C_3$-$C_7$ alkynyl, monocyclic cycloalkyl, monocyclic heterocycloalkyl, aryl, heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings and with $C_1$-$C_6$ alkyl chains.

The still more preferred compounds of formula (I) are those wherein:

$R^1$ is phenyl wherein the hydrogen at the para position of the ring is substituted with a group selected from C(O)R', C(O)NHR' or C(O)NR$^3$R$^4$, wherein:

R' is selected from the G6 groups defined above, $R^3$ and $R^4$, equal to or different from each other, are selected from the above mentioned G6 groups but excluding hydrogen, or $R^3$ and $R^4$ together with the nitrogen atom to which they are linked, form a ring having a number of atoms from 5 to 7, $R^2$ is phenyl wherein one of the hydrogen atoms at the meta position of the ring is optionally substituted with a group selected from: halogen, $C_1$-$C_3$ alkyl, cyano, $SO_2NH_2$, isothiocyanate, $OR^5$, $NO_2$, $NHR^5$ or $NR^6R^7$, wherein:

$R^5$ is selected from hydrogen or $C_1$-$C_3$ alkyl, $R^6$ and $R^7$ together with the nitrogen atom to which they are linked, form a ring having a number of atoms comprised between 5 and 7, or $R^6$ and $R^7$, equal to or different from each other, are $C_1$-$C_5$ alkyl, $D_1$ is as defined above, $T_1$ is a group selected from the following formulae:

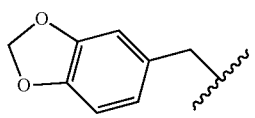
(T5)

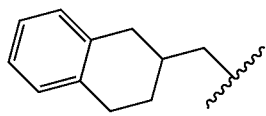
(T6)

or T₁ is a group selected from H, $C_1$-$C_7$ alkyl, $C_3$-$C_7$ alkenyl, $C_3$-$C_7$ alkynyl, phenyl, monocyclic heteroaryl, monocyclic cycloalkyl, monocyclic heterocycloalkyl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings and have $C_1$-$C_3$ alkyl chains.

The specific compounds of formula (I) are the following:

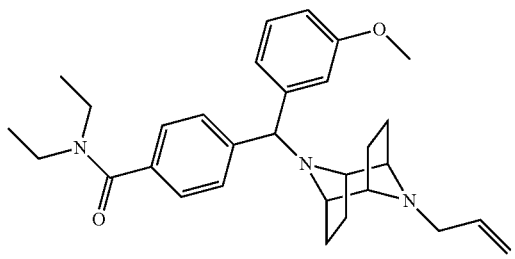
(I-I)

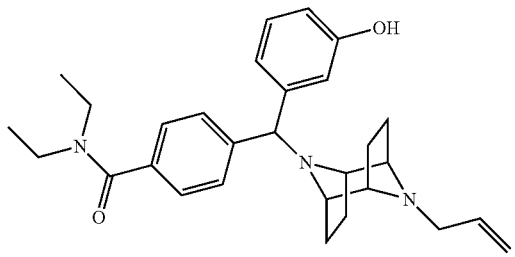
(I-II)

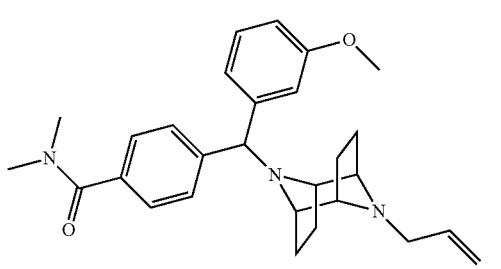
(I-III)

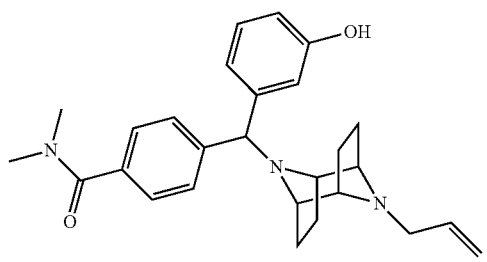
(I-IV)

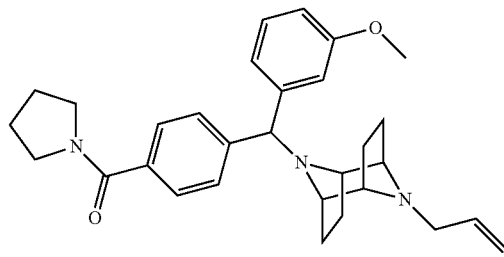
(I-V)

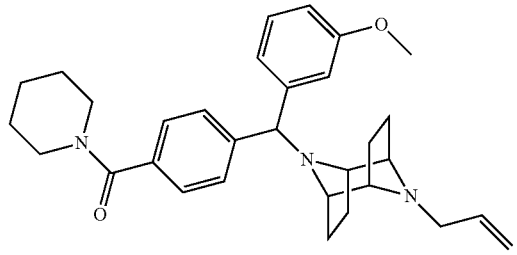
(I-VI)

(I-VII)

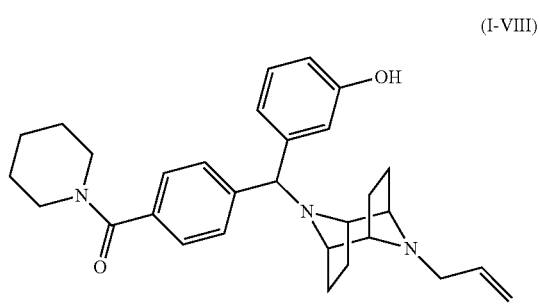
(I-VIII)

-continued
(I-IX)
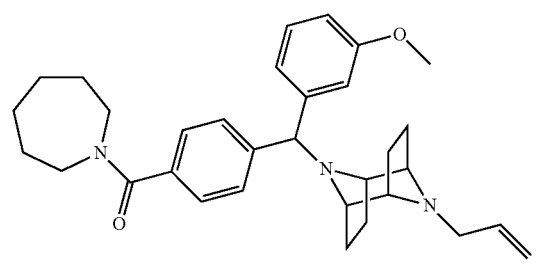
(I-XIV)
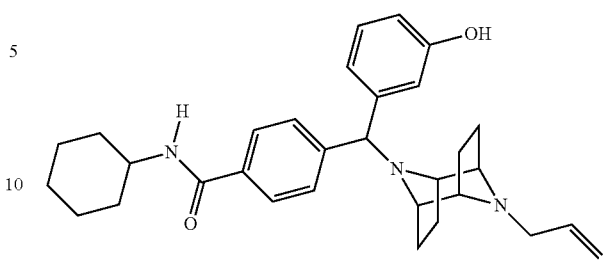
(I-X)
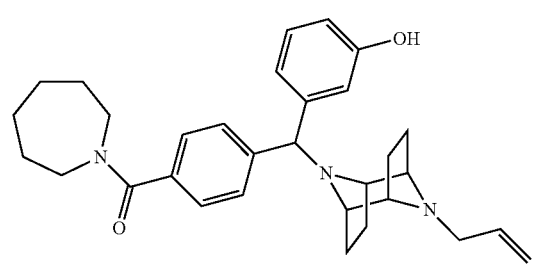
(I-XV)
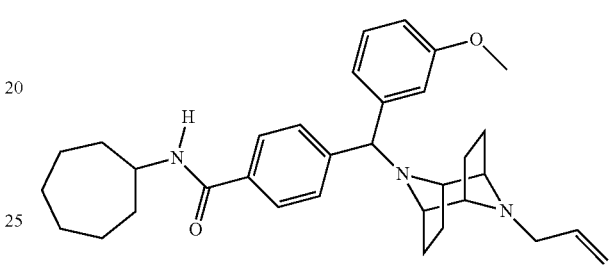
(I-XI)
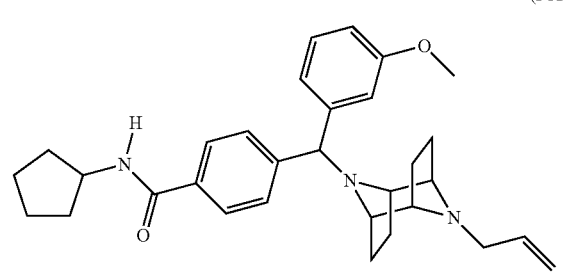
(I-XVI)
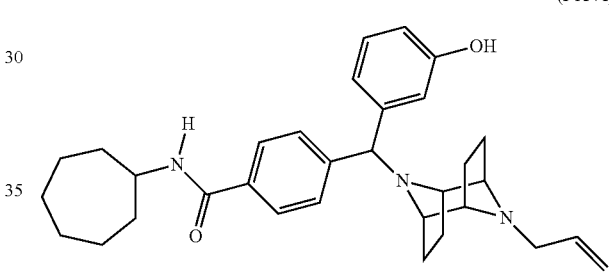
(I-XII)
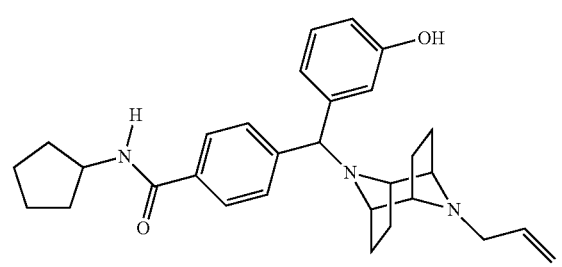
(I-XVII)
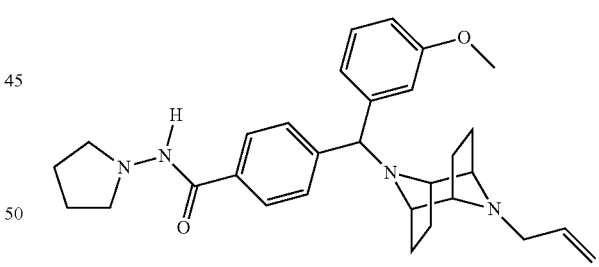
(I-XIII)
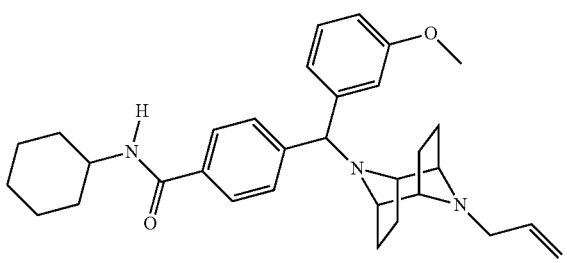
(I-XVIII)
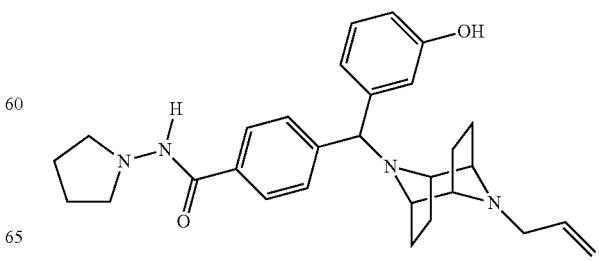

-continued
(I-XIX)
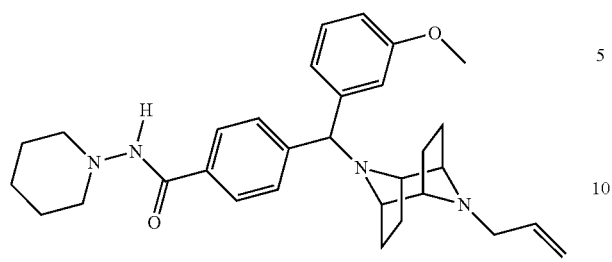
(I-XX)
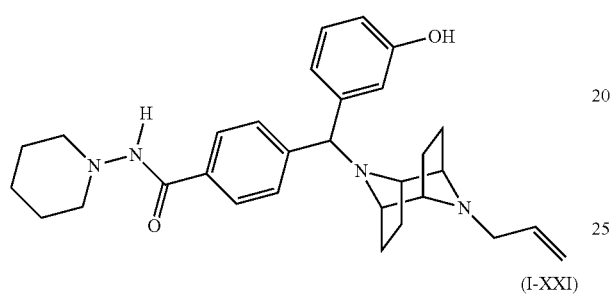
(I-XXI)
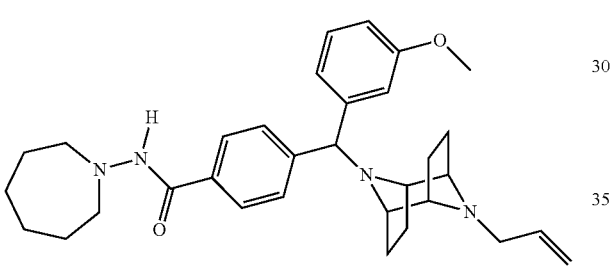
(I-XXII)
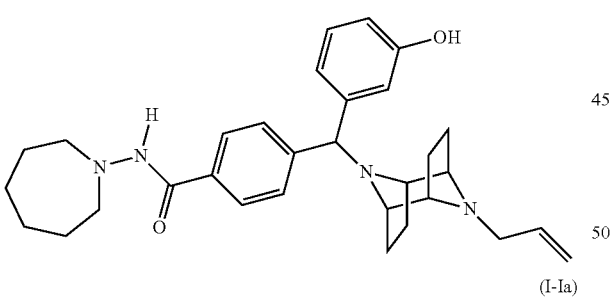
(I-Ia)
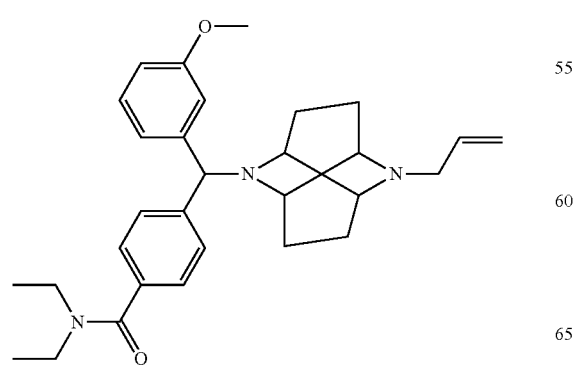
-continued
(I-IIa)
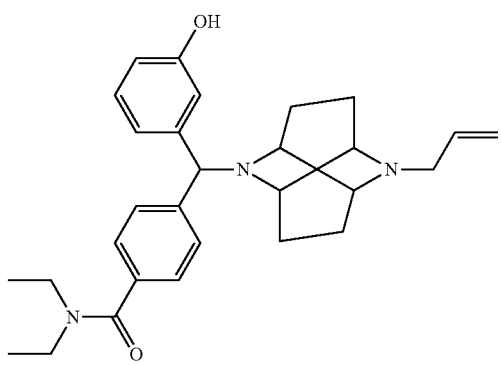
(I-IIIa)
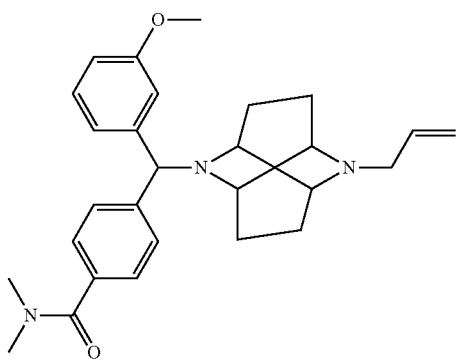
(I-IVa)
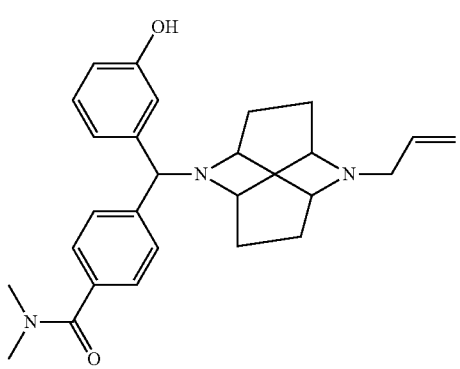
(I-Va)
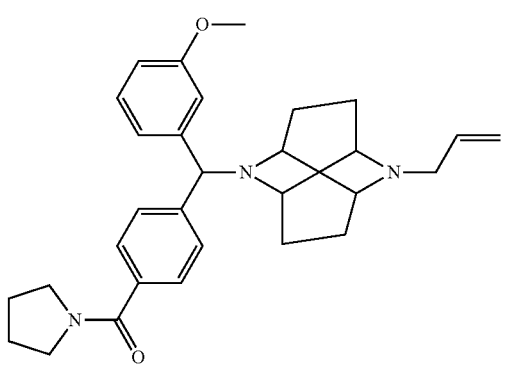

(I-VIa)

(I-VIIa)

(I-VIIIa)

(I-IXa)

(I-Xa)

(I-XIa)

(I-XIIa)

(I-XIIIa)
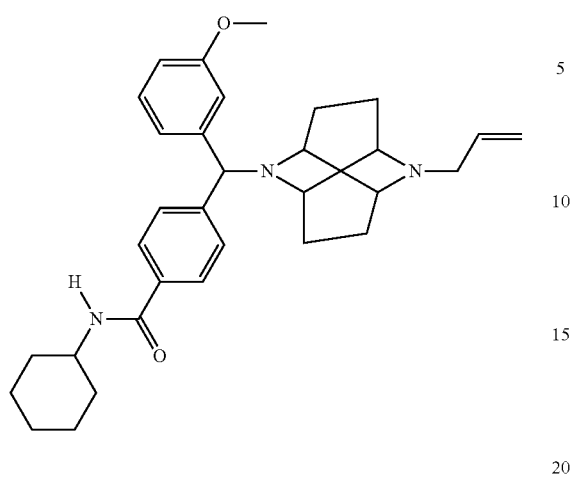
(I-XVIa)
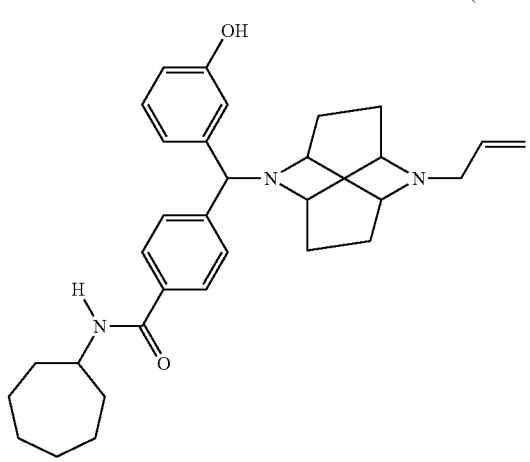
(I-XIVa)
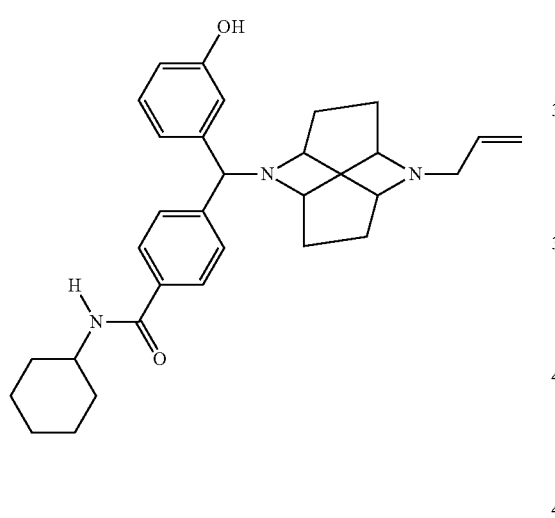
(I-XVIIa)
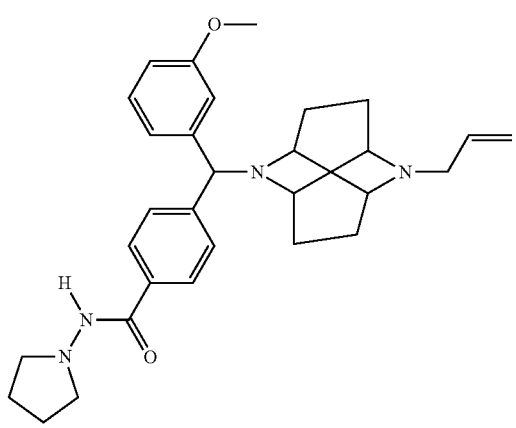
(I-XVa)
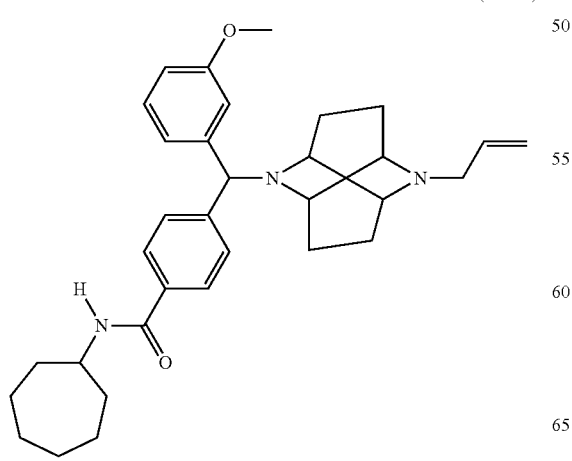
(I-XVIIIa)
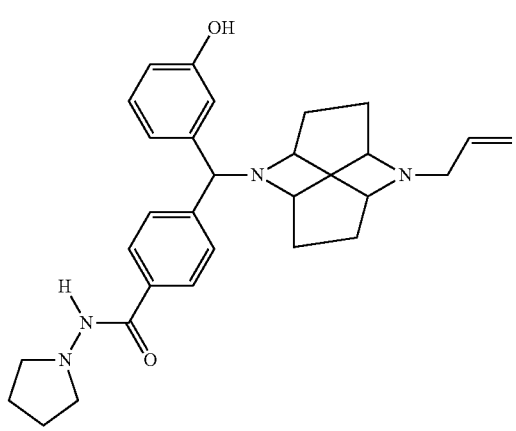

-continued
(I-XIXa)
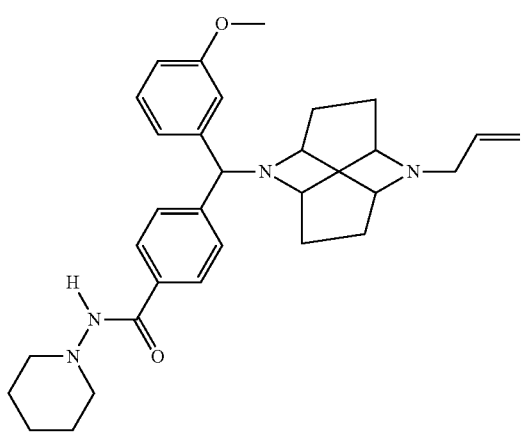
(I-XXa)
(I-XXIa)
-continued
(I-XXIIa)
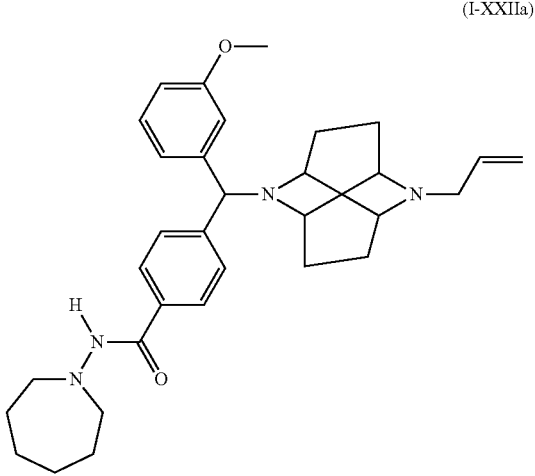
(I-Ib)
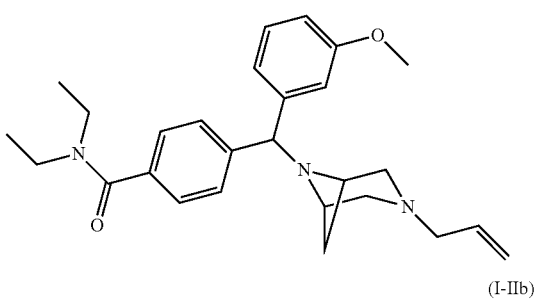
(I-IIb)
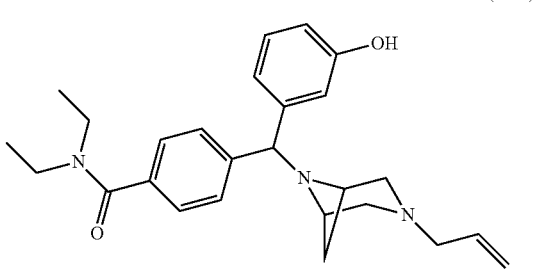
(I-IIIb)
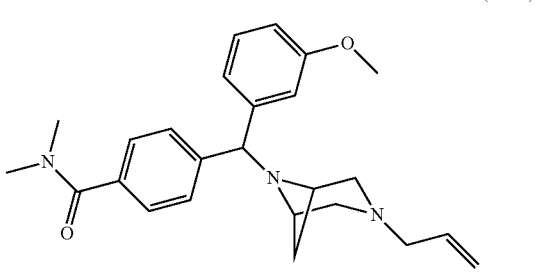
(I-IVb)
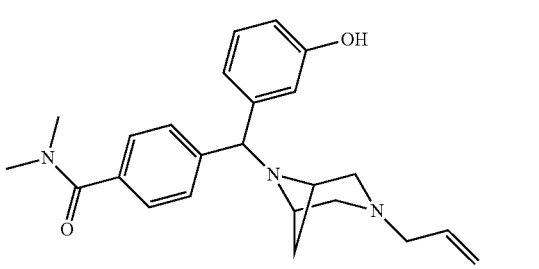

(I-Vb)
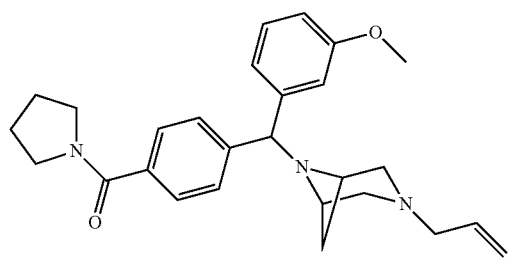
(I-VIb)
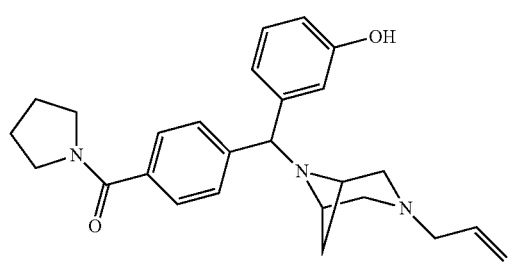
(I-VIIb)
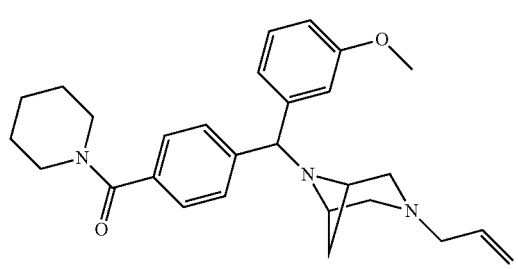
(I-VIIIb)
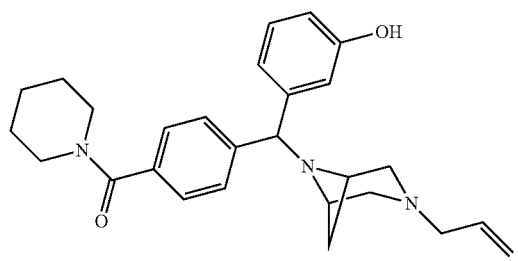
(I-IXb)
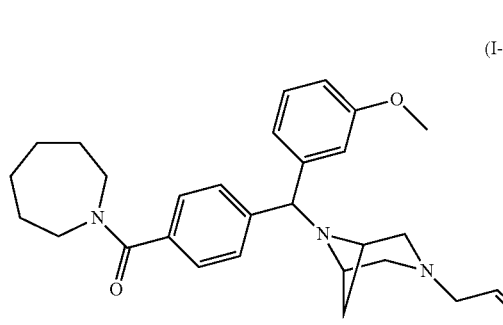
(I-Xb)
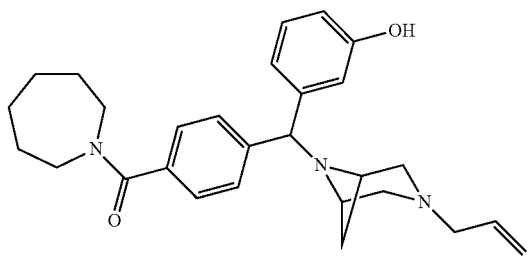
(I-XIb)
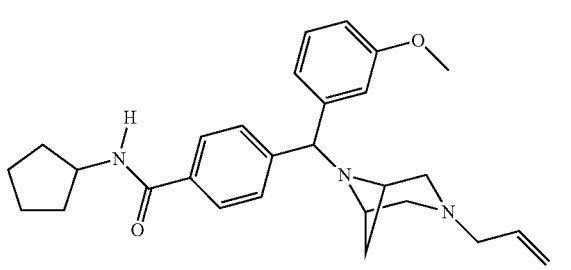
(I-XIIb)
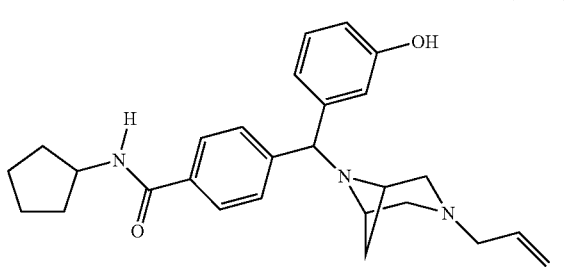
(I-XIIIb)
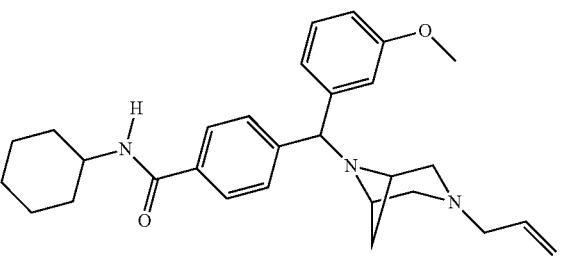
(I-XIVb)
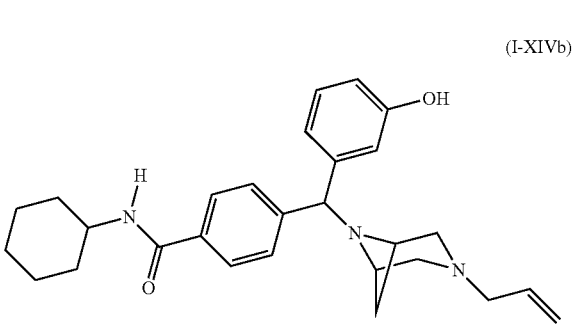

(I-XVb)
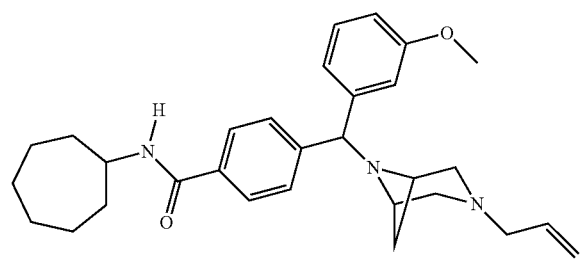
(I-XVIb)
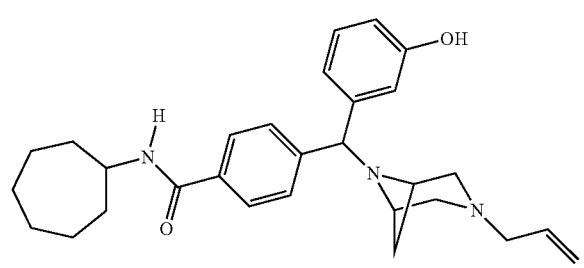
(I-XVIIb)
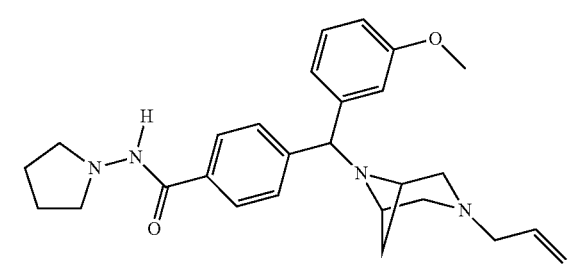
(I-XVIIIb)
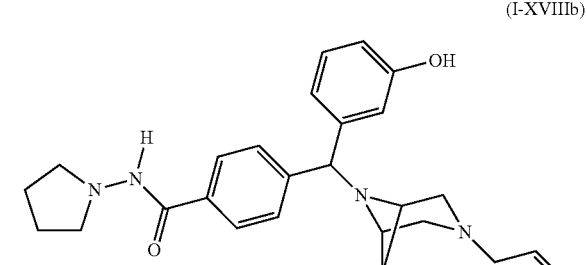
(I-XIXb)
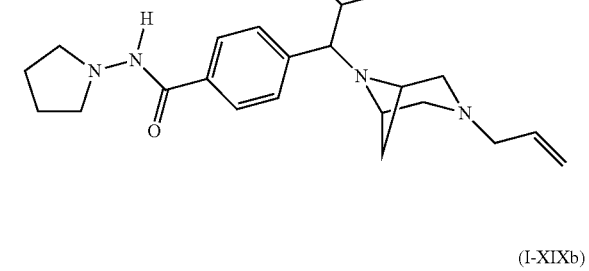
(I-XXb)
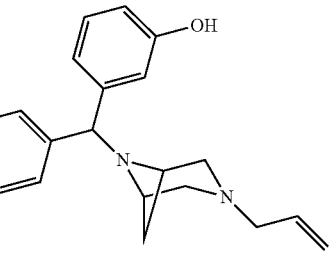
(I-XXIb)
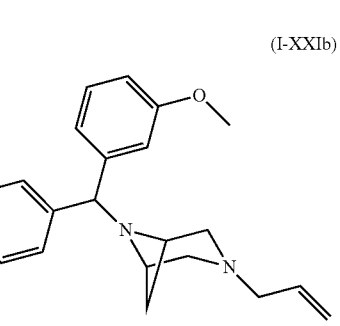
(I-XXIIb)
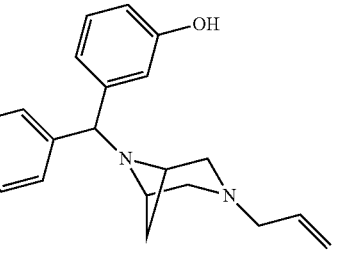
(I-Ic)
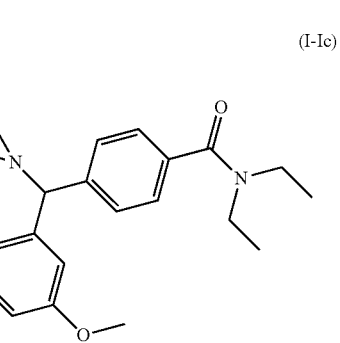
(I-IIc)
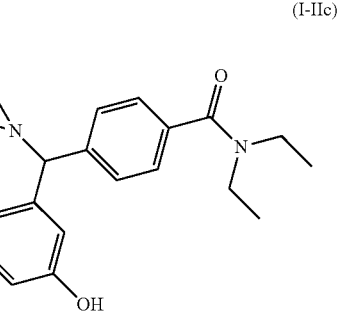

(I-IIIc)
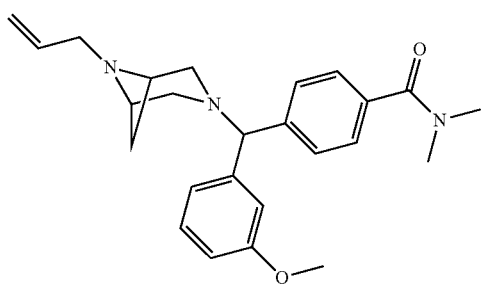
(I-IVc)
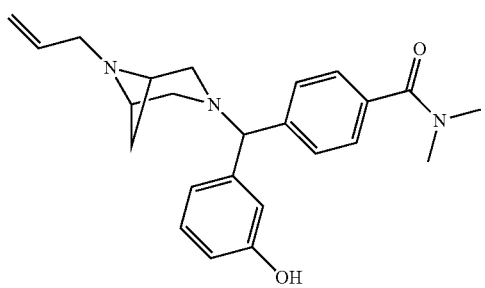
(I-Vc)
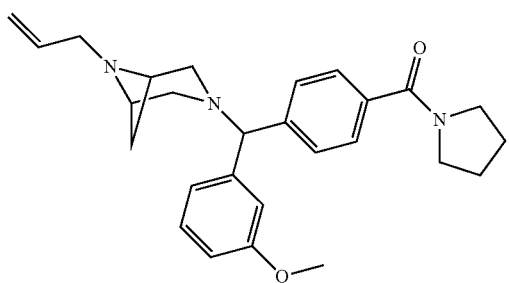
(I-VIc)
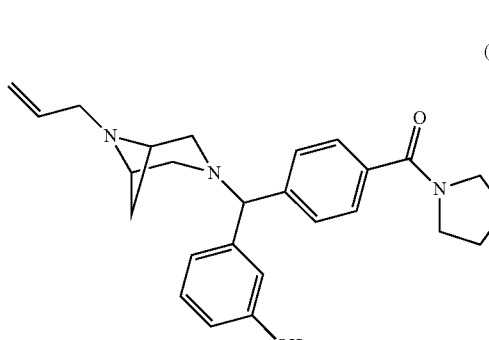
(I-VIIc)
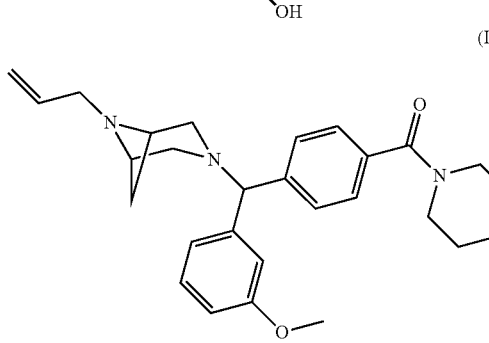
(I-VIIIc)
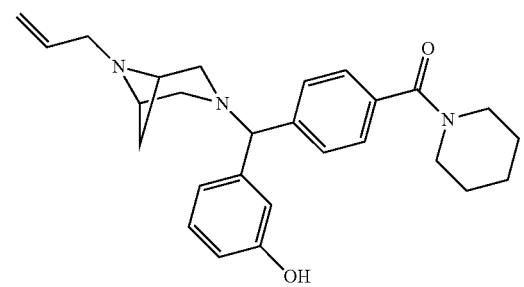
(I-IXc)
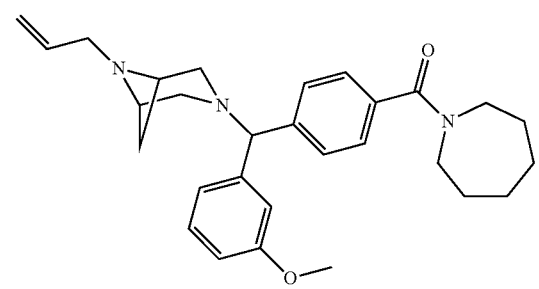
(I-Xc)
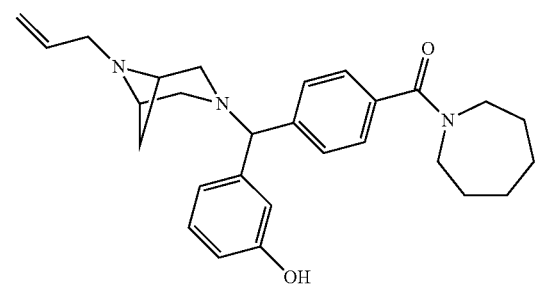
(I-XIc)
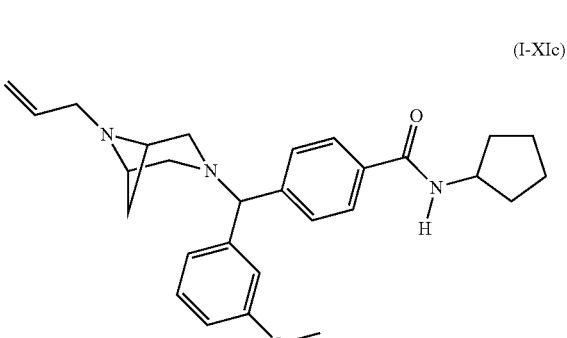
(I-XIIc)
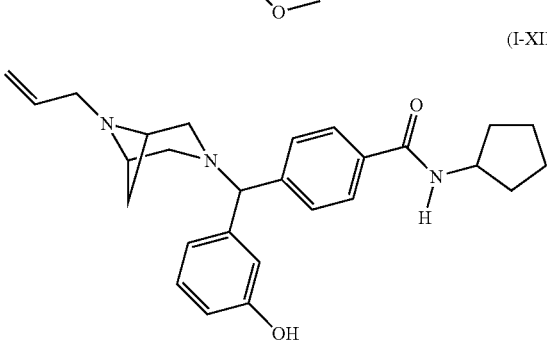

(I-XIIIc)
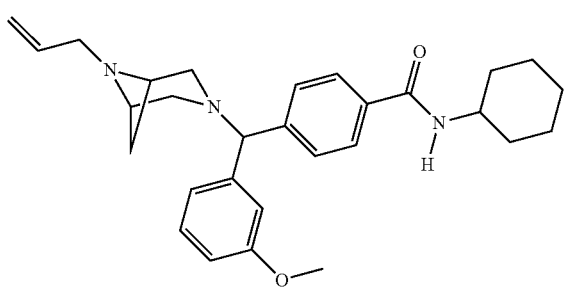
(I-XIVc)
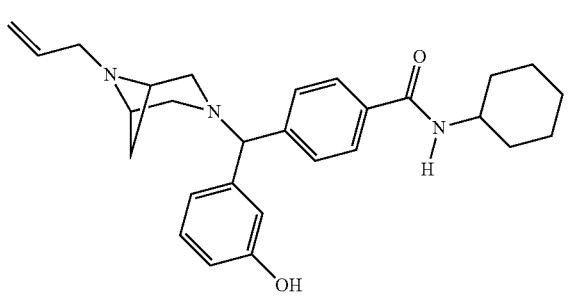
(I-XVc)
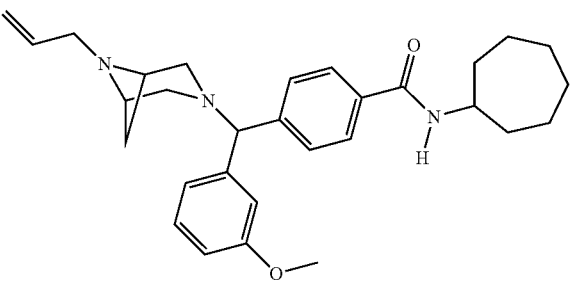
(I-XVIc)
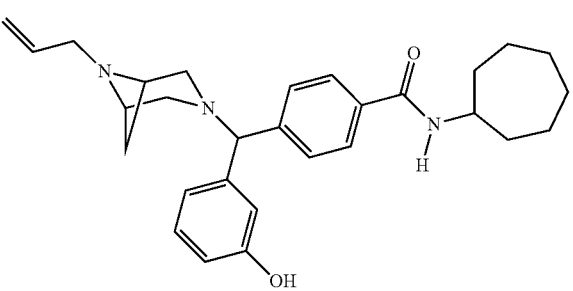
(I-XVIIc)
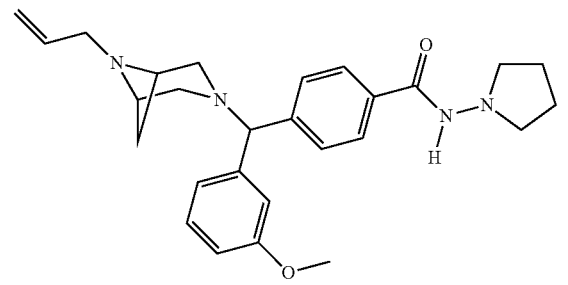
(I-XVIIIc)
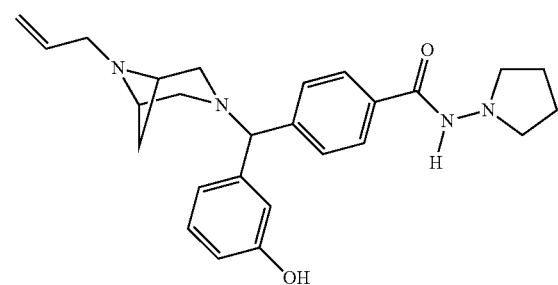
(I-XIXc)
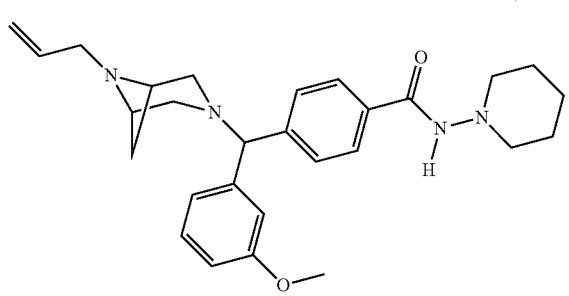
(I-XXc)
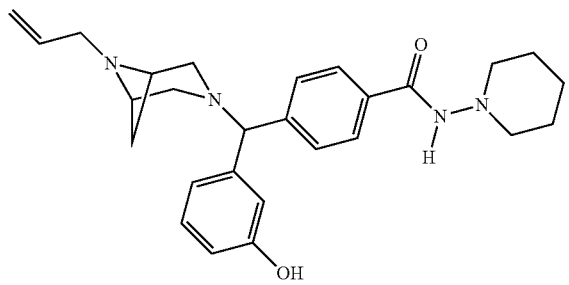
(I-XXIc)
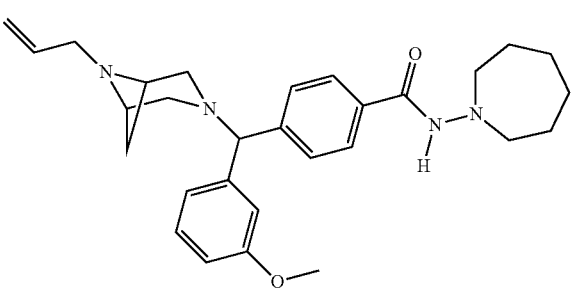
(I-XXIIc)
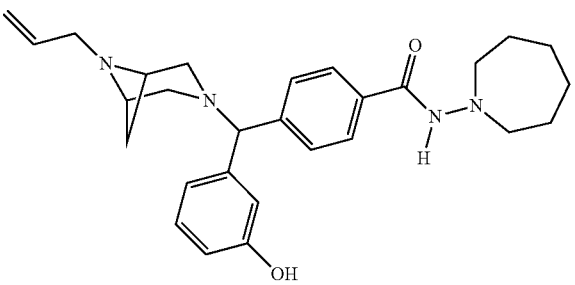

33
-continued
(I-Id)
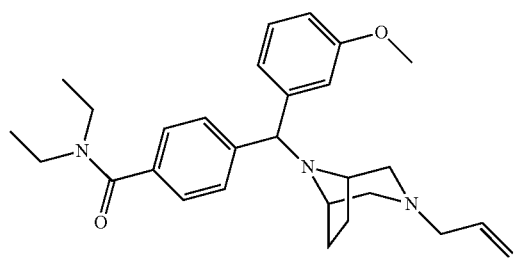
(I-IId)
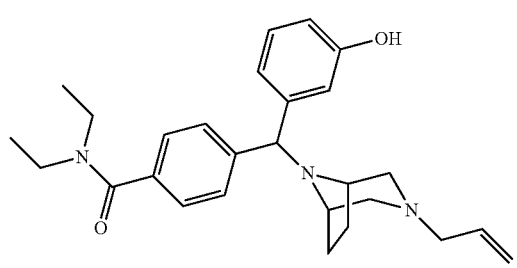
(I-IIId)
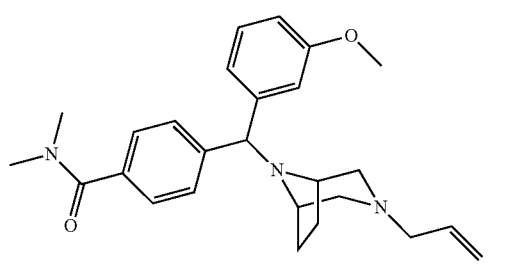
(I-IVd)
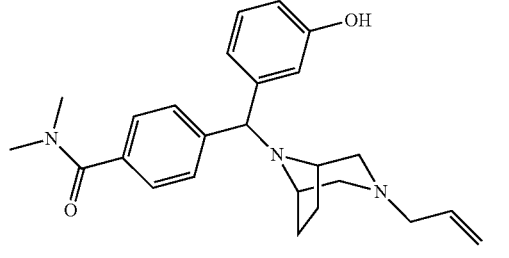
(I-Vd)
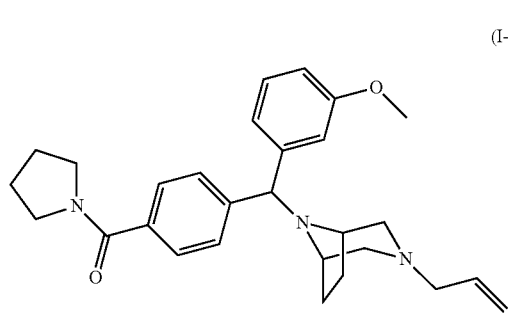
34
-continued
(I-VId)
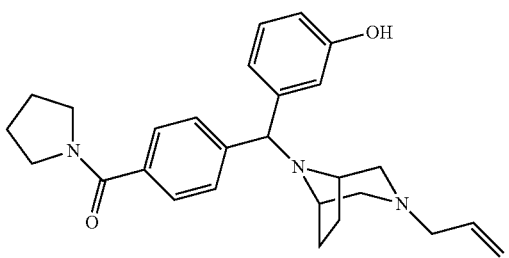
(I-VIId)
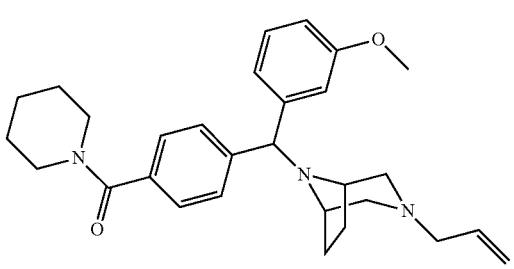
(I-VIIId)
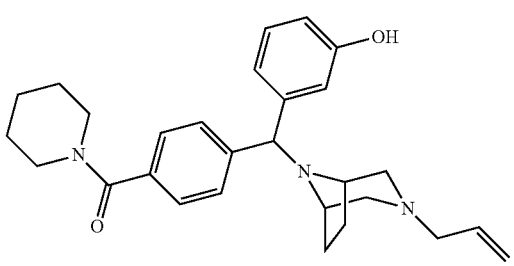
(I-IXd)
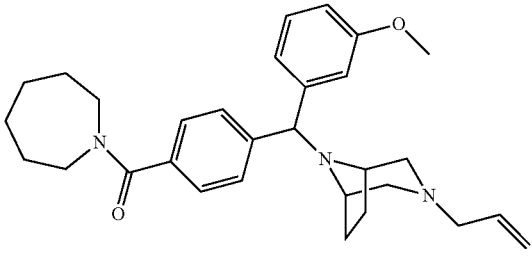
(I-Xd)
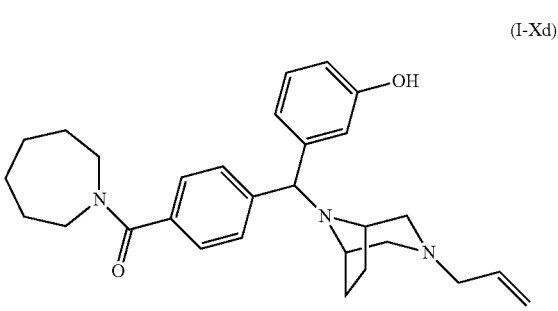

(I-XId)
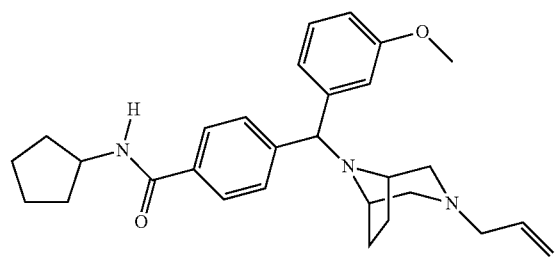
(I-XIId)
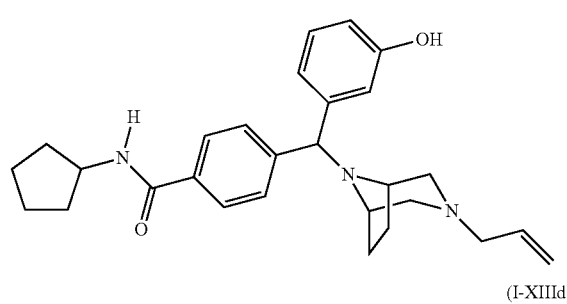
(I-XIIId)
(I-XIVd)
(I-XVd)
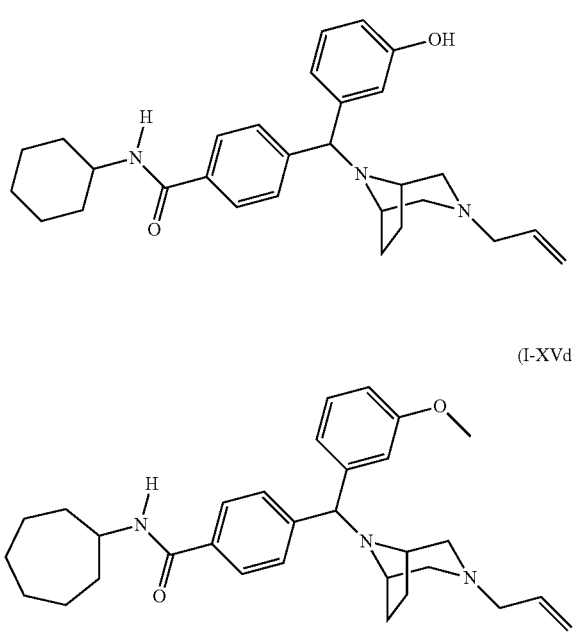
(I-XVId)
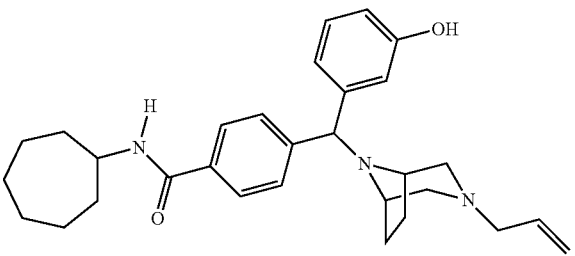
(I-XVIId)
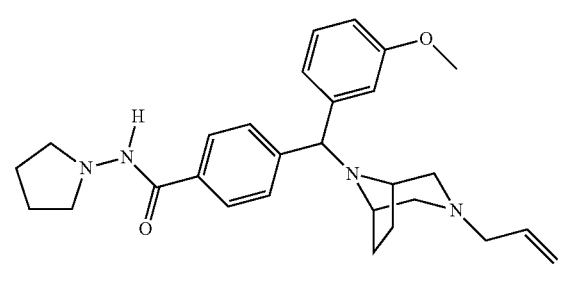
(I-XVIIId)
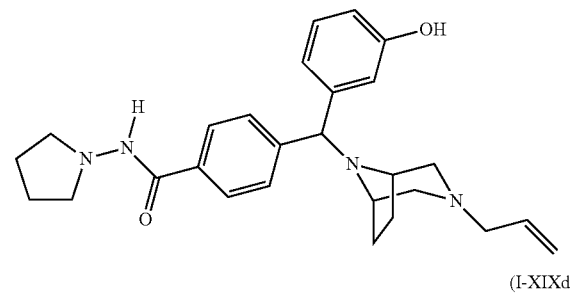
(I-XIXd)
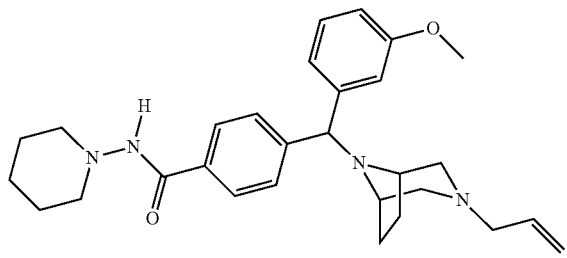
(I-XXd)
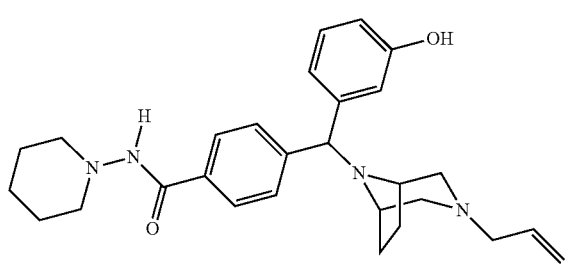

(I-XXId)
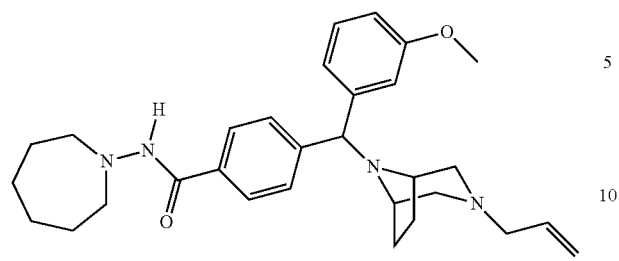
(I-IVe)
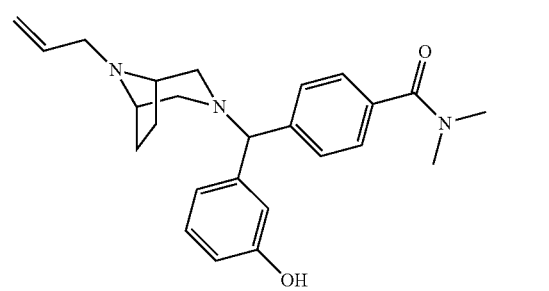
(I-XXIId)
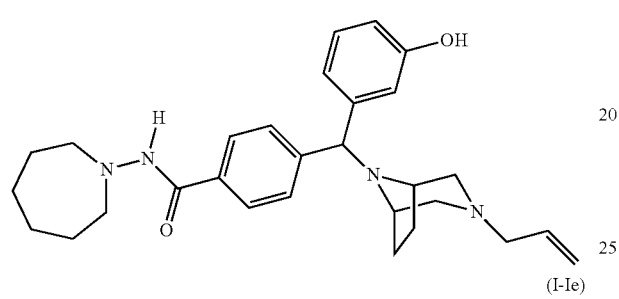
(I-Ve)
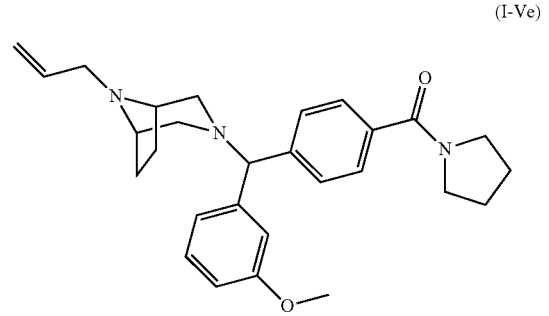
(I-Ie)
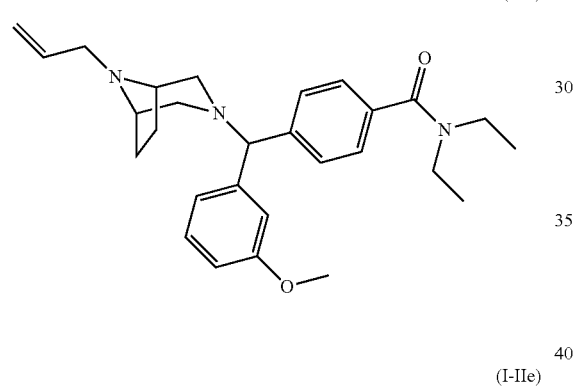
(I-VIe)
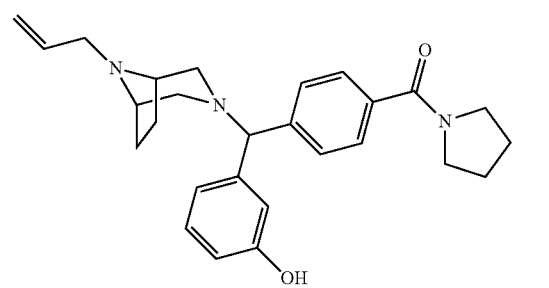
(I-IIe)
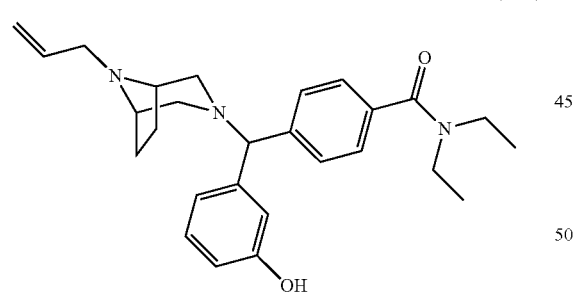
(I-VIe)
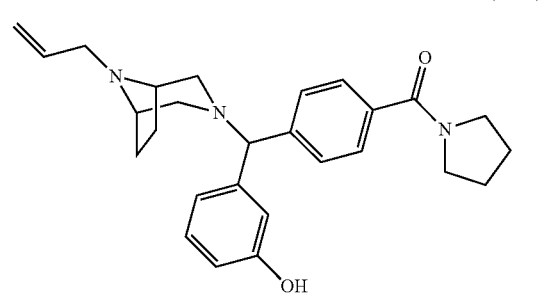
(I-IIIe)
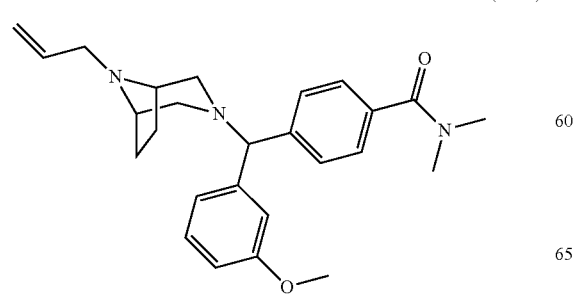
(I-VIIe)
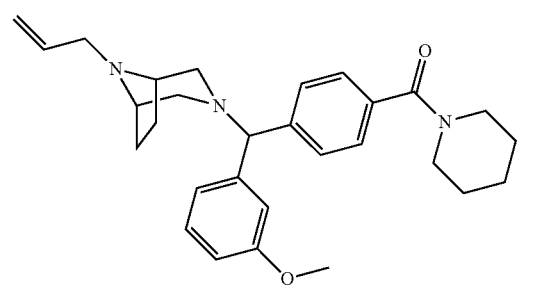

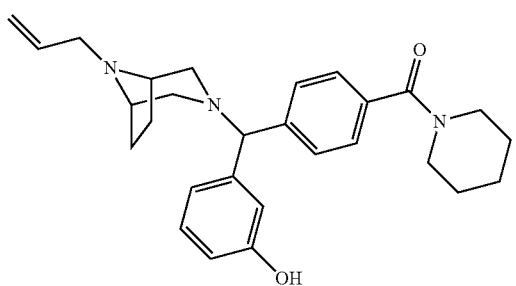
(I-VIIIe)
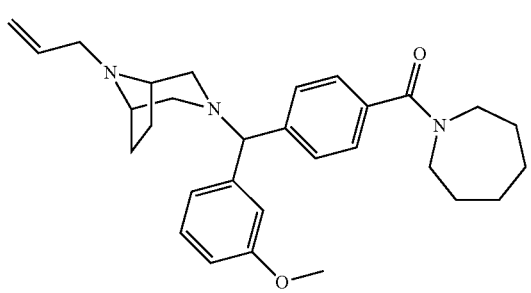
(I-IXe)
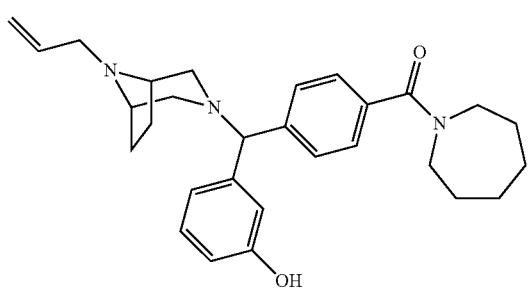
(I-Xe)
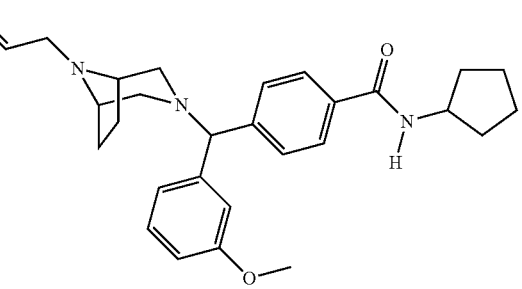
(I-XIe)
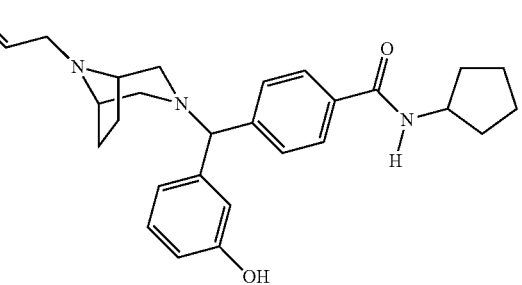
(I-XIIe)
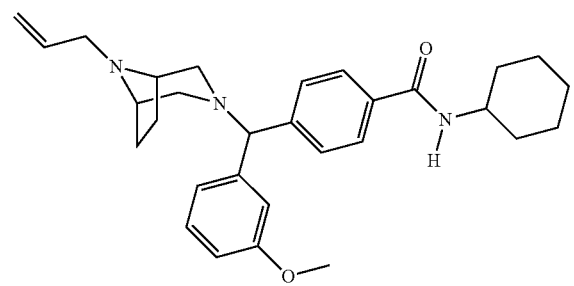
(I-XIIIe)
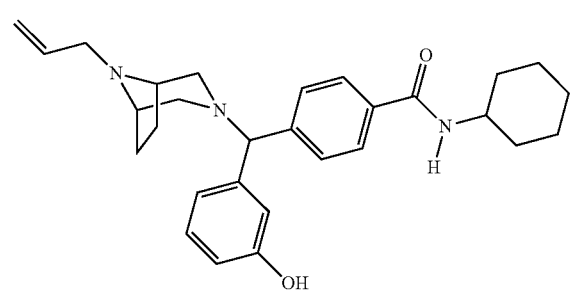
(I-XIVe)
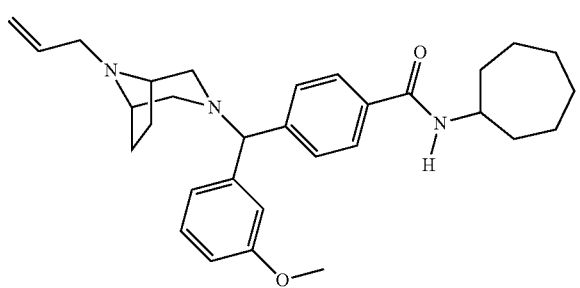
(I-XVe)
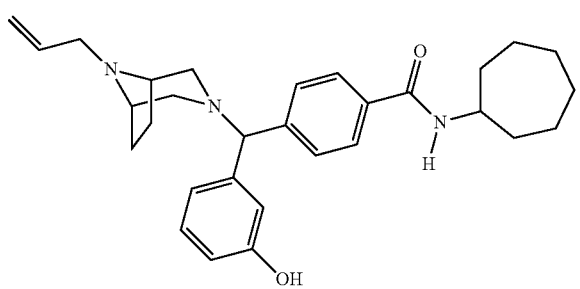
(I-XVIe)
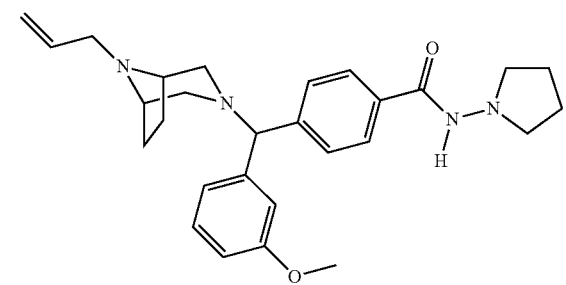
(I-XVIIe)

(I-XVIIIe)
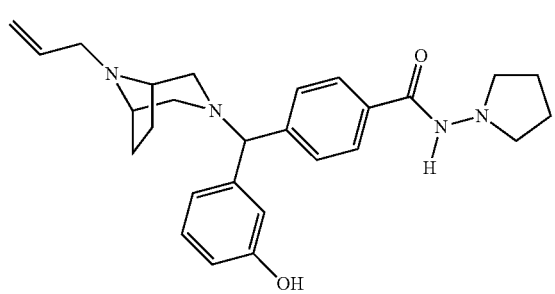
(I-XIXe)
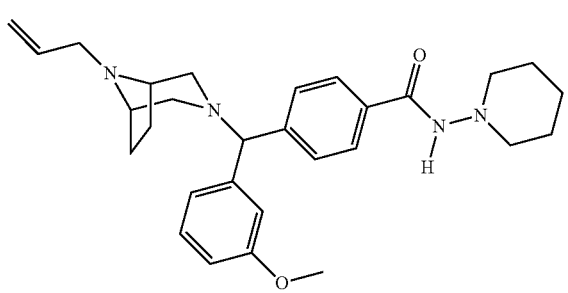
(I-XXe)
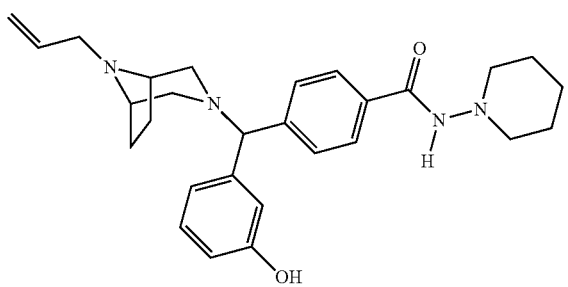
(I-XXIe)
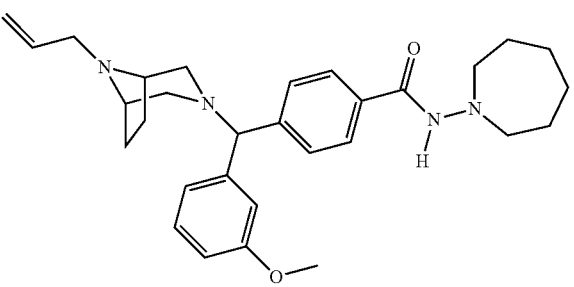
(I-XXIIe)
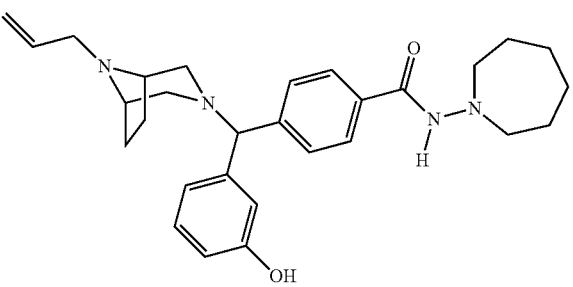
(I-If)
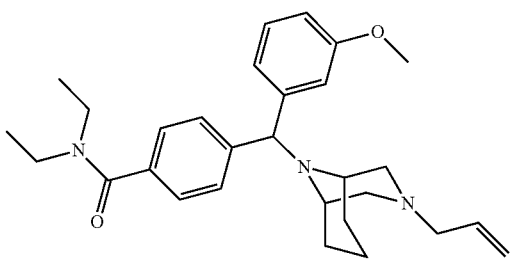
(I-IIf)
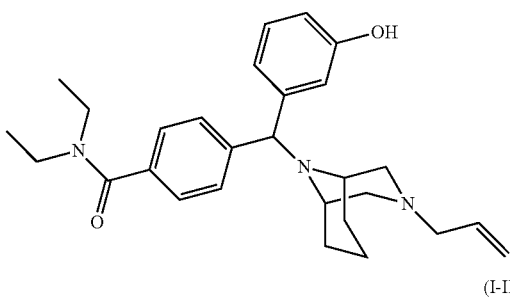
(I-IIIf)
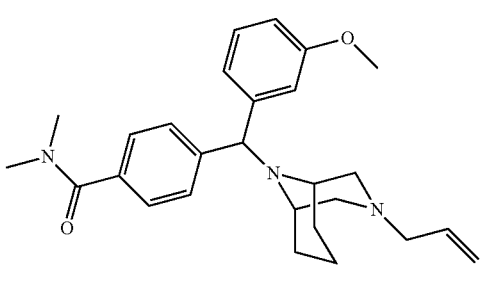
(I-IVf)
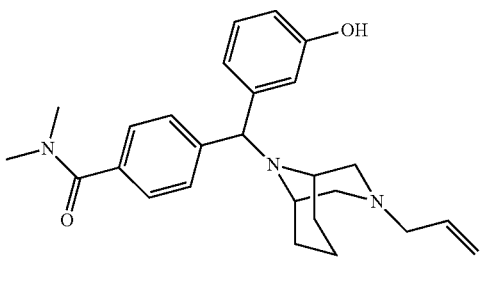
(I-Vf)
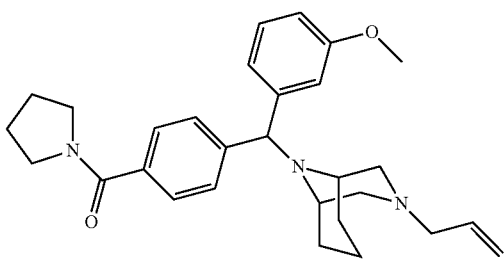

(I-VIf)
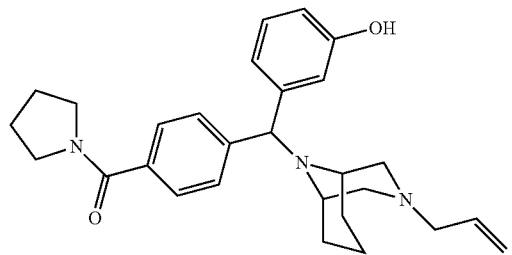
(I-XIf)
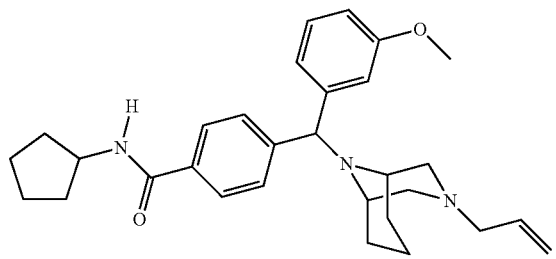
(I-VIIf)
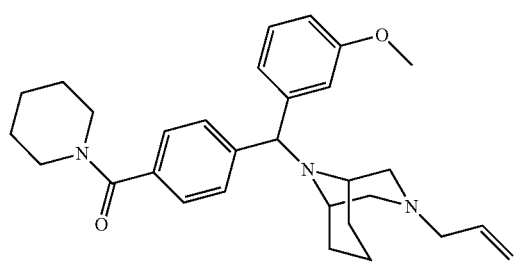
(I-XIIf)
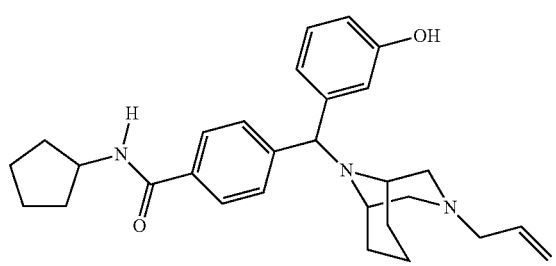
(I-VIIIf)
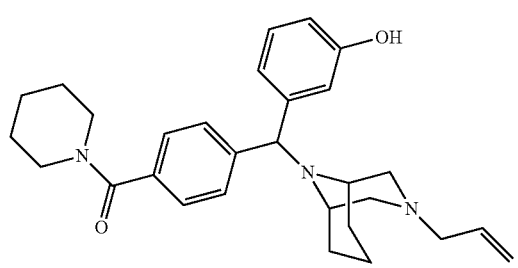
(I-XIIIf)
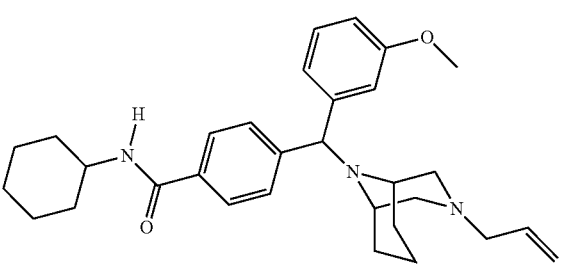
(I-IXf)
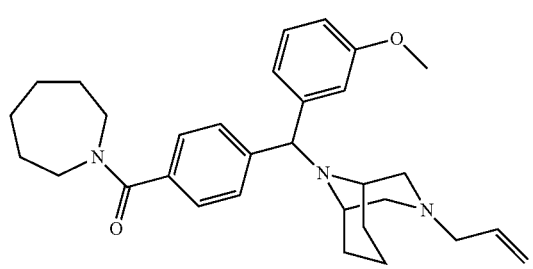
(I-XIVf)
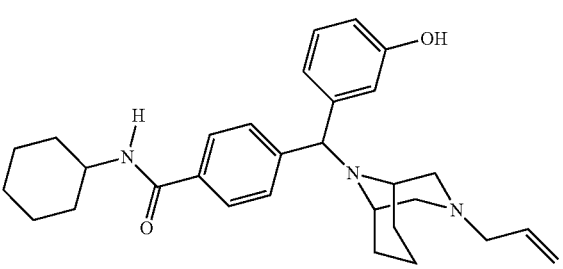
(I-Xf)
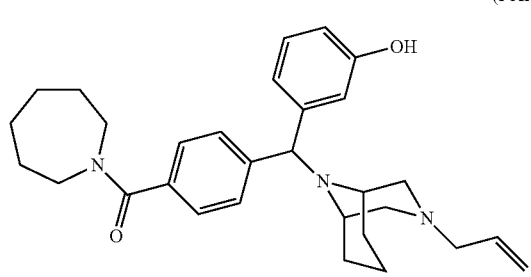
(I-XVf)
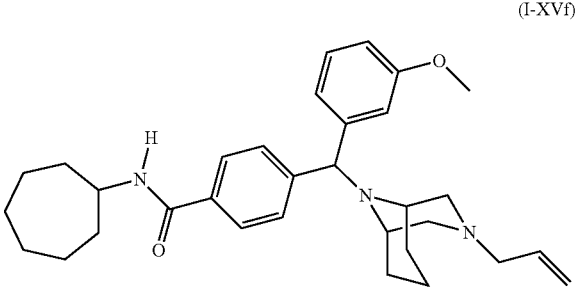

(I-XVIf)
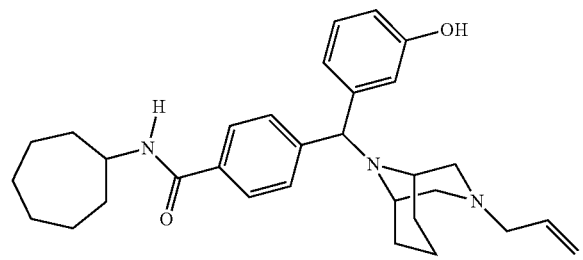
(I-XVIIf)
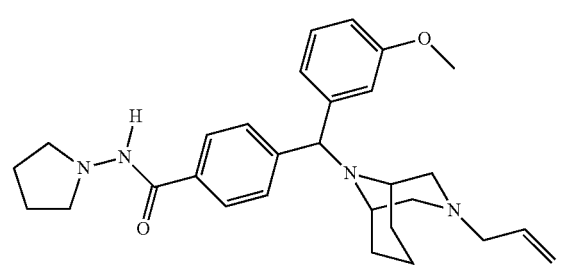
(I-XXIf)
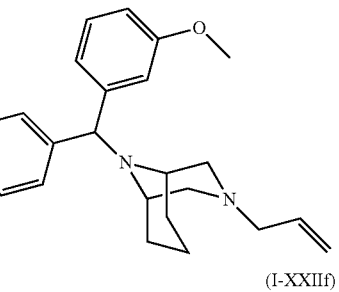
(I-XXIIf)
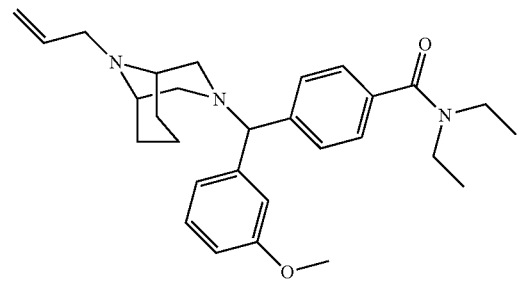
(I-XVIIIf)
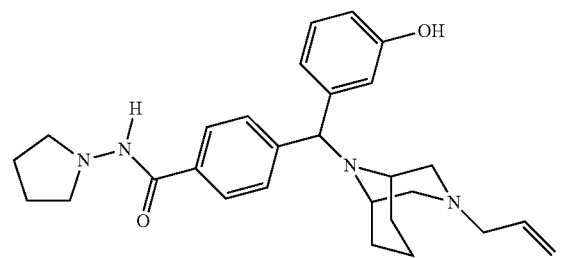
(I-Ig)
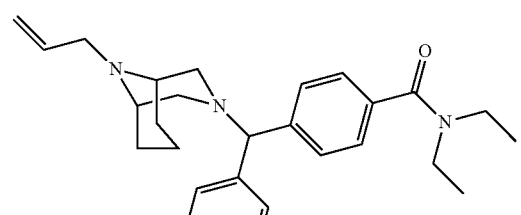
(I-XIXf)
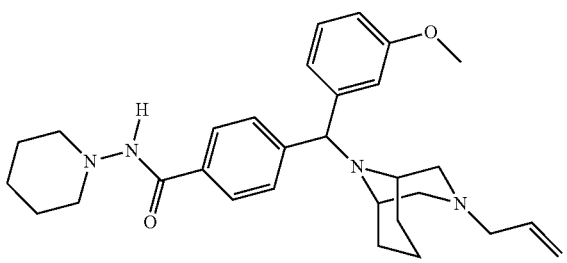
(I-IIg)
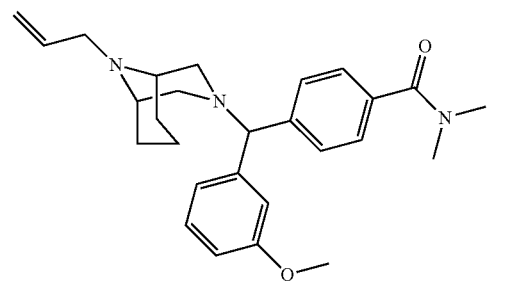
(I-XXf)
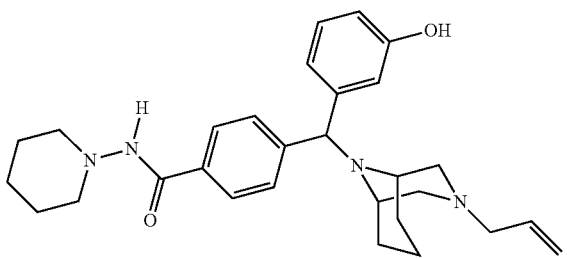
(I-IIIg)

(I-IVg)
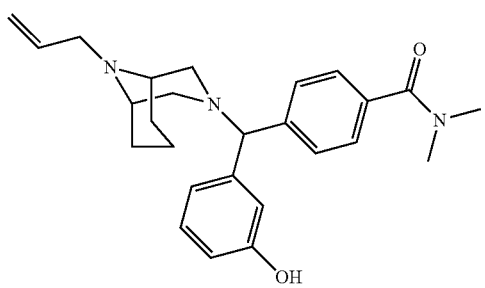
(I-Vg)
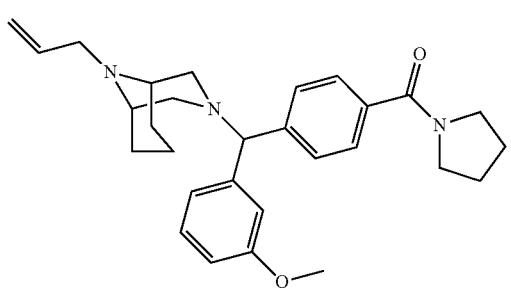
(I-VIg)
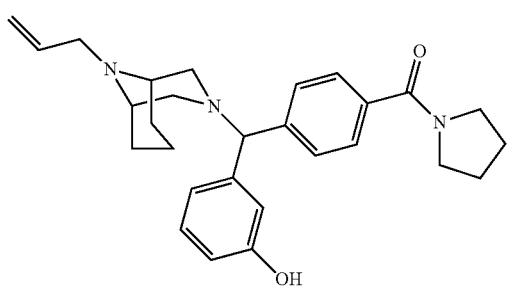
(I-VIIg)
(I-VIIIg)
(I-IXg)
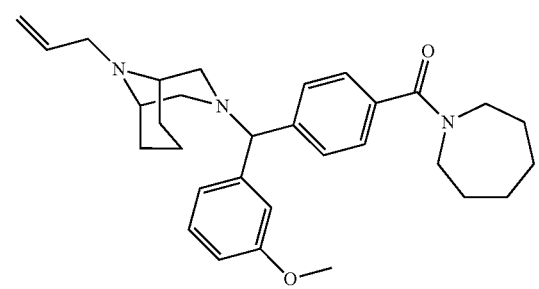
(I-Xg)
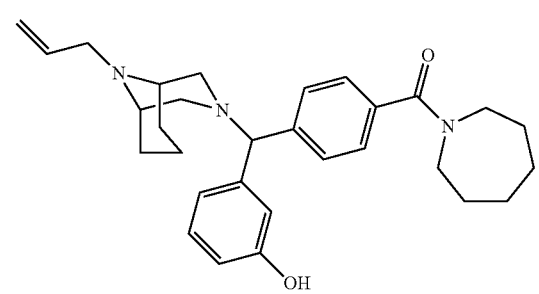
(I-XIg)
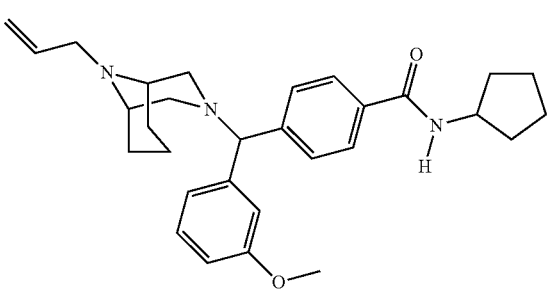
(I-XIIg)
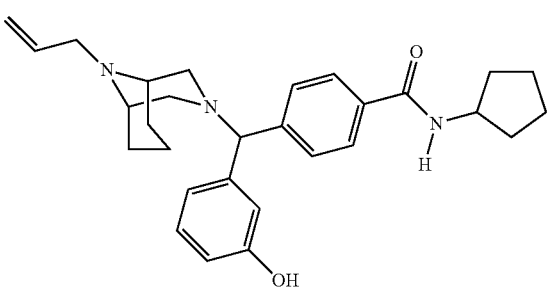
(I-XIIIg)
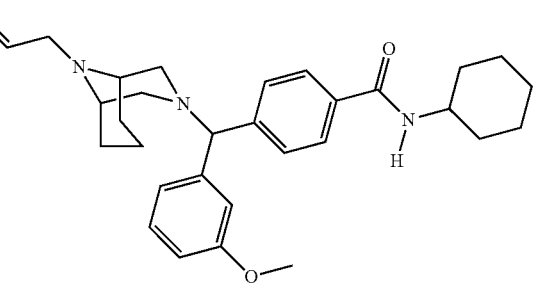

(I-XIVg)
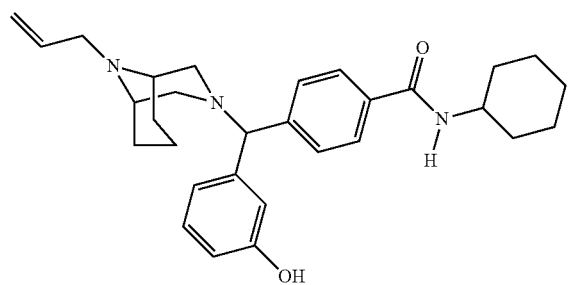
(I-XVg)
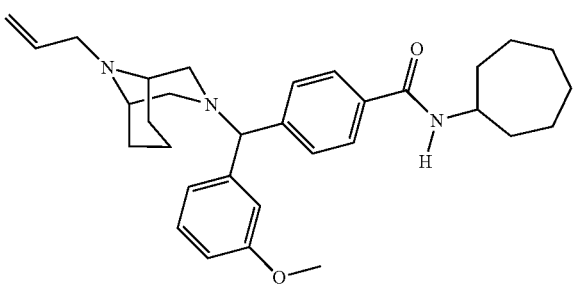
(I-XVIg)
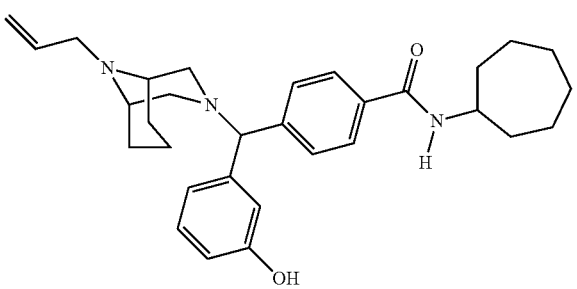
(I-XVIIg)
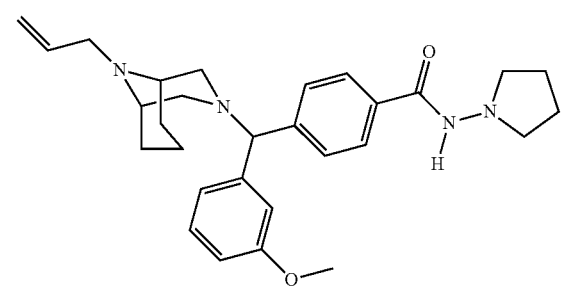
(I-XVIIIg)
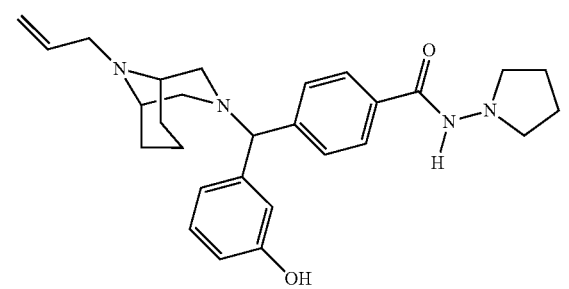
(I-XIXg)
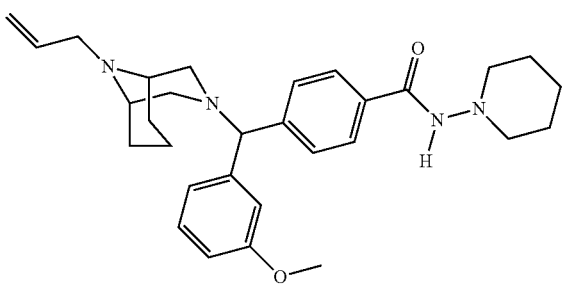
(I-XXg)
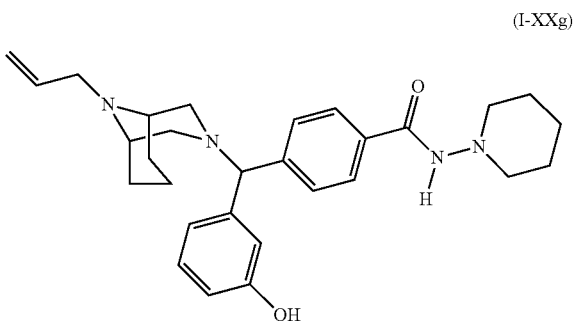
(I-XXIg)
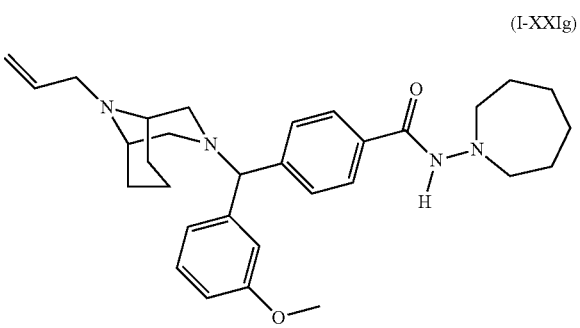
(I-XXIIg)
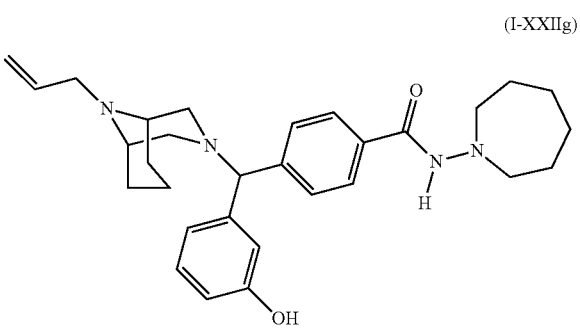
(I-Ih)
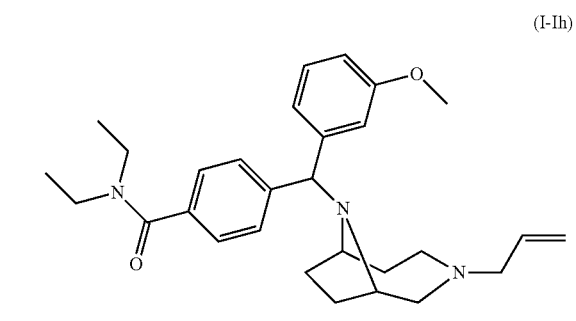

(I-IIh)
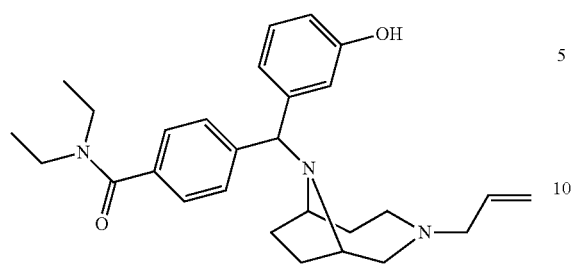
(I-IIIh)
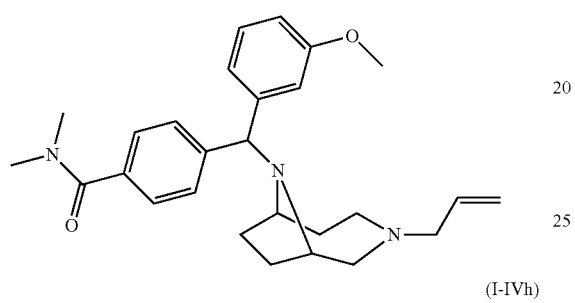
(I-IVh)
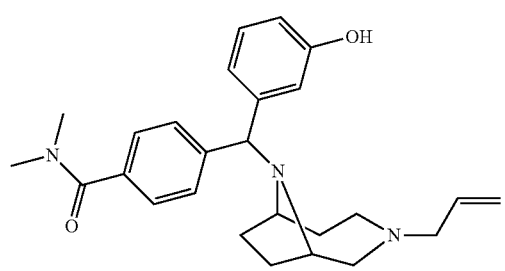
(I-Vh)
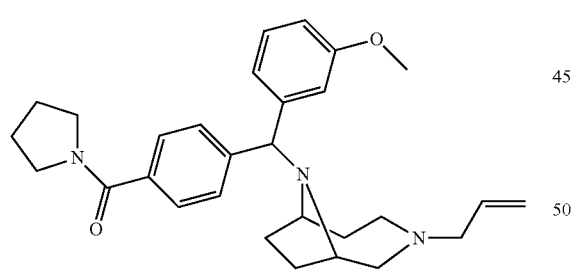
(I-VIh)
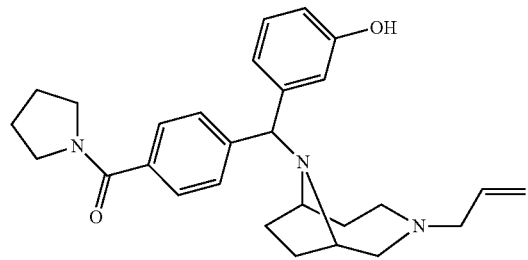
(I-VIIh)
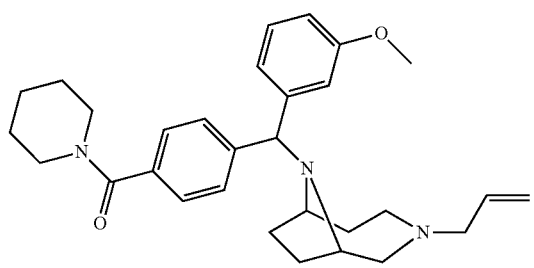
(I-VIIIh)
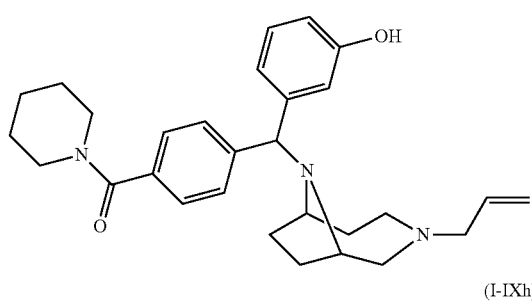
(I-IXh)
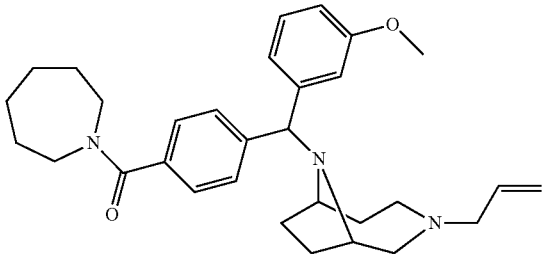
(I-Xh)
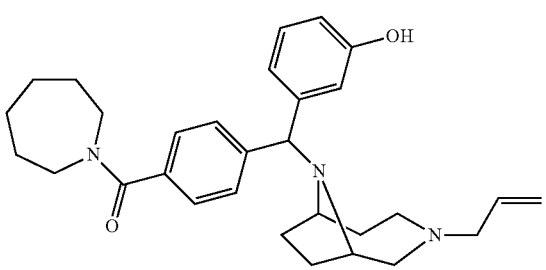
(I-XIh)
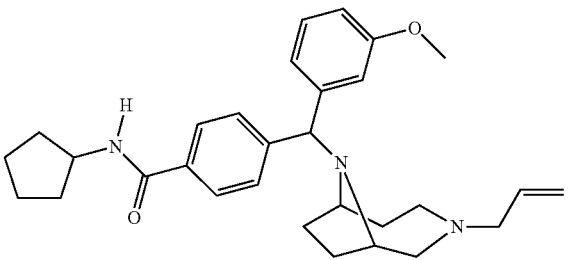

53
-continued
(I-XIIh)
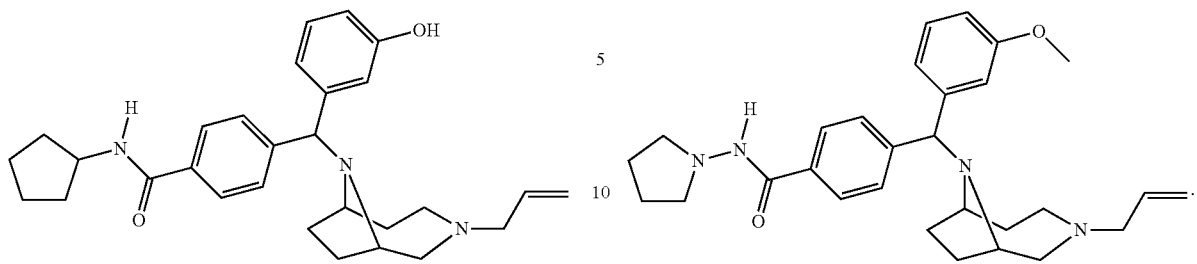
(I-XIIIh)
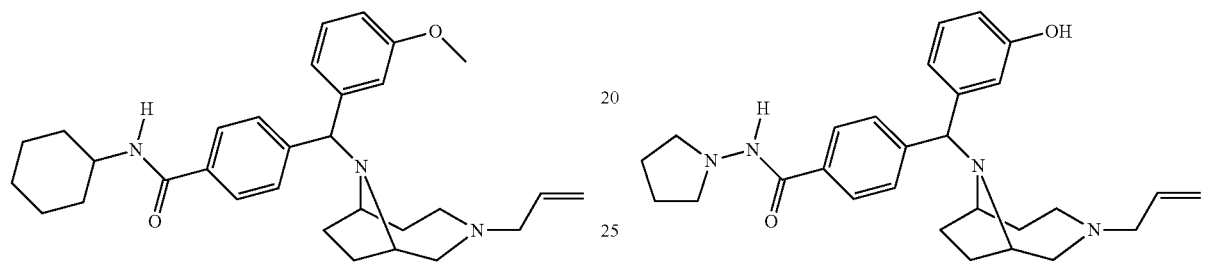
(I-XIVh)
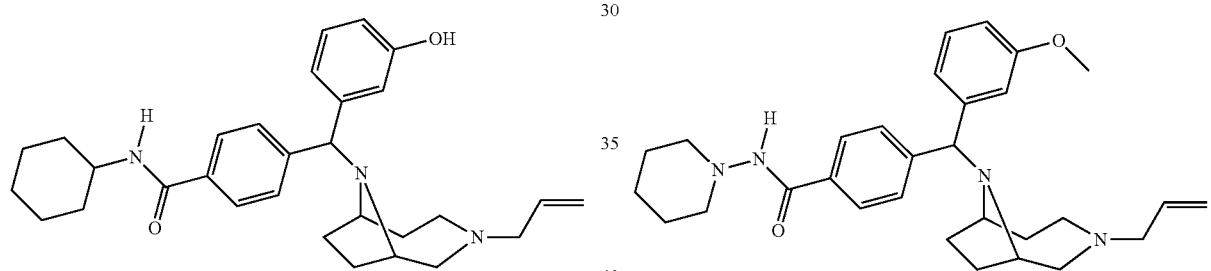
(I-XVh)
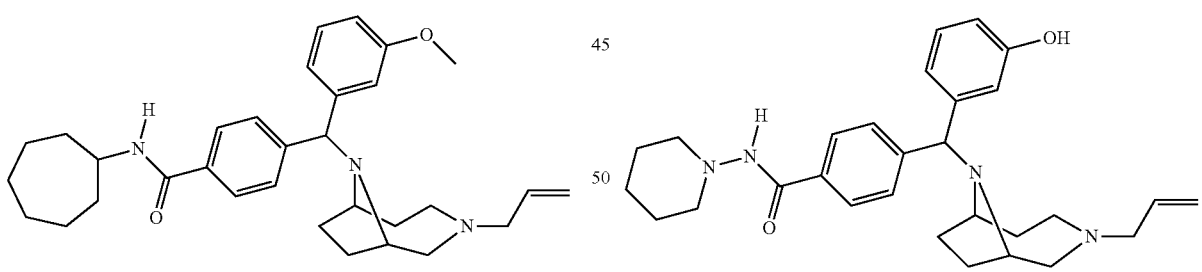
(I-XVIh)
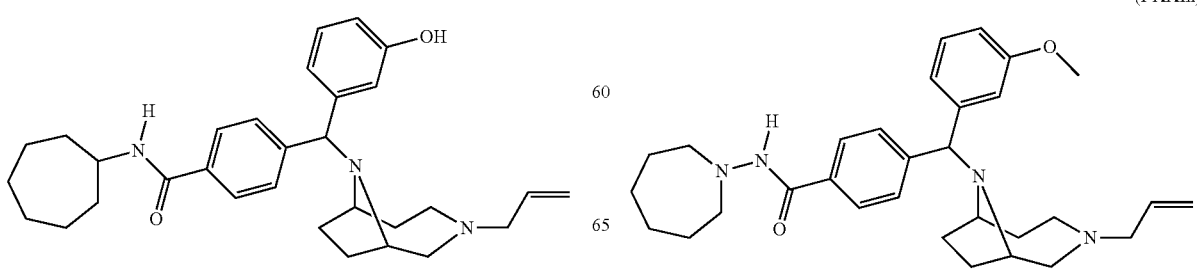
54
-continued
(I-XVIIh)
(I-XVIIIh)
(I-XIXh)
(I-XXh)
(I-XXIh)

(I-XXIIh)
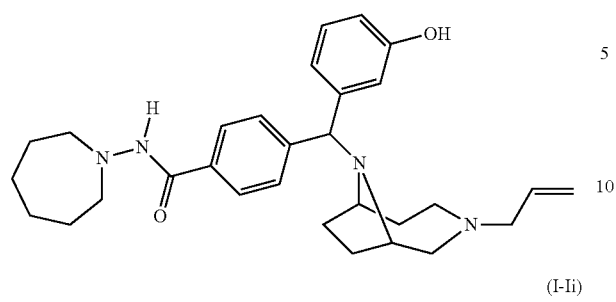
(I-Ii)
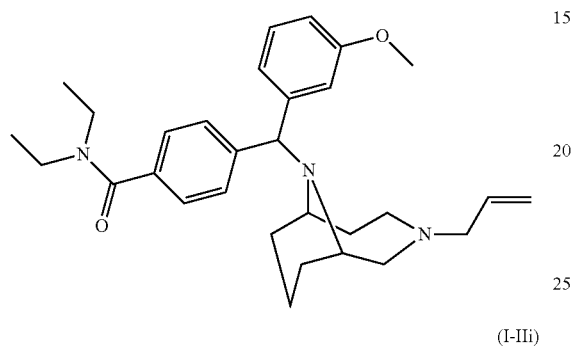
(I-IIi)
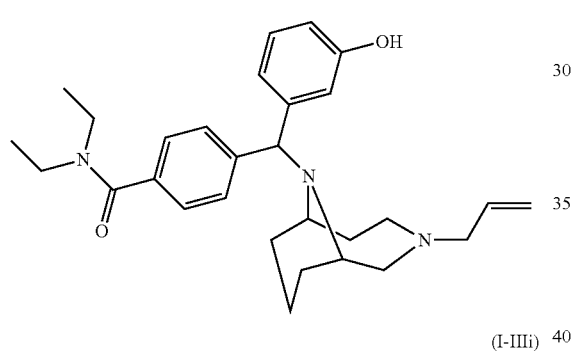
(I-IIIi)
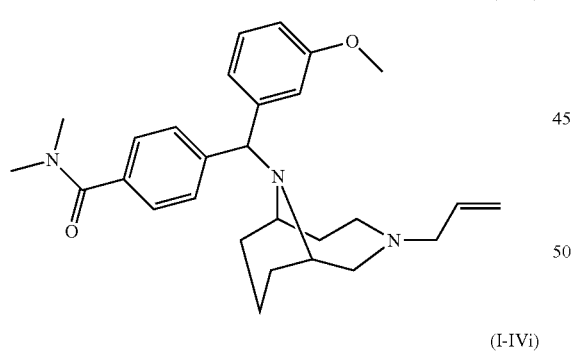
(I-IVi)
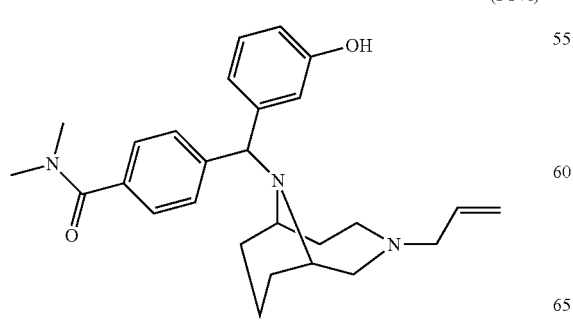
(I-Vi)
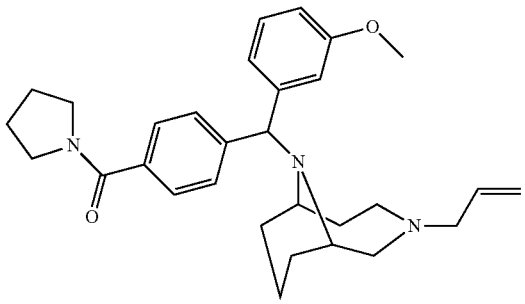
(I-VIi)
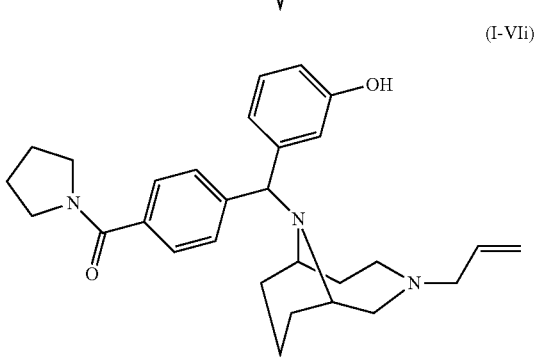
(I-VIIi)
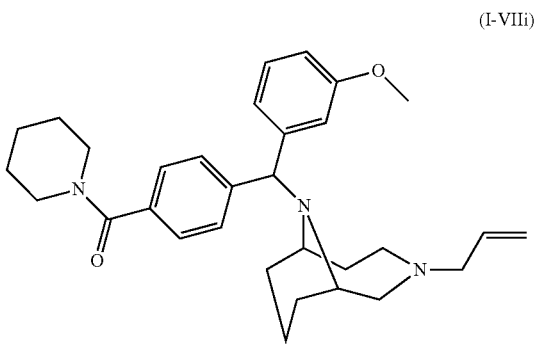
(I-VIIIi)
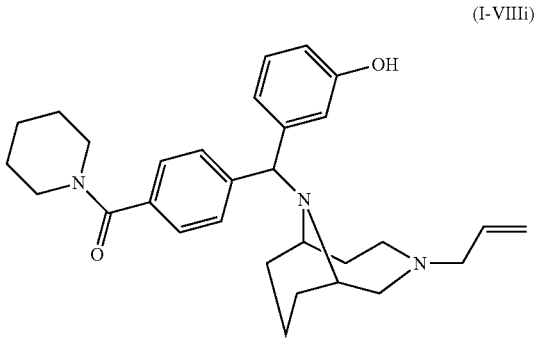
(I-IXi)
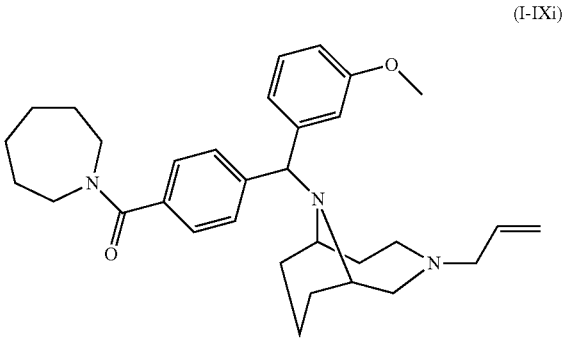

-continued
(I-XIi)
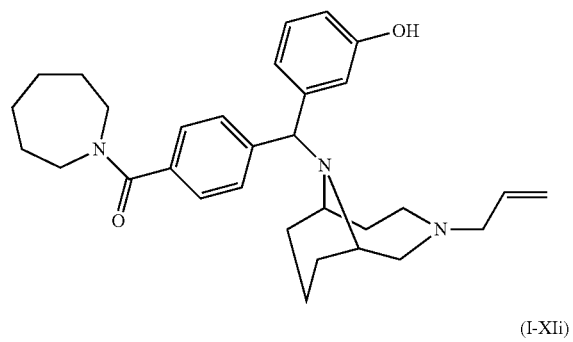
(I-XVi)
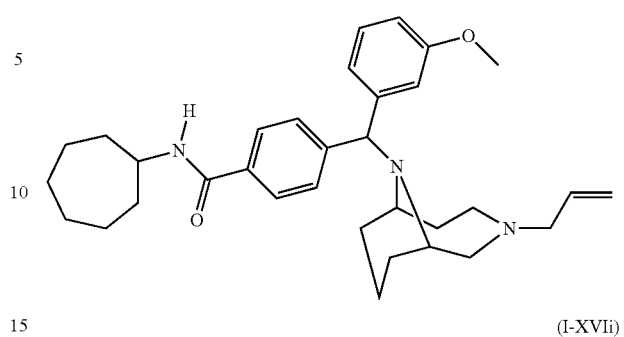
(I-XIIi)
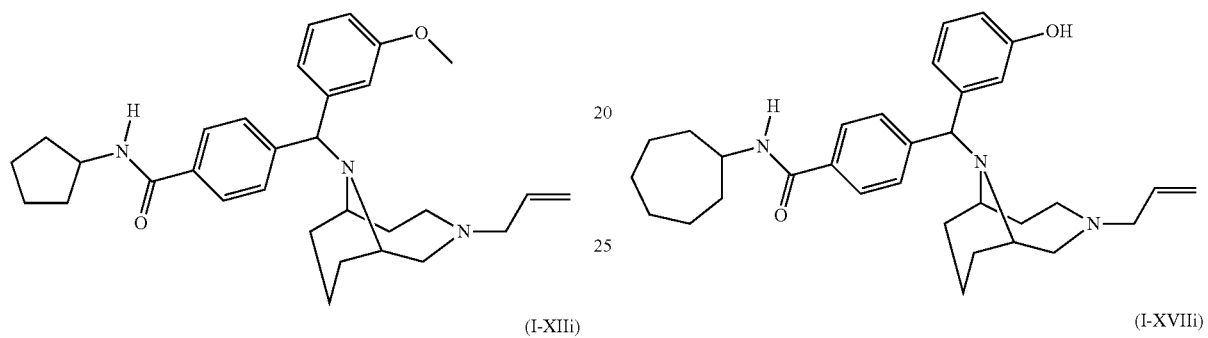
(I-XVIi)
(I-XIIIi)
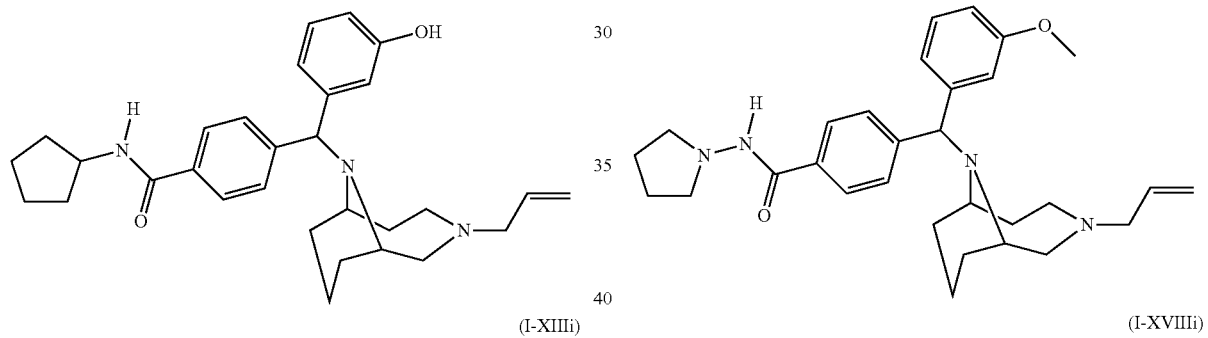
(I-XVIIi)
(I-XIVi)
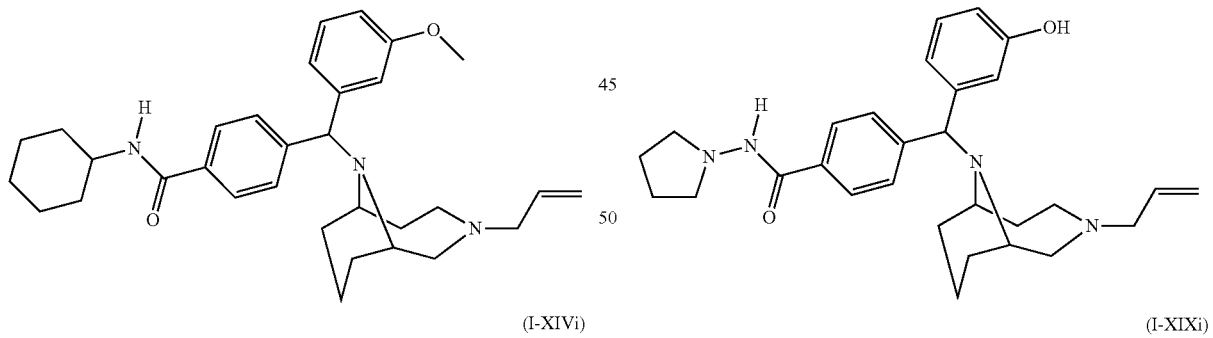
(I-XVIIIi)
(I-XIXi)
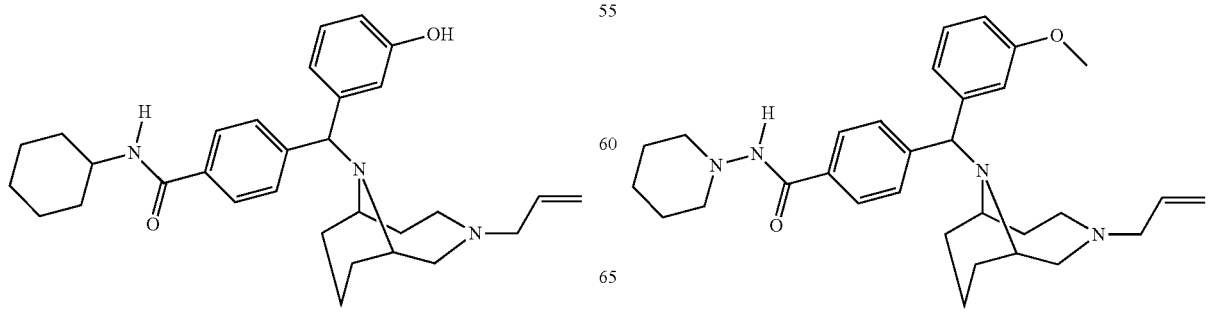

(I-XXi)
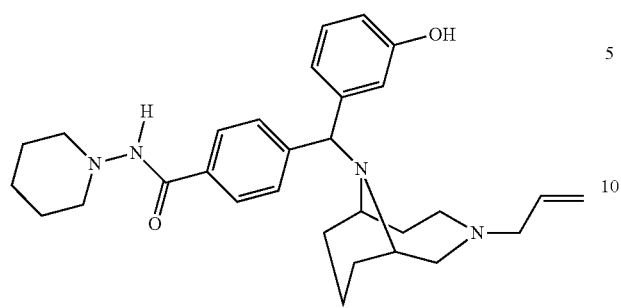
(I-XXIi)
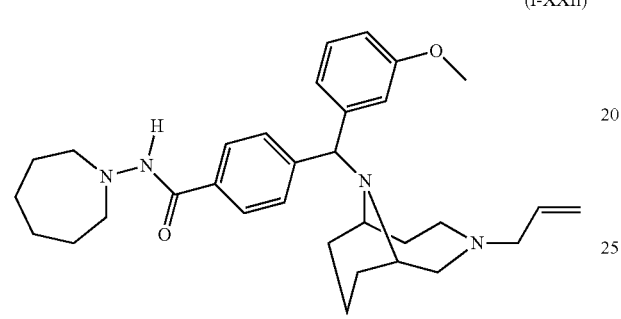
(I-XXIIi)
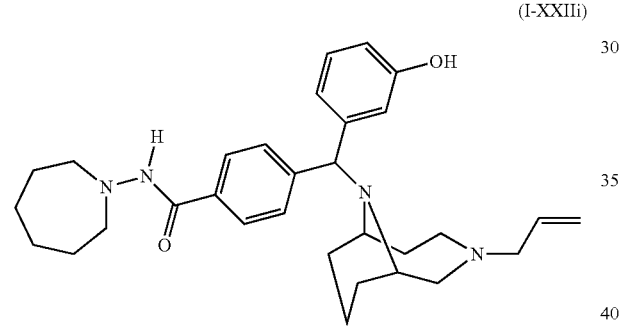
(I-Ij)
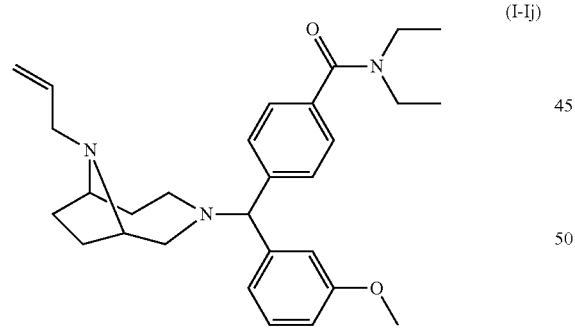
(I-IIj)
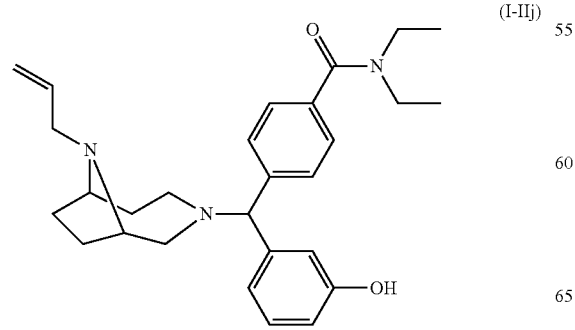
(I-IIIj)
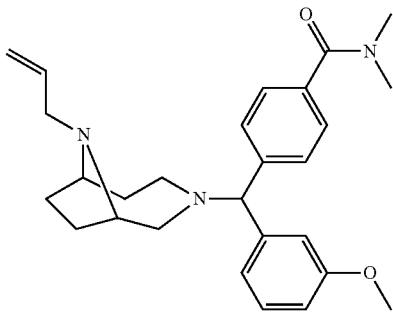
(I-IVj)
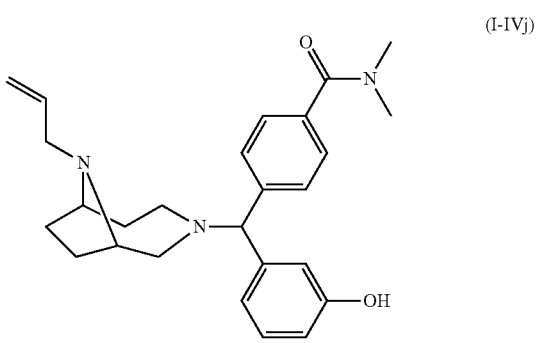
(I-Vj)
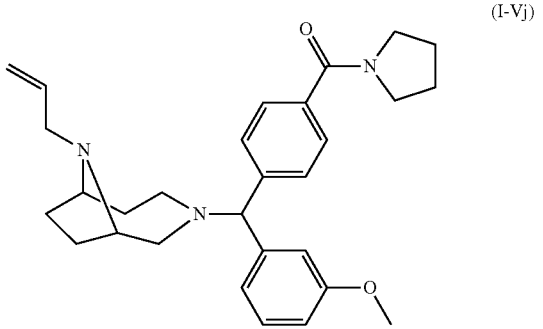
(I-VIj)
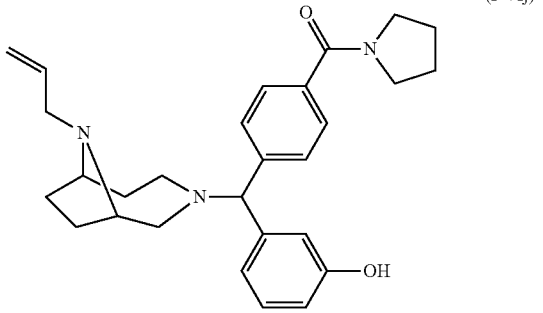
(I-VIIj)
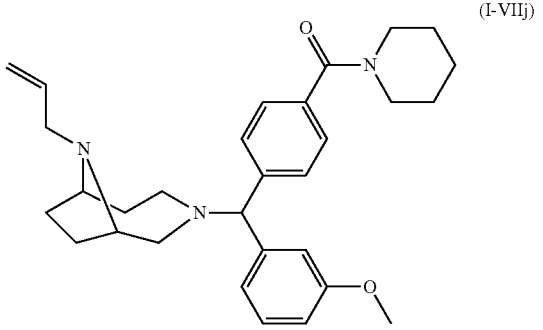

(I-VIIIj)
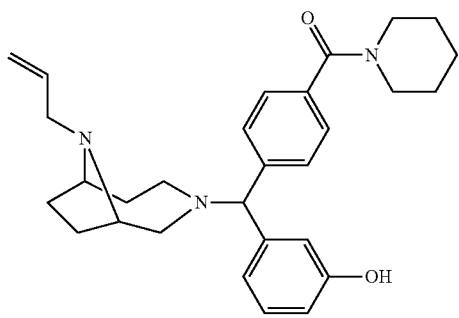
(I-IXj)
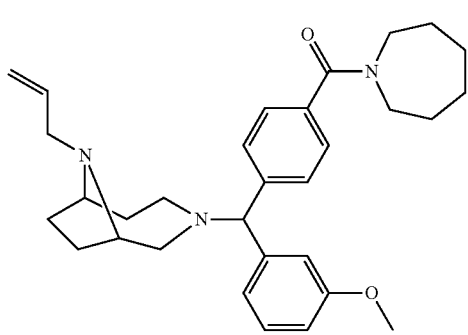
(I-Xj)
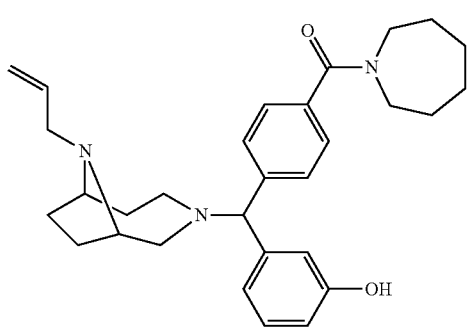
(I-XIj)
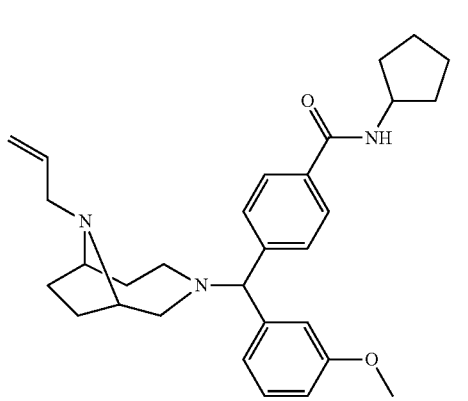
(I-XIIj)
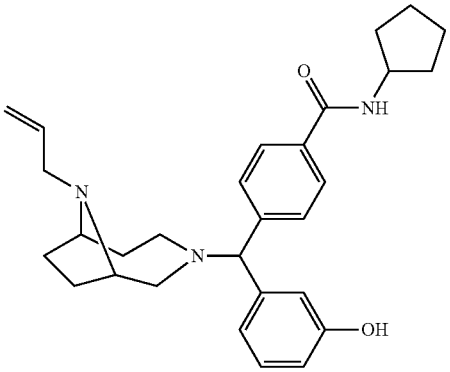
(I-XIIIj)
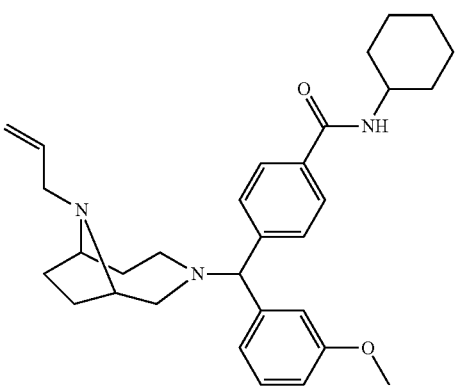
(I-XIVj)
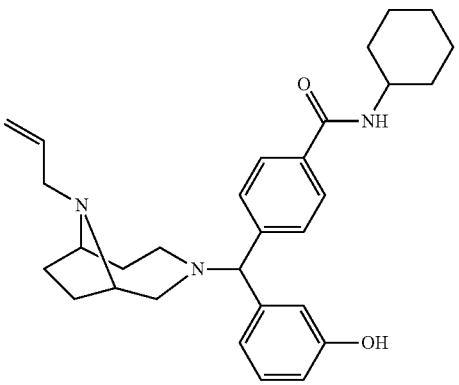
(I-XVj)
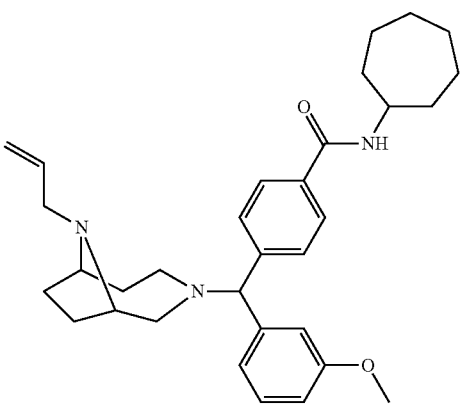

(I-XVIj)
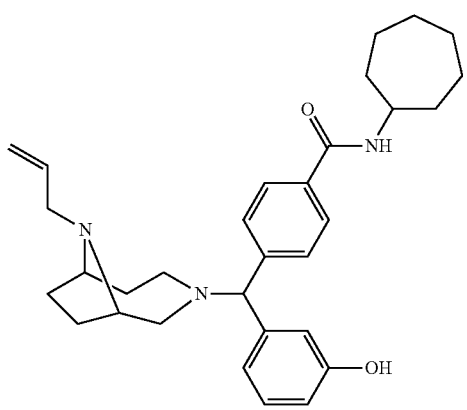
(I-XVIIj)
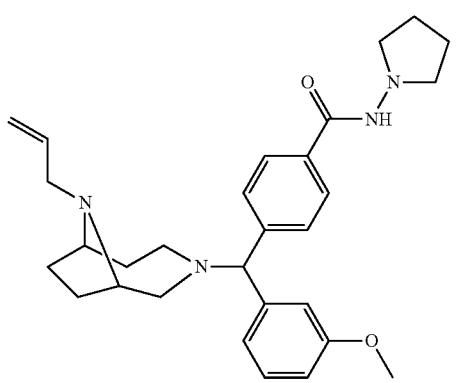
(I-XVIIIj)
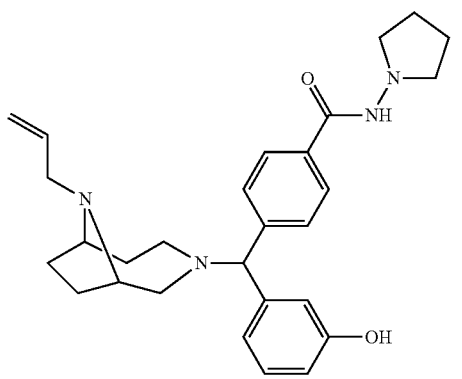
(I-XIXj)
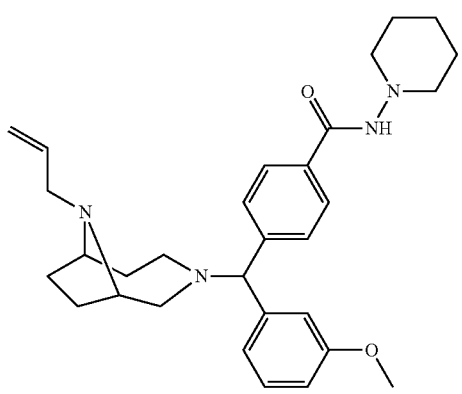
(I-XXj)
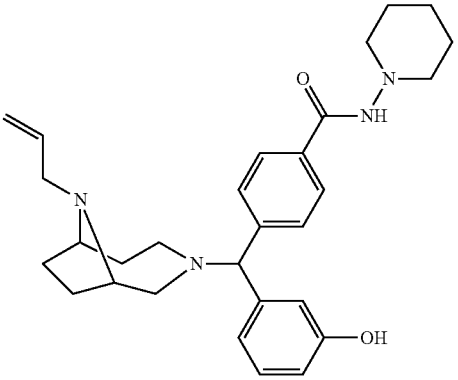
(I-XXIj)
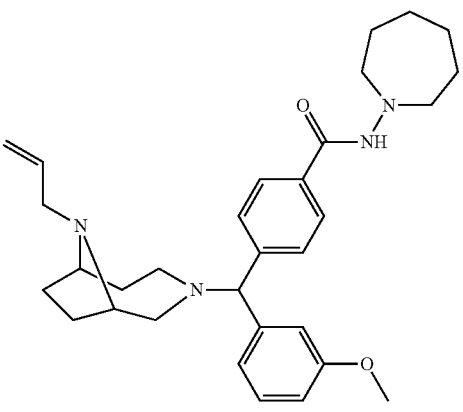
(I-XXIIj)
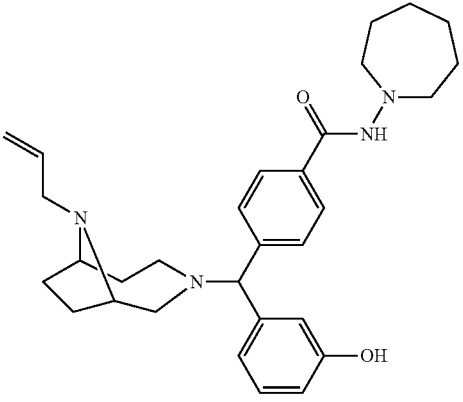
(I-Ik)
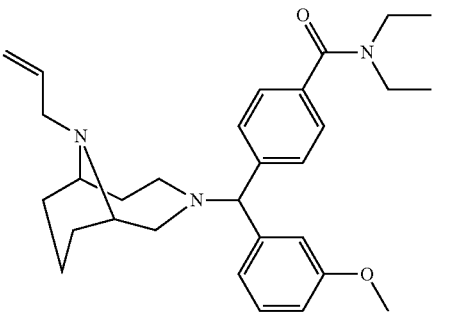

(I-IIk)
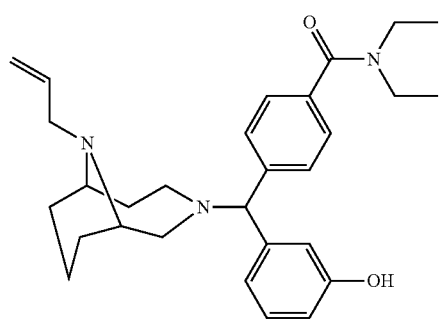
(I-IIIk)
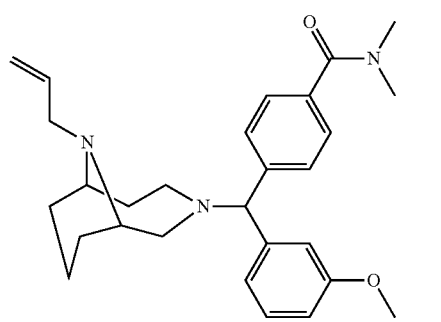
(I-IVk)
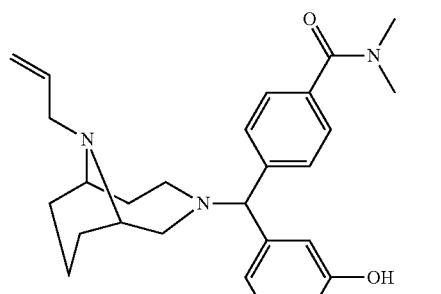
(I-Vk)
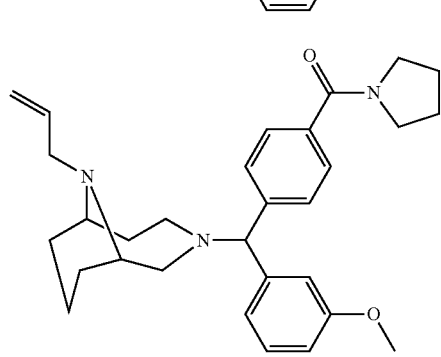
(I-VIk)
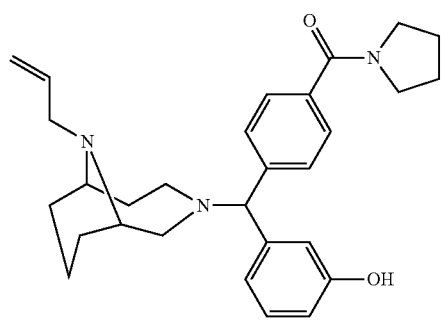
(I-VIIk)
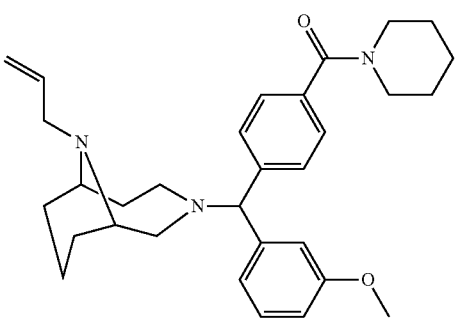
(I-VIIIk)
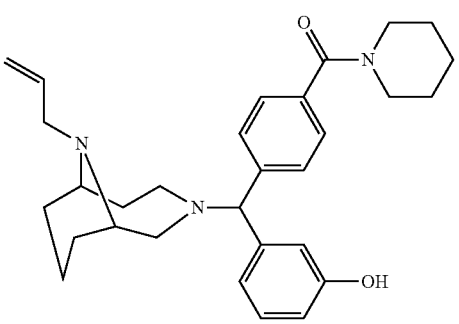
(I-IXk)
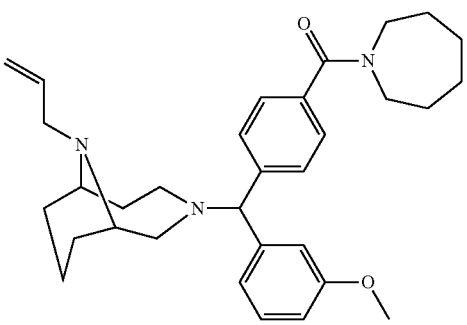
(I-Xk)
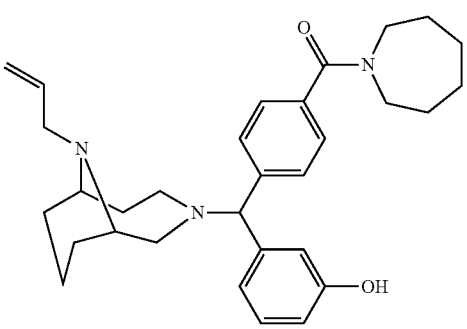

(I-XIk)
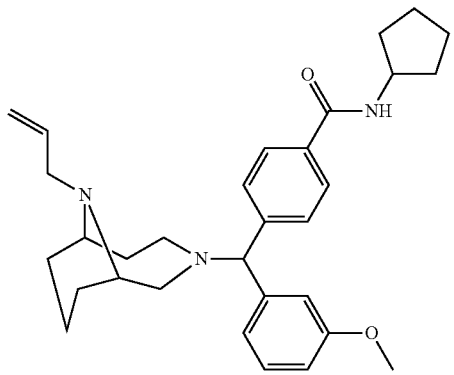
(I-XIIk)
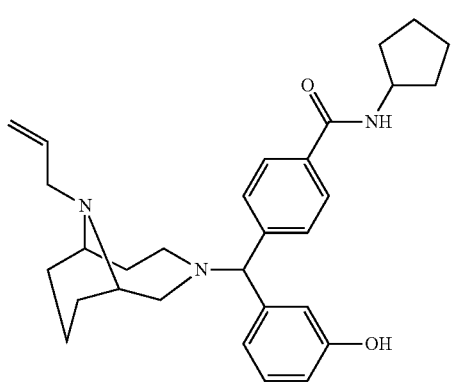
(I-XIIIk)
(I-XIVk)
(I-XVk)
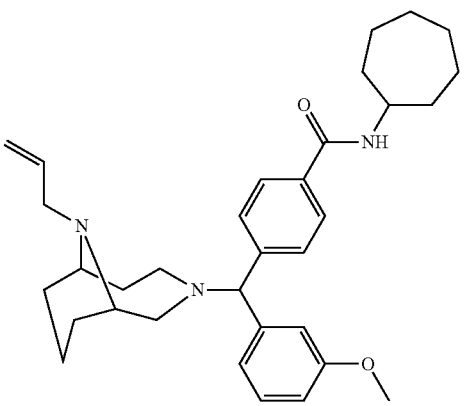
(I-XVIk)
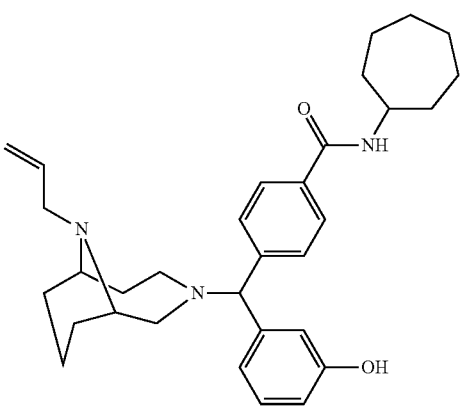
(I-XVIIk)
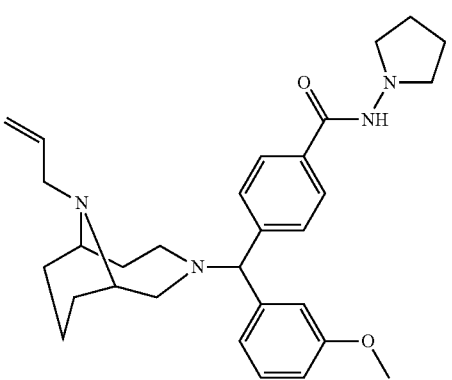
(I-XVIIIk)
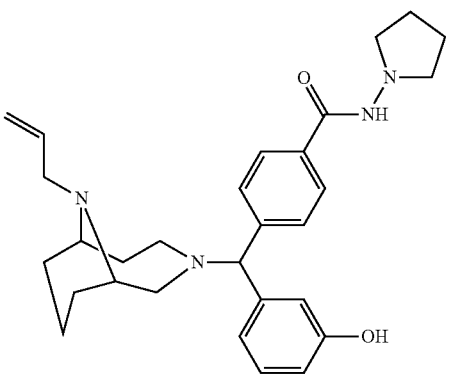

-continued (I-XIXk)

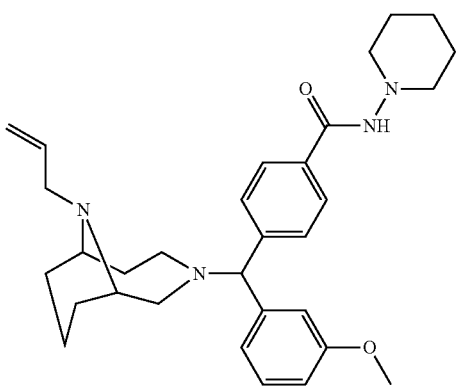

(I-XXk)

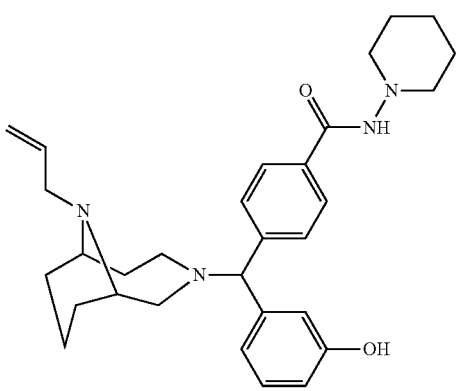

(I-XXIk)

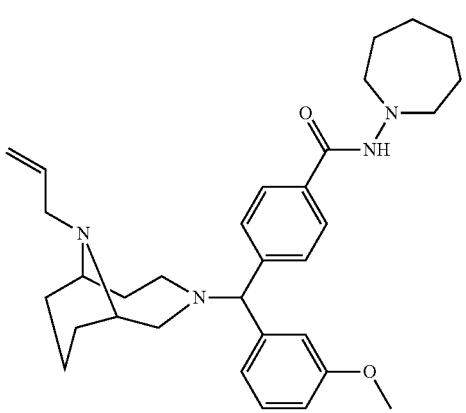

-continued (I-XXIIk)

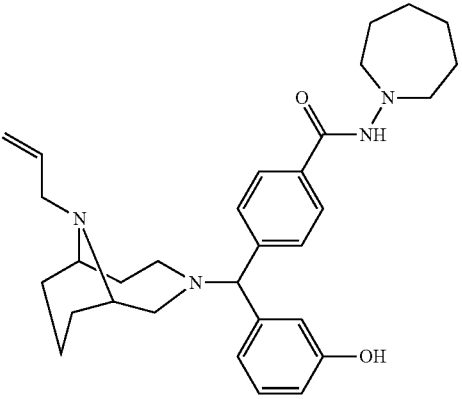

As said, the compounds of the present invention show the above combination of properties, i.e. high affinity, high selectivity and high activity for δ opioid receptors; reduced side effects compared to the compounds having affinity and selectivity for μ opioid receptors, in particular morphine.

As said, the hydrates, solvates and pharmaceutically acceptable salts of the compounds of formula (I), comprising the different isomers (cis and trans isomers, optical isomers when in the compounds one or more chiral centres are present), and mixtures thereof of the compounds of formula (I), are a further object of the present invention. The meaning of the hydrate and solvate terms is well known to the skilled in the art. In particular, by hydrate it is meant a compound containing one or more hydration water molecules, generally from 1 to 10 water molecules. By solvate it is meant that a compound contains one or more molecules of a solvent different from water.

By pharmaceutically acceptable salts are meant the salts obtained by treating the compounds of formula (I) with organic or inorganic acids acceptable from a pharmaceutical point of view. For example hydrochlorides, sulphates, fumarates, oxalates, citrates, hydrogensulphates, succinates, paratoluen-sulphonates, can be mentioned. See the volume: "Remington, The Science and Practice of Pharmacy", vol. II, 1995, page 1457.

The metabolites derived from the administration in human beings and in animals of the compounds of formula (I) are a further object of the present invention, excluding the end metabolites such as water and $CO_2$ and $NH_3$.

It has been surprisingly and unexpectedly found by the Applicant that the compound of formula (I) of the invention have an in vitro and/or in vivo affinity for the opioid receptors, in particular an high affinity and selectivity for the delta opioid receptors, with reduced side effects with respect to the morphine and to other compounds having affinity for the μ opioid receptors. It has furthermore been surprisingly and unexpectedly found by the Applicant that the compounds of formula (I) of the invention, when administered together with compounds having affinity and selectivity for μ opioid receptors, and/or morphine are capable to reduce the side effects of the latter, without negatively affecting the therapeutic activity of the latter compounds preferably increasing and/or prolonging in time said effects.

The compounds of the present invention can in fact provide a synergism of action with the compounds having activity and selectivity for μ opioid receptors, in particular μ opioidergic agonist compounds, such as morphine.

The compounds of formula (I) of the invention have a high affinity for the delta opioid receptors; in particular they have an affinity, expressed as $K_i$, <400 nM, more preferably <200 nM, still more preferably <100 nM. The compounds (I) of the invention have furthermore high selectivity for the δ opioid receptors; in particular they have selectivity ratios expressed as ratio $K_i$ for δ Opioid Receptors
$K_i$ for μ Opioid Receptors Lower than 0.20, more preferably lower than 0.10, still more preferably lower than 0.08.

A further object of the present invention is a process for preparing the compounds of formula (I).

When the substituent $R^2$ of the compounds of formula (I) does not contain OH groups, the process comprises the following steps:

a) alkylation of the nitrogen atom linked to one hydrogen atom of the following diazabicyclic or diazatricyclic compounds having formulae D1'-D6', wherein the other nitrogen atom is substituted with protecting groups $Z_9$ or $Z_1$:

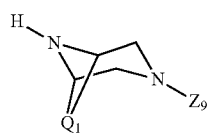
(D1')

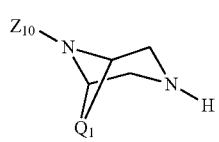
(D2')

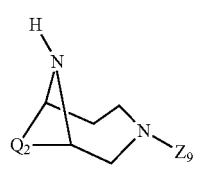
(D3')

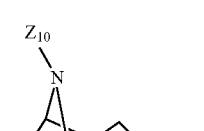
(D4')

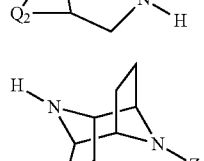
(D5')

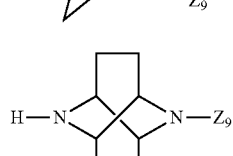
(D6')

wherein:
$Q_1$ is as defined above in the compound of formula (I) when $D_1$ has the meaning of D1 and t=1, $Q_2$ is equal to $Q_1$ but excluding —$CH_2$—
$Z_9$ and $Z_{10}$ are protecting groups of the nitrogen atom, by an alkylating compound of formula (II'):

(II')

wherein $R^1$ is as defined above, $R^{2a}$ has the same meanings as $R^2$ but excluding phenyl substituted with at least one or more OH groups, $T_y$ is a leaving group, and obtaining the compounds of formula (I'):

$$A_1\text{-}D_1\text{-}T_2 \qquad (I')$$

wherein $A_1$ and $D_1$ are as defined above and $T_2$ has the meaning of $Z_9$ or $Z_{10}$, b) deprotection of the nitrogen atom substituted with the groups $Z_9$ or $Z_{10}$ obtaining the compounds of formula (I) wherein $T_1$ is H:

$$A_1\text{-}D_1\text{-}T_1 \qquad (I)$$

c) substitution of the hydrogen atom linked to nitrogen of the compound $A_1$-$D_1$-H by reaction with a compound of formula $T_1$-$T_x$, wherein $T_1$ is as defined above and $T_x$ is a leaving group, obtaining the compounds of formula (I) wherein $T_1$ is different from H, wherein when the compounds of formula (I) desired has $T_1$=H step c is not carried out.

In step a) the alkylation reaction is preferably carried out under anhydrous conditions in the presence of a base, preferably potassium carbonate, by operating in an inert organic solvent such as acetonitrile. Preferably the reaction is carried out at reflux, preferably for 40-80 hours. Preferably the protecting groups $Z_9$ and $Z_{10}$ are selected from benzyl, methyl, terbutoxycarbonyl (BOC) or carboxybenzyl (CBZ). Preferably the leaving group $T_y$ of formula (II') is selected from halogen, mesyl or tosyl.

In step b) the deprotection of the nitrogen atom linked to the protecting groups $Z_9$ or $Z_{10}$ can be carried out by using the known reactions of the art in relation to the specific protective group. For example the removal of a benzyl protecting group can be carried out by catalytic hydrogenation, for example by catalytic hydrogenation on Pd/C. The removal of a methyl protecting group can for example be carried out with 2,2,2-trichloroethylchloroformate with formation of carbamate and subsequent treatment with metal zinc in acetic acid. The removal of a BOC protecting group can be carried out by using strong acids, for example trifluoroacetic acid or hydrochloric acid. The removal of a CBZ protecting group can be carried out by each of the deprotection reactions indicated above for benzyl or BOC.

In step c) the leaving groups $T_x$ are preferably selected from halogen, mesyl or tosyl. The reaction is preferably carried out in an inert organic solvent, preferably under anhydrous conditions, such as anhydrous acetone, preferably at reflux for 8-20 hours.

When in the compounds of formula (I) the substituent $R^2$ contains one or more OH groups, said compounds are obtainable with a process comprising, in sequence, the following steps: step a), step b), step c), carried out as described above, yielding a compound of formula (I) wherein in $R^2$, in the place of OH groups there are GS groups, stable under the reaction conditions adopted in the above mentioned steps, selected from the following: halogen, $NO_2$, $OR^6$, $NHR^5$ or $NR^6R^7$, wherein $R^5$, $R^6$, $R^7$ are as defined above, step d) conversion of GS groups into hydroxyl groups by known reactions, obtaining the compounds of formula (I) wherein the substituent $R^2$ contains one or more OH groups.

Preferably GS is the $OR^6$ group, more preferably methoxyl. In this latter case the conversion of the GS groups into OH groups occurs for example with mineral acids or Lewis acids. Concentrated HCl or boron tribromide are for example used. When boron tribromide is used, the reaction is preferably carried out in an inert organic solvent, for example dichloromethane, by operating at low temperatures, for example comprised between 0 and 5° C.

The diazabicyclic or diazatricyclic compounds having formulae from D1' to D6' used in the process of the present invention are known compounds. In particular, the compounds having formulae (D1') and (D2') and the preparation methods thereof are described in U.S. Pat. No. 5,672,601 and in patent applications US 2003/195,217 and WO 2005/108, 402. The compounds having formulae (D3') and (D4') and the preparation methods thereof are described in U.S. Pat. No. 7,358,243. The compounds of formula (D5') and (D6') and their preparation methods are described in U.S. Pat. No. 6,127,362.

The alkylating compounds of formula (II') can be obtained according to known methods in the art, in particular those described by S. N. Calderon et al. in J. Med. Chem. 37 (1994) 2125-2128 and in J. Med. Chem. 40 (1997) 695-704. For example, the compounds of formula (II') wherein $R^1$ has substituent groups C(O)R', C(O)OR', C(O)NHR', C(O)NR$^3$R$^4$ at para position, can be prepared according to scheme 1 reported hereinafter:

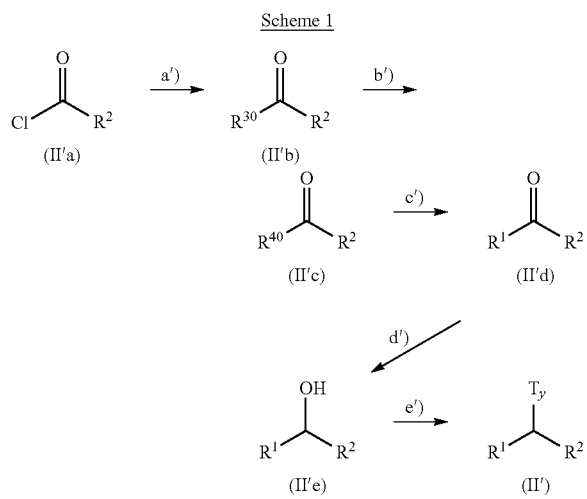

Scheme 1 wherein:
in step a') the benzophenone of formula (II'b), wherein $R^2$ is as defined above and $R^{30}$ is phenyl having in para position a methyl group, is obtained by reacting benzoyl chloride of formula (II'a) with toluene in the presence of aluminum trichloride (AlCl$_3$) in dichloromethane at room temperature, in step b') the methyl group of the substituent $R^{30}$ is oxidized to a carboxylic acid. In this step compound (II'c) is obtained wherein $R^2$ is as defined above and $R^{40}$ is a phenyl with a COOH group in para position. The reaction is carried out in the presence of an oxidizing agent, for example potassium permanganate at the reflux temperature in an hydroalcoholic solution, for example at the temperature of 90° C. in an ethanol/water 1:1 volume/volume mixture,
in step c') the COOH group of $R^{40}$ is converted into the groups C(O)R', C(O)OR', C(O)NHR', C(O)NR$^3$R$^4$ as defined above in $R^1$, according to methods known in the art, obtaining compound (II'd) wherein $R^1$ and $R^2$ are as defined above,
in step d') the alcohols of formula (II'e) are obtained by reduction of the carbonyl group $R_1$—C(O)—$R_2$ of formula (II'd) with a reducing agent, for example sodium borohydride, in an organic solvent, such as methanol or an ethanol/water mixture, for example by using an ethanol/water 1:1 volume/volume,
in step e') the alcohols of formula (II'e) are treated with concentrated HCl or with tosyl chloride or mesyl chloride to obtain the compound of formula (II'), wherein Ty is a leaving group herein above defined.

In step c') the conversion of the COOH group into C(O)NHR' or C(O)NR$^3$R$^4$ groups takes place by reaction of the acid (II'c) with the amines respectively of formula NH$_2$R' or NHR$^3$R$^4$ wherein R', R$^3$ and R$^4$ are as defined above. The reaction is carried out for example in the presence of 1-hydroxybenzotriazol hydrate and N-(3-dimethylaminopropyl)-N'-ethyl-carbodiimide (EDC).

In step c') the conversion of the COOH group into C(O)OR' groups takes place by reaction of the acid of formula (II'c) with an alcohol of formula R'—OH wherein R' is as defined above.

In step c') the conversion of the COOH group into C(O)R' groups takes place by reaction of the acid of formula (II'c) with N,O-dimethylhydroxylamine, for example in the hydrochloride, obtaining a Weinreb amide, and reacting the latter with organometallic compounds R'-M wherein M is for example lithium, Mg—Cl, Mg—Br, R'being as defined above.

A further object of the present invention relates to the compounds of formula (I) for use as a medicament.

The present invention relates also to the use of the compounds of formula (I) for preparing pharmaceutical compositions for diseases and disorders in mammals and in human beings of diseases and disorders wherein the opioid receptors are involved, more preferably wherein the delta opioid receptors are involved.

In this way it is obtained a prophylaxis therapy in mammals and in human beings for the above diseases.

A further object of the present invention are pharmaceutical compositions comprising the compounds of formula (I).

The pharmaceutical compositions of the present invention contain the compounds of formula (I) in an amount required for the specific pharmaceutical application.

In the pharmaceutical compositions the compound of formula (I) can be present as such or in the form of salt or solvate, or also as isomer, such as for example cis or trans isomer, or as an optical isomer when the compounds of formula (I) contain one or more chiral centres.

The additives contained in the pharmaceutical compositions are excipients, carriers, dyestuffs, preservatives, aromas, etc., the use of which in the pharmaceutical field is known. The used amounts of these various additives and excipients are those known for the specific applications.

The pharmaceutical compositions can be administered by oral, subcutaneous, sublingual, intramuscular, intravenous, topical, transdermal, rectal, ophthalmic, intranasal, vaginal, intraperitoneal route.

The pharmaceutical compositions of the present invention comprise for example dispersions, solutions, emulsions, microemulsions, powders, microparticles, nanoparticles, capsules, aerosol, suppositories, tablets, syrups, elixirs, creams, gels, ointments, plasters, foams, etc. See for example those described in patent application WO 2004/011,468, herein incorporated by reference.

The pharmaceutical compositions can be obtained according to the known processes of pharmaceutical art. For example they can be obtained according to the procedures mentioned in U.S. Pat. No. 6,028,084 herein incorporated by reference.

The pharmaceutical compositions can also be prepared by using the methods and the additives mentioned in patent application US 2003/0003,145, herein incorporated by reference. In these formulations sodium alkylsulphate or another surfactant commonly employed in the pharmaceutical field can be used.

For example pharmaceutical compositions, usable for the oral administration of the compounds of formula (I), their isomers or the corresponding hydrates or solvates or pharmaceutically acceptable salts, are constituted by: 0.5-20% by weight of a compound of formula (I), including all the different isomers and the corresponding mixtures or a corresponding hydrate or solvate or pharmaceutically acceptable salt; 0.05-0.5% by weight of sodium alkylsulphate or another surfactant; 2.5-10% by weight of a disintegrating agent such as cellulose, sodium carboxymethylcellulose or other cellulose derivatives. In all these formulations the sum of the active principle and the other usual excipients, in addition to those indicated above, give 100% of the composition.

Pharmaceutical formulations, usable for both the oral and intraocular administration, can comprise the compounds of formula (I), their isomers, including the salts thereof, hydrates, solvates, together with hydroxypropylmethylcellulose. In particular they can comprise from 0.1 to 20% of the compounds of formula (I) and from 0.5 to 10% of hydroxypropylmethylcellulose (HPMC), the difference to 100% w of the composition being given by the usual pharmaceutical excipients of such formulations for human use.

Specific pharmaceutical formulations for the oral administration in the form of capsules or tablets, besides the compounds of formula (I) and hydroxypropylmethylcellulose, they can comprise other excipients, such as for example monohydrate lactose, magnesium stearate, microcrystalline cellulose, titanium oxide. In these preparations HPMC can be present in the capsule or tablet core and/or in the tablet shell, when it is present.

Pharmaceutical compositions of the compounds of formula (I) are for example those obtainable by starting from emulsions or microemulsions, wherein the compounds of the invention, in the presence of surfactants and other additives, are admixed with an aqueous phase and optionally with an oily phase.

It is a further object of the present invention pharmaceutical formulations in the form of microemulsions or emulsions, or comprising microemulsions or emulsions, comprising the following components (% by weight):
S) from 0.01 to 95% of one or more pharmaceutically acceptable compounds, selected from the following classes:
  surfactants selected from non-ionic, anionic, cationic and amphotheric, optionally containing fluorine atoms,
  polymers (Pol) forming organized structures such as aggregates, micelles, liquid crystals, vesicles, in the liquid in which they are solubilized,
O) from 0 to 95% of one or more oils selected from the following classes of pharmaceutically acceptable compounds:
  esters of $C_4$-$C_{32}$ acids, optionally containing one or more unsaturations of ethylene type,
  $C_4$-$C_{32}$ acids, optionally containing one or more unsaturations of, ethylene type, which are included in the composition when the pH is comprised between 3 and 5,
PA) from 0.001 to 90% of compounds of formula (I),
AD) from 0 to 60% by weight of one or more compounds selected from the following classes:
  modifiers of the water and/or oil polarity,
  modifiers of the film curvature of component S),
  co-surfactants,
WA) from 0.001 to 99.9% of water or of a saline aqueous solution, optionally buffered,
the sum of the components being 100%.

The compositions of the invention in the form of microemulsions are limpid and transparent, preferably liquid. When the viscosity is very high, the microemulsions of the invention are in a gel form, optionally formed of liquid crystals, such as lamellar, hexagonal, cubic liquid crystals.

In component S) the surfactants containing fluorine atoms can have (per)fluorinated chains, for example (per)fluoropolyether chains.

The liquids wherein the polymers of component S) are solubilized to form the organized structures are water and/or oil. The kinds of usable oils are mentioned later on and can be of both natural and synthetic origin.

By microemulsion a system is meant that is constituted of two or more phases immiscible among each other, said system being transparent, isotropic, comprising at least one aqueous phase and at least one oil phase, wherein the various phases are stabilized by component S), optionally in the presence of one or more compounds AD), for example cosurfactants. See for example R. K. Mitra, Physicochemical investigations of microemulsification of eucalyptus oil and water using mixed surfactants (AOT+ Brij-35) and butanol, J. Colloid and Interface Science, 283 (2005) 565-577. The oil phase in the microemulsions for pharmaceutical use can consist of the active principle, when the compound has a lipophilic character, thus being insoluble in water or in an aqueous phase.

By emulsion it is meant a system formed of the same components of the microemulsion but the system appears opalescent or milky or it can also have a creamy appearance.

The processes for preparing the microemulsions or the emulsions of the present invention are described hereinafter.

Preferred microemulsions or emulsions according to the present invention have the following composition (% by weight):
  Component S) from 0.01 to 90%,
  Component O) from 0 to 90%,
  Component PA) from 0.001 to 50%,
  Component AD) from 0 to 30%,
  Component WA) from 0.1 to 99.9%,
the sum of the components being 100%.

More preferred microemulsions or emulsions have the following composition (% by weight):
  Component S) from 0.01 to 80%,
  Component O) from 0 to 70%,
  Component PA) from 0.05 to 40%,
  Component AD) from 0 to 20%,
  Component WA) from 10 to 99.9%,
the sum of the components being 100%

Still more preferred microemulsions or emulsions have the following composition (% by weight):
  Component S) from 0.01 to 70%,
  Component O) from 0.01 to 50%,
  Component PA) from 0.05 to 30%,
  Component AD) from 0 to 15%,
  Component WA) from 20 to 99.9%,
the sum of the components being 100%.

The preferred surfactants component S) are those non-ionic and anionic. Among the non-ionic surfactants, the most preferred are those containing polyoxyalkylene chains, preferably polyoxyethylene chains. The following ones can for example be mentioned:

polyoxyl 35 castor oil, known for example by the trademark Cremophor® EL (BASF), prepared by ethoxylation of castor oil, polyoxyl 40 hydrogenated castor oil, known for example by the trademark Cremophor® RH40 (BASF), prepared by ethoxylation of hydrogenated castor oil, polyethylenglycol 15 hydroxystearate, known for example by the trademark Solutol® HS15 (BASF), prepared by reaction of 15 moles of ethylene oxide with 1 mole of 12-hydroxystearic acid, polyoxyethylene polysorbate, such as Tween® 80, Tween® 20, Tween® 60, Tween® 85, sorbitan esters of fatty acids, as sorbitan monolaurate and sorbitan monostearate, (Span® 20 and Span® 60, respectively), vitamin E/TPGS: tocopheryl propylenglycol 1000 succinate, polyoxyethylen ethers of fatty acids, such as those of the series Brij®, quali Brij® 35, Brij® 76, Brij® 98, PEG-12-acyloxy-stearates, see for example C. E. McNamee et al. in "Physicochemical Characterization of PEG 1500-12-acyloxy-stearate micelles and liquid crystalline phases", Langmuir, 2005, 21, 8146-8154, among these the following can for example be mentioned:

PEG 1500 mono-12-capryloyloxy stearate (PEG 1500-$C_{18}C_8$)

PEG 1500 mono-12-caproyloxy stearate (PEG 1500-$C_{18}C_{10}$)

PEG 1500 mono-12-lauroyloxy stearate (PEG 1500-$C_{18}C_{12}$)

PEG 1500 mono-12-myristoyloxy stearate (PEG 1500-$C_{18}C_{14}$)

PEG 1500 mono-12-palmitoyloxy stearate (PEG 1500-$C_{18}C_{16}$).

Among the anionic surfactants the following can for example be mentioned: soya lecithin, (Epikuron® 200), bis-2-ethylhexylsulphosuccinate (AOT), sodium taurocholate.

Among cationic surfactants, hexadecyltrimethylammonium bromide (CTAB) and didodecylammonium bromide (DDAB) can for example be mentioned.

The polymers (Pol) which can be used as component S) must be soluble in the aqueous phase and/or in the oily phase. "Soluble" means that the polymers must reach in the phase in which they are soluble concentrations at least equal to those allowing the formation in that solvent of organized structures as aggregates, micelles, liquid crystals, vesicles. The presence of said organized structures may be detected by specific techniques of the physical chemistry of the dispersed systems, as for example Laser Light Scattering (LLS), Neutron Scattering, microscopy.

As said, the polymers component S) can be used also in combination with the mentioned surfactants. Also in this case the concentration of the solubilized polymer in the liquid phase must be such to lead to the formation of the above mentioned organized structures.

The polymers component S) are for example polyvinylpyrrolidone and vinylpyrrolidone/vinyl acetate copolymers, (Kollidon® 12PF and Kollidon® 17PF-BASF), and the block copolymers containing polyoxyalkylene chains, preferably containing polyoxyethylene chains (PEO), as for example the block copolymers PEO with polyoxypropylene chains (PPO) that are characterized by PEO-PPO-PEO structures (Pluronic® or Poloxamer® or Lutrol® F68 and Lutrol® F127, both commercialized by Basf).

In component O) the organic acid esters are preferably obtained by esterification of the corresponding carboxylic acid with an alcohol having an aliphatic chain, preferably $C_1$-$C_5$, or having a polyoxyethylene chain, or the esterification is carried out with glycerine. In this case mono-, di- or triglycerides are obtained.

The following can for example be mentioned:

oleoyl macrogol 6 glyceride (unsaturated polyglycosylated glyceride), commercialized for example under the trademark Labrafil® 1944 CS, (Gattefossé), propylenglycol caprylate caprate, (Labrafac® PG, Gattefossé), propylenglycol monoester of the caprylic acid, (Capmul® PG-8-Abitec), glycerol oleate (for example Peceol® Gattefossé)), medium chain mono- and diglycerides, for example capric and caprylic acid glycerides (for example Capmul® MCM (Abitec), Imwitor® 308 (Sasol)), polyglycerol oleate (for example Pluro® oleic (Gattefossé)), capric/caprylic acid triglycerides (for example Miglyol® 812 and Miglyol® 810 (Sasol), Labrafac® CC CS (Gattefossé)), ethyl butyrate, ethyl caprylate, ethyl oleate, tripalmitine, (DYNASAN® 116-Sasol).

Vegetable oils of pharmaceutical grade containing one or more of the above mentioned esters can also be used. The soya oil can for example be mentioned.

The acids component O) are preferably carboxylic acids, more preferably fatty acids.

Among the acids component O) stearic acid, the omega-3 and omega-6 acids, can be mentioned.

In component AD) the modifiers of the water and/or oil polarity can for example be polyethylenglycols. Lutrol®E300 and Lutrol® E400 (BASF) can be mentioned. Aliphatic alcohols, for example ethanol, can also be used.

In component AD) the modifiers of the film curvature of component S) are for example aliphatic alcohols, preferably $C_2$-$C_5$.

In component AD) the co-surfactants can for example be surfactant compounds as defined above, or aliphatic alcohols, preferably having a chain with at least 6 carbon atoms. There can be mentioned for example:

propylen glycol monolaurate, (Capmul® PG12 or Lauroglycol® 90 both of Gattefossé), caprylocaproyl macrogol 8 glyceride (saturated ethyldiglycosylated glyceride) (Labrasol®, Gelucire 44-14—Gattefossé), diethylenglycol monoethyl ether, (Transcutol®—Gattefossé).

The compositions formed of microemulsions are stable in a wide range of temperature, generally from 0° C. to 80° C., preferably from 4° C. to 45° C.

The microemulsions of the present invention can be prepared with a process comprising the following steps:

(IP) optional solubilization of the compound component PA) in component O)

(IIP) addition of component S) to component PA) or to its solution in component O) obtained in (IP), (IIIP) optional addition of component AD) to the phase obtained in (IIP), (IVP) addition, under stirring, of water or of saline aqueous solution to the phase obtained in (IIP) or optionally (IIIP), obtaining a limpid solution.

The steps of the process can be carried out at temperatures in the range 0° C.-90° C.

Microemulsions can be obtained also by varying the order of implementation of the above mentioned steps, or, for example, by proceeding as it follows:

(IP') optional solubilization of the compound component PA) in component O), (IIP') addition of component S) to water or to a saline aqueous solution, (IIIP') optional addition of component AD) to the aqueous phase, (IVP') mixing under stirring of component PA) or of the oily solution of step (IP') with the aqueous phase of step (IIP') or optionally of step (IIIP').

The temperature range at which the process is carried out is the same as indicated above for the microemulsions.

The emulsions of the present invention can be prepared by a process comprising the following steps:

(IP'') optional solubilization of the compound component PA) in component O), optionally in the presence of component AD), (IIP'') heating of component PA) or of the oily solution obtained in (IP'') at temperatures in the range 35° C.-90° C., more preferably 45-80° C., (IIIP'') addition of component S) to water or to a saline aqueous solution, optionally containing component AD), (IVP'') heating of the aqueous phase of step (IIIP'') at temperatures in the range 35° C.-90° C., more preferably 45-80° C., (VP'') addition under stirring of the phase obtained in step (IIP'') to the aqueous phase obtained in step (IVP''), obtaining an emulsion, (VIP'') cooling of the emulsion, preferably at temperatures comprised between 0° C. and 30° C.

Step (VP'') is preferably performed by using turboemulsifiers.

The thus emulsions obtained can optionally undergo a further homogeneization step at high pressure.

The emulsions can also be obtained by dilution of microemulsions with water or with aqueous solutions or with component O). Optionally component AD) can be included in each of the liquid phases.

Other pharmaceutical formulations comprising the compounds of formula (I) are those formed of micro- or nanoparticles of silica, or of lipids or of pharmaceutically acceptable polymers, wherein the compounds of the invention, present at concentrations comprised between 0.1 and 60% by weight with respect to silica, or to the lipids or to the polymers, are englobed inside and/or on the surface of the micro- and nano-particles.

As an example of lipid particles, those based on fatty acids or esters thereof having a melting point higher than 40° C., more preferably higher than 50° C., can for example be mentioned. As triglycerides of fatty acids, tripalmitine and lanoline can for example be mentioned. The lipid particles can also be formed of mixtures between fatty acids or fatty acid esters, having a melting point higher than 40° C., and an oil liquid at room temperature (20-25° C.), for example medium chain triglycerides, vegetable oils, Miglyol® 812 and Miglyol® 810 (Sasol). Alternatively, these lipid particles can be nanocapsules formed of a surface layer of soya lecithin englobing a liquid lipidic core, constituted for example by medium chain triglycerides, such as vegetable oils, Miglyol® 812 and Miglyol® 810 (See for example patent application US 2003/0152635).

The silica particles are preferably constituted by hydrophilic silica. They can optionally contain one or more compounds component O) (see above), and/or lipids used for preparing the above described lipidic particles. For example the LipoCeramic™ particles described by Simovic et al. in Mol. Pharmaceutics, 6, 2009, 861-872 can for example be used.

In the case of polymer particles, those formed of the following polymers Pol-A can for example be mentioned:

proteins, for instance albumin, optionally peghilated by functionalization with compounds having polyethylenglycol (PEG) chains, polysaccharides, such as chitosan, dextran, starch and derivatives such as hydroxyethylstarch (HES), dendrimers, for example those described by Woo-Dong Jang et al. in Progress in Polymer Science 34, 2009, 1-23, carbon nanotubes, polymerized cyclodextrins, such as beta-cyclodextrin polymers, optionally linked to PEG chains, see for example the article by T. Schluep et al. Clin. Cancer Res. 15, 2009, 181-189, synthetic polymers such as polyorganophosphazenes, polyanhydrides, polyamides, polyorthoesters, polyalkyl-cyano-acrylates, polyesters as polylactate (PLA) and the polylactate/polyglycolate copolymers (PLA/PLGA), polyhydroxyacids, polylactones, polyesteramides, polyaminoacids, polyanhydrides, polycarbonates, polyphosphazines, polyphosphoesters, polythioesters.

The particles containing the compounds of formula (I) can optionally be surface modified, on the following grounds:

to make easier their passage through the physiological barriers (for example the haematoencephalic barrier), to increase their residence time in the blood, to increase their absorption by the body, to target selectively cells, tissues or organs to be treated. The modification of the surface of the nano- and micro-particles can be carried out both by chemico-physical adsorption (for example Van Der Waals forces) of one or more surface modifiers, and by chemical functionalization with one or more specific modifiers. In the latter case the modifiers are linked with covalent bond to the particles. See for example E. Garcia et Al., "Colloidal carriers and blood-brain barrier (BBB) translocation: A way to deliver drugs to the brain", Int. J. of Pharmaceutics 298 (2005), 274-292.

Among the surface modifiers, the following can for example be mentioned:

compounds comprising polyoxyethylene or peghilated chains (PEG-based), such as Tween® 80, see for example J. Kreuter, "Nanoparticulate systems for brain delivery of drugs", *Advanced Drug Delivery Reviews,* 47, 2001, 65-81, M. T. Peracchia et al., "Synthesis of a Novel Poly (MePEG cyanoacrylate-co-alkyl cyanoacrylate) amphiphilic copolymer for nanoparticle technology", Macromolecules, 30, 1997, 846-851, proteins, such as plasma proteins, apolipoproteins, see US 2004/0131692, optionally peghilated, antibodies or fragments thereof, peptides, compounds recognized by specific receptors expressed at the level of physiological barriers, such as peptide compounds, proteins, synthetic or natural compounds with a structure different from a peptide. See for example L. Costantino et al., "Peptide-derivatized biodegradable nanoparticles able to cross the blood-brain barrier", Journal of Controlled Release, 108, 2005, 84-96, B. Stella et al., "Design of folic acid-conjugated nanoparticles for drug targeting", J. of Pharmaceutical Sciences 89 11, November 2000 1452-1464.

The surface modifiers can be directly linked to the particles, as for example in the case of PEG chains of the poly (MePEG cyanoacrylate-co-alkyl cyanoacrylate) particles described in M. T. Peracchia et al., "Synthesis of a Novel Poly(MePEG cyanoacrylate-co-alkyl cyanoacrylate) amphiphilic copolymer for nanoparticle technology", Macromolecules, 30, 1997, 846-851.

The bond between the surface modifiers and the particles can be formed by reacting a functional group of the material of the particles (polymers, lipids or silica), for example OH, SH, COOH functional end groups selected from ester, amide, amino, or end groups containing a double bond, with a functional group of the modifier, for example OH, SH, alkenyl, OC(O)$R_{10}$, $NR_{10}R_{11}$, wherein $R_{10}$ and $R_{11}$ equal to or different are selected from H or alkyl, with formation of ester, thioester, amide, etc. groups. Said reactions are carried out under procedures and conditions well known to the skilled in the art.

The surface modifiers can also be covalently linked to the particles through linker LK. Suitable linkers according to the present invention are preferably those stable in the plasma and pharmaceutically acceptable, the metabolically degradable linkers are still more preferred. Examples of linkers are the following: alkylene, alkenylene, alkynylene, heteroalkylene, arylene, heteroarylene, cycloalkylene, alkylcycloalkylene, heteroalkylcycloalkylene, heterocycloalkylene, arylalkylene, heteroarylalkylene. Optionally the preferred linkers contain S—S bonds and/or N—N bonds, peptide chains, optionally containing S—S bonds and/or N—N bonds, and/or the bivalent linkers of formula (DXI) and/or (DXII)

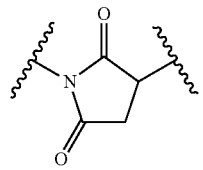
(DXI)

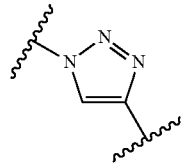
(DXII)

Examples of preferred linkers are those reported hereinafter (formulae from (XYZ1) to (XYZ22)):

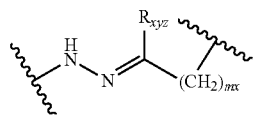
(XYZ1)

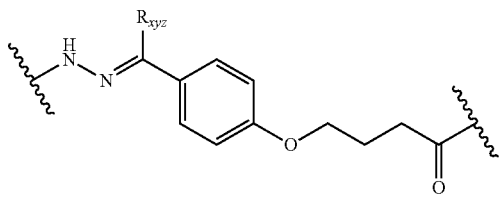
(XYZ2)

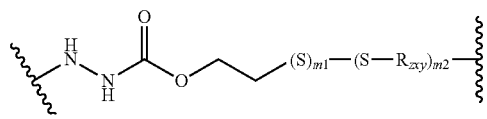
(XYZ3)

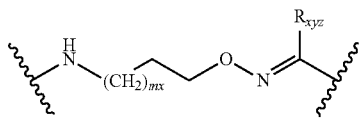
(XYZ4)

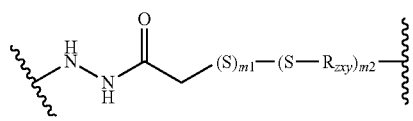
(XYZ5)

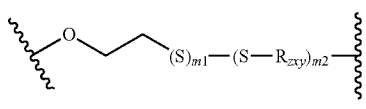
(XYZ6)

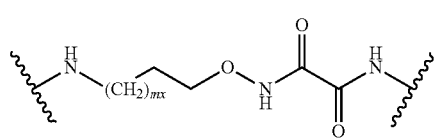
(XYZ7)

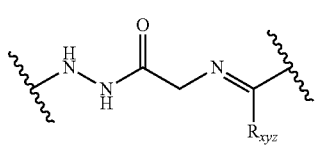
(XYZ8)

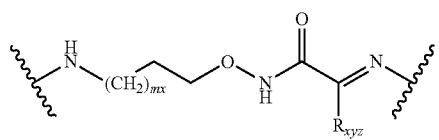
(XYZ9)

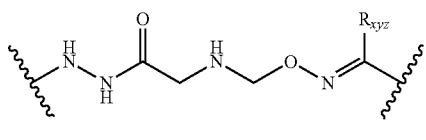
(XYZ10)

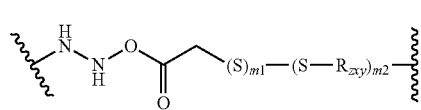
(XYZ11)

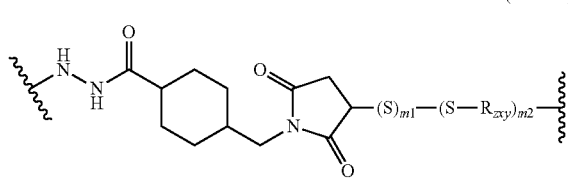
(XYZ12)

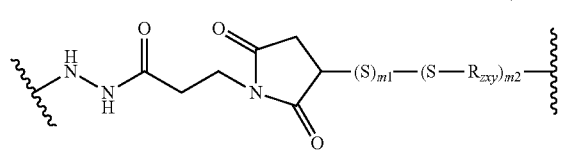
(XYZ13)

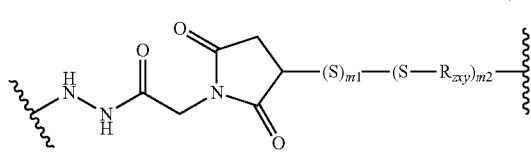
(XYZ14)

-continued
(XYZ15)
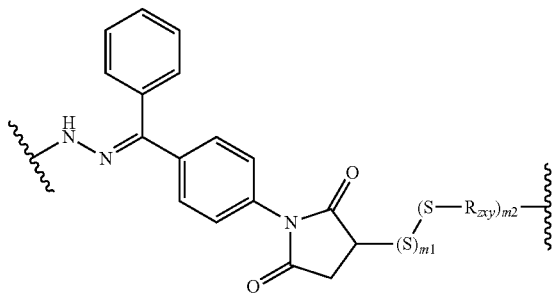
(XYZ16)
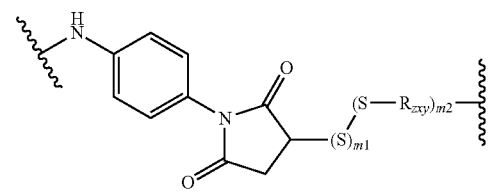
(XYZ17)
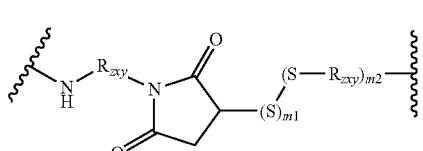
(XYZ18)
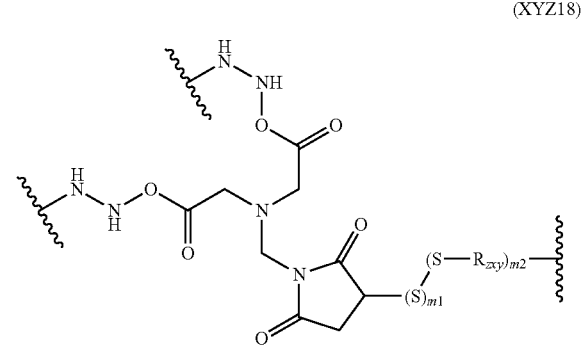
(XYZ19)
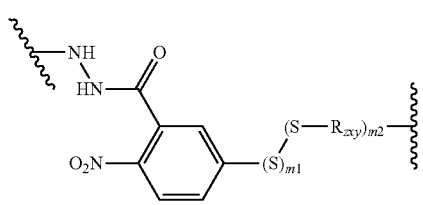
(XYZ20)
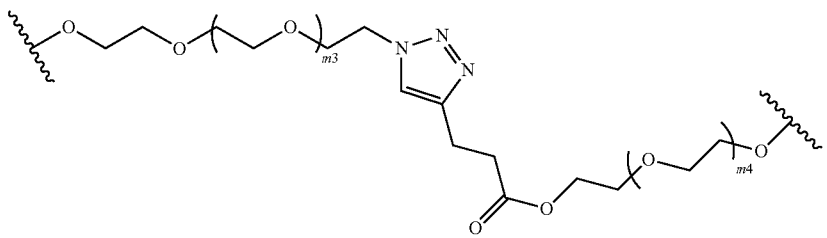
(XYZ21)
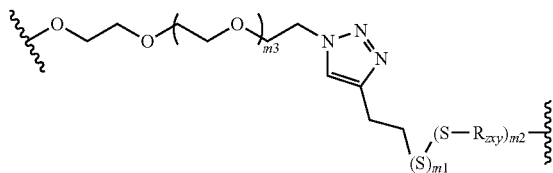
(XYZ22)
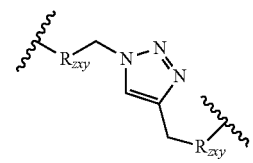

wherein:

mx is an integer from 0 to 20, preferably from 0 to 6, m1 and m2, equal to or different from each other, are zero or 1, m3 and m4, equal to or different from each other, are an integer from 0 to 200, preferably from 0 to 50, more preferably from 0 to 10, $R_{xyz}$ has the meaning of H or alkyl, wherein alkyl is preferably a linear or when possible branched $C_1$-$C_5$ chain, $R_{zxy}$ has the meaning of alkylene, alkenylene, alkynylene, heteroalkylene, arylene, heteroarylene, cycloalkylene, alkylcycloalkylene, heteroalkylcycloalkylene, heterocycloalkylene, arylalkylene, heteroarylalkylene.

The process for obtaining conjugated compounds made by the material constituting the particles, herein called MP (i.e. polymers, lipids or silica), the linker and surface modifiers MD, can be carried out by the following steps:

Con-1) reaction between a functional group of MP with a functional group $T_4$ of a LK precursor of formula $T_4$-LK-$T_3$, $T_3$ being another functional group optionally protected, with formation of a conjugated compound MP-LK-$T_3$, Con-2) reaction of the conjugated compound MP-LK-$T_3$ with MD with formation of the MP-LK-MD conjugated compound.

In Con-1) the reacting functional groups $T_4$ and of MP are for example selected from OH, SH, COOH, ester, amide, amino, containing a double bond in terminal position. By the reaction of said functional groups with each other ester, thioester, amide, etc. groups are for example formed.

In Con-2) the reaction takes place between the functional groups of MD and $T_3$. When $T_3$ is protected, the reaction takes place after deprotection of $T_3$. The functional group $T_3$ and the MD functional groups are selected for example from those mentioned in Con-1).

The reactions in step Con-1) and Con-2) are carried out under the procedures and conditions well known to the skilled in the field.

The pharmaceutical formulations of the invention can contain hyaluronic acid and/or cyclodextrins, such as alpha, beta or gamma cyclodextrins or modified cyclodextrins, for example containing alkyl and/or PEG chains.

The pharmaceutical compositions of the invention can optionally contain magnetic compounds, such as iron oxides.

It is a further object of the present invention the use of the compounds of formula (I) and of the pharmaceutical compositions containing them for the prophylaxis and therapy in mammals and in human beings of the diseases and disorders wherein the opioidergic receptors, more preferably the delta opioid receptors, are involved.

The diseases and disorders which can be treated with the compounds of formula (I), and with the pharmaceutical compositions containing them, are: pain, post-surgery pain, chronic pain, neuropathic pain, treatment of cases of abuse substances (such as heroin, cocaine), alcoholism, constipation, diarrhoea and other disorders of the gastrointestinal tract, nausea, vomit, cough, dermatitis, obesity and disorders related to food intake, anxiety, depression, smoke dependence (tabagism), sexual disfunctions, early ejaculation, shock, cerebral trauma, spinal lesions, eye pathologies and disorders, such as glaucoma and intraocular hypertension, tumours such as breast cancer, arthritis, psoriasis, asthma, cardiac disorders, incontinence and urogenital tract disorders, Alzheimer and Parkinson diseases and correlated disorders, diabetes, atherosclerosis, immune system disfunctions, neurologic diseases, hormonal disorders, disorders in neurotransmitter release, neurologic disfunctions, transplant rejection.

The compounds of formula (I) and their pharmaceutical compositions can be used in the regulation of the μ opioid receptors both in vivo and in vitro with lower side effects with respect to the compounds used in the prior art having affinity and selectivity for μ opioid receptors and/or morphine. In fact they are able to modulate the analgesic effect of morphine and/or of other μ opioidergic agonists which prevailingly act through the μ opioid receptors reducing the side effects of said latter drugs, such as dependence and pharmacological tolerance.

The use of the compounds of formula (I) and of their compositions for the treatment of the various pathologies can be made by using the known methods for said treatments. In particular the administration must be carried out so that the amount of the active principle is effective for the specific treatment. The dosages, the administration routes and the posology will be determined upon considering the disease typology, the pathology severity, the physical conditions and characteristics of the patient, for example age, weight, response to the active principle administration, the pharmacokinetics and toxicology of the active principle for the specific treatment. The preferred daily dosage is of 0.01-1,000 mg of compound of formula (I) per Kg of body weight of the mammal to be treated. In human beings, the preferred daily dosage range is 0.01-800 mg of compound for Kg of body weight, still more preferred from 1 to 600 mg.

Optionally, the treatment can be made in combination with other drugs or with other therapies. For example in pain treatment (analgesic effect) the compounds of formula (I) and their compositions can be used in association with other drugs used in said treatment, such as μ opioid receptor agonist drugs, in particular morphine, for reducing the side effects induced by the use of these latter compounds, in particular morphine.

The pharmaceutical compositions of the compounds of formula (I) can be used in combination with the drugs of the prior art used in the above reported therapies, in particular can be used in combination with morphine.

The compounds of formula (I) containing radioisotopes and their pharmaceutical formulations can be used for identifying and marking the δ opioidergic receptors both in vitro and in vivo in mammals and in human beings.

The compounds of formula (I) can be used for obtaining ligands detectable through immunochemical methods, to be used for example in the isolation, purification and characterization of the δ opioidergic receptors and in the identification of the corresponding active sites.

The following examples are reported for a better understanding of the present invention but are not meant to be limitative of the scope of the invention.

EXAMPLES

Example 1.1

Preparation of 2-azido-9-benzyl-5-bromo-9-azabicyclo[4.2.1]nonane and 2-azido-9-benzyl-6-bromo-9-azabicyclo[3.3.1]nonane

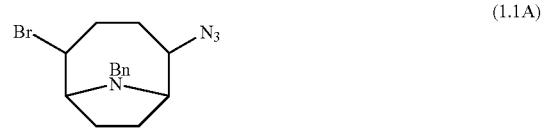

(1.1A)

-continued

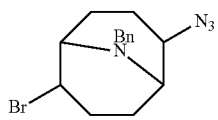
(1.1B)

a. Preparation of 5,6-epoxycyclooctene

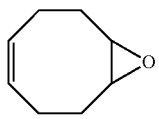
(1.1a)

To a solution of 1,5-cyclooctadiene (10 g, 92.44 mmoles) in $CH_2Cl_2$ (100 ml) 39.2 g of sodium carbonate are added under stirring. The obtained suspension is cooled down to 0° C. and 15.35 ml of a 40% by weight solution of $CH_3COOH$ are added dropwise in a time of 10 minutes. The suspension is stirred at room temperature for 16 hours and then filtered. The obtained solid is washed with $CH_2Cl_2$. The resulting organic solution is evaporated under vacuum to yield a yellow liquid (19 g), which is purified by flash chromatography (ligroin/$Et_2O$ 9/1 v/v). 9.18 g of 5,6-epoxycyclooctene in the form of a colourless liquid are obtained. Yield: 80%. $^1$H-NMR ($CDCl_3$) δ 1.80-2.25 (m, 5H); 2.25-2.53 (m, 3H); 2.90-3.10 (m, 2H); 5.55-5.59 (m, 2H). Anal. calc. for $C_8H_{12}O$: C, 77.38; H, 9.74. Found: C, 77.13; H, 9.72.

b. Preparation of the aminoalcohol trans-2-benzylamino-1-hydroxycyclooct-5-ene

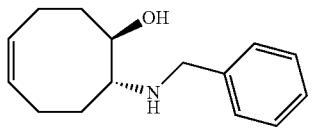
(1.1b)

A solution of hytterbium trifluoromethansulphonate (3.25 g, 5.23 mmoles) in anhydrous THF (55 ml) is prepared and further stirred for 5 minutes. To this solution 17.15 ml of benzylamine and 13 g of epoxide (1.1a) dissolved in 50 ml of anhydrous THF are added. The mixture is heated at reflux for 20 hours. At the end it is diluted with water, THF is removed by evaporation and the residue is extracted with $CH_2Cl_2$. The organic phase is dehydrated with sodium sulphate, filtered and evaporated under vacuum. The residual benzylamine is distilled. 23.77 g of trans-2-benzylamino-1-hydroxycyclooct-5-ene are recovered as a white solid. Yield: 98%. m.p.: 71-72° C.; $^1$H-NMR ($CDCl_3$) δ 1.30-1.50 (m, 2H); 2.00-2.45 (m, 6H); 2.55-2.67 (m, 1H); 3.35-3.45 (m, 1H); 3.80 (AB system, 2H, J=12.6 Hz); 5.45-5.75 (m, 2H); 7.25-7.35 (m, 5H). Anal. calc. for $C_{15}H_{21}NO$: C, 77.88; H, 9.15; N, 6.05. Found: C, 77.79; H, 9.14; N, 6.03.

c. Preparation of N-benzyl-9-azabicyclo[6.1.0]-4-nonene

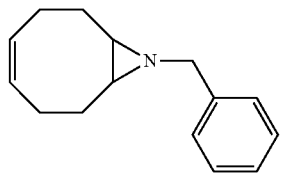
(1.1c)

To a solution of 3.17 grams of the aminoalcohol (1.1b) in anhydrous $CH_2Cl_2$ (52 ml), cooled down to 0° C. and kept under a nitrogen atmosphere, 1.38 ml of methansulphonyl-chloride and a catalytic amount of 4-dimethylaminopyridine (1% by moles based on the aminoalcohol) are added. To the colourless limpid solution 5.73 ml of triethylamine are added. The reaction is carried under stirring at room temperature for 14 hours. At the end of this period $CH_2Cl_2$ (50 ml) is added and the organic phase is washed with water (50 ml for three times). The organic phase is then dehydrated with $Na_2SO_4$ and then filtered. The solvent is then evaporated under vacuum. The residue is a yellow oil which is purified by flash chromatography (ligroin/ethyl acetate 9/1 v/v). 2.58 grams of N-benzyl-9-azabicyclo[6.1.0]-4-nonene (aziridine) are recovered. Yield: 88%. $^1$H-NMR ($CDCl_3$) δ 1.50-1.65 (m, 2H); 1.85-2.20 (m, 6H); 2.25-2.50 (m, 2H); 3.53 (s, 2H); 5.50-5.65 (m, 2H); 7.20-7.40 (m, 5H). Anal. calc. for $C_{15}H_{19}N$: C, 84.46; H, 8.98; N, 6.57. Found: C, 84.32; H, 8.96; N, 6.55.

d. Preparation of trans-2-azido-1-benzylaminocyclooct-5-ene

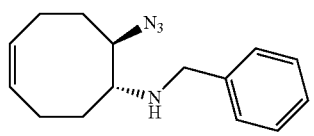
(1.1d)

A solution is prepared by dissolving in 240 ml of an EtOH/water 5/1 v/v mixture 4.0 grams of aziridine (1.1c), sodium azide (4.9 g) and ammonium chloride (4.0 g). The solution is heated at reflux for 4 hours. After this period it is cooled at room temperature and ethanol evaporated under vacuum. The residue is extracted with $CH_2Cl_2$ (3×60 ml), pooling the organic phases that are then dehydrated with $Na_2SO_4$. After filtration, the solvent is removed by evaporation under vacuum. 4.56 g of trans-2-azido-1-benzylaminocyclooct-5-ene are recovered. Yield: 95%. $^1$H-NMR ($CDCl_3$) δ 1.60-1.90 (m, 2H); 2.00-2.25 (m, 4H); 2.30-2.60 (m, 2H); 2.76-2.86 (m, 1H); 3.64 (dt, 1H, J=3.6 and 9 Hz); 3.77 (AB syst., 2H, J=12.8 Hz); 5.50-5.70 (m, 2H); 7.20-7.37 (m, 5H). Anal. calc. for $C_{15}H_{20}N_4$: C, 70.28; H, 7.86; N, 21.86. Found: C, 70.15; H, 7.84; N, 21.84.

e. Preparation of 2-azido-9-benzyl-5-bromo-9-azabicyclo[4.2.1]nonane and of 2-azido-9-benzyl-6-bromo-9-aza bicyclo[3.3.1]nonane 3 grams of trans-2-azido-1-benzylaminocyclooct-5-ene (1.1d) are dissolved in 150 ml of cyclohexane at 0° C. A solution of Br$_2$ (0.6 ml) in cyclohexane (10 ml) is dropwise added. The resulting solution is left under stirring at room temperature for 5 hours. The reaction mixture is filtered and the solid is dispersed in 200 ml of a H$_2$O/CH$_2$Cl$_2$ (1/1 volume/volume) mixture. The obtained suspension is brought to an alkaline pH by adding an aqueous solution of NaOH at 10% w/v. The organic and aqueous phase are then separated. The organic phase is recovered and dehydrated with sodium sulphate, filtered and the solvent evaporated under vacuum. The obtained yellow oil is purified by flash chromatography (ligroin/Et$_2$O 98.5/1.5 v/v). 0.92 g of 2-azido-9-benzyl-5-bromo-9-azabicyclo-[4.2.1]nonane (1.1A) and 0.62 g of 2-azido-9-benzyl-6-bromo-9-azabicyclo[3.3.1]nonane (1.1B), are recovered. The formulae of these compounds are reported above.

Compound (1.1A)

Yield: 23%. $^1$H-NMR (CDCl$_3$) δ 1.35-1.60 (m, 2H); 1.70-2.10 (m, 3H); 2.15-2.40 (m, 3H); 3.25-3.35 (m, 1H); 3.56 (q, 1H, J=4.8 Hz); 3.70-3.90 (m, 3H); 4.11 (t, 1H, J=7.2 Hz); 7.25-7.50 (m, 5H). Anal. calc. for C$_{15}$H$_{19}$BrN$_4$: C, 53.74; H, 5.71; N, 16.71. Found: C, 53.66; H, 5.69; N, 16.68.

Compound (1.1B)

Yield: 16%. $^1$H-NMR (CDCl$_3$) δ 1.60-2.00 (m, 3H); 2.00-2.50 (m, 5H); 2.85-2.95 (m, 1H); 3.05-3.15 (m, 1H); 3.90-4.20 (m, 3H); 4.35-4.45 (m, 1H); 7.20-7.50 (m, 5H). Anal. calc. for C$_{15}$H$_{19}$BrN$_4$: C, 53.74; H, 5.71; N, 16.71. Found: C, 53.68; H, 5.70; N, 16.69.

Example 2.1

Preparation of 9-benzyl-9,10-diazatricyclo[4.2.1.1$^{2,5}$]decane

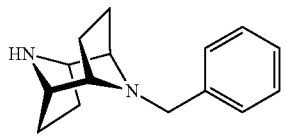

3.44 grams of the azide (1.1A) obtained in Ex. 1.1 are dissolved in 26 ml of anhydrous THF. To this solution 2.96 grams of triphenylphosphine, dissolved in 10 ml of anhydrous THF are added. The mixture is heated at reflux for 5 hours. At the end it is cooled at room temperature and 0.5 ml of water are added. It is further heated at reflux for 14 hours and then cooled at room temperature. The precipitate is filtered under vacuum and washed with THF, suspended in 50 ml of a CH$_2$Cl$_2$/H$_2$O (1/1 v/v) mixture and treated with a 10% by weight K$_2$CO$_3$ aqueous solution up to pH 8. The organic phase is separated, dehydrated with sodium sulphate, filtered and evaporated under vacuum. 2.13 g of 9-benzyl-9,10-diazatricyclo[4.2.1.1$^{2,5}$]decane are recovered. Yield: 91%. $^1$H-NMR (CDCl$_3$) δ 1.45-1.55 (m, 2H); 1.80-1.90 (m, 4H); 2.00-2.15 (m, 2H); 2.78-2.88 (m, 2H); 3.02-3.12 (m, 2H); 3.31 (s, 2H); 7.20-7.45 (m, 5H). Anal. calc. for C$_{15}$H$_{20}$N$_2$: C, 78.90; H, 8.83; N, 12.27. Found: C, 78.71; H, 8.80; N, 12.25.

Example 2.2

Preparation of 2-benzyl-2,7-diazatricyclo[4.4.0.0$^{3,8}$]decane

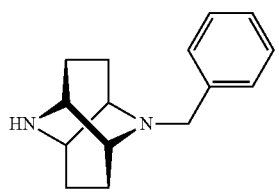

The synthesis described in Ex. 2.1 was repeated, but substituting the azide (1.1A) with the compound (1.1B) obtained in Ex. 1.1. The compound 2-benzyl-2,7-diaza-tricyclo-[4.4.0.0$^{3,8}$]decane is obtained. Yield: 68%. $^1$H-NMR (CDCl$_3$) δ 1.50-2.00 (m, 8H); 2.70-2.80 (m, 2H); 3.00-3.10 (m, 2H); 3.90 (AB system, 2H, J=13.8 Hz); 7.20-7.42 (m, 5H). Anal. calc. for C$_{15}$H$_{20}$N$_2$: C, 78.90; H, 8.83; N, 12.27. Found: C, 78.78; H, 8.81; N, 12.26.

Example 2.3

Synthesis of the compound 10-Benzyl-3,10-diazabiciclo[4.3.1]-decane

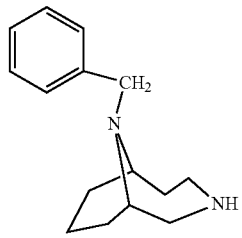 [SMILES: c1ccc(CN2C3CCCC2CNCC3)cc1]

a. Synthesis of the compound 10-Benzil-3,10-diazabicyclo-[4.3.1]decan-4-one

To a solution of 9-benzyl-9-azabicyclo[3.3.1]nonan-3-one (0.5 g) in chloroform (4.4 ml), cooled down to −5° C., 1 ml of conc. H$_2$SO$_4$ is dropwise added while maintaining the temperature below 15° C. Then NaN$_3$ (0.28 g) is slowly added, at small portions so to avoid temperatures in the reaction mixture higher than 35° C. The mixture is then heated at reflux for 2 hours. The reaction mixture is poured into a vessel containing about 200 ml of ice. Solid K$_2$CO$_3$ is added up to a strongly alkaline pH. An emulsion is formed, that is added of 25 ml of a 60% KOH aqueous solution. Stirring is effected for 10 minutes. At the end the formed inorganic salts are filtered and the reaction mixture extracted with chloroform. The organic phase is dehydrated with sodium sulphate and the solvent evaporated. 0.50 g of 10-benzyl-3,10-diazabicyclo[4.3.1]decan-4-one (1py1) are obtained as a light solid.

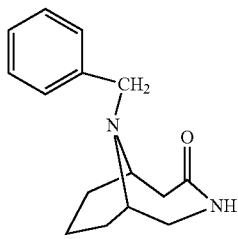

(1py1)

Yield: 95%; $R_f$: 0.42 (CHCl$_3$-MeOH 97:3); $^1$H-NMR (CDCl$_3$): δ (ppm) 1.43-1.70 (m, 3H), 1.90-2.23 (m, 3H), 2.37-2.53 (m, 1H), 2.80-3.15 (m, 4H), 3.75 (dt, 1H, J=3.8 and 15 Hz), 3.93 (s, 2H), 5.82 (bs, 1H), 7.20-7.40 (m, 5H).

b. Synthesis of the compound 10-Benzyl-3,10-diazabicyclo-[4.3.1]decane

A solution obtained by dissolving 0.50 g of 10-benzyl-3,10-diazabicyclo[4.3.1]decan-4-one (1py1) in THF (4 ml) is dripped in a suspension of LiAlH$_4$ (0.19 g) in anhydrous THF (9 ml), cooled at 0° C., kept under an argon inert atmosphere. The mixture is kept under stirring at room temperature for 14 hours. At the end the mixture is cooled to 0° C. About 0.9 ml of H$_2$O are cautiously added while stirring for 10 min. A precipitate is obtained which is filtered under vacuum and washed with dichloromethane. The recovered filtrate is evaporated, obtaining an oil which is dissolved in dichloromethane. The organic solution is dehydrated with sodium sulphate and the solvent then evaporated. 0.47 g of the compound 10-benzyl-3,10-diazabicyclo[4.3.1]decane are recovered. Yield: quantitative; $R_f$: 0.62 (CH$_2$Cl$_2$-MeOH 8:2); $^1$H-NMR (CDCl$_3$): δ (ppm) 1.17-2.18 (m, 8H), 2.62 (bs, 1H), 2.76-2.92 (m, 2H), 2.99-3.18 (m, 4H), 3.97 (s, 2H), 7.20-7.42 (m, 5H).

Example 2.4

Synthesis of the compound 9-Methyl-3,9-diazabicyclo-[4.2.1]-nonane

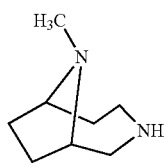

a. Synthesis of the compound 9-Methyl-3,9-diazabicyclo-[4.2.1]nonan-4-one

To a solution (5 g) in chloroform (50 ml) of tropinone (1px) of formula:

(1px)

cooled to −5° C., 11.3 ml of conc. H$_2$SO$_4$ are dropwise added, while maintaining the temperature below 15° C. NaN$_3$ (4.67 g) is then slowly added at small portions, so that the temperature of the solution does not exceed 35° C. The mixture is then heated at reflux for 2 hours. The obtained mixture is poured into a vessel containing about 200 ml of ice. Solid K$_2$CO$_3$ is added up to a strongly alkaline pH. An emulsion is formed. To this emulsion 25 ml of aqueous 60% w KOH are added. Stirring is then effected for 10 minutes, the formed inorganic salts are filtered out and the liquid phase is extracted with chloroform. The organic phase is recovered and dehydrated with sodium sulphate. The solvent is then evaporated. 3.64 g of the compound 9-Methyl-3,9-diazabicyclo[4.2.1]nonan-4-one (1px1) as a white crystalline solid, are obtained.

(1px1)

Yield: 95%; $R_f$: 0.26 (CHCl$_3$-MeOH 8:2); m.p.: 79-82° C.; $^1$H-NMR (CDCl$_3$): δ (ppm) 1.69-1.85 (m, 2H), 2.00-2.20 (m, 2H), 2.42 (s, 3H), 2.48-2.53 (m, 1H), 2.80-2.96 (m, 2H), 3.15-3.27 (m, 2H), 3.59 (bd, 1H, J=14 Hz).

b. Synthesis of the compound 9-Methyl-3,9-diazabicyclo[4.2.1]nonane

A solution of the compound 9-Methyl-3,9-diazabicyclo-[4.2.1]nonan-4-one (1px1) in THF (1.00 g of compound in 10 ml di THF) is dropwise added to a suspension of LiAlH$_4$ (0.61 g) in anhydrous THF (30 ml), cooled to 0° C., kept under an argon inert atmosphere. The mixture is heated at reflux for 48 hours and then cooled to 0° C. Water (3 ml) is then slowly added to the mixture. The mixture is afterward kept under stirring for 10 minutes. A precipitate is formed which is filtered under vacuum and washed with dichloromethane. The recovered filtrate is evaporated, obtaining an oil which is dissolved in dichloromethane. The solution in dichloromethane is dehydrated with sodium sulphate and the solvent is evaporated. The residual oil is distilled (45-50° C./0.1 mmHg). 0.63 g of the compound 9-Methyl-3,9-diazabicyclo[4.2.1]nonane are recovered as a colourless oil.

Yield: 69%; $R_f$: 0.22 (CHCl$_3$-MeOH 9:1+drop of NH$_4$OH); b.p.: 45-50° C./0.1 mmHg; $^1$H-NMR (CDCl$_3$): δ (ppm) 1.40-2.38 (m, 4H), 2.05-2.15 (m, 2H), 2.44 (s, 3H), 2.47 (bs, 1H, NH), 2.64-3.30 (m, 6H); $^{13}$C-NMR (CDCl$_3$): δ (ppm) 28.16; 30.65; 37.30; 43.69; 45.84; 55.57; 63.98; 66.69.

Example 3.1

Preparation of 4-[chloro-(3'-methoxyphenyl)methyl]-N,N-diethyl benzamide

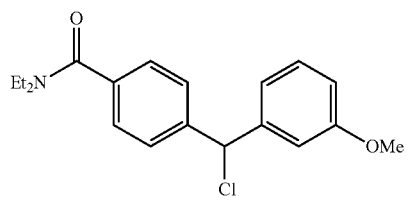

a. Preparation of 4-methyl-3'-methoxybenzophenone

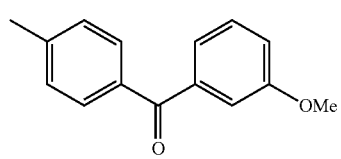

(3.1a)

To a suspension of AlCl$_3$ (1.1 equivalents) in CH$_2$Cl$_2$ (40 ml) a solution of m-anisoylchloride (12.0 g) and toluene (1 equivalent) in CH$_2$Cl$_2$ (10 ml) is dropwise added. The resulting mixture is stirred at room temperature for 4 hours, then poured into 200 ml of a mixture ice-37% by weight HCl (1/1 v/v). The organic phase and the aqueous phase are separated. The organic phase is dehydrated with sodium sulphate. Filtration is then effected and the organic solvent evaporated. 4-methyl-3'-methoxybenzophenone is obtained. Yield: quantitative. IR (nujol) (λ=cm$^{-1}$) 1690 (C=O); $^1$H-NMR (CDCl$_3$) δ 2.44 (s, 3H); 3.86 (s, 3H); 7.08-7.18 (m, 1H); 7.20-7.40 (m, 5H); 7.73 (d, 2H, J=8.4 Hz). Anal. calc. for C$_{15}$H$_{14}$O$_2$: C, 79.62; H, 6.24. Found: C, 79.53; H, 6.22.

b. Preparation of 4-(3'-methoxybenzoyl)benzoic acid

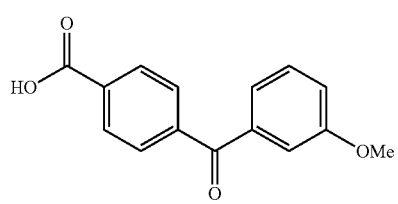

(3.1b)

4.0 grams of 4-methyl-3'-methoxybenzophenone (3.1a) are dissolved in 40 ml of a t-butanol/water 1/1 (v/v) mixture. 6.44 grams of potassium permanganate are added. The reaction mixture is heated at reflux for 7.5 hours, then filtered on celite and concentrated under vacuum. The residue is dissolved in a 5% weight NaOH aqueous solution. The obtained solution is washed with ethyl ether and brought to an acid pH with a 37% w HCl aqueous solution. 4-(3'-methoxybenzoyl) benzoic acid (3.1b) is recovered as a white precipitate. The solid is filtered off and recrystallized by a methanol/H$_2$O (1/1 v/v) solution. Yield: 76%. IR (nujol) (λ=cm$^{-1}$) 1690 (C=O), 1715 (C=O), 3300 (OH); $^1$H-NMR (CDCl$_3$) δ 3.57 (bs, 1H); 3.86 (s, 3H); 7.10-7.45 (m, 6H); 7.81 (d, 2H, J=8.4 Hz). Anal. calc. for C$_{15}$H$_{12}$O$_4$: C, 70.31; H, 4.72. Found: C, 70.16; H, 4.70.

c. Preparation of N,N-diethyl-4-(3'-methoxybenzoyl)benzamide

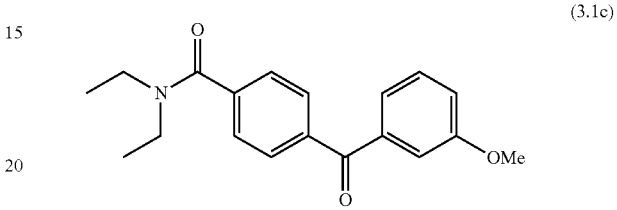

(3.1c)

A mixture of 0.23 grams of acid (3.1b), 1-Ethyl-3-(3-dimethylaminopropyl)carbodiimide (1.2 equivalents with respect to the acid) and 1-hydroxy benzotriazol hydrate (1.2 equivalents) in anhydrous CH$_2$Cl$_2$ (2 ml) is stirred at room temperature for 30 minutes. A solution of diethylamine (1.5 equivalents) in anhydrous CH$_2$Cl$_2$ (8 ml) is then dropwise added. The obtained mixture is stirred at room temperature for 14 hours and washed in a first step with saturated aqueous sodium bicarbonate and in a second step with water. The organic phase is dehydrated with sodium sulphate, filtered and evaporated under vacuum. The residue that is recovered is purified by flash chromatography (ligroin/ethyl acetate 1/1 v/v). N,N-diethyl-4-(3'-methoxybenzoyl)benzamide (3.1c) is obtained. Yield: 98%. IR (nujol) (λ=cm$^{-1}$) 1690 (C=O); $^1$H-NMR (CDCl$_3$) δ 1.00-1.38 (m, 6H); 3.20-3.38 (m, 2H); 3.50-3.70 (m, 2H); 3.86 (s, 3H); 7.10-7.40 (m, 4H); 7.48 (d, 2H, J=8.4 Hz); 7.84 (d, 2H, J=8.4 Hz). Anal. calc. for C$_{19}$H$_{21}$NO$_3$: C, 73.29; H, 6.80; N, 4.50. Found: C, 73.11; H, 6.78; N, 4.49.

d. Preparation of N,N-diethyl-4-[hydroxy-(3'-methoxyphenyl)methyl]benzamide

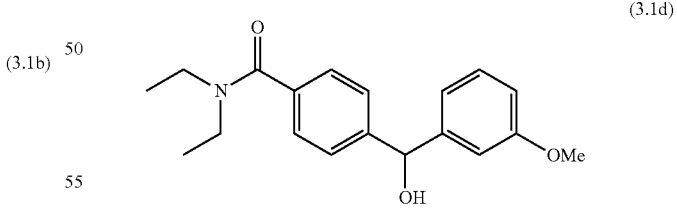

(3.1d)

To 5.16 grams of N,N-diethyl-4-(3'-methoxybenzoyl)benzamide (3.1c) dissolved in 56 ml of Ethanol/H$_2$O 3/1 v/v, NaBH$_4$ (6 equivalents with respect to (3.1c)) is slowly added. The reaction mixture is stirred at room temperature for 2 hours, then concentrated under vacuum and brought to pH 5 with acetic acid. A dispersion of N,N-diethyl-4-[hydroxy-(3'-methoxyphenyl)-methyl]benzamide is obtained. The dispersion is filtered and the solid that is recovered is dried in air. The compound (3.1d) is obtained. Yield: quantitative. IR (nujol) (λ=cm$^{-1}$) 1680 (C=O), 3300 (OH); $^1$H-NMR (CDCl$_3$) δ

1.00-1.35 (m, 6H); 2.39 (s, 1H); 3.10-3.18 (m, 2H); 3.20-3.30 (m, 2H); 3.79 (s, 3H); 5.82 (d, 1H, J=3.2 Hz); 6.75-7.00 (m, 3H); 7.24 (d, 2H, J=8.2 Hz); 7.25-7.38 (m, 1H); 7.41 (d, 2H, J=8.2 Hz). Anal. calc. for $C_{19}H_{23}NO_3$: C, 72.82; H, 7.40; N, 4.47. Found: C, 72.66; H, 7.38; N, 4.46.

e. Preparation of 4-[chloro-(3'-methoxyphenyl)methyl]-N,N-diethylbenzamide 5.08 grams of N,N-diethyl-4-[hydroxy-(3'-methoxyphenyl)methyl]benzamide (3.1d) are dissolved in 18 ml of chloroform. To this solution 37% by weight HCl (135 equivalents) is added. The reaction mixture is stirred at room temperature for 14 hours, then diluted with water and extracted with chloroform (50 ml for three times). The pooled organic phases are dehydrated with sodium sulphate, filtered and evaporated. 4-[chloro-(3'-methoxyphenyl)methyl]-N,N-diethylbenzamide is obtained. Yield: 95%. IR (nujol) ($\lambda=cm^{-1}$) 1680 (C=O); $^1$H-NMR (CDCl$_3$) δ 1.00-1.78 (m, 6H); 3.08-3.38 (m, 2H); 3.40-3.60 (m, 2H); 3.80 (s, 3H); 6.09 (s, 1H); 6.80-7.00 (m, 4H); 7.35 (d, 2H, J=8.4 Hz); 7.44 (d, 2H, J=8.4 Hz). Anal. calc. for $C_{19}H_{22}ClNO_2$: C, 68.77; H, 6.68; N, 4.22. Found: C, 68.59; H, 6.67; N, 4.21.

Example 3.2

Preparation of {4-[chloro-(3'-methoxyphenyl)methyl]phenyl}pyrrolidin-1-yl-methanone

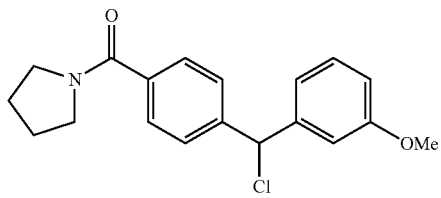

Ex. 3.1 has been repeated but substituting in step c. diethylamine with pyrrolidine. In said step instead of compound (3.1c) compound (3.2c) was obtained. In following step d) of this example instead of compound (3.1d), compound (3.2d) was obtained. Compounds (3.2c) and (3.2d) are herein below reported:

(3.2c)

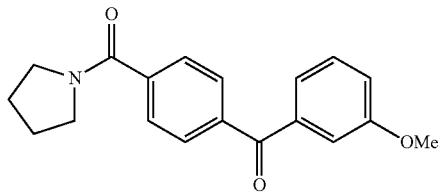

(3.2d)

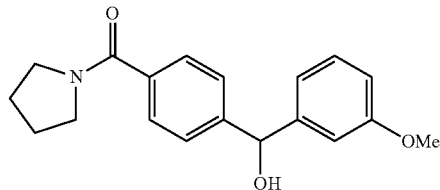 [SMILES: COc1cccc(C(Cl)c2ccc(C(=O)N3CCCC3)cc2)c1]

At the end of step c. compound {4-[chloro-(3'-methoxyphenyl)methyl]phenyl}pyrrolidin-1-yl-methanone was obtained. IR (nujol) ($\lambda=cm^{-1}$) 1680 (C=O); $^1$H-NMR (CDCl$_3$) δ 1.90-2.00 (m, 4H); 3.42 (t, 2H, J=6.4 Hz); 3.64 (t, 2H, J=6.4 Hz); 3.79 (s, 3H); 6.09 (s, 1H); 6.90-7.00 (m, 3H); 7.20-7.60 (m, 5H). Anal. calc. for $C_{19}H_{20}ClNO_2$: C, 69.19; H, 6.11; N, 4.25. Found: C, 69.01; H, 6.09; N, 4.24.

Example 3.3

Preparation of {4-[chloro-(3'-methoxyphenyl)methyl]phenyl}piperidin-1-yl-methanone

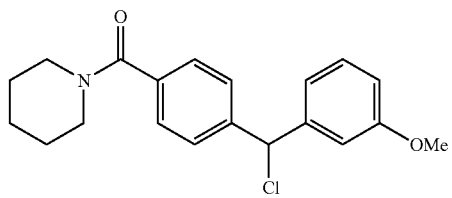 [SMILES: COc1cccc(C(Cl)c2ccc(C(=O)N3CCCCC3)cc2)c1]

Example 3.1 was repeated but substituting in step c. diethylamine with piperidine. Instead of the compounds (3.1c) and (3.1d), the following compounds (3.3c) and (3.3d) were respectively obtained:

(3.3c)

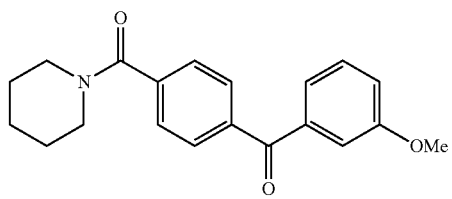

(3.3d)

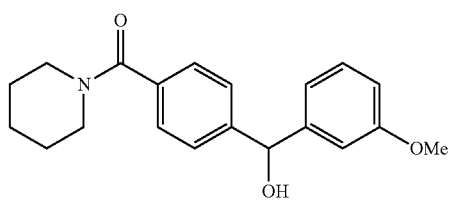

At the end of step c. compound {4-[chloro-(3'-methoxyphenyl)methyl]phenyl}piperidin-1-yl-methanone was obtained. IR (nujol) ($\lambda=cm^{-1}$) 1690 (C=O); $^1$H-NMR (CDCl$_3$) δ 1.40-1.80 (m, 6H); 3.30-3.45 (m, 2H); 3.60-3.78 (m, 2H); 3.80 (s, 3H); 6.09 (s, 1H); 6.80-7.00 (m, 3H); 7.20-

7.50 (m, 5H). Anal. calc. for $C_{20}H_{22}ClNO_2$: C, 69.86; H, 6.45; N, 4.07. Found: C, 69.64; H, 6.43; N, 4.06.

Example 3.4

Preparation of 4-[chloro-(3'-methoxyphenyl)methyl]-N-cyclohexyl benzamide

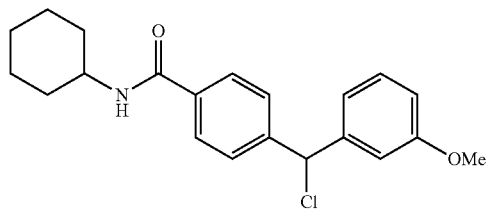 [SMILES: COc1cccc(C(Cl)c2ccc(C(=O)NC3CCCCC3)cc2)c1]

Example 3.1 was repeated, but substituting in step c. diethylamine with cyclohexylamine. In place of the compounds (3.1c) and (3.1d), the compounds (3.4c) and (3.4d) were, respectively, obtained:

(3.4c)

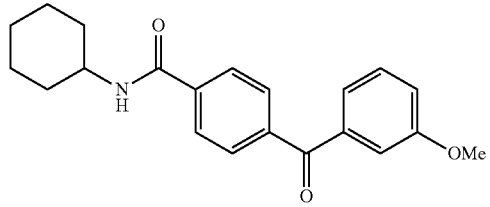

(3.4d)

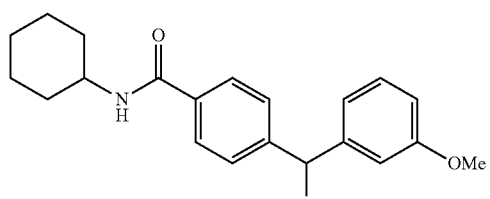

At the end of step c. the compound 4-[chloro-(3'-methoxyphenyl)methyl]-N-cyclohexylbenzamide was obtained.

IR (nujol) ($\lambda$=cm$^{-1}$) 1690 (C=O), 3100 (NH); $^1$H-NMR (CDCl$_3$) $\delta$ 1.00-1.80 (m, 8H); 1.95-2.10 (m, 2H); 3.78 (s, 3H); 3.85-4.05 (m, 1H); 5.90-6.00 (m, 1H); 6.09 (s, 1H); 6.80-7.00 (m, 3H); 7.20-7.30 (m, 1H); 7.46 (d, 2H, J=8.4 Hz); 7.72 (d, 2H, J=8.4 Hz). Anal. calc. for $C_{21}H_{24}ClNO_2$: C, 70.48; H, 6.76; N, 3.91. Found: C, 70.33; H, 6.74; N, 3.90.

Example 3.5

Preparation of 4-[chloro-(3'-methoxyphenyl)methyl]-N,N-dimethyl benzamide

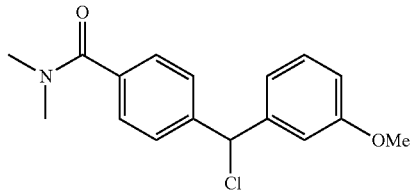

Example 3.1 was repeated, but substituting in step c. diethylamine with dimethylamine. In place of the compounds (3.1c) and (3.1d), the compounds (3.5c) and (3.5d) were respectively obtained:

(3.5c)

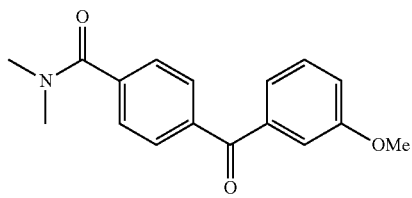 [SMILES: COc1cccc(C(Cl)c2ccc(C(=O)N(C)C)cc2)c1]

(3.5d)

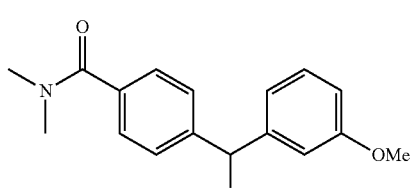

At the end of step c., the compound 4-[chloro-(3'-methoxyphenyl)methyl]-N,N-dimethylbenzamide was obtained.

IR (nujol) ($\lambda$=cm$^{-1}$) 1690 (C=O); $^1$H-NMR (CDCl$_3$) $\delta$ 2.90-3.20 (m, 6H); 3.79 (s, 3H); 6.53 (s, 1H); 6.70-7.60 (m, 8H). Anal. calc. for $C_{17}H_{18}ClNO_2$: C, 67.21; H, 5.97; N, 4.61. Found: C, 67.03; H, 5.95; N, 4.60.

Example 4.1

Preparation of 4-[(10-benzyl-9,10-diazatricyclo[4.2.1.1$^{2,5}$]dec-9-yl)-(3-methoxyphenyl)methyl]-N,N-diethylbenzamide

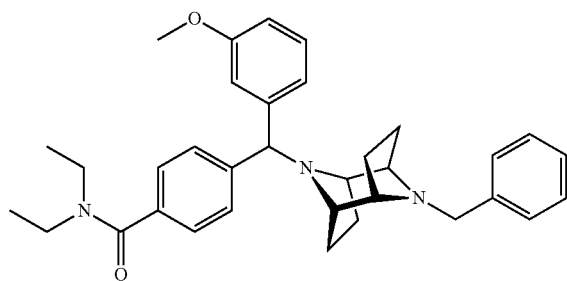

A mixture formed of 9-benzyl-9,10-diazatricyclo[4.2.1.1$^{2,5}$]decane prepared in Example 2.1 (2.19 mmoles), 4-[chloro-(3-methoxyphenyl)methyl]-N,N-diethylbenzamide obtained in Example 3.1 (1.5 equivalents), anhydrous potassium carbonate (3 equivalents) and acetonitrile (20 ml), is heated at reflux for 3 days. At the end the mixture was filtered under vacuum and the liquid phase recovered. The solvent was evaporated under vacuum and the residual oil purified by flash chromatography. The eluent was ligroin/ethyl acetate 7/3 (v/v). The compound 4-[(10-benzyl-9,10-diazatricyclo-[4.2.1.1$^{2,5}$]dec-9-yl)-(3-methoxyphenyl)methyl]-N,N-diethylbenzamide was obtained. Yield: 52%. IR (nujol) ($\lambda$=cm$^{-1}$) 1680 (C=O); $^1$H-NMR (CDCl$_3$) $\delta$ 1.00-1.30 (m, 6H); 1.60-2.20 (m, 8H); 2.75-2.85 (m, 4H); 3.20-3.36 (m, 2H); 3.37 (s, 2H); 3.40-3.60 (m, 2H); 3.80 (s, 3H); 4.28 (s, 1H); 6.70-6.80 (m, 1H); 7.00-7.40 (m, 10H); 7.55 (d, 2H, J=8.4 Hz). Anal. calc. for $C_{34}H_{41}N_3O_2$: C, 77.98; H, 7.89; N, 8.02. Found: C, 77.76; H, 7.91; N, 8.12.

Example 4.2

Preparation of {4-[(10-benzyl-9,10-diazatricyclo[4.2.1.1$^{2,5}$]dec-9-yl)-(3-methoxyphenyl)methyl]phenyl}-pyrrolidin-1-yl-methanone

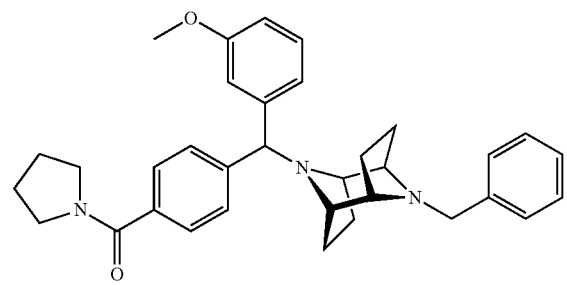

The same procedure of Example 4.1 was repeated, but using instead of the compound of Example 3.1 the compound [4-(chloro-(3-methoxyphenyl)methyl)phenyl](pyrrolidin-1-yl)methanone of Example 3.2. {4-[(10-benzyl-9,10-diazatricyclo-[4.2.1.1$^{2,5}$]-dec-9-yl)-(3-methoxyphenyl)methyl]phenyl}-pyrrolidin-1-yl-methanone was obtained. Yield: 44%. IR (nujol) ($\lambda$=cm$^{-1}$) 1680 (C=O); $^1$H-NMR (CDCl$_3$) $\delta$ 1.50-2.25 (m, 12H); 2.70-2.90 (m, 4H); 3.30-3.45 (m, 4H); 3.55-3.65 (m, 2H); 3.79 (s, 3H); 4.29 (s, 1H); 6.65-6.75 (m, 1H); 7.00-7.50 (m, 10H); 7.55 (d, 2H, J=8.4 Hz). Anal. calc. for $C_{34}H_{39}N_3O_2$: C, 78.28; H, 7.54; N, 8.05. Found: C, 78.31; H, 7.52; N, 8.07.

Example 4.3

Preparation of {4-[(10-benzyl-9,10-diazatricyclo[4.2.1.1$^{2,5}$]dec-9-yl)-(3-methoxyphenyl)methyl]phenyl}-piperidin-1-yl-methanone

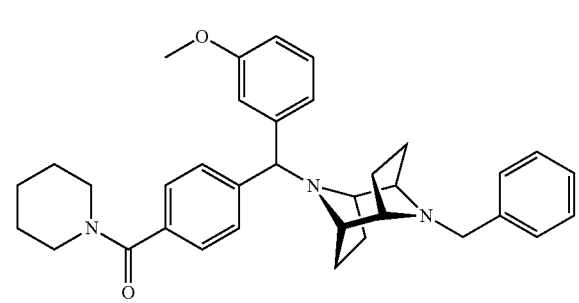

The procedure of Example 4.1 was repeated, but using instead of the compound of Example 3.1 the compound {4-[chloro-(3'-methoxyphenyl)methyl]phenyl)piperidin-1-yl-methanone of Example 3.3. The compound {4-[(10-benzyl-9,10-diazatricyclo[4.2.1.1$^{2,5}$]-dec-9-yl)-(3-methoxyphenyl)methyl]phenyl}-piperidin-1-yl-methanone was obtained. Yield: 85%. IR (nujol) ($\lambda$=cm$^{-1}$) 1650 (C=O); $^1$H-NMR (CDCl$_3$) $\delta$ 1.40-1.85 (m, 10H); 1.90-2.00 (m, 2H); 2.15-2.25 (m, 2H); 2.70-2.85 (m, 4H); 3.20-3.35 (m, 2H); 3.36 (s, 2H); 3.60-3.75 (m, 2H); 3.79 (s, 3H); 4.28 (s, 1H); 6.65-6.75 (m, 1H); 7.05-7.40 (m, 10H); 7.55 (d, 2H, J=8.0 Hz). Anal. calc. for $C_{35}H_{41}N_3O_2$: C, 78.47; H, 7.71; N, 7.84. Found: C, 78.21; H, 7.68; N, 7.79.

Example 4.4

Preparation of 4-[(10-benzyl-9,10-diazatricyclo[4.2.1.1$^{2,5}$]dec-9-yl)-(3-methoxyphenyl)methyl]-N-cyclohexylbenzamide

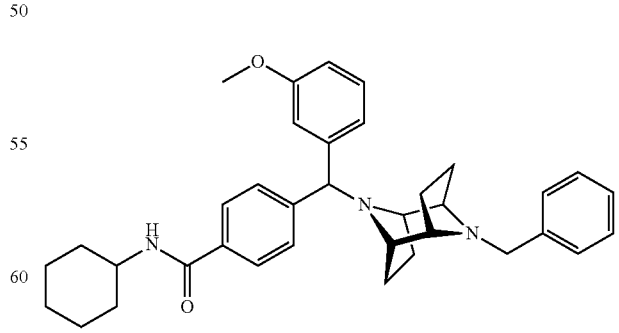

The procedure of Example 4.1 was repeated, but using instead of the compound of Example 3.1 the compound 4-[chloro-(3-methoxyphenyl)methyl]-N-cyclohexyl] benzamide of Example 3.4. The compound 4-[(10-benzyl-9,10- diazatricyclo[4.2.1.1$^{2,5}$]dec-9-yl)-(3-methoxy-phenyl)methyl]-N-cyclohexylbenzamide was obtained.

Yield: 42%. IR (nujol) (λ=cm$^{-1}$) 1680 (C=O); 3100 (NH); $^1$H-NMR (CDCl$_3$) δ 1.00-1.55 (m, 5H); 1.58-1.85 (m, 6H); 1.90-2.10 (m, 4H); 2.15-2.25 (m, 2H); 2.70-2.90 (m, 4H); 3.36 (s, 2H); 3.78 (s, 3H); 4.31 (s, 1H); 5.85 (d, 2H, J=7.4 Hz); 6.65-6.75 (m, 1H); 7.00-7.40 (m, 8H); 7.55-7.65 (m, 4H). Anal. calc. for C$_{36}$H$_{43}$N$_3$O$_2$: C, 78.65; H, 7.88; N, 7.64. Found: C, 7842; H, 7.85; N, 7.63.

Example 4.5

Preparation of 4-[(7-benzyl-2,7-diazatricyclo[4.4.0.0$^{3,8}$]dec-2-yl)-(3-methoxyphenyl)methyl]-N,N-diethylbenzamide

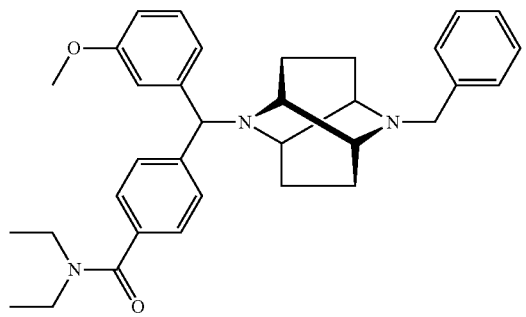

The procedure of Example 4.1 was repeated, but using instead of the compound of Example 2.1 2-benzyl-2,7-diazatricyclo[4.4.0.0$^{3,8}$]decane of Example 2.2. The compound 4-[(7-benzyl-2,7-diazatricyclo[4.4.0.0$^{3,8}$]dec-2-yl)-(3-methoxyphenyl)methyl]-N,N-diethylbenzamide was obtained. Yield: 65%. IR (nujol) (λ=cm$^{-1}$) 1680 (C=O); $^1$H-NMR (CDCl$_3$) δ 1.00-1.95 (m, 14H); 2.70-2.90 (m, 4H); 3.15-3.35 (m, 2H); 3.40-3.60 (m, 2H); 3.78 (s, 3H); 3.80-4.00 (m, 2H); 5.07 (s, 1H); 6.65-6.75 (m, 1H); 7.00-7.40 (m, 10H); 7.52 (d, 2H, J=8.2 Hz). Anal. calc. for C$_{34}$H$_{41}$N$_3$O$_2$: C, 77.98; H, 7.89; N, 8.02. Found: C, 78.02; H, 7.88; N, 8.04.

Example 4.6

Preparation of {4-[(7-benzyl-2,7-diazatricyclo[4.4.0.0$^{3,8}$]dec-2-yl)-(3-methoxyphenyl)methyl]phenyl}-piperidin-1-yl-methanone

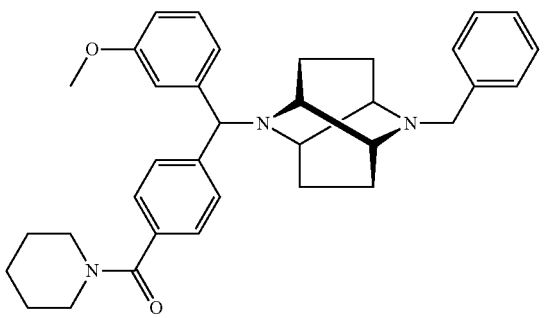

The procedure of Example 4.5 was repeated, but using in place of the compound of Example 3.1 {4-[chloro-(3'-methoxyphenyl)methyl]phenyl}piperidin-1-yl-methanone of Example 3.3. The compound {4-[(7-benzyl-2,7-diazatricyclo-[4.4.0.0$^{3,8}$]dec-2-yl)-(3-methoxyphenyl)methyl]phenyl}-piperidin-1-yl-methanone was obtained. Yield: 90%. IR (nujol) (λ=cm$^{-1}$) 1680 (C=O); $^1$H-NMR (CDCl$_3$) δ 1.30-2.10 (m, 14H); 2.75-2.90 (m, 4H); 3.20-3.45 (m, 2H); 3.55-3.75 (m, 2H); 3.77 (s, 3H); 3.79 (s, 2H); 5.10 (s, 1H); 6.65-7.40 (m, 11H); 8.00-8.20 (m, 2H). Anal. calc. for C$_{35}$H$_{41}$N$_3$O$_2$: C, 78.47; H, 7.71; N, 7.84. Found: C, 78.25; H, 7.72; N, 7.85.

Example 4.7

Preparation of 4-[(10-benzyl-9,10-diazatricyclo[4.2.1.1$^{2,5}$]dec-9-yl)-(3-methoxyphenyl)methyl]-N,N-dimethylbenzamide

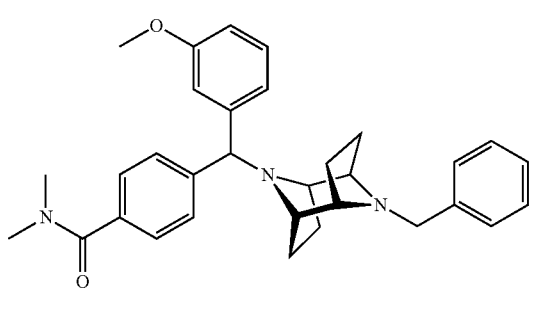

The procedure of Example 4.1 was repeated, but using in place of the compound of Example 3.1 4-[chloro-(3-methoxyphenyl)methyl]-N,N-dimethyl benzamide of Example 3.5. The compound 4-[(10-benzyl-9,10-diazatricyclo[4.2.1.1$^{2,5}$]dec-9-yl)-(3-methoxy-phenyl)methyl]-N,N-dimethylbenzamide was obtained. Yield: 50%; IR (nujol) (λ=cm$^{-1}$) 1700 (C=O); $^1$H-NMR (CDCl$_3$) δ 1.60-2.30 (m, 8H); 2.70-2.85 (m, 4H); 2.90-3.15 (m, 6H); 3.36 (s, 2H); 3.79 (s, 3H); 4.29 (s, 1H); 6.65-6.75 (m, 1H); 7.10-7.40 (m, 10H); 7.55 (d, 2H, J=8.4 Hz). Anal. calc. for C$_{32}$H$_{37}$N$_3$O$_2$: C, 77.54; H, 7.52; N, 8.48. Found: C, 77.70; H, 7.41; N, 8.54.

Example 4.8

Preparation of {4-[(7-benzyl-2,7-diazatricyclo[4.4.0.0$^{3,8}$]dec-2-yl)-(3-methoxyphenyl)methyl]phenyl}-pyrrolidin-1-yl-methanone

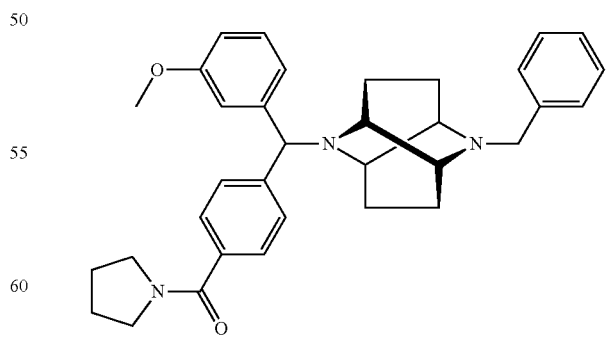

The procedure of Example 4.5 was repeated, but using instead of the compound of Example 3.1 the compound [4-(chloro-(3-methoxyphenyl)methyl)phenyl](pyrrolidin-1-yl)methanone of Example 3.2. The compound {4-[(7-benzyl-2, 7-diazatricyclo[4.4.0.0³,⁸]dec-2-yl)-(3-methoxyphenyl) methyl]phenyl}-pyrrolidin-1-yl-methanone was obtained. Yield: 44%; IR (nujol) ($\lambda=cm^{-1}$) 1680 (C=O); ¹H-NMR (CDCl₃) δ 1.40-2.00 (m, 12H); 2.75-3.10 (m, 4H); 3.30-3.50 (m, 2H); 3.55-3.75 (m, 2H); 3.78 (s, 3H); 4.00-4.20 (m, 2H); 5.07 (s, 1H); 6.90-7.60 (m, 13H). Anal. calc. for $C_{34}H_{39}N_3O_2$: C, 78.28; H, 7.54; N, 8.05. Found: C, 77.98; H, 7.52; N, 8.07.

Example 4.9

Preparation of 4-[(10-benzyl-3,10-diazabicyclo [4.3.1]dec-3-yl)-(3-methoxyphenyl)methyl]-N,N-diethylbenzamide

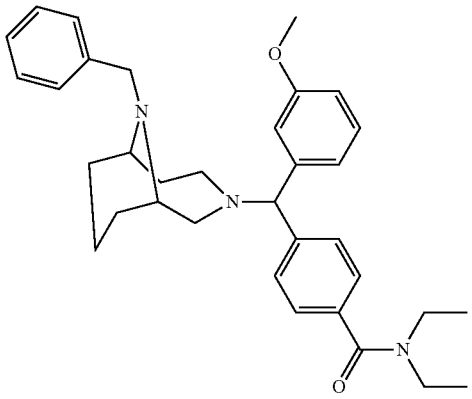 [SMILES: CCN(CC)C(=O)c1ccc(C(c2cccc(OC)c2)N2CCC3CCCC(C2)N3Cc2ccccc2)cc1]

The same procedure reported in Example 4.1 was repeated, but using the compound obtained in Example 2.3 instead of 9-benzyl-9,10-diazatricyclo[4.2.1.1²,⁵]-decane of Example 2.1. The compound 4-[(10-benzyl-3,10-diazabicyclo[4.3.1] dec-3-yl)-(3-methoxyphenyl)methyl]-N,N-diethylbenzamide was obtained. Yield: 28%; Rf=0.25 (CH₂Cl₂/acetone 9:1); IR (nujol) ($\lambda=cm^{-1}$) 1641 (C=O); ¹H-NMR (CDCl₃): δ 1.00-1.46 (m, 8H), 1.54-2.05 (m, 6H), 2.33-2.46 (m, 1H), 2.48-2.96 (m, 4H), 3.05-3.62 (m, 5H), 3.76 (s, 3H), 3.96 (s, 2H), 4.41 (s, 1H), 6.63-6.76 (m, 1H), 6.91-7.43 (m, 10H), 7.49 (d, 2H, J=7.6 Hz). Anal. calc. for $C_{34}H_{43}N_3O_2$: C, 77.68; H, 8.24; N, 7.99. Found: C, 7.7.61; H, 8.23; N, 7.97.

Example 4.10

Preparation of 4-[(9-methyl-3,9-diazabicyclo[4.2.1] non-3-yl)-(3-methoxyphenyl)methyl]-N,N-dimethyl-benzamide

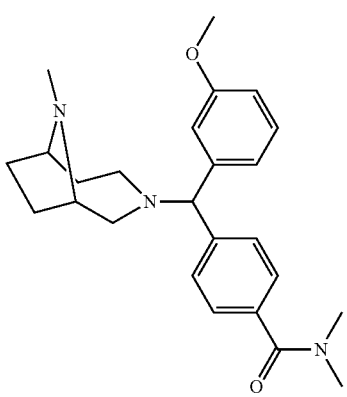 [SMILES: COc1cccc(C(c2ccc(C(=O)N(C)C)cc2)N2CCC3CCC(C2)N3C)c1]

The same procedure of Example 4.1 was repeated but using instead of 9-benzyl-9,10-diazatricyclo[4.2.1.1²,⁵]-decane and of 4-[chloro-(3-methoxyphenyl)methyl]-N, N-dietilbenzamide, the compounds obtained, respectively, in Examples 2.4 and 3.5.

The compound 4-[(9-methyl-3,9-diazabicyclo[4.2.1]non-3-yl)-(3-methoxyphenyl)methyl]-N,N-dimethylbenzamide was obtained. Yield: 71%; IR (nujol) ($\lambda=cm^{-1}$) 1639 (C=O); ¹H-NMR (CDCl₃): δ 1.40-1.65 (m, 3H), 1.75-1.95 (m, 1H), 2.10-2.30 (m, 2H), 2.44 (s, 3H), 2.73 (dd, 1H, J=2.2 and 10.8 Hz), 2.83-3.00 (m, 3H), 3.02 (s, 6H), 3.10-3.30 (m, 2H), 3.79 (s, 3H), 4.24 (s, 1H), 6.65-6.80 (m, 1H), 7.01-7.22 (m, 5H), 7.56 (d, 2H, J=8.0 Hz). Anal. calc. for $C_{25}H_{33}N_3O_2$: C, 73.68; H, 8.16; N, 10.31. Found: C, 73.56; H, 8.15; N, 10.28.

Example 4.11

Preparation of 4-[(9-benzyl-3,9-diazabicyclo[3.3.1] non-3-yl)-(3-methoxyphenyl)methyl]-N-cyclohexyl-benzamide

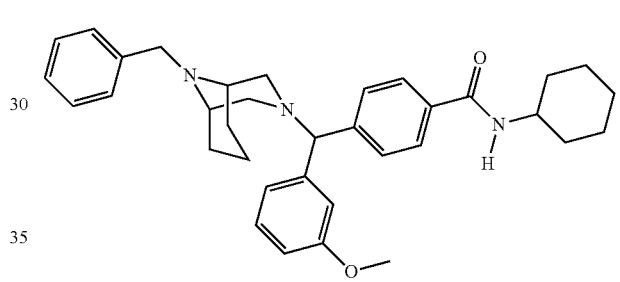

The same procedure of in Example 4.1 was repeated, but using instead of 4-[chloro-(3-methoxyphenyl)methyl]-N,N-diethylbenzamide the compound of in Example 3.4 and instead of 9-benzyl-9,10-diazatricyclo[4.2.1.1²,⁵]decane the following compound of formula (1pp)

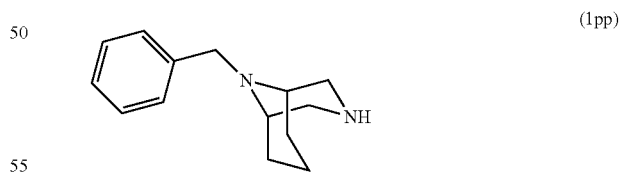

(1pp)

prepared as described in patent application US 2003/0195217. The compound 4-[(9-benzyl-3,9-diazabicyclo [3.3.1]non-3-yl)-(3-methoxyphenyl)methyl]-N-cyclohexyl-benzamide was obtained. Yield: 58%; IR (nujol) ($\lambda=cm^{-1}$) 1639 (C=O), 3200 (NH); ¹H-NMR (CDCl₃): δ 1.21-2.28 (m, 13H), 2.55-2.89 (m, 2H), 2.95-3.32 (m, 8H), 3.82 (s, 3H), 3.99 (s, 2H), 4.28 (s, 1H), 6.65-6.80 (m, 1H), 7.11-7.43 (m, 10H), 7.48 (bs, 1H, NH), 7.58 (d, 2H, J=7.6 Hz). Anal. calc. for C$_{35}$H$_{43}$N$_3$O$_2$: C, 78.18; H, 8.06; N, 7.81. Found: C, 78.02; H, 8.05; N, 7.80.

Example 4.12

Preparation of 4-[(3-benzyl-3,8-diazabicyclo[3.2.1]oct-8-yl)-(3-methoxyphenyl)methyl]-N,N-diethylbenzamide

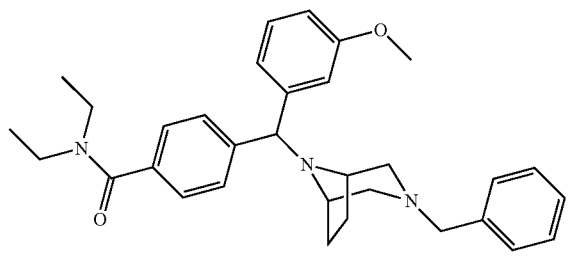 [SMILES: CCN(CC)C(=O)c1ccc(C(c2cccc(OC)c2)N2C3CCC2CN(Cc2ccccc2)C3)cc1]

The same procedure of Example 4.1 was repeated, but using instead of 9-benzyl-9,10-diazatricyclo[4.2.1.1$^{2,5}$]decane the following compound of formula (1pr)

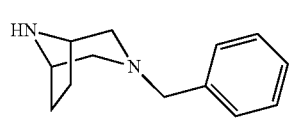
(1pr)

prepared as described by G. Cignarella et al. in J. Org. Chem., 26 (1961) 2747-2750.

The compound 4-[(3-benzyl-3,8-diazabicyclo[3.2.1]oct-8-yl)-(3-methoxyophenyl)methyl]-N,N-diethylbenzamide was obtained. Yield: 66%; IR (nujol) (λ=cm$^{-1}$) 1644 (C=O); $^1$H-NMR (CDCl$_3$): δ 1.05-2.12 (m, 12H), 2.66-2.86 (m, 2H), 2.95-3.22 (m, 6H), 3.78 (s, 3H), 3.99 (s, 2H), 4.33 (s, 1H), 6.74-6.89 (m, 1H), 7.09-7.49 (m, 10H), 7.56 (d, 2H, J=7.8 Hz). Anal. calc. for C$_{32}$H$_{39}$N$_3$O$_2$: C, 77.23; H, 7.90; N, 8.44. Found: C, 77.15; H, 7.88; N, 8.42.

Example 4.13

Preparation of 4-[(6-benzyl-3,6-diazabicyclo[3.1.1]hept-3-yl)-(3-methoxyphenyl)methyl]-N,N-diethylbenzamide

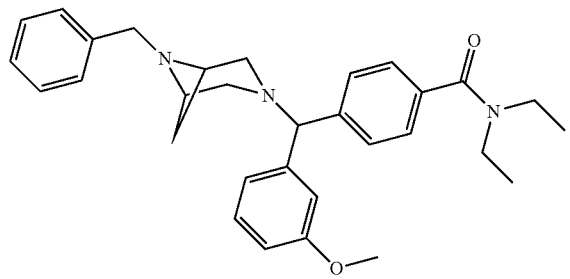 [SMILES: CCN(CC)C(=O)c1ccc(C(c2cccc(OC)c2)N2CC3CC(C2)N3Cc2ccccc2)cc1]

The same procedure reported in Example 4.1 was repeated, but using instead of 9-benzyl-9,10-diazatricyclo[4.2.1.1$^{2,5}$]-decane the following compound of formula (1pq)

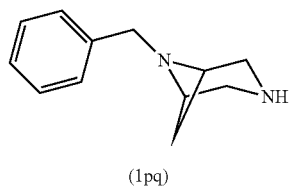 [SMILES: c1ccc(CN2C3CNCC2C3)cc1]
(1pq)

prepared as described in patent application WO 2005/108402. The compound 4-[(6-benzyl-3,6-diazabicyclo[3.1.1]hept-3-yl)-(3-methoxyphenyl)methyl]-N,N-diethylbenzamide was obtained. Yield: 71%; IR (nujol) (λ=cm$^{-1}$) 1639 (C=O); $^1$H-NMR (CDCl$_3$): δ 1.14-2.19 (m, 11H), 2.65-2.88 (m, 2H), 2.96-3.19 (m, 5H), 3.78 (s, 3H), 3.91 (s, 2H), 4.32 (s, 1H), 6.67-6.84 (m, 1H), 6.99-7.43 (m, 10H), 7.63 (d, 2H, J=7.9 Hz). Anal. calc. for C$_{31}$H$_{37}$N$_3$O$_2$: C, 76.98; H, 7.71; N, 8.69. Found: C, 76.88; H, 7.70; N, 8.67.

Example 4.14

Preparation of 4-[(9-benzyl-3,9-diazabicyclo[4.2.1]nonan-3-yl)(3-methoxyphenyl)methyl]-N,N-diethylbenzamide

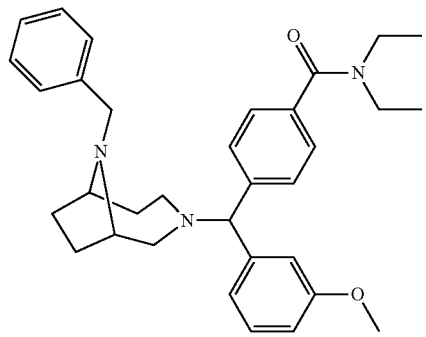 [SMILES: CCN(CC)C(=O)c1ccc(C(c2cccc(OC)c2)N2CCC3CCC(C2)N3Cc2ccccc2)cc1]

The same procedure of Ex. 4.1 was followed but substituting 9-benzyl-9,10-diazatricyclo[4.2.1.1$^{2,5}$]decane with 9-benzyl-3,9-diazabicyclo[4.2.1]nonane of formula (1ps) having the following formula:

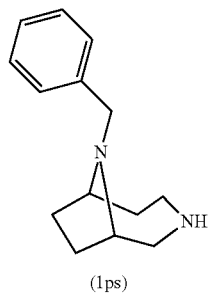 [SMILES: c1ccc(CN2C3CCNCC2CC3)cc1]
(1ps)

The preparation of 1ps was carried out according to Audouze K. et al. in J. Med. Chem, 49 (2006) 3159-3171.

The synthesis afforded the compound 4-[(9-benzyl-3,9-diazabicyclo[4.2.1]nonan-3-yl)(3-methoxyphenyl)methyl]-N,N-diethylbenzamide.

Yield: 50%; Rf=0.33 (CHCl$_3$/MeOH 9.8:0.2); IR (nujol) (λ=cm$^{-1}$) 1645 (C=O); $^1$H-NMR (CDCl$_3$): δ 1.00-1.42 (m, 6H), 1.43-1.49 (m, 1H), 1.64-1.82 (m, 2H), 1.87-2.06 (m, 2H), 2.13-2.38 (m, 2H), 2.45-2.65 (m, 2H), 2.70-2.85 (m, 1H), 3.05-3.14 (m, 1H), 3.17-3.37 (m, 3H), 3.44-3.60 (m, 2H), 3.74 (bs, 2H), 3.77 (s, 3H), 4.40 (s, 1H), 6.67-6.76 (m, 1H), 6.92-6.99 (m, 1H), 7.00-7.09 (m, 1H), 7.12-7.22 (m, 2H), 7.23-7.32 (m, 4H), 7.33-7.43 (m, 3H), 7.47 (d, 1H, J=8.1 Hz). Anal. calc. for $C_{33}H_{41}N_3O_2$: C, 77.46; H, 8.08; N, 8.21. Found: C, 77.39; H, 8.07; N, 8.19.

Example 5.1

Preparation of 4-[(9,10-diazatricyclo[4.2.1.1$^{2,5}$]dec-9-yl)-(3-methoxyphenyl)methyl]-N,N-diethylbenzamide

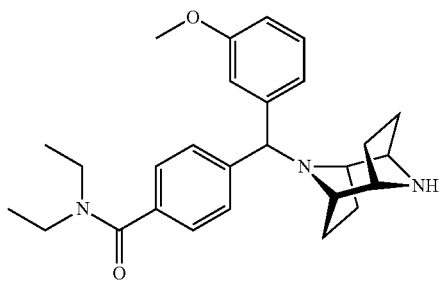

0.38 mmoles of the compound 4-[(10-benzyl-9,10-diazatricyclo[4.2.1.1$^{2,5}$]-dec-9-yl)-(3-methoxyphenyl)methyl]-N,N-diethylbenzamide obtained in Example 4.1 were mixed with palladium at 10% by weight on carbon (0.1 equivalents) in ethanol (5 ml). The mixture was submitted to hydrogenation at a pressure of 45 psi of $H_2$ and at a temperature of 60° C., for 6 hours. At the end of the reaction the catalyst was removed by filtration under vacuum. The solvent was then evaporated under vacuum obtaining the compound 4-[(9,10-diazatricyclo[4.2.1.1$^{2,5}$]dec-9-yl)-(3-methoxy phenyl)methyl]-N,N-diethylbenzamide. Yield: quantitative. IR (nujol) ($\lambda$=cm$^{-1}$) 1630 (C=O), 3200 (NH); $^1$H-NMR (CDCl$_3$) δ 1.00-1.45 (m, 6H); 1.90-2.43 (m, 10H); 2.90-3.10 (m, 2H); 3.10-3.30 (m, 2H); 3.40-3.60 (m, 2H); 3.66 (bs, 1H); 3.79 (s, 3H); 4.26 (s, 1H); 6.75-6.80 (m, 1H); 7.03-7.38 (m, 5H); 7.60 (d, 2H, J=8.0 Hz). Anal. calc. for $C_{27}H_{35}N_3O_2$: C, 74.79; H, 8.14; N, 9.69. Found: C, 75.04; H, 8.13; N, 9.67.

Example 5.2

Preparation of {4-[(9,10-diazatricyclo[4.2.1.1$^{2,5}$]dec-9-yl)-(3-methoxyphenyl)methyl]phenyl}-pyrrolidin-1-yl-methanone

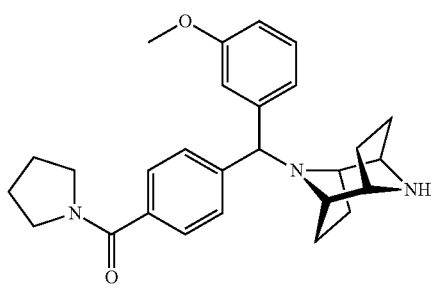

The procedure of Example 5.1 was repeated, but using the compound {4-[(10-benzyl-9,10-diazatricyclo[4.2.1.1$^{2,5}$]dec-9-yl)-(3-methoxyphenyl)methyl]phenyl}-pyrrolidin-1-il-methanone of Example 4.2 instead of the compound of Example 4.1. The compound {4-[(9,10-diazatricyclo[4.2.1.1$^{2,5}$]dec-9-yl)-(3-methoxyphenyl)-methyl]phenyl}-pyrrolidin-1-yl-methanone was obtained. Yield: quantitative. IR (nujol) ($\lambda$=cm$^{-1}$) 1650 (C=O), 3300 (NH); $^1$H-NMR (CDCl$_3$) δ 1.80-2.10 (m, 11H); 2.30-2.40 (m, 2H); 2.80-3.00 (m, 2H); 3.30-3.45 (m, 4H); 3.55-3.70 (m, 3H); 3.79 (s, 3H); 4.29 (s, 1H); 6.70-6.80 (m, 1H); 7.00-7.30 (m, 3H); 7.43 (d, 2H, J=8.0 Hz); 7.53 (d, 2H, J=8.0 Hz). Anal. calc. for $C_{27}H_{33}N_3O_2$: C, 75.15; H, 7.71; N, 9.74. Found: C, 75.09; H, 7.69; N, 9.71.

Example 5.3

Preparation of {4-[(9,10-diazatricyclo[4.2.1.1$^{2,5}$]dec-9-yl)-(3-methoxyphenyl)methyl]phenyl}-piperidin-1-yl-methanone

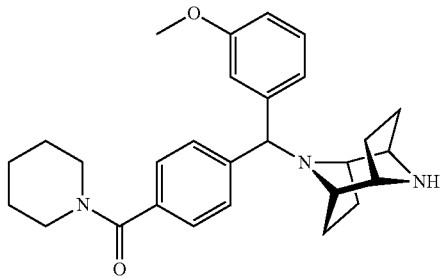

The procedure of Example 5.1 was repeated, but using instead of the compound prepared in Example 4.1 the compound {4-[(10-benzyl-9,10-diazatricyclo[4.2.1.1$^{2,5}$]dec-9-yl)-(3-methoxyphenyl)methyl]phenyl}-piperidin-1-yl-methanone of Example 4.3. The compound {4-[(9,10-diazatricyclo[4.2.1.1$^{2,5}$]dec-9-yl)-(3-methoxyphenyl)-methyl]phenyl}-piperidin-1-yl-methanone was obtained.

Yield: quantitative. IR (nujol) ($\lambda$=cm$^{-1}$) 1680 (C=O), 3100 (NH); $^1$H-NMR (CDCl$_3$) δ 1.40-1.90 (m, 13H); 2.20-2.40 (m, 2H); 2.75-2.95 (m, 2H); 3.06 (s, 2H); 3.22-3.45 (m, 2H); 3.60-3.75 (m, 2H); 3.80 (s, 3H); 4.22 (s, 1H); 6.70-6.80 (m, 1H); 7.00-7.40 (m, 5H); 7.55 (d, 2H, J=8.0 Hz). Anal. calc. for $C_{28}H_{35}N_3O_2$: C, 75.47; H, 7.92; N, 9.43. Found: C, 75.20; H, 7.90; N, 9.41.

Example 5.4

Preparation of 4-[(9,10-diazatricyclo[4.2.1.1$^{2,5}$]dec-9-yl)-(3-methoxyphenyl)methyl]-N-cyclohexylbenzamide

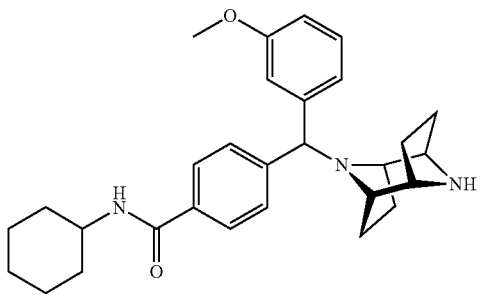

The procedure of Example 5.1 was repeated, but using instead of the compound prepared in Example 4.1 the compound 4-[(10-benzyl-9,10-diazatricyclo[4.2.1.1$^{2,5}$]dec-9-yl)-(3-methoxyphenyl)methyl]-N-cyclohexyl benzamide of Example 4.4.

The compound 4-[(9,10-diazatricyclo[4.2.1.1$^{2,5}$]dec-9-yl)-(3-methoxyphenyl)methyl]-N-cyclohexylbenzamide was obtained. Yield: 80%. IR (nujol) ($\lambda$=cm$^{-1}$) 1680 (C=O), 3100 (NH), 3300 (NH); $^1$H-NMR (CDCl$_3$) $\delta$ 1.05-1.45 (m, 6H); 1.50-2.00 (m, 6H); 2.00-2.35 (m, 6H); 2.40-2.55 (m, 2H); 3.60-3.77 (m, 3H); 3.78 (s, 3H); 4.33 (s, 1H); 6.74 (d, 1H, J=6.8 Hz); 7.08 (d, 1H, J=11.6 Hz); 7.10-7.25 (m, 3H); 7.57 (d, 2H, J=8.0 Hz); 7.75 (d, 2H, J=8.0 Hz). Anal. calc. for C$_{29}$H$_{37}$N$_3$O$_2$: C, 75.78; H, 8.11; N, 9.14. Found: C, 75.53; H, 8.09; N, 9.11.

Example 5.5

Preparation of 4-[(2,7-diazatricyclo[4.4.0.0$^{3,8}$]dec-2-yl)-(3-methoxyphenyl)methyl]-N,N-diethylbenzamide

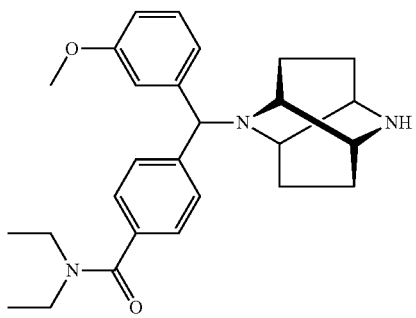

The same procedure of Example 5.1 was repeated, but using instead of the compound prepared in Example 4.1 the compound 4-[(7-benzyl-2,7-diazatricyclo[4.4.0.0$^{3,8}$]dec-2-yl)-(3-methoxy-phenyl)methyl]-N,N-diethyl benzamide of Example 4.5. The compound 4-[(2,7-diazatricyclo[4.4.0.0$^{3,8}$]dec-2-yl)-(3-methoxyphenyl)methyl]-N,N-diethylbenzamide was obtained. Yield: 90%. IR (nujol) ($\lambda$=cm$^{-1}$) 1670 (C=O), 3100 (NH); $^1$H-NMR (CDCl$_3$) $\delta$ 1.00-1.40 (m, 6H); 1.90-2.50 (m, 10H); 2.90-3.00 (m, 2H); 3.10-3.30 (m, 2H); 3.40-3.60 (m, 2H); 3.96 (s, 3H); 4.95 (s, 1H); 6.65-6.85 (m, 1H); 7.00-7.40 (m, 5H); 7.48 (d, 2H, J=6.0 Hz). Anal. calc. for C$_{27}$H$_{35}$N$_3$O$_2$: C, 74.79; H, 8.14; N, 9.69. Found: C, 74.81; H, 8.11; N, 9.68.

Example 5.6

Preparation of {4-[(2,7-diazatricyclo[4.4.0.0$^{3,8}$]dec-2-yl)-(3-methoxyphenyl)methyl]phenyl}-piperidin-1-yl-methanone

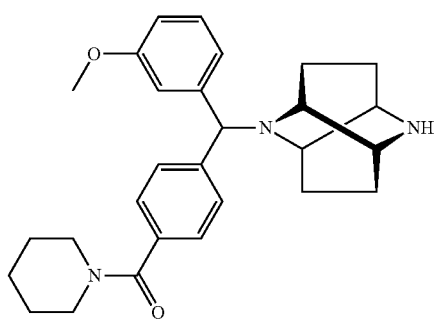

The procedure of Example 5.1 was repeated, but using instead of the compound prepared in Example 4.1 the compound {4-[(7-benzyl-2,7-diazatricyclo[4.4.0.0$^{3,8}$]dec-2-yl)-(3-methoxyphenyl)methyl]phenyl}-piperidin-1-yl-methanone of Example 4.6. The compound {4-[(2,7-diazatricyclo[4.4.0.0$^{3,8}$]dec-2-yl)-(3-methoxyphenyl)methyl]-phenyl}-piperidin-1-yl-methanone was obtained. Yield: quantitative. IR (nujol) ($\lambda$=cm$^{-1}$) 1680 (C=O), 3100 (NH); $^1$H-NMR (CDCl$_3$) $\delta$ 1.40-2.10 (m, 16H); 2.15-2.30 (m, 1H); 2.80-3.00 (m, 2H); 3.15-3.45 (m, 2H); 3.50-3.75 (m, 2H); 3.78 (s, 3H); 5.00-5.25 (m, 3H); 5.70-5.90 (m, 1H); 6.65-7.40 (m, 6H); 7.95-8.15 (m, 2H). Anal. calc. for C$_{28}$H$_{35}$N$_3$O$_2$: C, 75.47; H, 7.92; N, 9.43. Found: C, 75.23; H, 7.90; N, 9.41.

Example 5.7

Preparation of 4-[(9,10-diazatricyclo[4.2.1.1$^{2,5}$]dec-9-yl)-(3-methoxyphenyl)methyl]-N,N-dimethylbenzamide

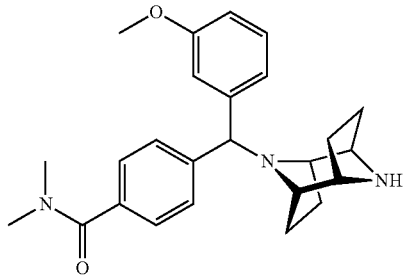

The procedure of Example 5.1 was repeated, but using in place of the compound prepared in Example 4.1 the compound {4-[(10-benzyl-9,10-diazatricyclo[4.2.1.1$^{2,5}$]dec-9-yl)-(3-methoxyphenyl)methyl]-N,N-dimethyl benzamide of Example 4.7.

The compound 4-[(9,10-diazatricyclo[4.2.1.1$^{2,5}$]dec-9-yl)-(3-methoxyphenyl)methyl]-N,N-dimethylbenzamide was obtained. Yield: quantitative; IR (nujol) (λ=cm$^{-1}$) 1620 (C=O), 3100 (NH); $^{1}$H-NMR (CDCl$_3$) δ 2.00-2.50 (m, 10H); 2.90-3.10 (m, 9H); 3.78 (s, 3H); 4.34 (s, 1H); 6.70-6.85 (m, 1H); 7.00-7.60 (m, 7H). Anal. calc. for C$_{25}$H$_{31}$N$_3$O$_2$: C, 74.04; H, 7.70; N, 10.36. Found: C, 74.21; H, 7.69; N, 10.39.

Example 5.8

Preparation of {4-[(2,7-diazatricyclo[4.4.0.0$^{3,8}$]dec-2-yl)-(3-methoxyphenyl)methyl]phenyl}-pyrrolidin-1-yl-methanone

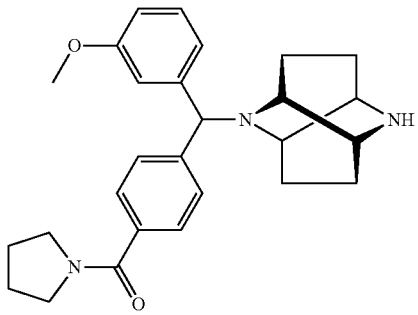

The procedure of Example 5.1 was repeated, but using in place of the compound prepared in Example 4.1 the compound {4-[(7-benzyl-2,7-diazatricyclo[4.4.0.0$^{3,8}$]dec-2-yl)-(3-methoxyphenyl)methyl]phenyl}-pyrrolidin-1-yl-methanone of Example 4.8. The compound {4-[(2,7-diazatricyclo[4.4.0.0$^{3,8}$]dec-2-yl)-(3-methoxyphenyl)methyl]phenyl}-pyrrolidin-1-yl-methanone was obtained. Yield: 90%; IR (nujol) (λ=cm$^{-1}$) 1680 (C=O), 3100 (NH); $^{1}$H-NMR (CDCl$_3$) δ 1.10-2.20 (m, 11H); 2.25-2.35 (m, 2H); 2.95-3.05 (m, 2H); 3.30-3.40 (m, 3H); 3.55-3.75 (m, 3H); 3.78 (s, 3H); 4.96 (s, 1H); 7.00-7.09 (m, 2H); 7.15-7.30 (m, 2H); 7.40-7.55 (m, 4H). Anal. calc. for C$_{27}$H$_{33}$N$_3$O$_2$: C, 75.14; H, 7.71; N, 9.74. Found: C, 74.98; H, 7.69; N, 93.73.

Example 5.9

Preparation of 4-[(3,10-diazabicyclo[4.3.1]dec-3-yl)-(3-methoxyphenyl)methyl]-N,N-diethylbenzamide

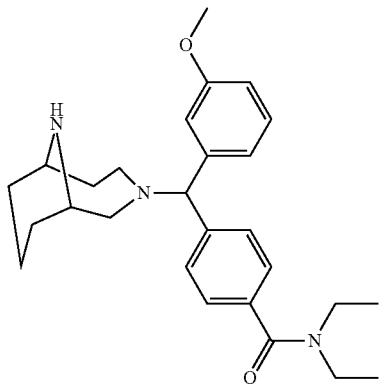 [SMILES: CCN(CC)C(=O)c1ccc(C(c2cccc(OC)c2)N2CCC3CCCC(C2)N3)cc1]

The procedure of Example 5.1 was repeated, but using the compound of Example 4.9 in place of the compound of Example 4.1. The compound 4-[(3,10-diazabicyclo[4.3.1] dec-3-yl)-(3-methoxy-phenyl)methyl]-N,N-diethylbenzamide was obtained. Yield: 35%; Rf=0.30 (CHCl$_3$/MeOH 9:1); IR (nujol) (λ=cm$^{-1}$) 1639 (C=O), 3130 (NH); $^{1}$H-NMR (CDCl$_3$): δ 1.00-1.32 (m, 8H), 1.42-2.35 (m, 7H), 2.47-2.64 (m, 1H), 2.72-3.06 (m, 4H), 3.12-3.32 (m, 2H), 3.40-3.62 (m, 3H), 3.76 (s, 3H), 4.50 (s, 1H), 6.68-6.78 (m, 1H), 6.90-7.07 (m, 2H), 7.14-7.24 (m, 1H), 7.26-7.34 (m, 2H), 7.35-7.52 (m, 2H). Anal. calc. for C$_{27}$H$_{37}$N$_3$O$_2$: C, 74.45; H, 8.56; N, 9.65. Found: C, 74.28; H, 8.54; N, 9.63.

Example 5.10

Preparation of 4-[(3,9-diazabicyclo[4.2.1]non-3-yl)-(3-methoxyphenyl)methyl]-N,N-dimethylbenzamide

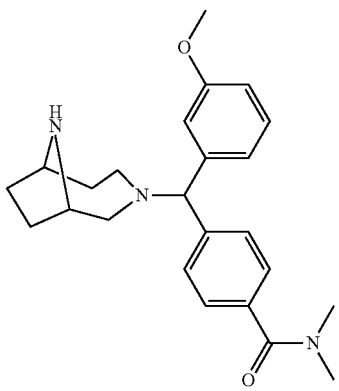 [SMILES: COc1cccc(C(c2ccc(C(=O)N(C)C)cc2)N2CCC3CCC(C2)N3)c1]

0.4 ml of 2,2,2-trichloroethylchloro formate and 0.52 g of K$_2$CO$_3$ were added to a solution of the compound obtained in Example 4.10 (1.02 g) in toluene (25 ml), kept under argon inert atmosphere. The mixture was heated at reflux for 16 hours and at the end cooled at room temperature. The mixture is washed in sequence with water, with an aqueous solution of 15% citric acid and then with brine. At the end of the washings the organic phase was recovered and dehydrated on sodium sulphate. After solvent evaporation 1.21 g of a light yellow oil (carbamate) were obtained. The oil was dissolved in 25 ml of glacial acetic acid. To the solution 0.82 g of zinc in powder were added. The mixture was kept under stirring at room temperature for 16 hours and at the end diluted with about 25 ml of toluene. The solvent was evaporated under vacuum. The residue was dissolved in the minimum volume of dichloromethane. The solution was extracted three times with an aqueous solution of 15% w citric acid. The aqueous phases were shaken with dichloromethane, then brought to an alkaline pH with conc. NH$_4$OH and extracted again with dichloromethane. The pooled organic phases were dehydrated with sodium sulphate and the solvent evaporated. 0.52 g of the compound 4-[(3,9-diazabicyclo[4.2.1]non-3-yyl)-(3-methoxy-phenyl)methyl]-N,N-dimethylbenzamide were obtained. Yield: 62%; IR (nujol) (λ=cm$^{-1}$) 1646 (C=O), 3120 (NH); $^{1}$H-NMR (CDCl$_3$): δ 1.39-1.65 (m, 3H), 1.74-1.97 (m, 1H), 2.11-2.30 (m, 2H), 2.66 (bs, 1H), 2.75 (dd, 1H, J=2.2 and 11.0 Hz), 2.81-3.04 (m, 3H), 3.05 (s, 6H), 3.11-3.32 (m, 2H), 3.81 (s, 3H), 4.27 (s, 1H), 6.63-6.79 (m, 1H), 7.00-7.20 (m, 5H), 7.55 (d, 2H, J=8.1 Hz). Anal. calc. for C$_{24}$H$_{31}$N$_3$O$_2$: C, 73.25; H, 7.94; N, 10.68. Found: C, 73.11; H, 7.92; N, 10.65.

Example 5.11

Preparation of 4-[(3,9-diazabicyclo[3.3.1]non-3-yl)-(3-methoxyphenyl)methyl]-N-cyclohexylbenzamide

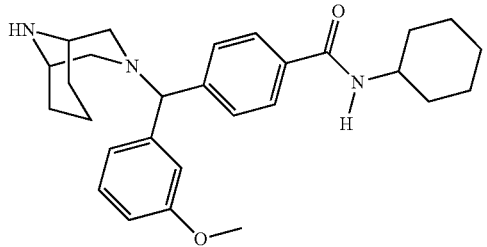 [SMILES: COc1cccc(C(c2ccc(C(=O)NC3CCCCC3)cc2)N2CC3CCCC(C2)N3)c1]

The procedure of Example 5.1 was repeated, but using the compound of Example 4.11 instead of the compound of Example 4.1. The compound 4-[(3,9-diazabicyclo[3.3.1]non-3-yl)-(3-methoxyphenyl)-methyl]-N-cyclohexylbenzamide was obtained.

Yield: 96%; IR (nujol) ($\lambda$=cm$^{-1}$) 1642 (C=O), 3230 (NH); $^1$H-NMR (CDCl$_3$): δ 1.19-2.27 (m, 13H), 2.53-2.88 (m, 2H), 2.90 (bs, 1H), 2.93-3.33 (m, 8H), 3.81 (s, 3H), 4.29 (s, 1H), 6.63-6.82 (m, 1H), 7.14-7.45 (m, 5H), 7.49 (bs, 1H, NH), 7.57 (d, 2H, J=7.8 Hz). Anal. calc. for C$_{28}$H$_{37}$N$_3$O$_2$: C, 75.13; H, 8.33; N, 939. Found: C, 75.08; H, 8.32; N, 9.37.

Example 5.12

Preparation of 4-[(3,8-diazabicyclo[3.2.1]oct-8-yl)-(3-methoxyphenyl)methyl]-N,N-diethylbenzamide

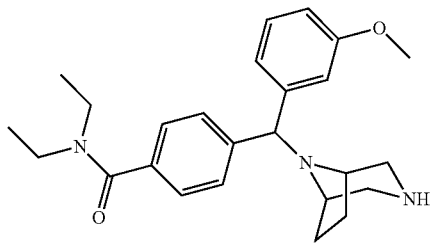 [SMILES: CCN(CC)C(=O)c1ccc(C(c2cccc(OC)c2)N2C3CCC2CNC3)cc1]

The procedure of Example 5.1 was repeated, but using the compound of Example 4.12 instead of the compound of Example 4.1. The compound 4-[(3,8-diazabicyclo[3.2.1]oct-8-yl)-(3-methoxyphenyl)-methyl]-N,N-diethylbenzamide was obtained.

Yield: 96%; IR (nujol) ($\lambda$=cm$^{-1}$) 1641 (C=O), 3220 (NH); $^1$H-NMR (CDCl$_3$): δ 1.12-2.11 (m, 12H), 2.69-2.82 (m, 2H), 2.95 (bs, 1H), 2.98-3.24 (m, 6H), 3.79 (s, 3H), 4.35 (s, 1H), 6.72-6.91 (m, 1H), 7.05-7.48 (m, 5H), 7.60 (d, 2H, J=8.0 Hz).

Anal. calc. for C$_{25}$H$_{33}$N$_3$O$_2$: C, 73.68; H, 8.16; N, 10.31. Found C, 73.60; H, 8.15; N, 10.29.

Example 5.13

Preparation of 4-[(3,6-diazabicyclo[3.1.1]hept-3-yl)-(3-methoxyphenyl)methyl]-N,N-diethylbenzamide

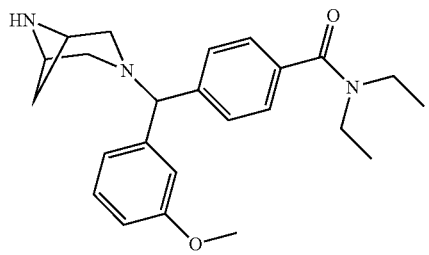 [SMILES: CCN(CC)C(=O)c1ccc(C(c2cccc(OC)c2)N2CC3CC(C2)N3)cc1]

The procedure of Example 5.1 was repeated, but using the compound of Example 4.13 instead of the compound prepared in Example 4.1. the compound 4-[(3,6-diazabicyclo[3.1.1]hept-3-yl)-(3-methoxy-phenyl)methyl]-N,N-diethyl-benzamide was obtained.

Yield: 92%; IR (nujol) ($\lambda$=cm$^{-1}$) 1641 (C=O), 3230 (NH); $^1$H-NMR (CDCl$_3$): δ 1.11-2.21 (m, 11H), 2.59 (bs, 1H), 2.61-2.89 (m, 2H), 2.95-3.20 (m, 5H), 3.79 (s, 3H), 4.30 (s, 1H), 6.65-6.85 (m, 1H), 6.98-7.45 (m, 5H), 7.60 (d, 2H, J=7.9 Hz). Anal. calc. for C$_{24}$H$_{31}$N$_3$O$_2$: C, 73.25; H, 7.94; N, 10.68. Found: C, 73.17; H, 7.93; N, 10.66.

Example 5.14

Preparation of 4-[(3,9-diazabicyclo[4.2.1]nonan-3-yl)-(3-methoxyphenyl)methyl]-N,N-diethylbenzamide

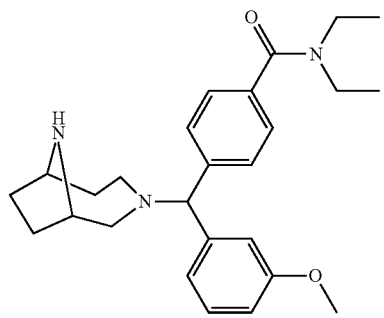 [SMILES: CCN(CC)C(=O)c1ccc(C(c2cccc(OC)c2)N2CCC3CCC(C2)N3)cc1]

The same procedure described in Ex. 5.1 was followed, but using the compound obtained in Ex. 4.14 instead of the compound prepared in Ex. 4.1.

The synthesis afforded the compound 4-[(3,9-diazabicyclo[4.2.1]nonan-3-yl)(3-methoxyphenyl)methyl]-N,N-diethyl-benzamide.

Yield: 41%; Rf=0.38 (CHCl$_3$/MeOH 9:1); IR (nujol) ($\lambda$=cm$^{-1}$) 1641 (C=O), 3133 (NH); $^1$H-NMR (CDCl$_3$): δ 1.01-1.31 (m, 6H), 1.47-1.60 (m, 1H), 1.82-2.25 (m, 4H), 2.33-2.61 (m, 2H), 2.63-2.92 (m, 4H), 3.14-3.28 (m, 2H), 3.30-3.40 (m, 1H), 3.42-3.62 (m, 3H), 3.76 (s, 3H), 4.42-4.50 (m, 1H), 6.68-6.74 (m, 1H), 6.91-7.03 (m, 2H), 7.13-7.21 (m,

Example 6.1

Preparation of 4-[(10-allyl-9,10-diazatricyclo[4.2.1.1$^{2,5}$]dec-9-yl)-(3-methoxyphenyl)methyl]-N,N-diethylbenzamide

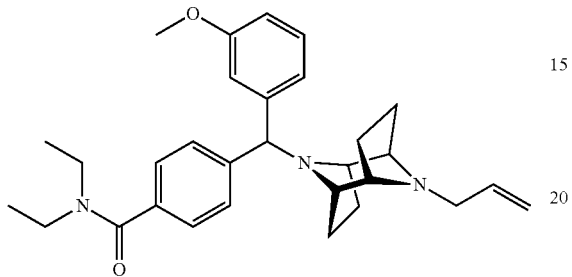

A mixture formed of the compound obtained in example 5.1 (0.98 mmoles), of allyl bromide (1.5 equivalents) and of anhydrous potassium carbonate (3 equivalents) in acetone (25 ml) is heated at reflux for 14 hours. At the end it is filtered and the filtrate is evaporated under vacuum. The compound 4-[(10-allyl-9,10-diazatricyclo[4.2.1.1$^{2,5}$]dec-9-yl)-(3-methoxyphenyl)methyl]-N,N-diethyl benzamide (light solid) is obtained.

Yield: 96%. m.p.: 99-101° C.; IR (nujol) (λ=cm$^{-1}$) 1680 (C=O); $^1$H-NMR (CDCl$_3$) δ 1.00-1.30 (m, 6H); 1.50-2.20 (m, 8H); 2.70-2.90 (m, 6H); 3.20-3.35 (m, 2H); 3.40-3.55 (m, 2H); 3.80 (s, 3H); 4.28 (s, 1H); 4.98-5.15 (m, 2H); 5.70-5.90 (m, 1H); 6.65-6.80 (m, 1H); 7.00-7.20 (m, 5H); 7.54 (d, 2H, J=8.0 Hz). Anal. calc. for C$_{30}$H$_{39}$N$_3$O$_2$: C, 76.07; H, 8.30; N, 8.87. Found: C, 75.95; H, 8.27; N, 8.85.

Example 6.2

Preparation of {4-[(10-allyl-9,10-diazatricyclo[4.2.1.1$^{2,5}$]dec-9-yl)-(3-methoxyphenyl)methyl]phenyl}-pyrrolidin-1-yl-methanone

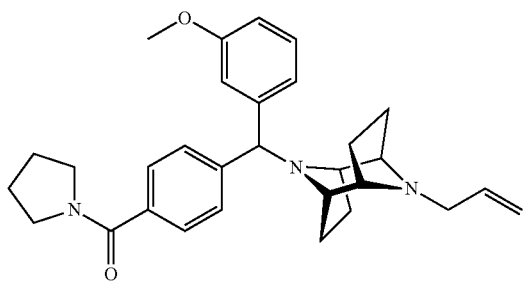

The procedure of Example 6.1 was repeated, but using the compound obtained in Example 5.2 instead of the compound of Example 5.1. The compound {4-[(10-allyl-9,10-diazatricyclo[4.2.1.1$^{2,5}$]dec-9-yl)-(3-methoxyphenyl)methyl]phenyl}-pyrrolidin-1-yl-methanone was obtained.

Yield: 94%. m.p.: 46-48° C.; IR (nujol) (λ=cm$^{-1}$) 1680 (C=O); $^1$H-NMR (CDCl$_3$) δ 1.60-2.30 (m, 12H); 2.70-2.95 (m, 6H); 3.30-3.45 (m, 2H); 3.50-3.70 (m, 2H); 3.79 (s, 3H); 4.28 (s, 1H); 4.95-5.15 (m, 2H); 5.70-5.95 (m, 1H); 6.65-6.75 (m, 1H); 7.00-7.15 (m, 3H); 7.41 (d, 2H, J=8.0 Hz); 7.55 (d, 2H, J=8.0 Hz). Anal. calc. for C$_{30}$H$_{37}$N$_3$O$_2$: C, 76.40; H, 7.91; N, 8.91. Found: C, 76.27; H, 8.02; N, 8.80.

Example 6.3

Preparation of {4-[(10-allyl-9,10-diazatricyclo[4.2.1.1$^{2,5}$]dec-9-yl)-(3-methoxyphenyl)methyl]phenyl}-piperidin-1-yl-methanone

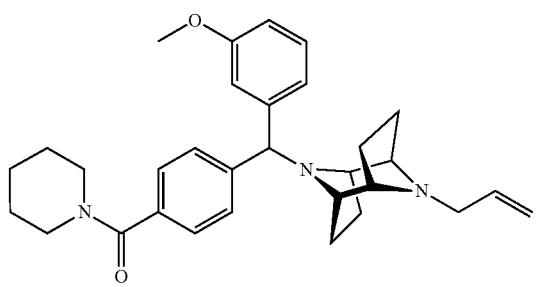

The procedure of Example 6.1 was repeated, but using the compound obtained in Example 5.3 instead of the compound of Example 5.1. The compound {4-[(10-allyl-9,10-diazatricyclo[4.2.1.1$^{2,5}$]dec-9-yl)-(3-methoxyphenyl)methyl]-phenyl}-piperidin-1-yl-methanone was obtained. Yield: quantitative. m.p.: 134-136° C.; IR (nujol) (λ=cm$^{-1}$) 1650 (C=O); $^1$H-NMR (CDCl$_3$) δ 1.40-1.90 (m, 10H); 1.91-2.00 (m, 2H); 2.10-2.25 (m, 2H); 2.70-2.95 (m, 6H); 3.20-3.45 (m, 2H); 3.55-3.75 (m, 2H); 3.80 (s, 3H); 4.28 (s, 1H); 5.00-5.20 (m, 2H); 5.70-5.90 (m, 1H); 6.70-6.80 (m, 1H); 7.00-7.40 (m, 5H); 7.55 (d, 2H, J=8.0 Hz). Anal. calc. for C$_{31}$H$_{39}$N$_3$O$_2$: C, 76.67; H, 8.09; N, 8.65. Found: C, 76.45; H, 8.11; N, 8.67.

Example 6.4

Preparation of 4-[(10-allyl-9,10-diazatricyclo[4.2.1.1$^{2,5}$]dec-9-yl)-(3-methoxyphenyl)methyl]-N-cyclohexylbenzamide

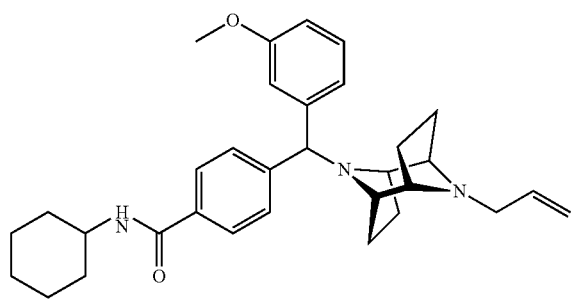

The procedure of Example 6.1 was repeated, but using the compound obtained in Example 5.4 instead of the compound of Example 5.1. The compound 4-[(10-allyl-9,10-diazatricyclo[4.2.1.1$^{2,5}$]dec-9-yl)-(3-methoxyphenyl)methyl]-N-cyclohexylbenzamide was obtained. Yield: quantitative. m.p.: 58-60° C.; IR (nujol) (λ=cm$^{-1}$) 1680 (C=O); $^1$H-NMR (CDCl$_3$) δ 1.10-1.80 (m, 14H); 1.85-2.10 (m, 4H); 2.15-2.20 (m, 2H); 2.70-2.95 (m, 5H); 3.78 (s, 3H); 4.31 (s, 1H); 5.00-

5.20 (m, 2H); 5.70-5.95 (m, 2H); 6.65-6.75 (m, 1H); 7.00-7.25 (m, 3H); 7.50-7.70 (m, 4H). Anal. calc. for $C_{32}H_{41}N_3O_2$: C, 76.92; H, 8.27; N, 8.41. Found: C, 76.71; H, 8.30; N, 8.39.

Example 6.5

Preparation of 4-[(7-allyl-2,7-diazatricyclo[4.4.0.0$^{3,8}$]dec-2-yl)-(3-methoxyphenyl)methyl]-N,N-diethylbenzamide

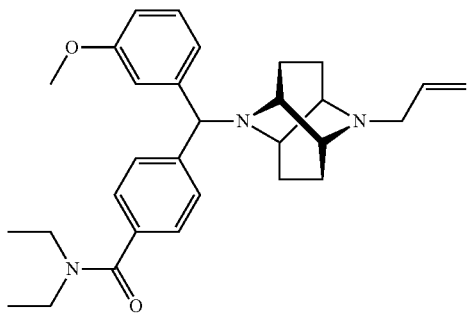

The procedure of Example 6.1 was repeated, but using the compound obtained in Example 5.5 instead of the compound of Example 5.1. The compound 4-[(7-allyl-2,7-diazatricyclo[4.4.0.0$^{3,8}$]dec-2-yl)-(3-methoxyphenyl)methyl]-N,N-diethyl benzamide was obtained. Yield: 80%. m.p.: 217-220° C.; IR (nujol) ($\lambda$=cm$^{-1}$) 1680 (C=O); $^1$H-NMR (CDCl$_3$) δ 1.00-1.95 (m, 16H); 2.77-2.89 (m, 2H); 3.15-3.30 (m, 2H); 3.32-3.40 (m, 2H); 3.40-3.60 (m, 2H); 3.79 (s, 3H); 5.00-5.25 (m, 3H); 5.70-5.90 (m, 1H); 6.65-6.75 (m, 1H); 7.00-7.30 (m, 5H); 7.53 (dd, 2H, J=2.0 and 8.0 Hz). Anal. calc. for $C_{30}H_{39}N_3O_2$: C, 76.07; H, 8.30; N, 8.87. Found: C, 76.21; H, 8.29; N, 8.89.

Example 6.6

Preparation of {4-[(7-allyl-2,7-diazatricyclo[4.4.0.0$^{3,8}$]dec-2-yl)-(3-methoxyphenyl)methyl]phenyl}-piperidin-1-yl-methanone

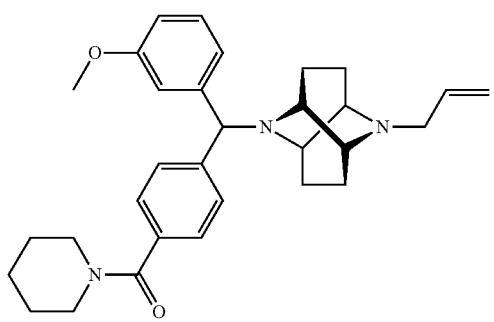

The procedure of Example 6.1 was repeated, but using the compound obtained in Example 5.6 instead of the compound of Example 5.1. The compound {4-[(7-allyl-2,7-diazatricyclo[4.4.0.0$^{3,8}$]dec-2-yl)-(3-methoxyphenyl)methyl]phenyl}-piperidin-1-yl-methanone was obtained. Yield: 90%. m.p.: 94-96° C.; IR (nujol) ($\lambda$=cm$^{-1}$) 1680 (C=O); $^1$H-NMR (CDCl$_3$) δ 1.15-2.00 (m, 18H); 2.75-2.85 (m, 2H); 3.20-3.40 (m, 2H); 3.60-3.75 (m, 2H); 3.78 (s, 3H); 5.00-5.25 (m, 3H); 5.70-5.90 (m, 1H); 6.65-7.40 (m, 6H); 7.95-8.15 (m, 2H). Anal. calc. for $C_{31}H_{39}N_3O_2$: C, 76.67; H, 8.09; N, 8.65. Found: C, 76.76; H, 8.12; N, 8.59.

Example 6.7

Preparation of 4-[(10-allyl-9,10-diazatricyclo[4.2.1.1$^{2,5}$]dec-9-yl)-(3-methoxyphenyl)methyl]-N,N-dimethylbenzamide

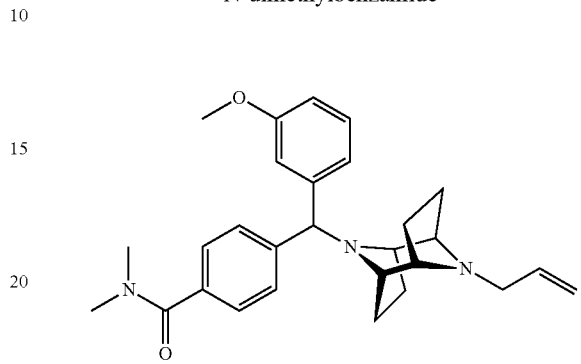

The procedure of Example 6.1 was repeated, but using the compound obtained in Example 5.7 instead of the compound of Example 5.1. The compound 4-[(10-allyl-9,10-diazatricyclo[4.2.1.1$^{2,5}$]dec-9-yl)-(3-methoxyphenyl)methyl]-N,N-dimethylbenzamide was obtained. Yield: 88%; m.p.: 100-103° C.; IR (nujol) ($\lambda$=cm$^{-1}$) 1670 (C=O); $^1$H-NMR (CDCl$_3$) δ 1.50-2.10 (m, 8H); 2.70-3.10 (m, 12H); 3.79 (s, 3H); 4.29 (s, 1H); 4.95-5.15 (m, 2H); 5.70-5.95 (m, 1H); 6.60-6.68 (m, 1H); 7.00-7.40 (m, 5H); 7.56 (d, 2H, J=7.4 Hz). Anal. calc. for $C_{28}H_{35}N_3O_2$: C, 75.47; H, 7.92; N, 9.43. Found: C, 75.16; H, 7.94; N, 9.39.

Example 6.8

Preparation of {4-[(7-allyl-2,7-diazatricyclo[4.4.0.0$^{3,8}$]dec-2-yl)-(3-methoxyphenyl)methyl]phenyl}-pyrrolidin-1-yl-methanone

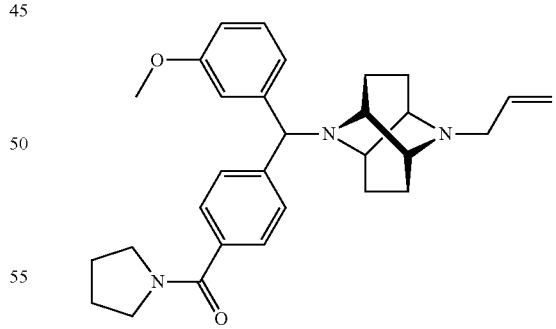

The procedure of Example 6.1 was repeated, but using the compound obtained in Example 5.8 instead of the compound of Example 5.1. The compound {4-[(7-allyl-2,7-diazatricyclo[4.4.0.0$^{3,8}$]dec-2-yl)-(3-methoxyphenyl)methyl]phenyl}-pyrrolidin-1-yl-methanone was obtained. Yield: quantitative; m.p.: 126-128° C.; IR (nujol) ($\lambda$=cm$^{-1}$) 1680 (C=O); $^1$H-NMR (CDCl$_3$) δ 1.10-2.00 (m, 12H); 2.70-3.00 (m, 4H); 3.20-3.50 (m, 4H); 3.50-3.70 (m, 2H); 3.77 (s, 3H); 5.00-5.25 (m, 3H); 5.70-5.90 (m, 1H); 6.65-6.80 (m, 1H); 7.00-7.35 (m, 3H); 7.40 (d, 2H, J=8.0 Hz); 7.53 (d, 2H, J=8.0 Hz). Anal. calc. for $C_{30}H_{37}N_3O_2$: C, 76.40; H, 7.91; N, 8.91. Found: C, 76.56; H, 7.88; N, 8.92.

Example 6.9

Preparation of 4-[(10-allyl-9,10-diazatricyclo [4.2.1.1$^{2,5}$]dec-9-yl)-(3-hydroxyphenyl)methyl]-N,N-diethylbenzamide

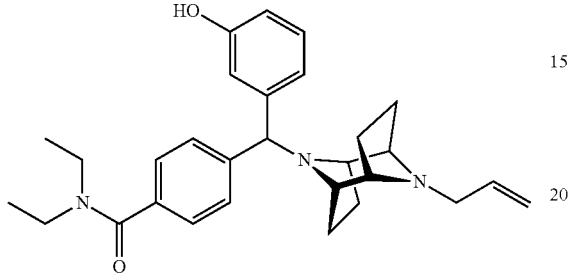

A solution of the compound obtained in Example 6.1 (0.50 mmoles) in dichloromethane (10 ml) is prepared and cooled to 0° C. Boron tribromide (2 equivalents) is added. The solution is stirred at 0° C. for 1.5 hours. 20 ml of an aqueous solution 1% by weight of potassium hydroxide are then added. The reaction mixture is diluted with 20 ml of dichloromethane and washed with water (15 ml for three times). The pooled organic phases are dehydrated with sodium sulphate, filtered and evaporated under vacuum. The obtained residue is recrystallized from a solvent mixture acetonitrile/water 1/1 (v/v). The compound 4-[(10-allyl-9,10-diazatricyclo [4.2.1.1$^{2,5}$]dec-9-yl)-(3-hydroxyphenyl)methyl]-N,N-diethyl-benzamide is obtained. Yield: quantitative. m.p.: 112-115° C.; IR (nujol) ($\lambda$=cm$^{-1}$) 1680 (C=O), 3400 (OH); $^1$H-NMR (CDCl$_3$) $\delta$ 1.00-1.35 (m, 6H); 1.60-2.30 (m, 8H); 2.70-3.10 (m, 6H); 3.20-3.35 (m, 2H); 3.45-3.75 (m, 2H); 4.26 (s, 1H); 5.30-5.50 (m, 2H); 6.40-6.60 (m, 2H); 6.65-6.75 (m, 1H); 6.90-7.40 (m, 5H); 7.51 (d, 2H, J=8.0 Hz). Anal. calc. for $C_{29}H_{37}N_3O_2$: C, 75.78; H, 8.11; N, 9.14. Found: C, 75.49; H, 8.13; N, 9.17.

Example 6.10

Preparation of 4-[(10-allyl-9,10-diazatricyclo [4.2.1.1$^{2,5}$]dec-9-yl)-(3-hydroxyphenyl)methyl]-N,N-dimethylbenzamide

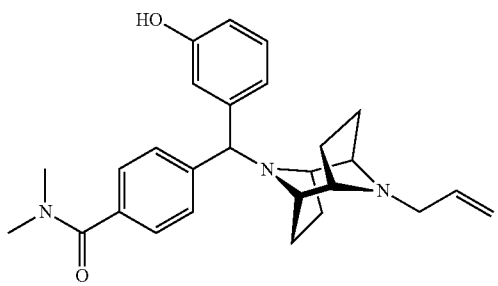

The procedure of Example 6.9 was repeated, but using the compound obtained in Example 6.7 instead of the compound of Example 6.1. The compound 4-[(10-allyl-9,10-diazatricyclo[4.2.1.1$^{2,5}$]dec-9-yl)-(3-hydroxyphenyl)methyl]-N,N-dimethylbenzamide was obtained. Yield: 90%. m.p.: 99-101° C.; IR (nujol) ($\lambda$=cm$^{-1}$) 1650 (C=O), 3300 (OH); $^1$H-NMR (CDCl$_3$) $\delta$ 1.50-2.10 (m, 8H); 2.50-3.10 (m, 12H); 4.30 (s, 1H); 5.30-5.55 (m, 2H); 6.40-6.60 (m, 1H); 6.65-6.80 (m, 1H); 7.00-7.80 (m, 7H); 8.70 (bs, 1H). Anal. calc. for $C_{27}H_{33}N_3O_2$: C, 75.14; H, 7.71; N, 9.74. Found: C, 74.98; H, 7.68; N, 9.58.

Example 6.11

Preparation of {4-[(10-allyl-9,10-diazatricyclo [4.2.1.1$^{2,5}$]dec-9-yl)-(3-hydroxyphenyl)methyl]phenyl}-pyrrolidin-1-yl-methanone

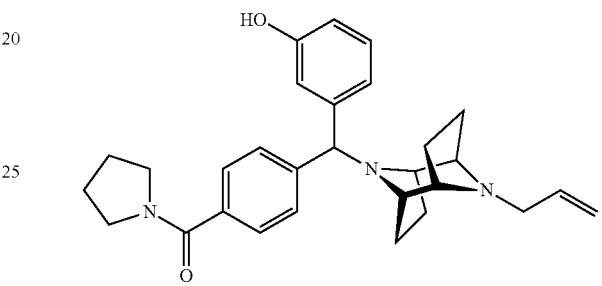

The procedure of Example 6.9 was repeated, but using the compound obtained in Example 6.2 instead of the compound of Example 6.1. The compound {4-[(10-allyl-9,10-diazatricyclo[4.2.1.1$^{2,5}$]dec-9-yl)-(3-hydroxyphenyl)methyl]phenyl}-pyrrolidin-1-yl-methanone was obtained. Yield: 93%. m.p.: 156-158° C.; IR (nujol) ($\lambda$=cm$^{-1}$) 1650 (C=O), 3300 (OH); $^1$H-NMR (CDCl$_3$) $\delta$ 1.60-2.20 (m, 12H); 2.50-3.10 (m, 5H); 3.55-3.80 (m, 3H); 4.28 (s, 1H); 5.20-5.60 (m, 2H); 6.40-6.60 (m, 1H); 6.85-7.00 (m, 1H); 7.20-7.60 (m, 6H); 8.53 (bs, 1H). Anal. calc. for $C_{29}H_{35}N_3O_2$: C, 76.12; H, 7.71; N, 9.18. Found: C, 76.24; H, 7.73; N, 9.17.

Example 6.12

Preparation of {4-[(10-allyl-9,10-diazatricyclo [4.2.1.1$^{2,5}$]dec-9-yl)-(3-hydroxyphenyl)methyl]phenyl}-piperidin-1-yl-methanone

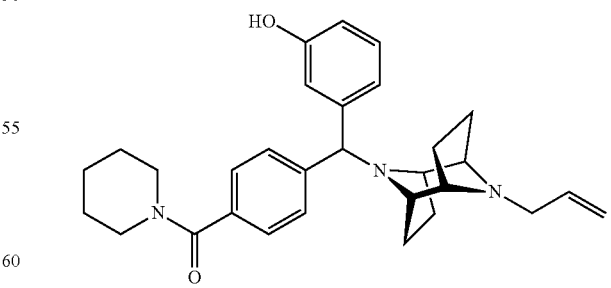

The procedure of Example 6.9 was repeated, but using the compound obtained in Example 6.3 instead of the compound of Example 6.1. The compound {4-[(10-allyl-9,10-diazatricyclo[4.2.1.1$^{2,5}$]dec-9-yl)-(3-hydroxyphenyl)methyl]phenyl}-piperidin-1-yl-methanone was obtained. Yield: quantitative. m.p.: 133-135° C.; IR (nujol) (λ=cm$^{-1}$) 1680 (C=O), 3300 (OH); $^1$H-NMR (CDCl$_3$) δ 1.40-1.90 (m, 10H); 1.95-2.00 (m, 4H); 2.55-2.75 (m, 4H); 3.00-3.20 (m, 2H); 3.22-3.80 (m, 4H); 4.35 (s, 1H); 5.35-5.60 (m, 2H); 6.45-6.70 (m, 1H); 6.75-6.85 (m, 1H); 7.00-7.40 (m, 5H); 7.53 (d, 2H, J=8.2 Hz); 8.95 (bs, 1H). Anal. calc. for C$_{30}$H$_{37}$N$_3$O$_2$: C, 76.40; H, 7.91; N, 8.91. Found: C, 76.55; H, 7.87; N, 8.92.

Example 6.13

Preparation of 4-[(10-allyl-9,10-diazatricyclo[4.2.1.1$^{2,5}$]dec-9-yl)-(3-hydroxyphenyl)methyl]-N-cyclohexylbenzamide

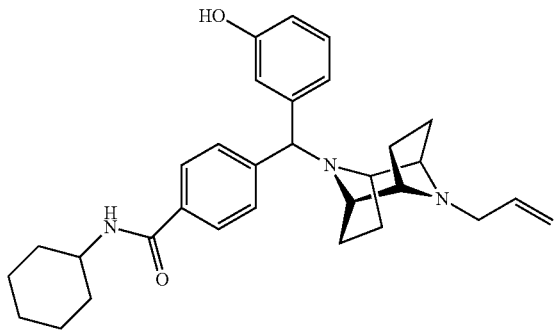

The procedure of example 6.9 was repeated, but using the compound obtained in Example 6.4 instead of the compound of Example 6.1. The compound 4-[(10-allyl-9,10-diazatricyclo[4.2.1.1$^{2,5}$]dec-9-yl)-(3-hydroxyphenyl)methyl]-N-cyclohexylbenzamide was obtained. Yield: 80%. m.p.: 68-70° C.; IR (nujol) (λ=cm$^{-1}$) 1690 (C=O), 3300 (OH); $^1$H-NMR (CDCl$_3$) δ 1.00-1.50 (m, 10H); 1.55-2.05 (m, 9H); 2.08-2.25 (m, 2H); 2.40-2.80 (m, 4H); 4.31 (s, 1H); 5.40-5.60 (m, 2H); 6.20-6.45 (m, 1H); 6.70 (d, 1H, J=7.8 Hz); 6.90-7.25 (m, 4H); 7.56 (d, 2H, J=8.0 Hz); 7.74 (d, 2H, J=8.0 Hz). Anal. calc. for C$_{31}$H$_{39}$N$_3$O$_2$: C, 76.67; H, 8.09; N, 8.65. Found: C, 76.85; H, 8.11; N, 8.63.

Example 6.14

Preparation of 4-[(7-allyl-2,7-diazatricyclo[4.4.0.0$^{3,8}$]dec-2-yl)-(3-hydroxyphenyl)methyl]-N,N-diethylbenzamide

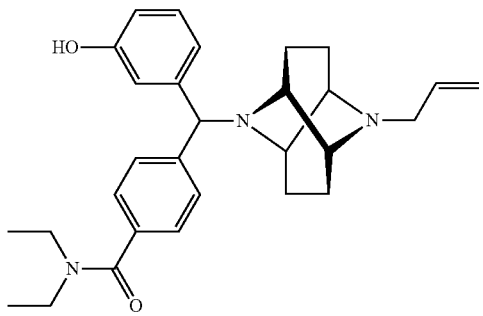

The procedure of Example 6.9 was repeated, but using the compound obtained in Example 6.5 instead of the compound of Example 6.1. The compound 4-[(7-allyl-2,7-diazatricyclo-[4.4.0.0$^{3,8}$]dec-2-yl)-(3-hydroxyphenyl)methyl]-N,N-diethylbenzamide was obtained. Yield: 75%. m.p: 147-150° C.; IR (nujol) (λ=cm$^{-1}$) 1685 (C=O), 3330 (OH); $^1$H-NMR (CDCl$_3$) δ 1.10-2.30 (m, 16H); 2.85-4.00 (m, 8H); 4.85 (s, 1H); 5.30-5.60 (m, 2H); 6.40-7.60 (m, 9H); 9.55 (bs, 1H). Anal. calc. for C$_{29}$H$_{37}$N$_3$O$_2$: C, 75.78; H, 8.11; N, 9.14. Found: C, 75.81; H, 8.06; N, 9.13.

Example 6.15

Preparation of {4-[(7-allyl-2,7-diazatricyclo[4.4.0.0$^{3,8}$]dec-2-yl)-(3-hydroxyphenyl)methyl]phenyl}-pyrrolidin-1-yl-methanone

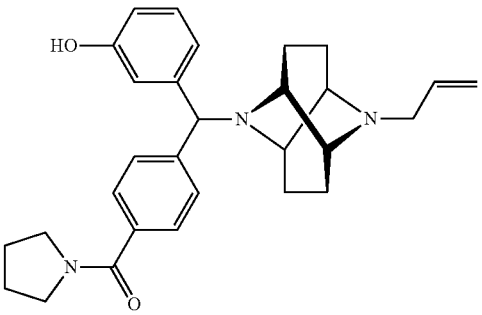

The procedure of Example 6.9 was repeated, but using the compound obtained in Example 6.8 instead of the compound of Example 6.1. The compound {4-[(7-allyl-2,7-diazatricyclo-[4.4.0.0$^{3,8}$]dec-2-yl)-(3-hydroxyphenyl)methyl]phenyl}-pyrrolidin-1-yl-methanone was obtained. Yield: quantitative. m.p.: 140-142° C.; IR (nujol) (λ=cm$^{-1}$) 1670 (C=O), 3300 (OH); $^1$H-NMR (CDCl$_3$) δ 1.30-2.40 (m, 12H); 2.80-3.15 (m, 2H); 3.20-4.00 (m, 8H); 4.90 (s, 1H); 5.35-5.60 (m, 2H); 6.30-6.55 (m, 1H); 6.70-6.80 (m, 1H); 6.85-6.95 (m, 1H); 7.00-7.15 (m, 1H); 7.20-7.40 (m, 3H); 7.50-7.60 (m, 2H); 9.20 (bs, 1H). Anal. calc. for C$_{29}$H$_{35}$N$_3$O$_2$: C, 76.12; H, 7.71; N, 9.81. Found: C, 75.89; H, 7.73; N, 9.70.

Example 6.16

Preparation of {4-[(7-allyl-2,7-diazatricyclo[4.4.0.0$^{3,8}$]dec-2-yl)-(3-hydroxyphenyl)methyl]phenyl}-piperidin-1-yl-methanone

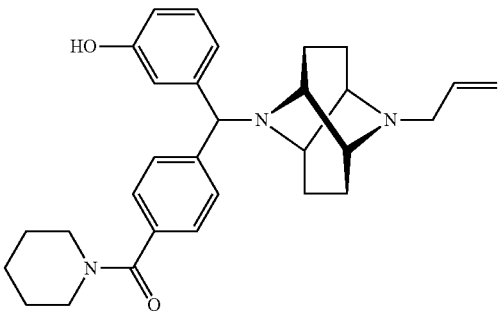

The procedure of Example 6.9 was repeated, but using the compound obtained in Example 6.6 instead of the compound of Example 6.1. The compound {4-[(7-allyl-2,7-diazatricyclo[4.4.0.0$^{3,8}$]dec-2-yl)-(3-hydroxy-phenyl)methyl]phenyl}-piperidin-1-yl-methanone was obtained. Yield: 91%. m.p.: 70-73° C.; IR (nujol) ($\lambda$=cm$^{-1}$) 1680 (C=O), 3400 (OH); $^1$H-NMR (CDCl$_3$) $\delta$ 1.20-1.90 (m, 20H); 3.15-3.40 (m, 2H); 3.55-3.80 (m, 2H); 5.20-5.45 (m, 3H); 6.10-6.20 (m, 1H); 6.60-7.30 (m, 6H); 7.80-8.00 (m, 3H). Anal. calc. for C$_{30}$H$_{37}$N$_3$O$_2$: C, 76.40; H, 7.91; N, 8.91. Found: C, 76.38; H, 7.89; N, 8.92.

Example 6.17

Preparation of 4-[(10-allyl-3,10-diazabicyclo[4.3.1] dec-3-yl)-(3-methoxyphenyl)methyl]-N,N-diethyl-benzamide

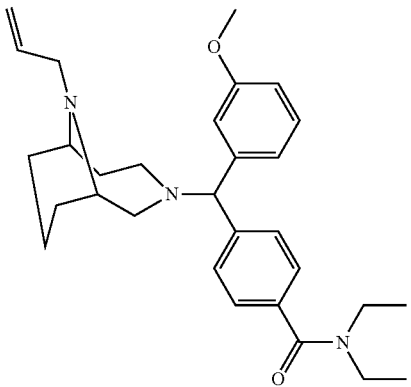 [SMILES: C=CCN1C2CCCC1CN(C(c1ccc(C(=O)N(CC)CC)cc1)c1cccc(OC)c1)CC2]

The procedure of Example 6.1 was repeated, but using the compound obtained in Example 5.9 instead of the compound of Example 5.1. The compound 4-[(10-allyl-3,10-diazabicyclo-[4.3.1]dec-3-yl)-(3-methoxyphenyl)methyl]-N,N-diethylbenzamide was obtained.

Yield: 50%; Rf=0.27 (CHCl$_3$/MeOH 9.5:0.5); IR (nujol) ($\lambda$=cm$^{-1}$) 1655 (C=O); $^1$H-NMR (CDCl$_3$): $\delta$ 1.00-1.48 (m, 7H), 1.51-1.72 (m, 3H), 1.72-1.95 (m, 3H), 1.95-2.14 (m, 2H), 2.41-2.92 (m, 4H), 3.14-3.38 (m, 3H), 3.38-3.65 (m, 4H), 3.78 (s, 3H), 4.42 (bs, 1H), 5.04-5.30 (m, 2H), 5.80-6.05 (m, 1H), 6.66-6.79 (m, 1H), 6.94-7.10 (m, 2H), 7.13-7.24 (m, 1H), 7.25-7.35 (m, 2H), 7.39-7.58 (m, 2H). Anal. calc. for C$_{30}$H$_{41}$N$_3$O$_2$: C, 75.75; H, 8.69; N, 8.83. Found: C, 75.69; H, 8.67; N, 8.82.

Example 6.18

Preparation of 4-[(9-allyl-3,9-diazabicyclo[4.2.1] non-3-yl)-(3-methoxyphenyl)methyl]-N,N-dimethyl-benzamide

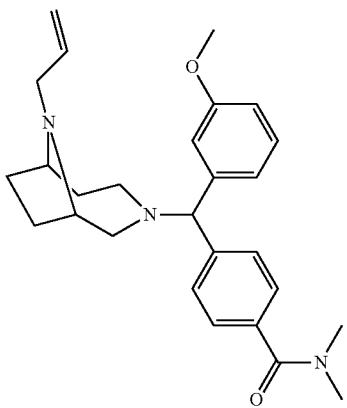 [SMILES: C=CCN1C2CCC1CN(C(c1ccc(C(=O)N(C)C)cc1)c1cccc(OC)c1)CC2]

The procedure of Example 6.1 was repeated, but using the compound obtained in Example 5.10 instead of the compound of Example 5.1. The compound 4-[(9-allyl-3,9-diazabicyclo-[4.2.1]non-3-yl)-(3-methoxyphenyl)methyl]-N,N-dimethylbenzamide was obtained.

Yield: 91%; IR (nujol) ($\lambda$=cm$^{-1}$) 1639 (C=O); $^1$H-NMR (CDCl$_3$): $\delta$ 1.41-1.65 (m, 3H), 1.75-1.94 (m, 1H), 2.09-2.28 (m, 2H), 2.72 (dd, 1H, J=2.2 and 10.9 Hz), 2.84-3.02 (m, 3H), 3.04 (s, 6H), 3.10-3.30 (m, 2H), 3.20 (d, 2H, J=8.0 Hz), 3.78 (s, 3H), 4.22 (s, 1H), 4.99-5.17 (m, 2H), 5.70-5.89 (m, 1H), 6.64-6.79 (m, 1H), 7.01-7.21 (m, 5H), 7.56 (d, 2H, J=8.2 Hz). Anal. calc. for C$_{27}$H$_{35}$N$_3$O$_2$: C, 74.79; H, 8.14; N, 9.69. Found: C, 74.66; H, 8.13; N, 9.67.

Example 6.19

Preparation of 4-[(9-allyl-3,9-diazabicyclo[3.3.1] non-3-yl)-(3-methoxyphenyl)methyl]-N-cyclohexyl-benzamide

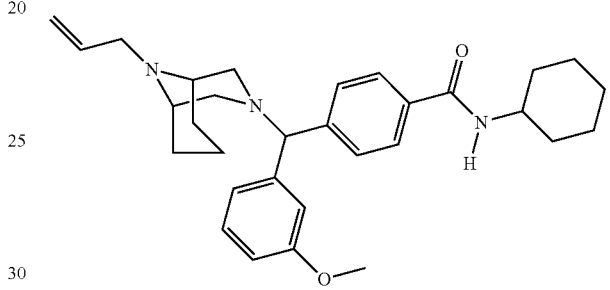

The procedure of Example 6.1 was repeated, but using the compound obtained in Example 5.11 instead of the compound of Example 5.1. The compound 4-[(9-allyl-3,9-diazabicyclo-[3.3.1]non-3-yl)-(3-methoxyphenyl)-methyl]-N-cyclohexylbenzamide was obtained. Yield: 93%; IR (nujol) ($\lambda$=cm$^{-1}$) 1639 (C=O); $^1$H-NMR (CDCl$_3$): $\delta$ 1.15-2.29 (m, 13H), 2.52-2.85 (m, 2H), 2.92-3.33 (m, 10H), 3.80 (s, 3H), 4.31 (s, 1H), 4.99-5.17 (m, 2H), 5.71-5.92 (m, 1H), 6.59-6.83 (m, 1H), 7.16-7.44 (m, 5H), 7.47 (bs, 1H, NH), 7.54 (d, 2H, J=7.9 Hz). Anal. calc. for C$_{31}$H$_{41}$N$_3$O$_2$: C, 76.35; H, 8.47; N, 8.62. Found: C, 76.29; H, 8.45; N, 8.61.

Example 6.20

Preparation of 4-[(3-allyl-3,8-diazabicyclo[3.2.1]oct-8-yl)-(3-methoxyphenyl)methyl]-N,N-diethylbenza-mide

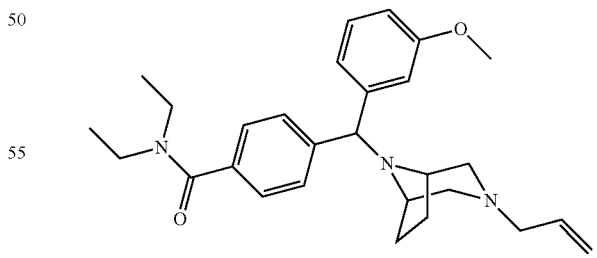

The procedure of Example 6.1 was repeated, but using the compound of Example 5.12 instead of the compound of Example 5.1. The compound 4-[(3-allyl-3,8-diazabicyclo [3.2.1]oct-8-yl)-(3-methoxyphenyl)-methyl]-N,N-diethyl-benzamide was obtained.

Yield: 89%; IR (nujol) ($\lambda$=cm$^{-1}$) 1643 (C=O); $^1$H-NMR (CDCl$_3$): $\delta$ 1.10-2.20 (m, 12H), 2.66-2.80 (m, 2H), 2.96-3.22

(m, 8H), 3.79 (s, 3H), 4.34 (s, 1H), 4.98-5.21 (m, 2H), 5.75-5.99 (m, 1H), 6.70-6.90 (m, 1H), 7.03-7.47 (m, 5H), 7.58 (d, 2H, J=8.0 Hz). Anal. calc. for $C_{28}H_{37}N_3O_2$: C, 75.13; H, 8.33; N, 9.39. Found: C, 75.08; H, 8.32; N, 9.36.

Example 6.21

Preparation of 4-[(6-allyl-3,6-diazabicyclo[3.1.1]hept-3-yl)-(3-methoxyphenyl)methyl]-N,N-diethylbenzamide

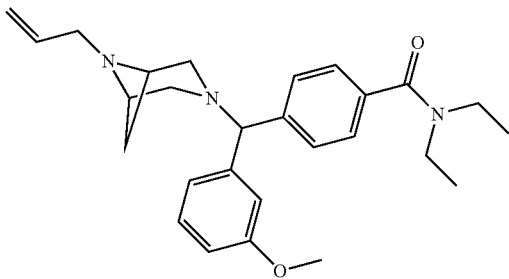 [SMILES: C=CCN1C2CC1CN(C(c1ccc(C(=O)N(CC)CC)cc1)c1cccc(OC)c1)C2]

The procedure of Example 6.1 was repeated, but using the compound obtained in Example 5.13 instead of the compound of Example 5.1. The compound 4-[(6-allyl-3,6-diazabicyclo-[3.1.1]hept-3-yl)-(3-methoxyphenyl)methyl]-N,N-diethylbenzamide was obtained.

Yield: 93%; IR (nujol) ($\lambda=cm^{-1}$) 1646 (C=O); $^1$H-NMR (CDCl$_3$): δ 1.15-2.25 (m, 11H), 2.57-2.88 (m, 2H), 2.94-3.21 (m, 7H), 3.80 (s, 3H), 4.27 (s, 1H), 4.95-5.12 (m, 2H), 5.78-5.98 (m, 1H), 6.64-6.88 (m, 1H), 6.94-7.41 (m, 5H), 7.56 (d, 2H, J=8.2 Hz). Anal. calc. for $C_{27}H_{35}N_3O_2$: C, 74.79; H, 8.14; N, 9.69. Found: C, 74.66; H, 8.13; N, 9.68.

Example 6.22

Preparation of 4-[(9-allyl-3,9-diazabicyclo[4.2.1]nonan-3-yl) (3-methoxyphenyl)methyl]-N,N-diethylbenzamide

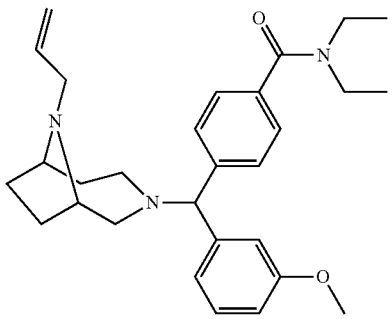 [SMILES: C=CCN1C2CCC1CN(C(c1ccc(C(=O)N(CC)CC)cc1)c1cccc(OC)c1)CC2]

The same procedure reported in Ex. 6.1 was repeated but using the compound obtained in Ex. 5.14 instead of the compound prepared in Ex. 5.1.

The synthesis afforded the compound 4-[(9-allyl-3,9-diazabicyclo[4.2.1]nonan-3-yl)-(3-methoxyphenyl)methyl]-N,N-diethylbenzamide.

Yield: 20%; Rf=0.32 (CHCl$_3$/MeOH 9.5:0.5); IR (nujol) ($\lambda$cm$^{-1}$) 1643 (C=O); $^1$H-NMR (CDCl$_3$): δ 1.03-1.26 (m, 6H), 1.40-1.51 (m, 1H), 1.70-1.91 (m, 2H), 1.92-2.02 (m, 2H), 2.21-2.40 (m, 2H), 2.47-2.60 (m, 2H), 2.72-2.85 (m, 1H), 3.17-3.32 (m, 5H), 3.39-3.56 (m, 3H), 3.77 (s, 3H), 4.40 (s, 1H), 5.06-5.22 (m, 2H), 5.87-6.02 (m, 1H), 6.68-6.74 (m, 1H), 6.92-6.96 (m, 1H), 6.98-7.05 (m, 1H), 7.14-7.21 (m, 1H), 7.26-7.29 (m, 2H), 7.37-7.41 (m, 1H), 7.42-7.48 (m, 1H). Anal. calc. for $C_{29}H_{39}N_3O_2$: C, 75.45; H, 8.52; N, 9.10. Found: C, 75.33; H, 8.51; N, 9.08.

Example 7

Affinity Towards the Opioidergic Receptors μ, δ, k

The affinity of the compounds synthesized towards the opioidergic receptors μ, δ, k has been evaluated in vitro by radioreceptorial binding studies by using the method reported hereinunder.

The receptorial binding method allows to establish if and with what affinity and specificity a specific compound binds to a particular receptor.

For evaluating the affinity of a compound to a particular receptor(s) it is used a preparation of a tissue wherein the particular receptor(s) is (are) present, with which the compound is contacted. The tested compound is challenged with a radioactive labelled compound whose affinity for the same receptor(s) is known. The ability of the tested compound to displace the radioactive compound from the receptor gives an index of the affinity of the compound under test for the specific receptor. The amount of radioactivity present in the receptor-compound complex allows furthermore to calculate with great accuracy the amount of compound bound to the receptor. By said method it is therefore possible to quickly establish the affinity of a new compound towards a specific receptor and thus determine its pharmacological activity. With the same experimental protocol it is possible to evaluate the affinity of the compound towards other receptors and thus establishing the specificity degree of the compound towards these further receptors.

The receptorial binding, technique, besides being used for the screening of new molecules with pharmacological activity, can give useful information on the changes taking place at receptorial level, related for example to a prolonged exposure to drugs and/or to particular pathologies. In these conditions, indeed, changes in the amount of the receptors present, or conformational changes can take place that alter the binding affinity of the agonists or antagonists, therefore affecting the functionality of the receptors themselves.

The experimentation has been carried out according to the guide lines of the European Community for the animal experimentation (EEC n. 86/609), by using laboratory animals (CD1 Charles River Italy male mice, Calco, LC, Italy) lodged twenty per cage, under standard stabulation conditions (temperature 22±2° C., relative humidity 60%, artificial lighting with light/dark cycle of 12 hours). The food and water were ad libitum.

The binding experiments were carried out according to the following methods:

Receptors k: CD1 male mice weighing 20-25 g were used. The animals were sacrificed by cervical dislocation and the complete brain (excluding the cerebellum) was quickly dissected and stored in ice. The tissue was homogeneized in 40 volumes (w/v) of Tris-HCl buffer (50 Mm, pH 7.4) by an Ultra-Turrax, then centrifuged for 20 minutes at 48,000×g in a centrifuge refrigerated at 4° C. The supernatant was resuspended in the same buffer and incubated at 37° C. for 30 minutes in an oscillating bath. At the end of the incubation the suspension was centrifuged at 48,000×g for 15 minutes and the obtained pellets resuspended in 10 volumes of Tris-HCl buffer. The binding experiment was carried out in a 1 ml volume of the suspension at the temperature of 25° C. with a protein content in the sample of about 800-1000 µg. Incubation was carried out for 60 minutes in the presence of various concentrations of the ligand $^3$H-U 69.593 (41.7 Ci/mmole). The non specific binding was determined in the presence of U69593 (10 µM). Incubation was then interrupted by performing a quick filtration by filtration apparatus Brandell®, Gaithersburg, Md., USA), by using GF/C filters (Whatman®).

Receptors µ and δ: the experiments were carried out according to the method described by Unterwald (1995), by using CD1 male mice weighing 20-25 g, lodged twenty in a cage, under standard stabulation conditions (temperature 22±2° C., relative humidity 60%, artificial lighting with light/dark cycle of 12 hours). After sacrifice, the complete brain (excluding the cerebellum) was quickly dissected. The so obtained tissues were rapidly homogenized, by a Polytron® equipment in 50 volumes of Tris HCl buffer (50 mM), pH 7.4 and the homogenate centrifuged at 48,000×g for 20 minutes at 4° C. The pellets obtained after centrifugation were suspended in 50 volumes of the same buffer and the so prepared suspensions were incubated at 37° C. for 45 minutes, in an oscillating bath, for making easier the separation of the endogenous opioids from the receptors. At the end of the incubation the suspensions were centrifuged at 48,000×g, for 20 minutes at 4° C. and the resulting pellets resuspended in 40 volumes of the Tris HCl (50 mM) buffer, pH 7.4. The suspension of cerebral membranes was used for the binding tests.

The binding experiment was carried out in a 2 ml volume, at the temperature of 25° C., with 50-100 µg of proteins in each sample; the incubation was carried out for 60 minutes in the presence of 1 nM [$^3$H]-DAMGO (54.5 Ci/mmole) or 1 nM [$^3$H]-DPDPE (45 Ci/mmole), respectively, for the study of the µ and δ receptors.

The non specific binding was determined in the presence of naloxone (10 µM). For determining the challenging curves, at least eight different concentrations were used for each of the compounds under test. Morphine at concentrations comprised between $10^{-10}$ and $10^{-5}$ M was used as a reference compound.

The incubation was interrupted by rapidly filtering the suspension through GF/B filters (Whatman®), by means of a filtration device (Brandel®, Gaithersburg, Md., USA). The filters were washed three times with 5 ml of cold Tris HCl (50 mM) buffer, pH 7.4.

The radioactivity was determined by a liquid scintillating counter (Tricarb® 2100, Packard, Meridien, Ill., USA) by using three ml of scintillating fluid (Ultima Gold MV, Packard, Meridien, Ill., USA).

The protein determination was carried out by the Bradford method (1976) by using the protocol and the reactants supplied by Bio-Rad (Milano, Italy).

The affinity of the compounds towards the µ, δ, κ receptors was expressed in $K_i$ terms.

The results of the binding experiments are shown in Table 1.

TABLE 1

Affinity of the compound of the invention towards the µ, δ and k opioidergic receptors. The affinity values are expressed as $K_i$

| Compound (Example) | $K_i$ µ (nM) | $K_i$ δ (nM) | $K_i$ k (nM) |
|---|---|---|---|
| 6.1 | 1633 ± 186 | 0.203 ± 0.032 | 55 ± 25 |
| 6.2 | 585 ± 101 | 1.00 ± 0.04 | 1000 ± 100 |
| 6.3 | 650 ± 96 | 1.03 ± 0.10 | 706 ± 101 |
| 6.4 | 2000 ± 289 | 45.0 ± 3.8 | 300 ± 58 |
| 6.5 | 533 ± 33 | 0.630 ± 0.030 | 1267 ± 67 |
| 6.6 | 293 ± 52 | 22.0 ± 4.0 | 4750 ± 250 |
| 6.9 | 20.0 ± 0.5 | 0.230 ± 0.030 | 4.80 ± 0.90 |
| 6.10 | 173.3 ± 14.5 | 0.900 ± 0.100 | 68.3 ± 9.0 |
| 6.11 | 23.7 ± 14.5 | 0.208 ± 0.020 | 4.70 ± 0.40 |
| 6.12 | 160.0 ± 15.3 | 1.30 ± 0.13 | 56.0 ± 8.0 |
| 6.13 | 36.7 ± 1.7 | 0.830 ± 0.200 | 3.60 ± 0.50 |
| 6.14 | 61.6 ± 13.0 | 0.270 ± 0.030 | 93.3 ± 17.6 |
| 6.15 | 63.2 ± 12.0 | 0.700 ± 0.080 | 50.0 ± 6.0 |
| 6.16 | 170 ± 10 | 2.50 ± 0.20 | 182 ± 9 |

Example 7A

Evaluation of the Activity of the Compounds of Formula (I) on the δ Opioidergic Receptors Through an Ex-Vivo Model (Isolated Organ: Mouse Vas Deferens)

It is known that agonist compounds of the delta opioid receptors are able to reduce the contractions electrically induced on the musculature of the mouse vas deferens in an ex-vivo model (E. J. Bilsky et al.; J.P.E.T.; 1995 April, 273 (1):359-366). Said effect is antagonized by selective antagonists of the delta opioid receptors, for example the compounds ICI 17.4864 and Naltrindol.

For evaluating the activity of the compounds of the invention on the delta opioid receptors, the compounds respectively obtained in Examples 6.1 and 6.9 were subjected to tests carried out on the basis of the method described by E. J. Bilsky et al. (J.P.E.T., 1995 April; 273 (1):359-366). The experiments were carried out on samples of vas deferent segments taken from CD1 mice (25-30 grams) immediately after sacrifice. After the explant, the vas deferent segments were transferred in a Petri dish containing a Krebs oxygenated solution (118.2 mM NaCl, 4.75 mM KCl, 1.19 mM $KH_2PO_4$, 25.0 mM $NaHCO_3$, 11.0 mM glucose, and 2.54 mM $CaCl_2$) in order to proceed to the cleaning of the samples and their subsequent dissection in segments. Segments of vas deferens were so obtained having a length of 1.0-1.2 cm. They were thus immersed in tubs containing 10 ml of an oxygenated Krebs solution (95% $O_2$ and 5% $CO_2$) and kept at a temperature of 37° C. One end of the vas deferens segment was attached to a fixed support, at the tub bottom, while the other end was connected to an isometric force transducer (WPI Fort10, Biological Instruments, Besozzo, Italy) for the registration of the contractions induced by electric stimuli. The samples were then allowed to equilibrate for 60 minutes, changing the Krebs solution every 15 minutes. The samples were then subjected to treatment cycles wherein the electrical stimulation lasted 3 minutes, with an interval of 15 minutes before the following stimulation. The isometric contractions were evoked with sequences of 3 pulses (sequence frequency 0.1 Hz; pulse duration 2 ms) by means of platinum electrodes placed at the sides of the samples. The electrical stimuli were generated by a Grass S88K stimulator and amplified (multiplexing pulse booster 316S; Ugo Basile, Comerio, Italy). The musculature contractions of the vas deferens were monitored by a computer, recorded and analyzed by an analysis system (PowerLab 400). The compounds of the invention were added to the vas deferens in cumulative doses, in the absence or in the presence of one of the following antagonists of the delta opioid receptors: ICI 17.4864 and Naltrindol.

The effect of the tested compounds on the contractions of vas deferens musculature was expressed in percent, calculated by referring the amplitude of the contractions induced by the electrical stimulations after each addition of the test compound to the amplitude of the contractions obtained in the absence of the same compound (100%).

The results obtained with the compounds of Examples 6.1 and 6.9 are reported, respectively, in Table 2 and in Table 3. The results are an average of the data obtained in seven different experiments.

The obtained results show that both compounds of Examples 6.1 and 6.9 inhibited the contractions induced by electrically stimulating the vas deferens musculature of mice. Said inhibitory action was antagonized by the compounds selective for the delta opioidergic receptor ICI 17.4864 or Naltrindol. The obtained results show that both compounds have an agonist activity towards the delta opioid receptors.

TABLE 2

Model ex-vivo (isolated organ: mouse vas deferens) % contraction inhibition in the presence of the compound of Ex. 6.1 (conc. moles/litre) and after addition of Naltrindol NTI (conc. NTI = $5 \times 10^{-8}$ M). The average values of the results obtained in 7 experiments are reported in the Table.

| | Concentration compound Ex. 6.1 | | | | | |
|---|---|---|---|---|---|---|
| | $10^{-11}$ | $10^{-10}$ | $10^{-9}$ | $10^{-8}$ | $10^{-7}$ | $10^{-6}$ |
| Compound Ex. 6.1 | 5.5 | 16.0 | 32.0 | 51.0 | 71.5 | 86.0 |
| Compound Ex. 6.1 + NTI | 4.0 | 5.0 | 11.5 | 19.0 | 24.9 | 41.0 |

TABLE 3 model ex-vivo (isolated organ: mouse vas deferens) % contraction inhibition in the presence of the compound of Ex. 6.9(conc. moles/litre) and after addition, respectively, of Naltrindol NTI (conc. NTI = $5 \times 10^{-8}$ M) and of ICI 17.4864 (conc. IC 17.4864 = $2 \times 10^{-6}$ M). The average values of the results obtained in 7 experiments are reported in the Table

| | Concentration compound Ex. 6.9 | | | | | |
|---|---|---|---|---|---|---|
| | $10^{-11}$ | $10^{-10}$ | $10^{-9}$ | $10^{-8}$ | $10^{-7}$ | $10^{-6}$ |
| Compound Ex. 6.9 | 7.5 | 17.0 | 40.0 | 70.0 | 83.0 | 85.0 |
| Compound Ex. 6.9 + NTI | 3.0 | 4.5 | 5.2 | 8.9 | 29.0 | 67.5 |
| Compound Ex. 6.9 + ICI 17.4864) | 1.8 | 2.5 | 4.0 | 9.5 | 28.2 | 52.2 |

Example 8

Preparation of an Emulsion Containing the Compounds of Formula (I)

0.05 g of the compound obtained in Ex. 6.1 were dissolved in 1.95 grams of Miglyol® 812S (triglycerides of the capric/caprylic acid— Sasol). The oily phase was heated to 70° C., and an aqueous solution of 1 g of nonionic surfactant Solutol® HS15 ((polyethylenglycol 660 hydroxystearate—Basf) in 7 ml of distilled water, kept at the same temperature, was dripped under stirring (1 drop/second). Stirring was effected by an ultraturrax Politron turboemulsifier (10,000 rpm with 7 mm probe) for further 15 minutes. 10 g of emulsion were obtained.

The emulsion was transferred into a 25 ml glass cylinder cooled to 4° C. After one hour the emulsion was warmed to 25° C.

The composition % by weight) of the emulsion was the following:

| Oil Miglyol ® 812S: | 19.5% |
| Surfactant Solutol ® HS15: | 10% |
| Water: | 70% |
| Compound Ex. 6.1: | 0.5% |

The emulsion was stored at the temperature of 25° C. and did not show phase separation at least for five days from the preparation.

Example 9

Preparation of an Emulsion Containing the Compounds of Formula (I)

0.05 grams of the compound obtained in Example 6.16 are dissolved in a mixture of 1.45 g of soya oils (pharmaceutical grade). After heating to 60° C., the oily phase was dripped under stirring, by using the turboemulsifier of Ex. 8, to a solution of 2.5 g of the block copolymer with polyoxyethylene and polyoxypropylene chains Lutrol® F127 (Basf) (surfactant) in 6 ml of physiological solution (aqueous phase), kept at the same temperature.

At the end the emulsion was cooled to 4° C. and then warmed to the temperature of 25° C. as described in Ex. 8. 10 g of emulsion were obtained.

The composition (% by weight) of the components of the emulsion is the following:

| Soya oil: | 14.5% |
| Lutrol ® F127: | 25% |
| Aqueous phase: | 60% |
| Compound Example 6.16: | 0.5% |

The emulsion does not show phase separation at least for five days from the preparation if kept at the temperature of 25° C.

Example 10

Preparation of a Microemulsion Containing the Compounds of Formula (I)

4.0 mg of the compound obtained in Ex. 6.1 were solubilized at 25° C. in 6.0 mg of the triglyceride Miglyol® 812S (Sasol Germany GmbH). To the oily solution 45.0 mg of the non-ionic surfactant Solutol® HS15 (Basf) and 2.445 g of physiological solution were added under stirring as in Example 9. The liquid mixture was heated for 5 minutes at 40° C. and then cooled at room temperature. The final liquid phase, completely liquid and isotropic at 25° C., was a microemulsion having the following composition (% by weight):

| | |
|---|---|
| Compound Ex. 6.1 | 0.16% |
| Oil (Miglyol ® 812S) | 0.24% |
| Surfactant Solutol ® HS15 | 1.80% |
| Aqueous phase (physiological solution) | 97.80% |

Example 11

Preparation of a Microemulsion Containing the Compounds of Formula (I)

The procedure of Ex. 10 was repeated, but substituting the oil Miglyol® 810 (Sasol Germany GmbH) with a mixture formed of equal weight amounts of Miglyol® 810 oil and Imwitor® 308 oil (monoglyceride of the caprylic acid—Sasol Germany GmbH). The microemulsion was completely liquid and isotropic at 25° C. The composition was the following (% by weight):

| | |
|---|---|
| Compound Ex. 6.1 | 0.16% |
| Oil Miglyol ® 810 | 0.12% |
| Oil Imwitor ® 308 | 0.12% |
| Surfactant Solutol ® HS15 | 1.80% |
| Aqueous phase (physiological solution) | 97.80% |

Example 12

Preparation of Particles of Polylactate-Polyglycolate Containing the Compounds of Formula (I)

10 mg of the compound obtained in Ex. 6.13 (active principle) and 100 mg of copolymer PLA-PLGA 50:50 having average molecular weight in the range 40,000-75,000 (Sigma Aldrich), were dissolved in 4 ml of ethyl acetate. The obtained organic solution was emulsified in 8 ml of an aqueous solution at 5% by weight of Solutol® HS15 (Basf) by mixing for 30 minutes by means of an ultraturrax Politron turboemulsifier (10,000 rpm with 7 mm probe).

From the emulsion the organic solvent (ethyl acetate) was then removed by heating to 50° C. in a rotating evaporator. An aqueous dispersion of PLA-PLGA particles containing the compound of Example 6.13 was then formed. The aqueous dispersion was subjected to three washing cycles by centrifuging in centrifuge AMICON™ test tubes, having membranes with 100,000 MWCO cut off. Each washing cycle was carried out at 4,000 rpm for 20 minutes, by adding each time 15 ml of distilled water in the upper compartment containing the particles.

At the end of the washings the particle aqueous dispersion was lyophilized under the following conditions: temperature: −40° C., pressure: $5 \times 10^{-2}$ mbar, time: 24 hours.

The obtained particles were characterized both by transmission electronic microscopy (TEM), and by Photon Correlation Spettroscopy (PCS). The average diameters determined for the particles were the following: 100±20 nm by TEM and 152±5 nm by PCS.

The active principle content englobed in the particles was determined by dissolving in dichloromethane a known amount of the final sample and analyzing then by UV/visible spectrophotometry the obtained organic solution. The amount of active principle present in the lyophilized sample of nanoparticles was equal to 50% of that initially solubilized in ethylacetate.

Example 13

Evaluation of the Analgesic Effect of the Compounds of Formula (I) In Vivo

One of the most important therapeutic indications of agonist compounds of the opioidergic receptors is pain treatment. Morphine is the reference compound of this class of opioidergic derivatives and its use is recommended for treating acute and chronic pain.

In order to evaluate the therapeutic properties of the compounds of formula (I) agonists of the delta opioid receptors in pain treatment, the Tail Flick test has been used, which is of wide use in the evaluation of pain threshold in laboratory animals.

In the Tail Flick test it is determined the time elapsed between the exposure of one part of the mouse tail (2 cm measured from the tail tip) to a small heat source and the time when the animal moves away the tail (Ruiu) S. et al. in J. Pharmacol. Exp. Ther.; 306 (1) (2003) 363-370). This time interval is automatically calculated by a specific equipment for the Tail-Flick test (Apparatus for the Tail Flick, Ugo Basile, Italy). The equipment is provided with an infrared lamp that is the heat regulatable source. For avoiding lesions to the tail tissues a maximum latency time has been fixed (cut-off=12 sec), after which the tail is moved away from the heat source.

The values of the latency time obtained in the experimentation were expressed in MPE % (maximum possible effect %), according to the formula:

$$MPE \ \% = \frac{[\text{Test Latency (sec.)} - \text{Base Latency(sec.)}]}{\text{Cut off (sec.)} - \text{Base Latency (sec.)}} \times 100$$

wherein:

Test Latency is the time in seconds elapsed before the animal moves away the tail from the heat source, Base Latency is the time in seconds elapsed before the same, untreated animal moves away the tail from the heat source.

The analgesic potency of the compound obtained in Example 6.1 was evaluated. The compound was solubilized in an aqueous solution (carrier), formed of a mixture of a physiological solution, ethanol and Cremophor® EL in the ratios by volume: 18.5:1.0:0.5. The blank or control was the carrier. The test compound was administered by intraperitoneal (i.p.) route, by using a solution volume to obtain a dose of 5 mg/kg.

The duration of the analgesic effect was evaluated by determining the MPE % values obtained at different times (20, 40, 60, 120 minutes) from administration of the compound and of the corresponding control (carrier).

The results are reported in Table 4 and show that the compounds of formula (I) are able to significantly increase the pain threshold, since the MPE % values within 120 minutes from the administration are significantly higher than those of the corresponding control (carrier). The compounds of the present invention can therefore be used as analgesic drugs.

TABLE 4

Tail Flick Test. The compound of Ex. 6.1 was administered at the dose of 5 mg/Kg. The reported values are the average ± SEM of 6 animals for each experimental group and observation time.

| | MPE % | | | |
|---|---|---|---|---|
| | 20 min | 40 min | 60 min | 120 min |
| Control (Carrier) | −1.8 ± 1.1 | −0.7 ± 0.5 | −2.0 ± 0.8 | 0.5 ± 0.3 |
| Compound Ex. 6.1 | 15.1 ± 3.5 | 50.1 ± 12.0 | 20.0 ± 3.0 | 13.2 ± 2.8 |

Example 14

Evaluation In Vivo of the Analgesic Effect of the Compounds of Formula (I)

Example 13 was repeated but using the compound synthesized in Ex. 6.9. The analgesic activity was evaluated at 30, 60, 120 and 240 minutes from the administration of the compound. The compound was administered at the dose of 5 mg/Kg after solubilization in an aqueous solution (carrier) formed of physiological solution, ethanol and Cremophor® EL in the same ratios as indicated in Example 13.

The results are reported in Table 5 and confirm that the compounds of formula (I) increase significantly the pain threshold as the MPE % values within 120 minutes from the administration are significantly higher than those of the corresponding carrier. Therefore they have analgesic properties.

Example 15

Evaluation In Vivo of the Activity of the Compounds of the Invention in the Analgesic Effect Modulation of the Morphine In order to evaluate the property of the compounds of formula (I) in the modulation of the analgesic effect of morphine, the Tail Flick test was carried out by using either only morphine or morphine in association with the compound of Ex. 6.9. The procedure described in Ex. 13 was repeated by recording the MPE % values at different times from the administration of the tested compounds: 30, 60, 120 and 240 minutes. The compounds were administered by intraperitoneal (i.p.) route at the following doses:

Morphine: 10 mg/kg,
Morphine+compound Ex. 6.9: respectively 10 mg/kg and 5 mg/kg.
Compound Ex. 6.9 5 mg/Kg.

The obtained results are reported in Table 5. They show that the administration of morphine in association with the compounds of formula (I) produces an analgesic effect higher than that of morphine only.

By comparing the MPE % values determined at 120 minutes from the administration, respectively, of the morphine and of the corresponding mixture with the compound of Ex. 6.9, it is observed that by using morphine, the latter mixture maintains for a longer time the analgesic effect in the experimental animal in comparison with morphine alone. Besides the two compounds in the mixture show a synergism of action at 120 minutes from administration, since the MPE % is higher than the sum of the MPE % of morphine and of the compound of Example 6.9, respectively.

The compounds of formula (I), having affinity and selectivity for the delta opioid receptors, are therefore able to modulate the analgesic effect of the morphine.

TABLE 5

Tail Flick Test. The morphine has been administered at the dose of 10 mg/Kg in both experiments, while the compound of Ex. 6.9 has been administered at the dose of 5 mg/Kg. The reported values are the average ± SEM of 6 animals for each experimental group and observation time.

| | MPE % | | | |
|---|---|---|---|---|
| | 30 min | 60 min | 120 min | 240 min |
| Control | −0.8 ± 0.6 | −7.0 ± 2.0 | −2.5 ± 1.0 | −1.8 ± 0.8 |
| Morphine | 60.1 ± 6.0 | 85.1 ± 10.1 | 48.0 ± 7.0 | −3.8 ± 1.8 |
| Morphine + Compound Ex. 6.9 | 62.5 ± 6.2 | 98.1 ± 1.6 | 97.0 ± 2.0 | 1.0 ± 0.8 |
| Ex. 6.9 | 30.1 ± 2.7 | 32.8 ± 10.0 | 18.5 ± 2.0 | 1.2 ± 0.6 |

The invention claimed is:

1. A compound of formula (I):

$$A_1\text{-}D_1\text{-}T_1 \tag{I}$$

wherein:
$A_1$ is a group of formula (II):

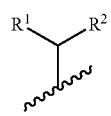

(II)

wherein:
$R^1$ is phenyl wherein one of the ring hydrogen atoms is substituted with a group selected from C(O)R', C(O)OR', C(O)NHR' or C(O)NR$^3$R$^4$, wherein:
R' is selected from H, alkyl, alkenyl, alkylthio, and from the following optionally substituted groups: cycloalkyl, heterocycloalkyl, aryl, heteroaryl, cycloalkylalkyl, heterocycloalkylalkyl, arylalkyl or heteroarylalkyl,
$R^3$ and $R^4$, equal to or different from each other, are selected from alkyl, alkenyl, alkylthio, and from the following optionally substituted groups: cycloalkyl, heterocycloalkyl, aryl, heteroaryl, cycloalkylalkyl, heterocycloalkylalkyl, arylalkyl, heteroarylalkyl, or together with the nitrogen atom to which they are linked, they form a 5-7 membered ring,
$R^2$ is phenyl, wherein one or more hydrogen atoms of the ring are optionally substituted with groups selected from: halogen, alkyl, cycloalkyl, heterocycloalkyl, phenyl, benzyl, heteroaryl, alkenyl, alkylthio, cyano, SO$_2$NH$_2$, isothiocyanate, OR$^5$, NO$_2$, NHR$^5$ or NR$^6$R$^7$, wherein:
$R^5$ is selected from H, alkyl, alkenyl, alkylthio, and from the following optionally substituted groups: cycloalkyl, heterocycloalkyl, aryl, heteroaryl, cycloalkylalkyl, heterocycloalkylalkyl, arylalkyl or heteroarylalkyl,
$R^6$ and $R^7$, equal to or different from each other, are selected from alkyl, alkenyl, alkylthio, and from the following optionally substituted groups: cycloalkyl, heterocycloalkyl, aryl, heteroaryl, cycloalkylalkyl, heterocycloalkylalkyl, arylalkyl, heteroarylalkyl, or together with the nitrogen atom to which they are linked, they form a 5-7 membered ring.

$D_1$ is a structure of formula (D1):

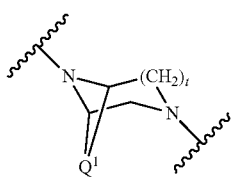

wherein t is 1 and,
$Q_1$ is —$CH_2$—$CH_2$,
$T_1$ is a group selected from H, alkyl, alkenyl, alkynyl, and from the following optionally substituted groups: cycloalkyl, heterocycloalkyl, aryl, heteroaryl, cycloalkylalkyl, heterocycloalkylalkyl, arylalkyl or heteroarylalkyl,
wherein
when R', $R^3$, $R^4$, $T_1$ have the meaning of cycloalkyl, heterocycloalkyl, aryl, heteroaryl, cycloalkylalkyl, heterocycloalkylalkyl, arylalkyl, heteroarylalkyl groups,
when $R^2$ is substituted with cycloalkyl, heteroacycloalkyl, phenyl, benzyl or heteroaryl,
one or more hydrogen atoms of the ring are optionally substituted with one or more groups selected from halogen, alkyl, cycloalkyl, heterocycloalkyl, phenyl, benzyl, heteroaryl, alkenyl, alkylthio, cyano, $SO_2NH_2$, isothiocyanate, $OR^5$, $NO_2$, $NHR^5$ or $NR^6R^7$, wherein $R^5$, $R^6$ and $R^7$ are as above defined,
and pharmaceutically acceptable salts or stereoisomers thereof.

2. The compound according to claim 1, wherein:
alkylthio is a —S—$R^8$ group wherein $R^8$ is selected from alkyl, cycloalkyl, alkenyl, or heterocycloalkyl.

3. The compound according to claim 1, wherein:
$R^1$ is phenyl wherein the hydrogen atom at the pare position, of the ring is substituted with a group selected from C(O)R', C(O)OR', C(O)NHR' or C(O)$NR^3R^4$, wherein:
R' is selected from: H, $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings with $C_1$-$C_8$ alkyl chains, $R^3$ and $R^4$, equal to or different from each are other, are selected from $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl or heteroarylalkyl, wherein said cycloalkylalkyl, heterocycloalkylalkyl arylalkyl, heteroarylalkyl are monocyclic rings with $C_1$-$C_8$ alkyl chains, or $R^3$ and $R^4$ with the nitrogen atom to which they are linked form a 5-7 membered ring,
$R^2$ is phenyl, wherein one or more hydrogen atoms of the ring are optionally substituted with the following groups: halogen, $C_1$-$C_7$ alkyl, $C_3$-$C_8$ monocyclic cycloalkyl, $C_2$-$C_7$ alkenyl, cyano, $SO_2NH_2$, isothiocyanate, $OR^5$, $NO_2$, $NHR^5$, $NR^6R^7$ or —S—$R^9$ wherein $R^9$ is $C_1$-$C_7$ alkyl, wherein:
$R^5$ is selected from H, $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylakyl, arylalkyl or heteroarylalkyl, wherein said cycloalkylalkyl, heterocycloalkylalkyl, arylalkyl, heteroarylalkyl are monocyclic rings with $C_1$-$C_8$ alkyl chains, $R^6$ and $R^7$, equal to or different from each other, are selected from $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings with $C_1$-$C_8$ alkyl chains, or $R^6$ and $R^7$ together with the nitrogen atom to which they are linked form a 5-7 membered ring,
$T_1$ is selected from H, $C_1$-$C_{10}$ alkyl, $C_3$-$C_{10}$ alkenyl, $C_3$-$C_{10}$ alkynyl, monocyclic cycloalkyl, heterocycloalkyl, aryl, heteroaryl, cycloalkylalkyl, heterocycloalkylalkyl, arylalkyl, heteroarylalkyl.

4. The compound according to claim 1, wherein:
$R^1$ is phenyl wherein the hydrogen at the para position of the ring is subtituted with a group selected from C(O)R', C(O)OR', C(O)NHR' or C(O)$NR^3R^4$, wherein:
R' is selected from: $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl, heteroarylalkyl, wherein said cycloalkylalkyl, heterocycloalkylalkyl, arylalkyl, heteroarylalkyl are monocyclic rings with $C_1$-$C_3$ alkyl chains,
$R^3$ and $R^4$, equal to or different from each other, are selected from $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl, heteroarylalkyl, wherein said cycloalkylalkyl, heterocycloalkylalkylarylalkyl, heteroarylalkyl are monocyclic rings with $C_1$-$C_3$ alkyl chains, or $R^3$ and $R^4$ together with the nitrogen atom to which they are linked form a 5-7 membered ring,
$R^2$ is phenyl wherein one or more hydrogen atoms of the ring are optionally substituted with one or more groups, equal to or different from each other, selected from: halogen, $C_1$-$C_7$ alkyl, cyano, $SO_2NH_2$, isothiocyanate, $OR^5$, $NO_2$, $NHR^5$ or $NR^6R^7$, wherein: $R^5$ is a substituent group selected from hydrogen or $C_1$-$C_7$ alkyl, $R^6$ and $R^7$ together with the nitrogen atom to which they are linked form a 5-7 membered ring, or $R^6$ and $R^7$, equal to or different from each other, are $C_1$-$C_7$ alkyl,
$T^1$ is a group selected from H, $C_1$-$C_7$ alkyl, $C_3$-$C_7$ alkenyl, $C_3$-$C_7$ alkynyl, monocyclic cycloalkyl, monocyclic heterocycloalkyl, aryl, heteroaryl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic rings substituted with $C_1$-$C_6$ alkyl chains.

5. The compound according to claim 1, wherein:
$R^1$ is phenyl wherein the hydrogen at the para position of the ring is substituted with a group selected from C(O)R', C(O)NHR' or C(O)$NR^3R^4$, wherein:
R' is selected from $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl, heteroarylalkyl, wherein said cycloalkylalkyl, heterocycloalkylalkyl, arylalkyl, heteroarylalkyl are monocyclic rings with $C_1$-$C_3$ alkyl chains, $R^3$ and $R^4$, equal to or different from each other, are selected from $C_1$-$C_7$ alkyl, $C_3$-$C_8$ monocyclic cycloalkyl, $C_3$-$C_8$ monocyclic heterocycloalkyl, phenyl, monocyclic heteroaryl, cycloalkylalkyl, heterocycloalkylalkyl, arylalkyl, heteroarylalkyl, wherein said cycloalkylalkyl, heterocycloalkylalkyl, arylalkyl, heteroarylalkyl are monocyclic rings with $C_1$-$C_3$ alkyl chains, or $R^3$ and $R^4$ together with the nitrogen atom to which they are linked form a 5-7 membered ring, $R^2$ is phenyl wherein one of the hydrogen atoms at the meta position of the ring is optionally substituted with a group selected from: halogen, $C_1$-$C_3$ alkyl, cyano, $SO_2NH_2$, isothiocyanate, $OR^5$, $NO_2$, $NHR^5$, $NR^6R^7$, wherein: $R^5$ is selected from hydrogen or $C_1$-$C_3$ alkyl, $R^6$ and $R^7$ together with the nitrogen atom to which they are linked form a 5-7 membered ring, or $R^6$ and $R^7$, equal to or different from each other, are $C_1$-$C_5$ alkyl, $T^1$ is a group selected from the following formulae:

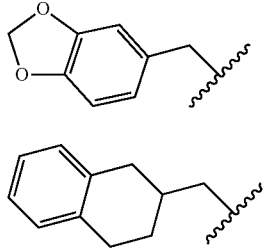

(T5)

(T6)

or $T^1$ is a group selected from H, $C_1$-$C_7$ alkyl, $C_3$-$C_7$ alkenyl, $C_3$-$C_7$ alkynyl, phenyl, monocyclic heteroaryl, monocyclic cycloalkyl, monocyclic heterocycloalkyl, cycloalkylalkyl, heterocycloalkylalkyl, arylalkyl or heteroarylalkyl, wherein said cycloalkylalkyl, heterocycloalkylalkyl, arylalkyl, heteroarylalkyl are monocyclic ring with $C_1$-$C_3$ alkyl chains.

6. The compound according to claim 1 selected from the following:

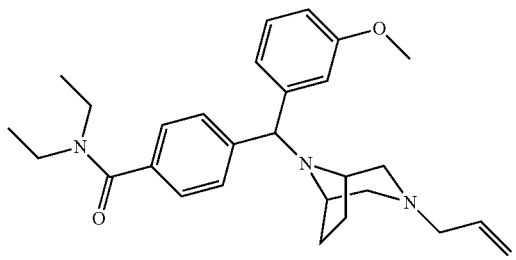

(I-Id)

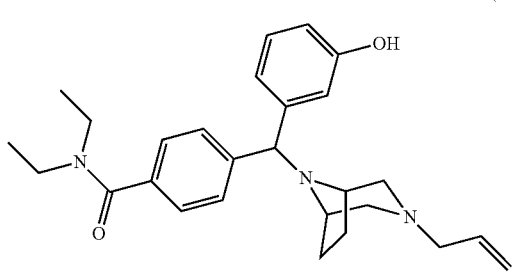

(I-IId)

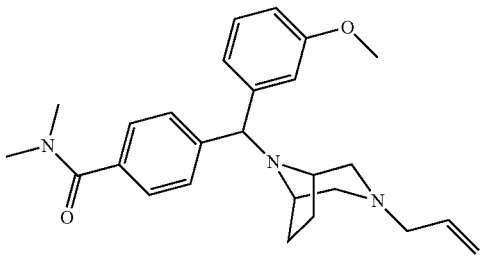

(I-IIId)

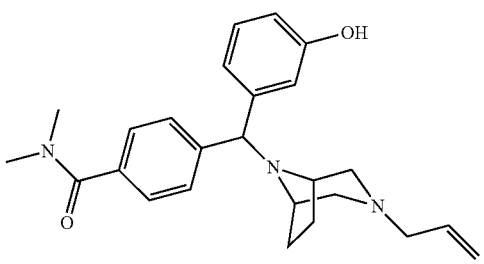

(I-IVd)

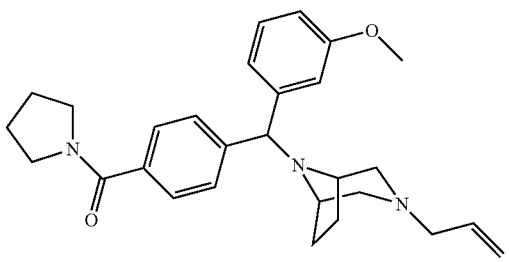

(I-Vd)

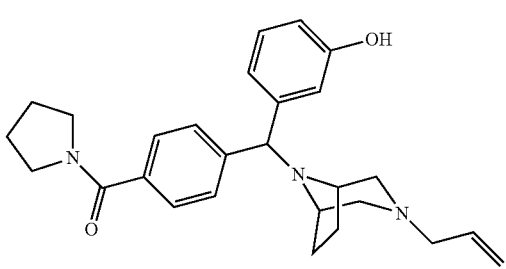

(I-VId)

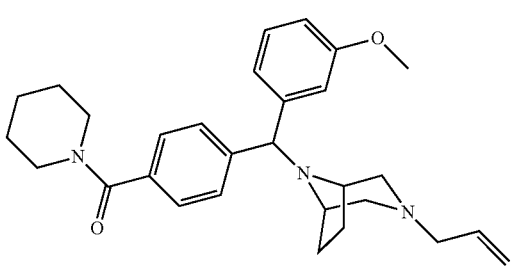

(I-VIId)

-continued
(I-VIIId)
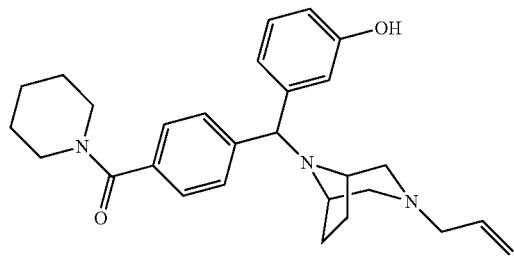
(I-IXd)
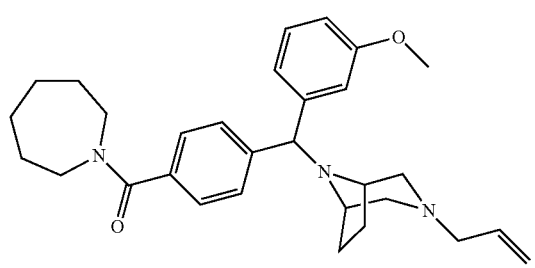
(I-Xd)
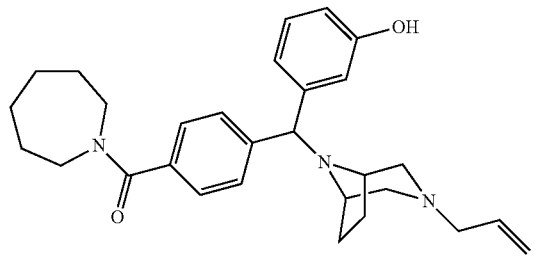
(I-XId)
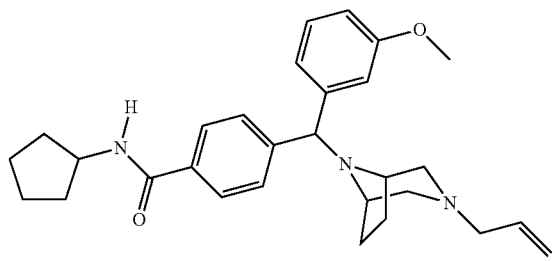
(I-XIId)
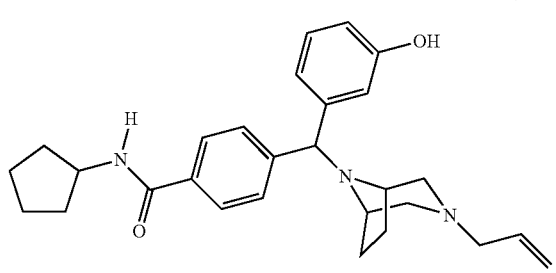
-continued
(I-XIIId)
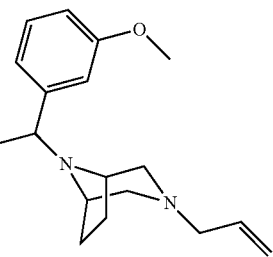
(I-XIVd)
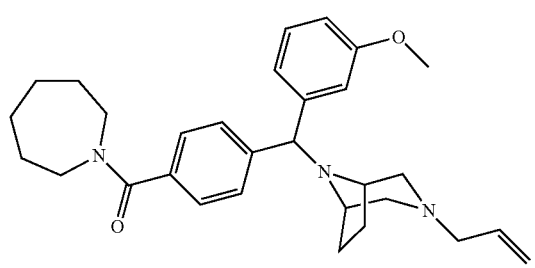
(I-XVd)
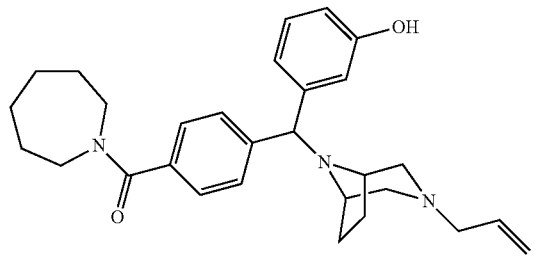
(I-XVId)
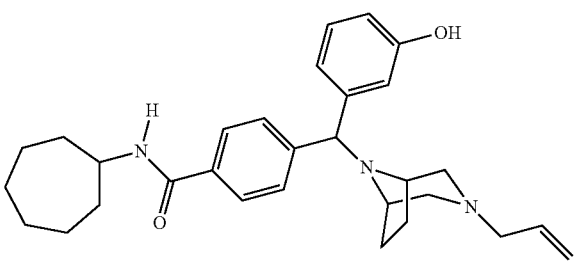
(I-XVIId)
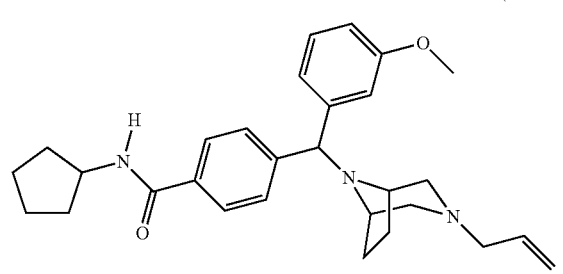

-continued
(I-XVIIId)
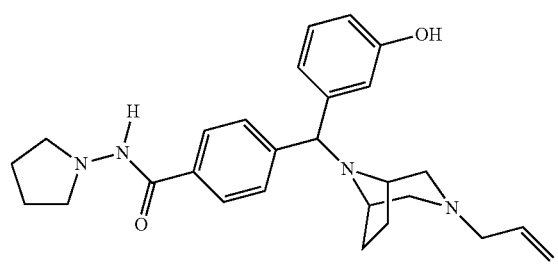
(I-XIXd)
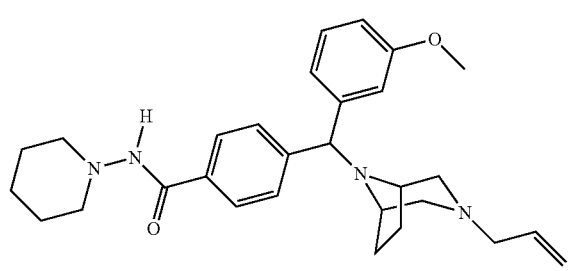
(I-XXd)
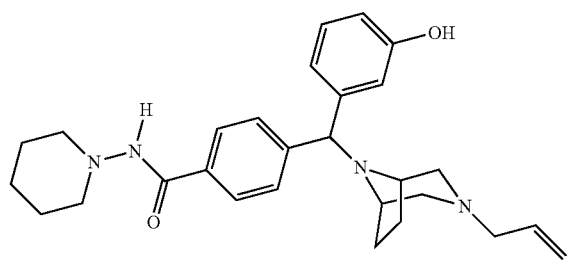
(I-XXId)
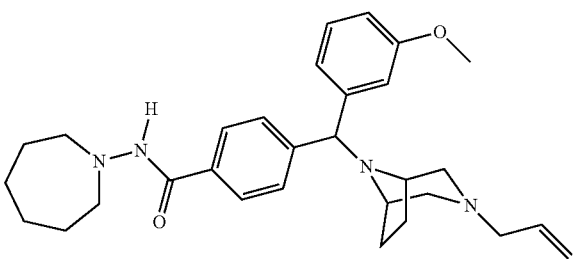
(I-XXIId)
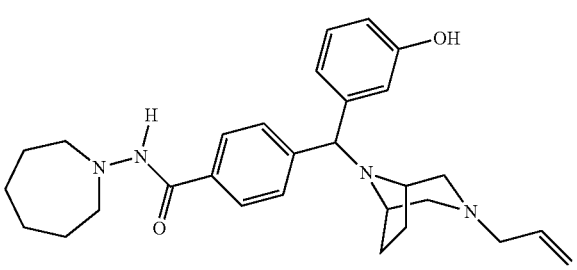
-continued
(I-Ie)
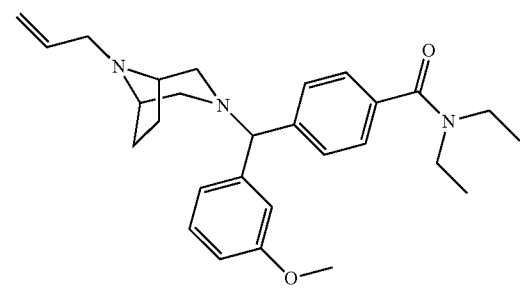
(I-IIe)
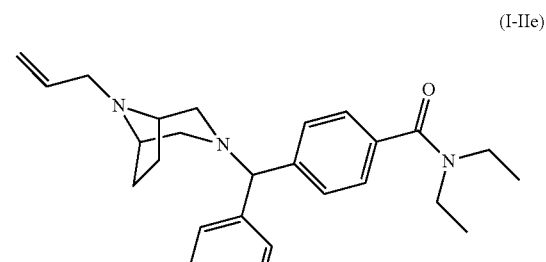
(I-IIIe)
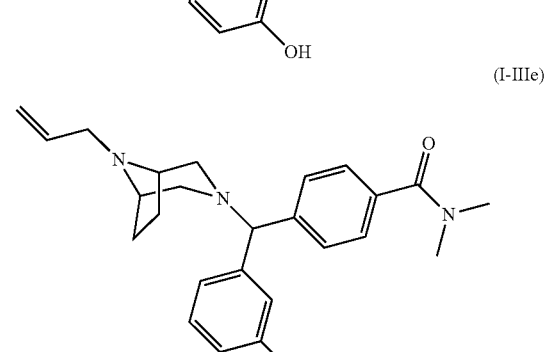
(I-IVe)
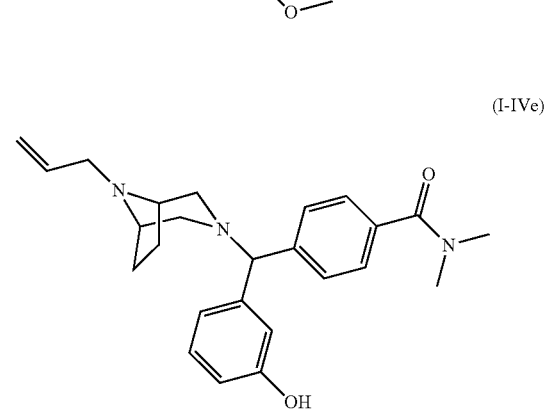
(I-Ve)
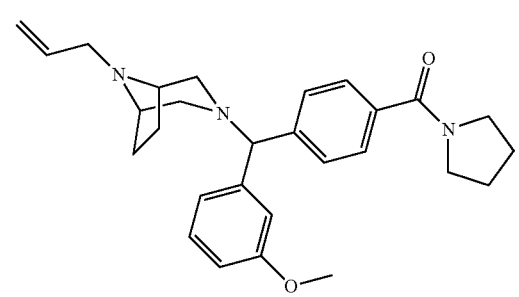

-continued
(I-VIe)
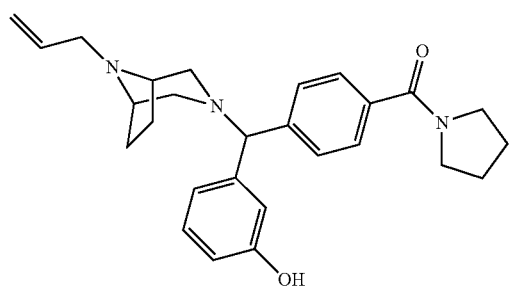
(I-VIIe)
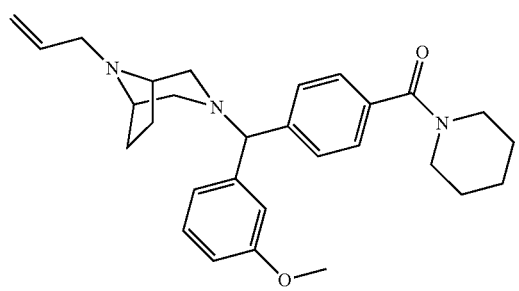
(I-VIIIe)
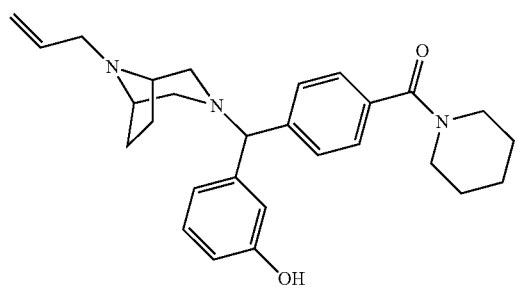
(I-IXe)
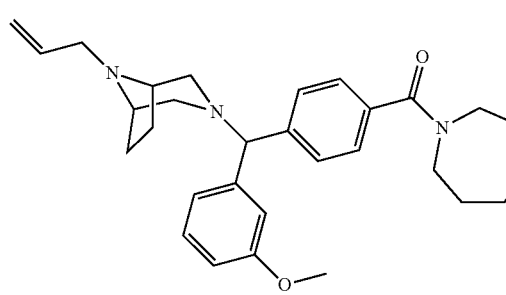
(I-Xe)
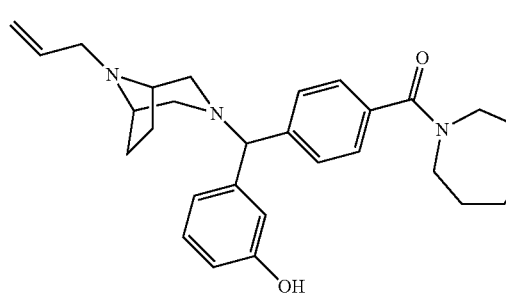
-continued
(I-XIe)
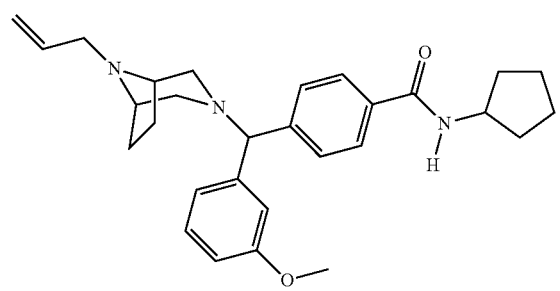
(I-XIIe)
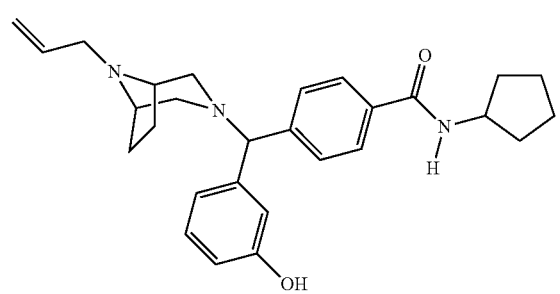
(I-XIIIe)
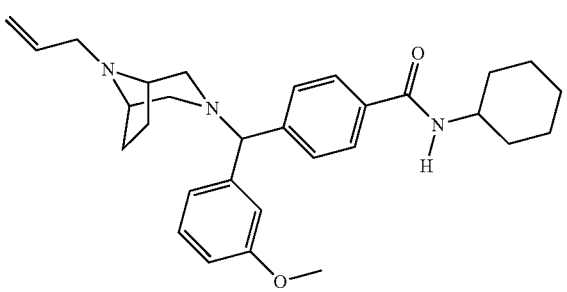
(I-XIVe)
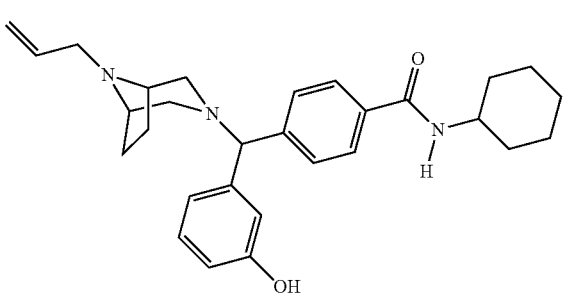
(I-XVe)
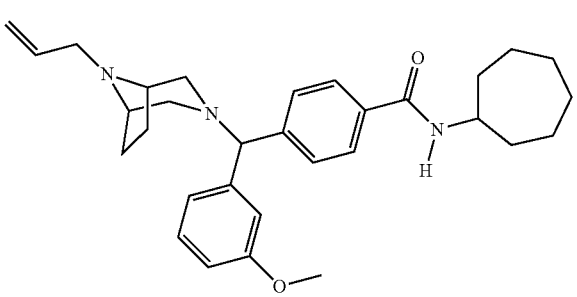

(I-XVIe)

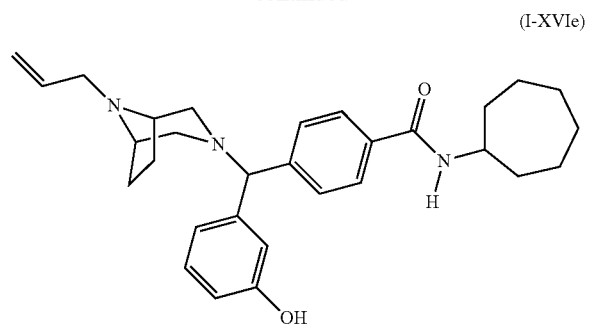

(I-XXe)

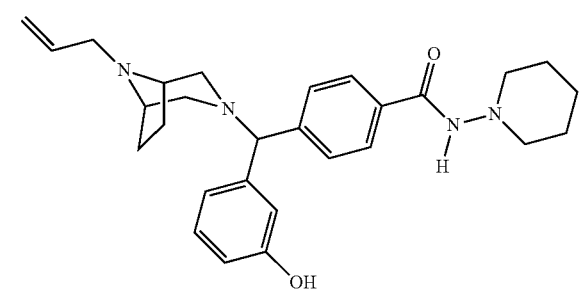

(I-XVIIe)

(I-XXIe)

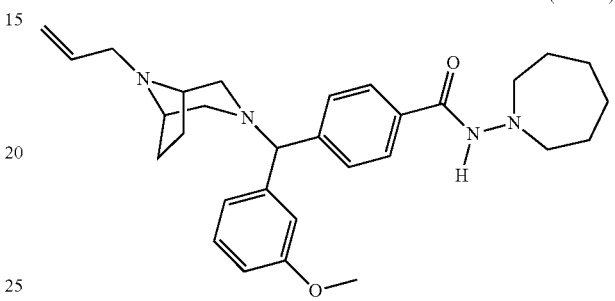

(I-XVIIIe)

(I-XXIIe)

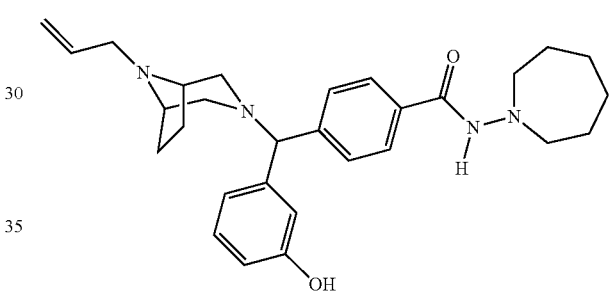

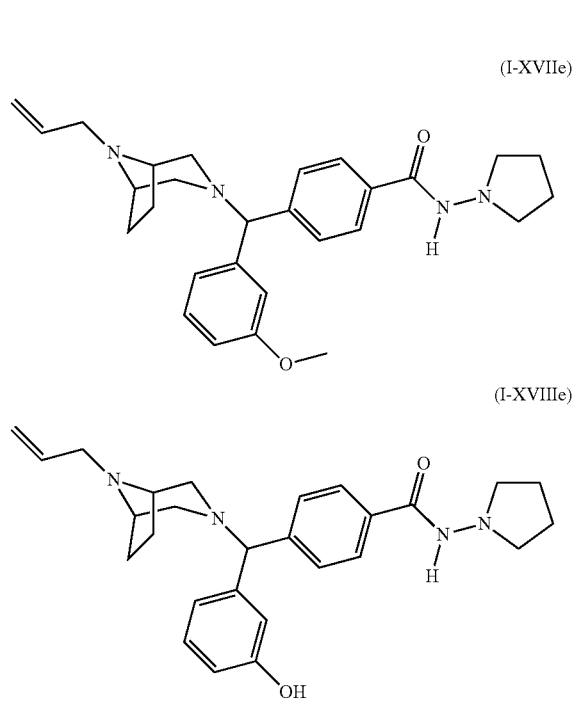

(I-XIXe)

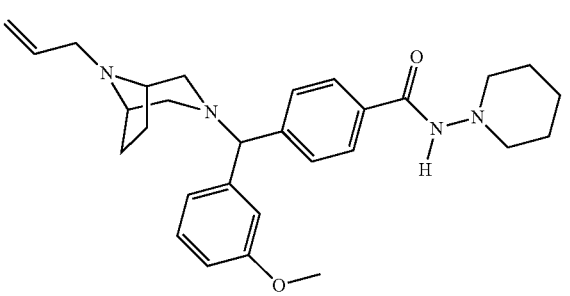

7. A pharmaceutical composition comprising the compound of claim 1 and pharmaceutically acceptable excipients.

8. The pharmaceutical composition according to claim 7, in the form of dispersions, solutions, emulsions, microemulsions, powders, microparticles, nanoparticles, capsules, aerosols, suppositories, tablets, syrups, elixirs, creams, gels, ointments, plasters, foams.

9. The pharmaceutical composition according to claim 7, in the form of micro- or nano-particles made of silica, or of lipids or of pharmaceutically acceptable polymers, wherein the compounds of formula (I) are englobed inside and/or on the surface of said micro- and nano-particles.

10. The pharmaceutical composition according to claim 9, wherein the micro- or nano-particles are modified on the surface by chemico-physical adsorption adsorption of one or more surface modifiers or by chemical functionalization with one or more modifiers.

* * * * *